US012304929B2

(12) United States Patent
Seo et al.

(10) Patent No.: US 12,304,929 B2
(45) Date of Patent: May 20, 2025

(54) RECOMBINANT RSV LIVE VACCINE STRAIN AND THE PREPARING METHOD THEREOF

(71) Applicant: SK BIOSCIENCE CO., LTD., Seongnam-si (KR)

(72) Inventors: Ki-weon Seo, Seongnam-si (KR); Eun-som Kim, Seongnam-si (KR); Teawoo Kwon, Seongnam-si (KR)

(73) Assignee: SK BIOSCIENCE CO., LTD., Seongnam-si (KR)

( * ) Notice: Subject to any disclaimer, the term of this patent is extended or adjusted under 35 U.S.C. 154(b) by 0 days.

(21) Appl. No.: 17/717,504

(22) Filed: Apr. 11, 2022

(65) Prior Publication Data

US 2022/0324917 A1 Oct. 13, 2022

Related U.S. Application Data

(60) Provisional application No. 63/173,577, filed on Apr. 12, 2021.

(30) Foreign Application Priority Data

Sep. 29, 2021 (KR) ........................ 10-2021-0129272

(51) Int. Cl.

| | |
|---|---|
| ***C07K 14/005*** | (2006.01) |
| ***A61K 39/00*** | (2006.01) |
| ***A61K 39/155*** | (2006.01) |
| ***A61P 31/14*** | (2006.01) |
| ***C12N 7/00*** | (2006.01) |

(52) U.S. Cl.

CPC .......... *C07K 14/005* (2013.01); *A61K 39/155* (2013.01); *A61P 31/14* (2018.01); *C12N 7/00* (2013.01); *A61K 2039/5254* (2013.01); *C12N 2760/18521* (2013.01); *C12N 2760/18522* (2013.01); *C12N 2760/18534* (2013.01); *C12N 2760/18571* (2013.01); *C12N 2760/20222* (2013.01)

(58) Field of Classification Search

CPC ..... C07K 14/005; A61P 31/14; A61K 39/155; A61K 2039/5254; C12N 7/00; C12N 2760/18521; C12N 2760/18522; C12N 2760/18534; C12N 2760/18571; C12N 2760/20222

See application file for complete search history.

(56) References Cited

U.S. PATENT DOCUMENTS 11,471,524 B2 * 10/2022 Moore ................. C07K 14/005
2021/0355169 A1 * 11/2021 Seo ........................ A61K 39/12

FOREIGN PATENT DOCUMENTS

WO WO-2011138251 A1 * 11/2011 ........... A61K 39/015
WO WO-2014160463 A1 * 10/2014 ............. A61K 39/12
WO WO-2017075125 A1 * 5/2017 ............. A61K 39/12

OTHER PUBLICATIONS

GenBank Accession No. KU950464.1. Das et al. Direct Submission. Submitted Mar. 21, 2016. (Year: 2016).*

Begoña Ruiz-Argüello, M. et al. (2002). Effect of proteolytic processing at two distinct sites on shape and aggregation of an anchorless fusion protein of human respiratory syncytial virus and fate of the intervening segment. Virology, 298(2), 317-326. (Year: 2002).*

Rawling, J. et al. (2008). Insertion of the two cleavage sites of the respiratory syncytial virus fusion protein in Sendai virus fusion protein leads to enhanced cell-cell fusion and a decreased dependency on the HN attachment protein for activity. Journal of virology, 82(12), 5986-5998. (Year: 2008).*

Chaiwatpongsakorn, S., Epand, R. F., Collins, P. L., Epand, R. M., & Peeples, M. E. (2011). Soluble respiratory syncytial virus fusion protein in the fully cleaved, pretriggered state is triggered by exposure to low-molarity buffer. Journal of virology, 85(8), 3968-3977. (Year: 2011).*

Widjaja, I. et al. (2015). Recombinant Soluble Respiratory Syncytial Virus F Protein That Lacks Heptad Repeat B, Contains a GCN4 Trimerization Motif and Is Not Cleaved Displays Prefusion-Like Characteristics. PloS one, 10(6), e0130829. (Year: 2015).*

Sugrue, R. J., Brown, C., Brown, G., Aitken, J., & McL. Rixon, H. W. (2001). Furin cleavage of the respiratory syncytial virus fusion protein is not a requirement for its transport to the surface of virus-infected cells. Journal of General Virology, 82(6), 1375-1386. (Year: 2001).*

Zimmer, G., Conzelmann, K.-K., & Herrler, G. (2002). Cleavage at the Furin Consensus Sequence RAR/KR109 and Presence of the Intervening Peptide of the Respiratory Syncytial Virus Fusion Protein Are Dispensable for Virus Replication in Cell Culture. Journal of Virology, 76(18), 9218-9224. (Year: 2002).*

König, P. et al. (2004). A novel protein expression strategy using recombinant bovine respiratory syncytial virus (BRSV): modifications of the peptide sequence between the two furin . . . function of the BRSV fusion protein. The Journal of general virology, 85(Pt 7), 1815-1824. (Year: 2004).*

(Continued)

*Primary Examiner* — Janet L Andres
*Assistant Examiner* — Carey Alexander Stuart
(74) *Attorney, Agent, or Firm* — MH2 Technology Law Group, LLP

(57) ABSTRACT

The present invention provides a recombinant attenuated respiratory syncytial virus (RSV) comprising F protein of stabilized pre-fusion RSV, or comprising protein consisting of the amino acid sequence represented by SEQ ID NO: 2 or functional fragment thereof, and provides genome of the recombinant RSV and a recombinant vector comprising the genome. The recombinant attenuated RSV can be provided as a live vaccine strain which maintains infectability and has excellent safety and stability.

14 Claims, 10 Drawing Sheets

Specification includes a Sequence Listing.

(56) References Cited

OTHER PUBLICATIONS

Rigter, A. et al. (2013). A protective and safe intranasal RSV vaccine based on a recombinant prefusion-like form of the F protein bound to bacterium-like particles. PloS One, 8(8), e71072. (Year: 2013).*

Ruiz-Argüello MB et al. (2004). Thermostability of the human respiratory syncytial virus fusion protein before and after activation: implications for the membrane-fusion mechanism. J Gen Virol. Dec. 2004;85(Pt 12):3677-3687. (Year: 2004).*

Stobart et al., "BAC-Based Recovery of Recombinant Respiratory Syncytial Virus (RSV)," In: Perez D. R. (ed.), Reverse Genetics of RNA Viruses: Methods and Protocols, Methods in Molecular Biology, 2017, vol. 1602, pp. 111-124.

Collins et al., "Respiratory Syncytial Virus: Virology, Reverse Genetics, and Pathogenesis of Disease," In: Anderson et al., (eds.) Challenges and Opportunities for Respiratory Syncytial Virus Vaccines, Current Topics in Microbiology and Immunology, 2013, vol. 372, 36 pages.

Hu et al., "Development of a reverse genetics system for respiratory syncytial virus long strain and an immunogenicity study of the recombinant virus," Virology Journal, 2014, vol. 11, No. 142, 16 pages.

* cited by examiner

【FIG. 1】
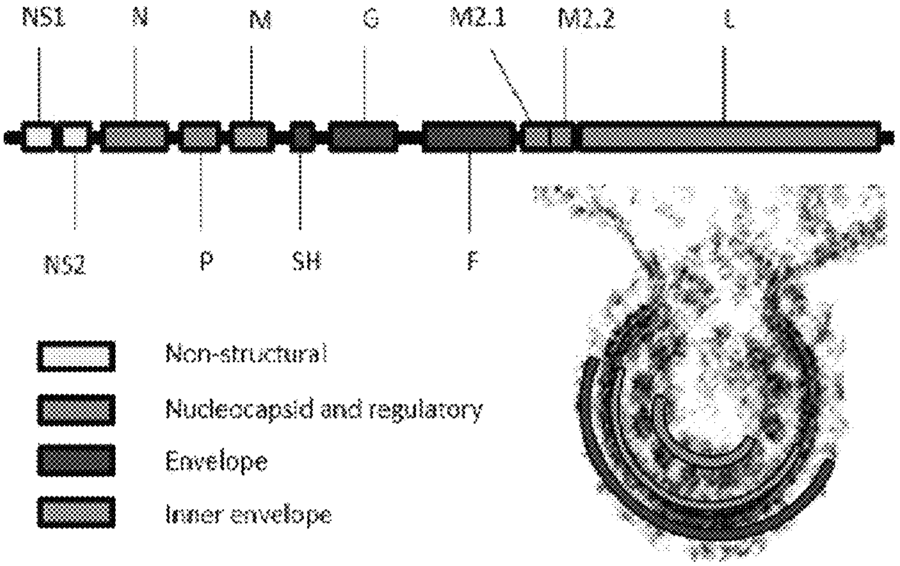

【FIG. 2】
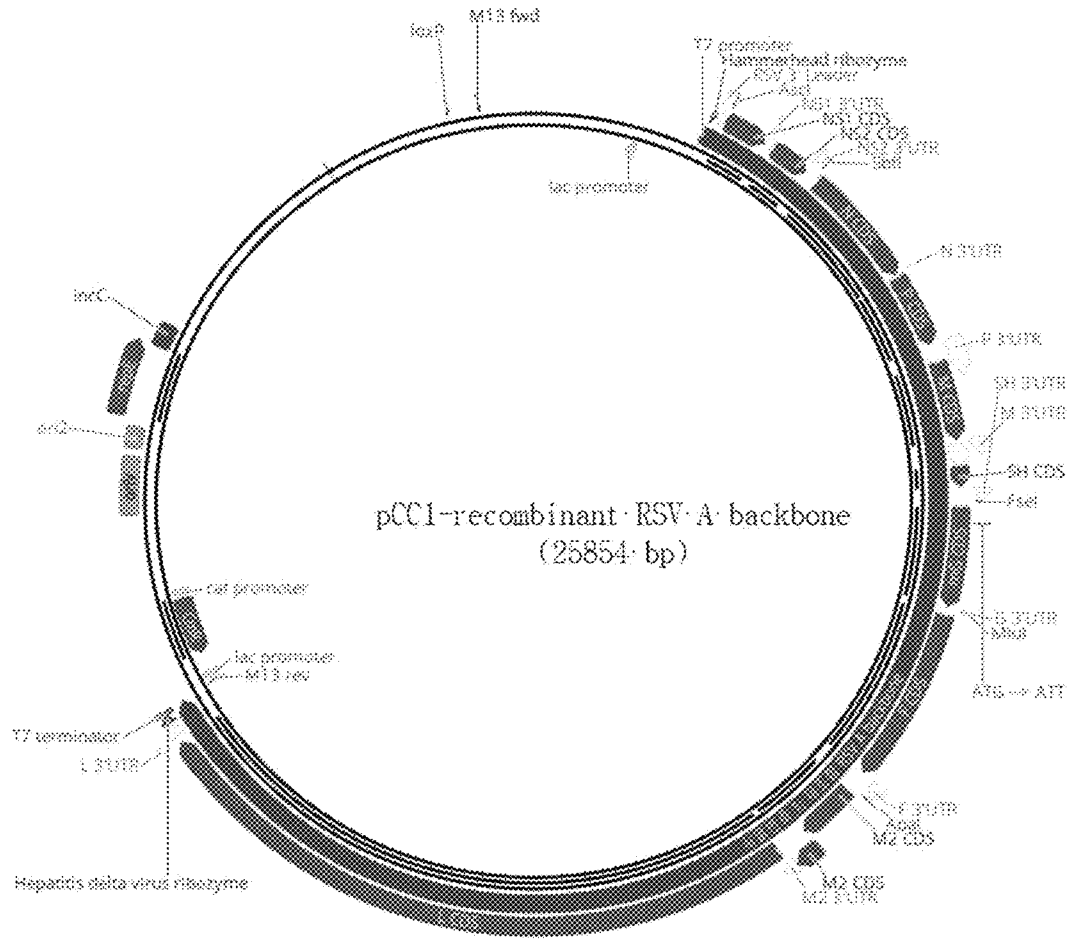

【FIG. 3】
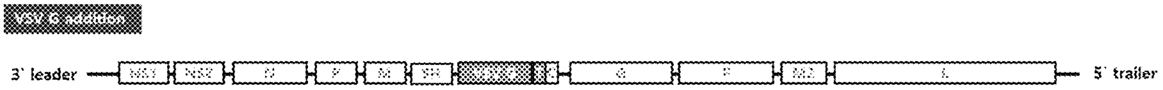
【FIG. 4】
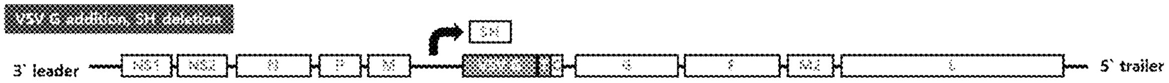
【FIG. 5】
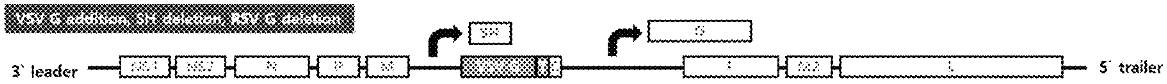
【FIG. 6】
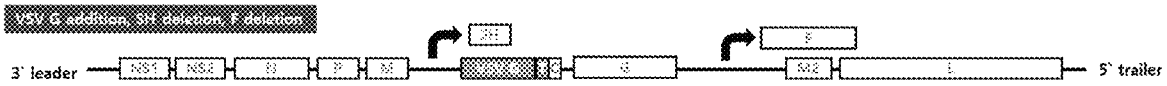
【FIG. 7】
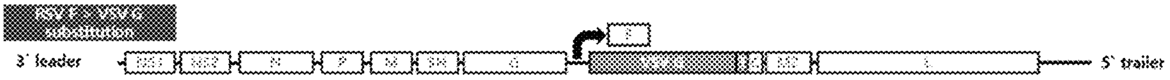

【FIG. 8】
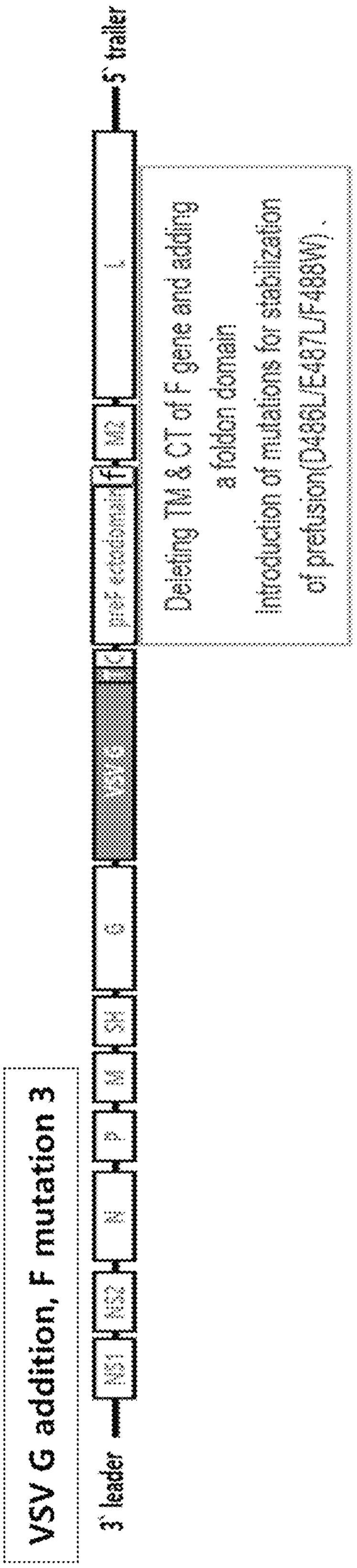
[FIG. 8]
VSV G addition, F mutation 3
3' leader — NS1 — NS2 — N — P — M — SH — G — RSV F — F — M2 — L — 5' trailer
Deleting TM & CT of F gene and adding a foldon domain
Introduction of mutations for stabilization of prefusion(D486L/E487L/F488W).

【FIG. 9】
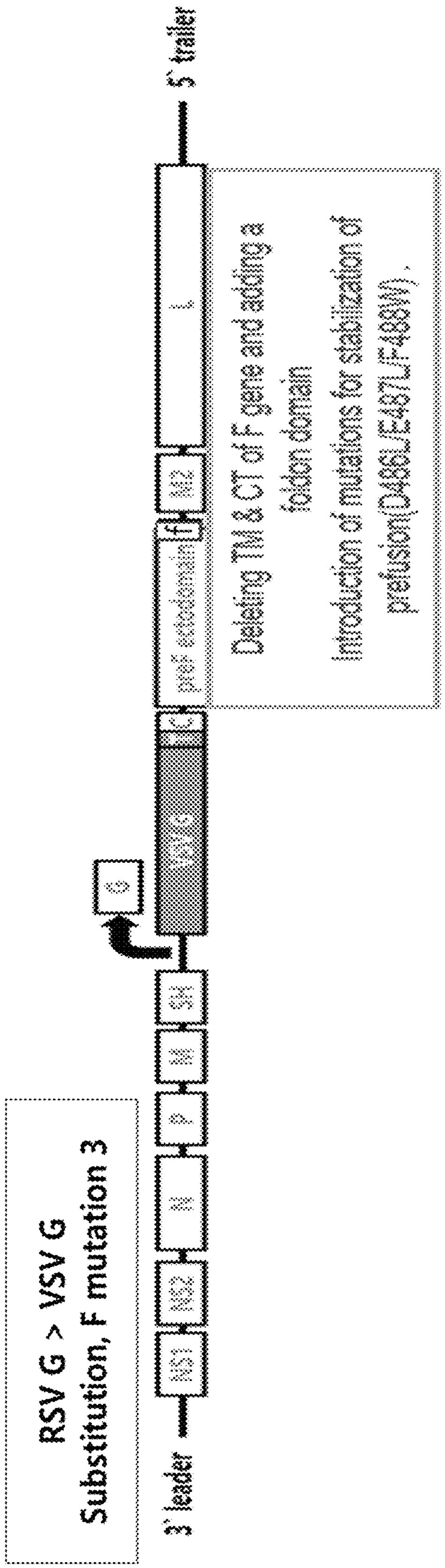
[FIG. 9]
RSV G > VSV G Substitution, F mutation 3
Deleting TM & CT of F gene and adding a foldon domain
Introduction of mutations for stabilization of prefusion (D486L/E487L/F488W).

【FIG. 10】
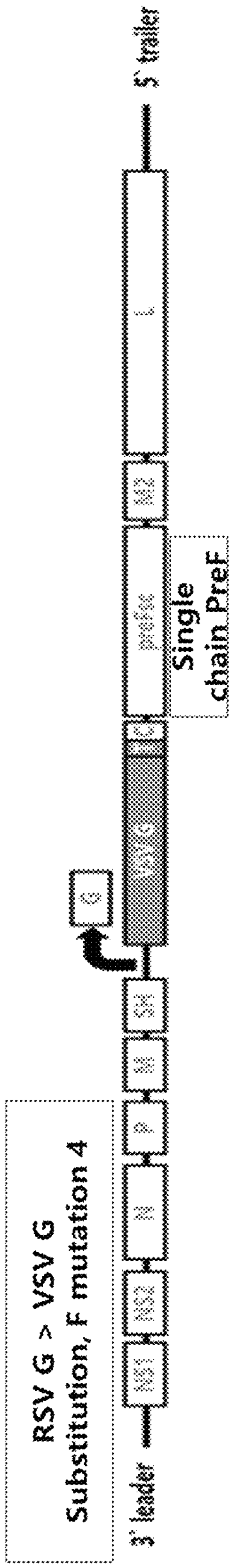

【FIG. 11】
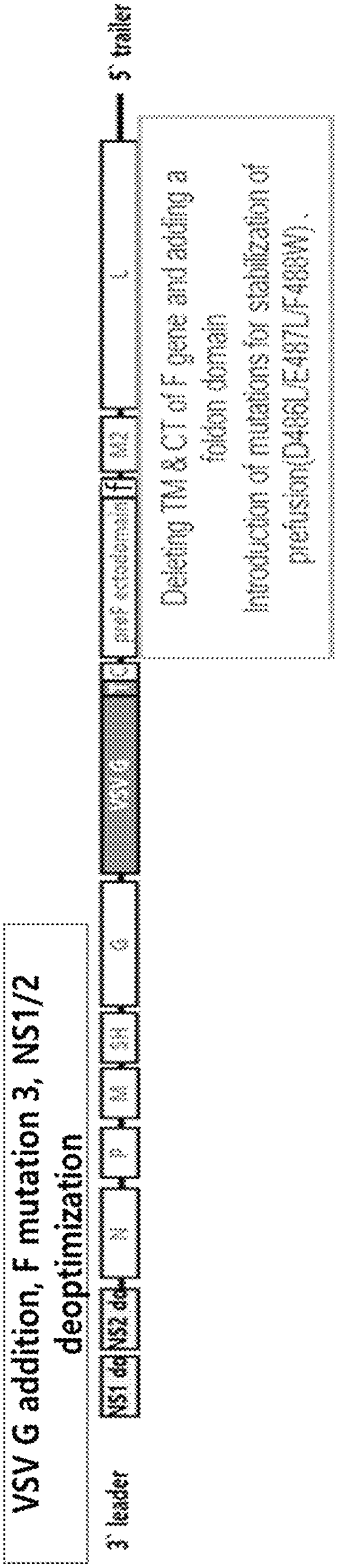

【FIG. 12】
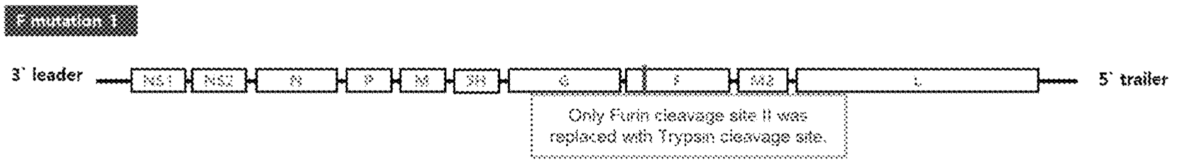
【FIG. 13】
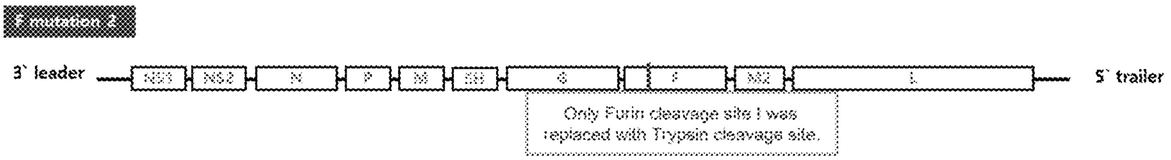

【FIG. 14】
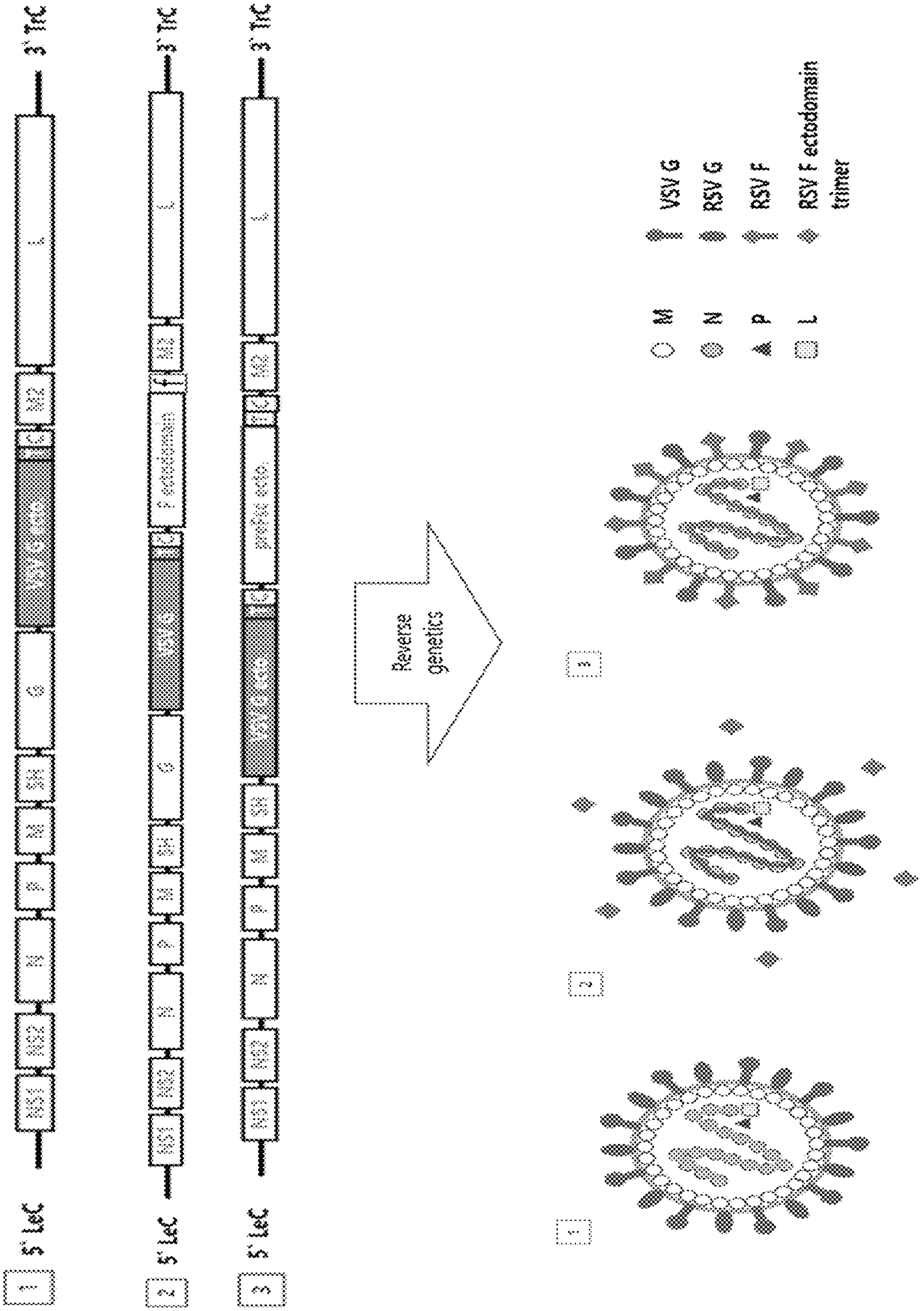

【FIG. 15】
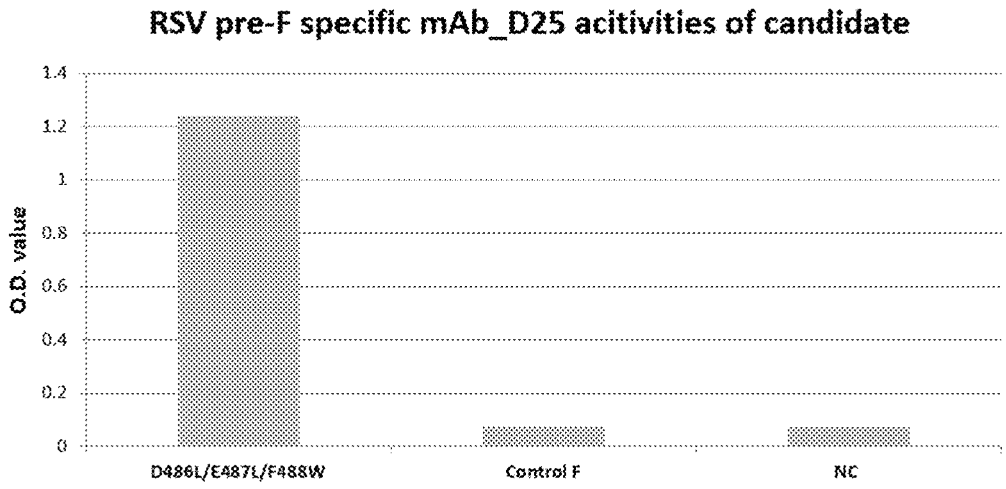

SEQUENCE LISTING

```
<160> NUMBER OF SEQ ID NOS: 58

<210> SEQ ID NO 1
<211> LENGTH: 15311
<212> TYPE: DNA
<213> ORGANISM: respiratory syncytial virus

<400> SEQUENCE: 1

acgcgaaaaa atgcgtacaa caaacttgcg taaaccaaaa aaatggggca aataagaatt     60
tgataagtac cacttaaatt taactccttt ggttagaggc gcgccatggg cagcaactca    120
ttgagtatga taaaagttag attgcaaaat ctgtttgaca atgatgaagt agcattgtta    180
aaaataacat gctatactga caaattaata cagttaacta atgctttggc taaggcagtt    240
atacatacaa tcaaattgaa tggcattgta tttgtgcatg ttattacaag tagtgatatt    300
tgccctaata ataatattgt agtgaaatcc aatttcacaa caatgccagt attacaaaat    360
ggaggttata tatgggaaat gatggaatta acacactgct ctcaacctaa tggcctaata    420
gatgacaatt gtgaaattaa attctccaaa aaactaagtg attcaacaat gaccaattat    480
atgaatcaat tatctgaatt acttggattt gacctcaatc cataaatcat aataaatatc    540
aactagcaaa tcaatgtcac taacaccatt agttaatata aaacttgaca gaagataaaa    600
atggggcaaa taaatcaatt cagccgaccc aaccatggac acaacacaca atgataccac    660
accacaaaga ctgatgatca cagacatgag gccattatcg cttgagacta taataacatc    720
tctaaccaga gatatcataa cacataaatt tatatacttg ataaatcatg aatgcatagt    780
aagaaaactt gatgaaagac aggccacatt tacatttctg gtcaactatg aaatgaaact    840
attgcacaaa gtgggaagca ctaaatataa aaaatatact gaatacaaca caaaatatgg    900
cactttccct atgccaatat ttatcaatca tgatgggttc ttagaatgca ttggcattaa    960
gcctaccaag cacacaccca taatatacaa gtatgatctc aatccatgaa tatcaaacca   1020
agattcaaac aatccgaaat aacaacttta tgcataatca cactccatag tccaaatgga   1080
gcctgaaaat tatagttatt taaaattcct gcaggaagga gagacataag atgaaagatg   1140
gggcaaatac aaaaatggct cttagcaaag tcaagttgaa tgatacactc aacaaagatc   1200
aacttctatc atccagcaaa tataccatcc aacggagcac aggagacagc attgacactc   1260
ctaattatga tgtgcagaaa cacattaata agttatgtgg catgttatta atcacagaag   1320
atgctaatca taaattcact gggttaatag gtatgttata tgctatgtct agattaggaa   1380
gagaagacac cataaaaata ctcaaagatg cgggatatca tgttaaggca aatggagtgg   1440
atgtaacaac acatcgtcaa gacattaatg ggaaagaaat gaaatttgaa gtgttaacat   1500
tagcaagctt aacaactgaa attcaaatca acattgagat agaatctaga aaatcctaca   1560
```

-continued

```
aaaaaatgct aaaagaaatg ggagaggtgg ctccagaata caggcatgac tctcctgatt   1620
gtgggatgat aatattatgt atagcggcat tagtaataac caaattagca gcaggagata   1680
gatcaggtct tacagctgtg attaggagag ctaataatgt cctaaaaaat gaaatgaaac   1740
gttataaagg tttattaccc aaggatatag ccaacagctt ctatgaagtg tttgaaaaat   1800
atcctcactt tatagatgtt tttgttcatt ttggtatagc acaatcttct accagaggtg   1860
gcagtagagt tgaagggatt tttgcaggat tgtttatgaa tgcctatggt gcagggcaag   1920
tgatgttacg gtgggggtc ttagcaaaat cagttaaaaa cattatgtta ggacacgcta    1980
gtgtacaagc agaaatggaa caagttgtgg aggtgtatga gtatgctcag aaattgggtg   2040
gagaagcagg attctaccat atattgaaca acccaaaagc atcactatta tctttgactc   2100
aatttcctca cttctctagt gtagtattgg gcaatgctgc tggcctaggc ataatgggag   2160
aatacagagg tacaccaagg aatcaagatt tatatgatgc tgcaaaagca tatgctgaac   2220
aactcaaaga aaatggtgtg attaactaca gtgtattaga tttgacagca gaagaactag   2280
aggctatcaa acatcagctt aatccaaaag ataatgatgt agagctttga gttaataaaa   2340
aagtggggca aataaatcat catggaaaag tttgctcctg aattccatgg agaagatgca   2400
aacaacagag ccaccaaatt cctagaatca ataaagggca aattcacatc acccaaagat   2460
cccaagaaaa aagatagtat catatctgtc aactcaatag atatagaagt aaccaaagaa   2520
agccctataa catcaaattc aaccattata aacccaataa atgagacaga tgatactgta   2580
gggaacaagc ccaattatca aagaaagcct ctagtaagtt tcaaagaaga ccctacgcca   2640
agtgataatc ctttttcaaa actatacaaa gaaaccatag aaacatttga taacaatgaa   2700
gaagaatcta gctattcata tgaagaaata aatgatcaga caaacgataa tataacagca   2760
agattagata ggattgatga gaaattaagt gaaatactag gaatgcttca cacattagta   2820
gtagcgagtg caggacccac atctgctcgg gatggtataa gagatgccat ggttggttta   2880
agagaagaaa tgatagaaaa aatcagaact gaagcattaa tgaccaatga cagactagaa   2940
gctatggcaa gactcaggaa tgaagaaagt gaaaagatgg caaaagacac atcagatgaa   3000
gtgtctctca atccaacatc agagaaactg aacaacctgt tggaagggaa tgatagtgac   3060
aatgatctat cacttgaaga tttctgatta gctaccaaac tgtacatcaa aacacaacac   3120
caatagaaaa ccaacaaaca aaccaactca cccatccaac caaacatcta tctgctgatt   3180
agccaaccag ccaaaaaaca accagccaat ctaaaactag ccacccggaa aaaatcgata   3240
ctatagttac aaaaaaagat ggggcaaata tggaaacata cgtgaataaa cttcacgagg   3300
gctccacata cacagctgct gttcaataca atgtcctaga aaaagacgat gatcctgcat   3360
cacttacaat atgggtgccc atgttccaat catccatgcc agcagatcta ctcataaaag   3420
aactagccaa tgtcaatata ctagtgaaac aaatatccac acccaaggga ccctcattaa   3480
gagtcatgat aaactcaaga agtgcagtgc tagcacaaat gcccagcaaa tttaccatat   3540
gtgccaatgt gtccttggat gaaagaagca agctggcata tgatgtaacc acaccctgtg   3600
aaattaaggc atgcagtcta acatgcctaa aatcaaaaaa tatgttaact acagttaaag   3660
atctcactat gaaaacactc aacccaacac atgacatcat tgctttatgt gaatttgaaa   3720
atatagtaac atcaaaaaaa gtcataatac caacatacct aagatctatc agcgtcagaa   3780
ataaagatct gaacacactt gaaaatataa caaccactga attcaaaaat gccattacaa   3840
atgcaaaaat catcccttac tcaggattat tgttagtcat cacagtgact gacaacaaag   3900
gagcattcaa atacataaag ccacaaagtc aattcatagt agatcttgga gcttacctag   3960
```

```
aaaaagaaag tatatattat gttacaacaa attggaagca cacagctaca cgatttgcaa   4020
tcaaacccat ggaagattaa ccttttttcct ctacatcaat gagtagattc atacaaactt   4080
tctaactaca ttcttcactt cacaatcata atcaccaacc ctctgtggtt caatcaatca   4140
aacaaaactc atcaagagtt ccagatcatc ccaagtcatt gttcatcaga tccagtactc   4200
aaataagtta ataaaaaatc cacatggggc aaataatcat tgagggaaat ccaactaatc   4260
acaacatctg tcaacataga caagtcaaca cgctagataa aatcaaccaa tggaaaatac   4320
atccataact atagaattct caagcaaatt ctggccttac tttacactaa tacacatgat   4380
aacaacaata atctctttga taatcataat ctccatcatg attgcaatac taaacaaact   4440
ctgcgaatat aatgtattcc ataacaaaac ctttgagcta ccaagagctc gagtcaatac   4500
atagcattca ccaatctgat agctcaaaac agtaaccttg catttgtaaa tgaactaccc   4560
tcacttcttc acaaaaccac atcaacatct caccatgcaa gccatcatct ataccataaa   4620
gtagttaatt aaaaatggcc ggccagtcat aacaatgaac taggatatta agaccaaaaa   4680
caacgctggg gcaaatgcaa acatgtccaa aaccgaggac caacgcaccg ccaagacact   4740
agaaaggacc tgggacactt ttaatcatct attattcata tcatcgtgct tatacaagtt   4800
aaatcttaaa tctatagcac aaatcacatt atctattttg gcaattataa tctcaacctc   4860
acttataatt gcagccatca tattcatagc ctcggcaaac cacaaagtca cactaacaac   4920
tgcaatcata caagatgcaa cgaaccagat caagaacaca accccaacat acctcaccca   4980
gaatccccag catggaatca gcttctccaa tctgtccgga actacatcac aatccaccac   5040
catactagct tcaacaacac caagtgctga ttcaacccca caatccacaa cagtcaagat   5100
caaaaacaca acaacaaccc aaatattacc tagcaaaccc accacaaaac aacgccaaaa   5160
taaaccacaa aacaaaccca acaatgattt tcactttgaa gtgttcaatt ttgtaccctg   5220
cagcatatgc agcaacaatc caacctgctg ggccatctgc aagagaatac caaacaaaaa   5280
acctggaaag aaaaccacca ccaagcccac aaaaaaacca accctcaaga caaccaaaaa   5340
agatcccaaa tcccaaacca caaaaccaaa ggaagtactc actaccaagc ctacaggaaa   5400
gccaaccatc aacaccacta aaacaaacat cagaactaca ctgctcacct ccaacaccaa   5460
aggaaatcca gaacacacaa gtcaagagga aaccctccac tcaaccacct ccgaaggcta   5520
tccaagccca tcacaagtcc acacaacatc cggtcaagag gaaaccctcc actcaaccac   5580
ctccgaaggc tatccaagcc catcacaagt ctacacaaca tccgagtacc tatcacaatc   5640
tctatcttca tccaacacaa caaaatgata gtcattaaaa agcacgcgtg tattgttgca   5700
aaaagccatg accaaatcaa acagaatcaa aatcaactct ggggcaaata acaatggagt   5760
tgccaatcct caaaacaaat gctattacca caatccttgc tgcagtcaca ctctgtttcg   5820
cttccagtca aaacatcact gaagaatttt atcaatcaac atgcagtgca gtcagcaaag   5880
gctatcttag tgctctaaga actggttggt atactagtgt tataactata gaattaagta   5940
atatcaagga aaataagtgt aatggtacag acgctaaggt aaaattaata aaacaagaat   6000
tagataaata taaaaatgct gtaacagaat tgcagttgct catgcaaagc acaccagcag   6060
ccaacaatcg agccagaaga gaactaccaa gatttatgaa ttatacactc aacaatacca   6120
aaaacaccaa tgtaacatta agtaagaaaa ggaaaagaag atttcttgga tttttgttag   6180
gtgttggatc tgcaatcgcc agtggcattg ccgtatccaa ggtcctgcac ctagaagggg   6240
aagtgaacaa aatcaaaagt gctctactat ccacaaacaa ggctgtagtc agcttatcta   6300
```

-continued

```
atggagtcag tgtcttaacc agcaaggtgt tagacctcaa aaactatata gataaacagt   6360
tgttacctat tgttaacaag caaagctgca gcatatcaaa cattgaaact gtgatagagt   6420
tccaacaaaa gaacaacaga ctactagaga ttaccagaga atttagtgtt aatgcaggtg   6480
taactactcc tgtaagcact tatatgttaa ctaatagtga gttattatca ttaatcaatg   6540
atatgcctat aacaaatgat cagaaaaagt taatgtccag caatgttcaa atagttagac   6600
agcaaagtta ctctatcatg tcaataataa aagaggaagt cttggcatat gtagtacaat   6660
taccactata tggtgtaata gatactcctt gttggaaact acacacatcc cctttatgta   6720
caaccaacac aaaggaagga tccaacatct gcttaacaag aaccgacaga ggatggtact   6780
gtgacaatgc aggatcagta tcctttttcc cacaagctga aacatgtaaa gttcaatcga   6840
atcgggtgtt ttgtgacaca atgaacagtt taacattacc aagtgaggta aatctctgca   6900
acattgacat attcaacccc aaatatgatt gcaaaattat gacttcaaaa acagatgtaa   6960
gcagctccgt tatcacatct ctaggagcca ttgtgtcatg ctatggcaaa accaaatgta   7020
cagcatccaa taaaaatcgt gggatcataa agacattctc taacgggtgt gattatgtat   7080
caaataaggg ggtggatact gtgtctgtag gtaatacatt atattatgta aataagcaag   7140
aaggcaaaag tctctatgta aaaggtgaac caataataaa tttctatgat ccattagtgt   7200
tcccctctga tgaatttgat gcatcaatat ctcaagtcaa tgagaaaatt aatcagagtc   7260
tagcatttat ccgtaaatca gatgaattat tacataatgt aaatgctggt aaatccacca   7320
caaatatcat gataactacc ataattatag taattatagt aatattgtta gcattaattg   7380
cagttggact gcttctatac tgcaaggcca gaagcacacc agtcacatta agtaaggatc   7440
aactgagtgg tataaataat attgcattta gtaactgaat aaaaatagca cctaatcata   7500
ttcttacaat ggttcgctat ttgaccatag ataacccatc tatcattaga ttatcctaaa   7560
atttgaactt catcacaact ttcatctata aaccatctca cttacacttt ttaagtagat   7620
ttctatttta tagttatata aaacagggcc cattgaatac caaattaact tactatttgt   7680
aaaaatgaga attggggcaa atatgtcacg aaggaatcct tgcaaattcg aaattcgagg   7740
tcattgcttg aatggtaaaa ggtgtcattt tagtcataat tattttgaat ggccacccca   7800
tgcactgctt gtaagacaaa actttatgtt aaacagaata cttaagtcta tggataaaag   7860
catagatact ttgtcagaaa taagtggagc tgcagagttg gacagaacag aagagtatgc   7920
cctcggtgta gttggagtgc tagagagtta tataggatca ataaataata taactaaaca   7980
atcagcatgt gttgccatga gcaaactcct tactgaactc aacagcgatg acatcaaaaa   8040
actaagggac aatgaagagc caaactcacc caaagtaaga gtgtacaata ctgtcatatc   8100
atatattgaa agcaacagga agaacaataa acaaactatc catctgttaa aaagattgcc   8160
agcagacgta ttgaagaaaa ccatcaaaaa cacattggat atccacaaga gcataaccat   8220
caataaccca aaagaatcaa ctgttagtga tacgaacgac catgccaaaa ataatgatac   8280
tacctgacaa atatccttgt agtataaatt ccatactaat aacaagtaat tgtagagtca   8340
ctatgtataa tcaaaaaaac acactatata tcaatcaaaa caaccaaaat agccatatat   8400
acccaccgga tcaaccattc aatgaaatcc attggacctc tcaagacttg attgatgcaa   8460
ctcaaaattt tctacaacat ctaggtatta ctgatgatat atacacaata tatatattag   8520
tgtcataata ctcaatccta atacttacca catcatcaaa ttattaactc aaacaattca   8580
agctatggga caaaatggat cccattatta gtggaaattc tgctaatgtt tatctaactg   8640
atagttattt aaaaggtgtt atttctttct cagaatgtaa cgctttagga agttacatat   8700
```

-continued

```
tcaatggtcc ttatctcaaa aatgattata ccaacttaat tagtagacaa aatccattaa   8760
tagaacacat aaatctaaag aaactaaata taacacagtc cttaatatct aagtatcata   8820
aaggtgaaat aaaaatagaa gaacctactt actttcagtc attacttatg acatacaaga   8880
gtatgacctc ttcagaacag actactacta ctaatttact taaaaagata ataagaagag   8940
ctatagaaat cagtgatgtc aaagtctatg ctatattgaa taaactgggg ctcaaagaaa   9000
aagacaagat taaatccaat aatggacaag atgaagacaa ctcagtcatt actaccataa   9060
tcaaagatga tatactttta gctgtcaagg ataatcaatc tcatcttaaa gcagacaaaa   9120
atcaatccac aaaacaaaaa gatacaatca aaacaacact tttgaagaaa ttaatgtgtt   9180
cgatgcaaca tcctccatca tggttaatac attggtttaa tttatacaca aaattaaaca   9240
gcatattaac acaatatcga tctagtgagg taaaaaacca tggttttata ttgatagata   9300
atcatactct tagtggattc caatttattt tgaatcaata tggttgtata gtttatcata   9360
aggaactcaa aagaattact gtgacaactt ataatcaatt cttgacatgg aaagatatta   9420
gccttagtag attaaatgtt tgtttgatta catggattag taactgtttg aacacattaa   9480
acaaaagctt aggcttaaga tgtggattca ataatgttat cttgacacaa ttattccttt   9540
atggagattg tatactaaaa ctattccaca atgaggggtt ctacataata aaagaggtag   9600
agggatttat tatgtctcta attttaaata taacagaaga agatcaattc agaaaacggt   9660
tttataatag tatgctcaac aacatcacag atgccgccaa caaagctcaa aaaaatctgc   9720
tatcaagagt atgtcataca ttattagata agacaatatc agataatata ataaatggca   9780
gatggataat tctattgagt aagttcctaa aattaattaa gcttgcaggt gacaataacc   9840
tcaacaatct gagtgaatta tattttttgt tcagaatatt tggacaccca atggtagatg   9900
aaagacaagc catggatgct gttaaagtta attgcaacga gaccaaattt tatttgttaa   9960
gtagtttgag tatgttaaga ggagctttta tatatagaat tataaaaggg tttgtaaata  10020
attacaacag atggcctact ttaagaaatg ccattgtctt acccttaaga tggttaactt  10080
actataaact aaacacttat ccttccttgt tggaacttac agaaagagat ttgattgttc  10140
tatcaggact acgtttctat cgagagtttc ggttgcctaa aaaagtggat cttgaaatga  10200
tcataaatga taaggctata tcacctccta aaaatttaat atggactagt ttccctagaa  10260
attatatgcc gtcacacata caaaattata tagaacatga aaaattaaaa ttctctgata  10320
gtgataaatc aagaagagta ttagagtatt atttaagaga taacaaattc aatgaatgtg  10380
atttacacaa ctgtgtagtt aatcaaagtt atcttaacaa cccgaatcat gtggtatcat  10440
tgacaggcaa agaaagagaa ctcagtgtag gtagaatgtt tgcaatgcaa ccaggaatgt  10500
tcagacaagt tcaaatatta gcagagaaaa tgatagcaga aaacatatta caatttttcc  10560
ctgaaagtct tacaagatat ggtgatctag aactacagaa aatattagaa ttgaaagcag  10620
gaataagtaa caaatcaaat cgttacaatg ataattacaa caattacatt agtaagtgct  10680
ctatcatcac agatctcagc aaattcaatc aagcatttcg atatgaaaca tcatgtattt  10740
gtagtgatgt actggatgaa ctgcatggtg tacaatctct attttcctgg ttacatttaa  10800
ctattcctca tgtcacaata atatgcacat ataggcatgc acccccctat ataaaggatc  10860
atattgtaga tcttaacaat gtagatgagc aaagtggact atatagatat catatgggtg  10920
gtatcgaagg gtggtgtcaa aaactatgga ccatagaagc tatatcacta ttagatctaa  10980
tatctctcaa agggaaattc tcaattactg ctttaattaa tggtgacaat caatcaatag  11040
```

-continued

```
atataagtaa accagtcaga ctcatggaag gtcaaactca tgctcaagca gattatttgc  11100
tagcattaaa tagtctcaaa ttactgtata aagagtatgc aggaataggc cacaaattaa  11160
aaggaactga gacttatata tcgagagata tgcaatttat gagtaaaacg atccaacata  11220
acggtgtata ttacccagct agtataaaga aagtcctaag agtgggaccg tggataaaca  11280
ctatacttga tgacttcaaa gtgagtctag aatctatagg tagtttgaca caagaattag  11340
aatatagagg tgaaagtcta ttatgcagtt taatatttag aaatgtatgg ttatataatc  11400
aaattgcatt acaacttaaa aatcatgcat tatgtaacaa caaattatat ttggatatat  11460
taaaagttct aaaacactta aaaacctttt ttaatcttga taacattgat acagcattaa  11520
cattgtatat gaatttgccc atgttatttg gtggtggtga tcccaacttg ttatatcgaa  11580
gtttctatag aagaactcct gatttcctca cagaggctat agttcactct gtgttcatac  11640
ttagttatta tacaaaccat gatttaaaag ataaacttca agatctgtca gatgatagat  11700
tgaataagtt cttaacatgc ataatcacgt ttgataaaaa ccccaatgct gaattcgtta  11760
cattgatgag agatcctcaa gctttaggat ctgagaggca agctaaaatt actagcgaaa  11820
tcaatagact ggcagttacc gaggttttga gcacagctcc aaacaaaata ttttccaaaa  11880
gtgcacaaca ctataccact acagagatag atcttaatga tattatgcaa aatatagaac  11940
ctacatatcc tcacgggcta agagttgttt atgagagttt accccttttat aaagcagaga  12000
aaatagtaaa tcttatatcc ggtacaaaat ctataactaa catactggaa aagacttctg  12060
ccatagactt aacagatatt gatagagcca ctgagatgat gaggaaaaac ataactttgc  12120
ttataaggat attaccatta gattgtaaca gagataaaag agaaatattg agtatggaaa  12180
acctaagtat tactgaatta agcaaatacg ttagagaaag atcttggtct ttatccaata  12240
tagttggtgt tacatcaccc agtatcatgt atacaatgga cataaaatat acaacaagca  12300
ctatagctag tggcataatc atagagaaat ataatgtcaa cagtttaaca cgtggtgaga  12360
gaggacccac taaaccatgg gttggttcat ctacacaaga gaaaaagaca atgccagttt  12420
ataatagaca agttttaacc aaaaaacaga gagatcaaat agatctatta gcaaaattgg  12480
attgggtgta tgcatctata gataacaagg atgaatttat ggaggaactt agcataggaa  12540
ctcttgggtt aacatatgag aaggccaaaa aattattccc acaatatttg agtgttaact  12600
atttgcatcg tcttacagtc agtagtagac catgtgaatt ccctgcatct ataccagctt  12660
atagaactac aaattatcac tttgatacta gccctattaa tcgcatatta acagaaaagt  12720
atggtgatga agatattgat atagtattcc aaaactgtat aagctttggc cttagcttaa  12780
tgtctgtagt agaacaattt actaatgtat gtcctaacag aattattctc atacccaagc  12840
ttaatgagat acatttgatg aaacctccca tattcacagg cgatgttgat attcacaagt  12900
taaaacaagt gatacaaaaa caacatatgt ttttaccaga caaaataagt ttgactcaat  12960
atgtggaatt attcttaagt aataaaacac tcaaatctgg atctaatgtt aattctaatt  13020
taatattggc gcataagata tctgactatt ttcataatac ttacattttg agtactaatt  13080
tagctggaca ttggattctt attatacaac ttatgaaaga ttctaagggt atttttgaaa  13140
aagattgggg agagggatat ataactgatc atatgttcat taatttgaaa gttttcttca  13200
atgcttataa gacatatctc ttgtgttttc ataaaggtta cggcagagca aagctggagt  13260
gtgatatgaa tacttcagat ctcctatgtg tattggaatt aatagacagt agttattgga  13320
agtctatgtc taaggtgttt ttagaacaaa aagttatcaa atacattctt agccaggatg  13380
caagtttaca tagagtaaaa ggatgtcata gcttcaaact atggtttctt aaacgtctta  13440
```

```
atgtagcaga attcacagtt tgcccttggg ttgttaacat agattatcat ccaacacata  13500
tgaaagcaat attaacttat attgatcttg ttagaatggg attgataaat atagatagaa  13560
tatacattaa aaataaacac aagttcaatg atgagtttta tacttctaat ctgttttaca  13620
ttaattataa cttctcagat aatactcatc tattaactaa acatataagg attgctaatt  13680
ccgaattaga aagtaattac aacaaattat atcatcctac accagaaacc ctagaaaata  13740
tactaaccaa tccggttaaa agtaatgaga aaaagacact gagtgactat tgtataggta  13800
aaaatgttga ctcaataatg ttaccatcgt tatctaataa gaagcttatt aaatcgtcta  13860
caatgattag aaccaattac agcagacaag atttgtataa tttatttcct acggttgtga  13920
ttgataaaat tatagatcat tcaggtaata cagccaaatc taaccaactt tacactacta  13980
cttctcatca aatatcctta gtgcacaata gcacatcact ttattgcatg cttccttggc  14040
atcatattaa tagattcaat tttgtattta gttctacagg ttgtaaaatt agtatagagt  14100
atattttaaa agatcttaaa attaaggatc ctaattgtat agcattcata ggtgaaggag  14160
cagggaattt attattgcgt acagtagtgg aacttcatcc tgatataaga tatatttaca  14220
gaagtctgaa agattgcaat gatcatagtt taccaattga gtttttaagg ctgtacaatg  14280
gacatatcaa cattgattat ggtgaaaatt tgaccattcc tgctacagat gcaaccaaca  14340
acattcattg gtcttattta catataaagt ttgctgaacc tatcagtctt tttgtctgtg  14400
atgctgaatt gcctgtaaca gtcaactgga gtaagattat aatagagtgg agcaagcatg  14460
taagaaaatg caagtactgt tcttcagtta ataaatgtac attgatagta aaatatcatg  14520
ctcaagatga tatcgatttc aaattagaca acataactat attaaaaact tatgtatgct  14580
taggtagtaa gttaaaggga tctgaagttt acttagtcct tacaataggt cctgcaaatg  14640
tgttcccagt atttaatgta gtacaaaatg ctaaattgat actatcaaga actaaaaatt  14700
tcatcatgcc taaaaaagct gataaagagt ctattgatgc aaatattaag agtttgatac  14760
cctttctttg ttaccctata acaaaaaaag gaattaatac tgcattgtct aaattaaaga  14820
gtgttgttag tggagatata ctatcatatt ctatagctgg acgtaatgaa gttttcagca  14880
ataaacttat aaatcataag catatgaaca tcttaaagtg gttcaatcat gttttaaatt  14940
tcagatcaac agaattaaac tataatcatt tatatatggt agaatctact tatcctcatc  15000
taagtgaatt gttaaacagc ttgacaacca atgaacttaa aaaactgatt aaaatcacag  15060
gtagtttgtt atacaacttt tataatgaat aatgagcaaa aatcttataa caaaaatagc  15120
tacacactaa cattgtattc aattatagtt attgaaaatt aataattata taatttttaa  15180
taacttctag tgaactaatc ctaaaattat cattttgatc taggaagaat aagtttaaat  15240
ccaaatctaa ttggtttata tgtatattaa ctaaattacg agatattagt ttttgacact  15300
tttttctcg t                                                        15311
```

<210> SEQ ID NO 2
<211> LENGTH: 514
<212> TYPE: PRT
<213> ORGANISM: Artificial Sequence
<220> FEATURE:
<223> OTHER INFORMATION: Chimeric G protein of Vesicular stomatitis
      Indiana virus

<400> SEQUENCE: 2

```
Met Lys Cys Leu Leu Tyr Leu Ala Phe Leu Phe Ile Gly Val Asn Cys
1               5                   10                  15
```

-continued

```
Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
        35                  40                  45

His Asn Asp Leu Ile Gly Thr Ala Leu Gln Val Lys Met Pro Lys Ser
    50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr His
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Val Ile Val Gln
    130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Tyr Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Met Asp Ile Thr Phe Phe Ser Glu Asp
        195                 200                 205

Gly Glu Leu Ser Ser Leu Gly Lys Glu Gly Thr Gly Phe Arg Ser Asn
    210                 215                 220

Tyr Phe Ala Tyr Glu Thr Gly Gly Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
    290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
        355                 360                 365

Glu Arg Glu Leu Trp Asp Asp Trp Ala Pro Tyr Glu Asp Val Glu Ile
    370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
            420                 425                 430

Leu Pro Asp Asp Glu Ser Leu Phe Phe Gly Asp Thr Gly Leu Ser Lys
```

```
        435                 440                 445

Asn Pro Ile Glu Leu Val Glu Gly Trp Phe Ser Ser Trp Lys Ser Ser
    450                 455                 460

Ile Ala Ser Phe Phe Phe Ile Ile Gly Leu Ile Ile Gly Leu Phe Leu
465                 470                 475                 480

Val Leu Arg Val Gly Ile His Leu Cys Ile Lys Ala Arg Ser Thr Pro
                485                 490                 495

Val Thr Leu Ser Lys Asp Gln Leu Ser Gly Ile Asn Asn Ile Ala Phe
            500                 505                 510

Ser Asn
```

<210> SEQ ID NO 3
<211> LENGTH: 1545
<212> TYPE: DNA
<213> ORGANISM: Artificial Sequence
<220> FEATURE:
<223> OTHER INFORMATION: cDNA encoding a Chimeric G protein of Vesicular stomatitis Indiana virus

<400> SEQUENCE: 3

```
atgaagtgcc ttttgtactt agccttttta ttcattgggg tgaattgcaa gttcaccata     60

gtttttccac acaaccaaaa aggaaactgg aaaaatgttc cttctaatta ccattattgc    120

ccgtcaagct cagatttaaa ttggcataat gacttaatag gcacagcctt acaagtcaaa    180

atgcccaaga gtcacaaggc tattcaagca gacggttgga tgtgtcatgc ttccaaatgg    240

gtcactactt gtgatttccg ctggtatgga ccgaagtata taacacattc catccgatcc    300

ttcactccat ctgtagaaca atgcaaggaa agcattgaac aaacgaaaca aggaacttgg    360

ctgaatccag gcttccctcc tcaaagttgt ggatatgcaa ctgtgacgga tgccgaagca    420

gtgattgtcc aggtgactcc tcaccatgtg ctggttgatg aatacacagg agaatgggtt    480

gattcacagt tcatcaacgg aaaatgcagc aattacatat gccccactgt ccataactct    540

acaacctggc attctgacta taaggtcaaa gggctatgtg attctaacct catttccatg    600

gacatcacct tcttctcaga ggacggagag ctatcatccc tgggaaagga gggcacaggg    660

ttcagaagta actactttgc ttatgaaact ggaggcaagg cctgcaaaat gcaatactgc    720

aagcattggg gagtcagact cccatcaggt gtctggttcg agatggctga taaggatctc    780

tttgctgcag ccagattccc tgaatgccca gaagggtcaa gtatctctgc tccatctcag    840

acctcagtgg atgtaagtct aattcaggac gttgagagga tcttggatta ttccctctgc    900

caagaaacct ggagcaaaat cagagcgggt cttccaatct ctccagtgga tctcagctat    960

cttgctccta aaaacccagg aaccggtcct gctttcacca taatcaatgg taccctaaaa   1020

tactttgaga ccagatacat cagagtcgat attgctgctc caatcctctc aagaatggtc   1080

ggaatgatca gtggaactac cacagaaagg gaactgtggg atgactgggc accatatgaa   1140

gacgtggaaa ttggacccaa tggagttctg aggaccagtt caggatataa gtttccttta   1200

tacatgattg gacatggtat gttggactcc gatcttcatc ttagctcaaa ggctcaggtg   1260

ttcgaacatc ctcacattca agacgctgct tcgcaacttc ctgatgatga gagtttattt   1320

tttggtgata ctgggctatc caaaaatcca atcgagcttg tagaaggttg gttcagtagt   1380

tggaaaagct ctattgcctc tttttcttt atcatagggt taatcattgg actattcttg   1440

gttctccgag ttggtatcca tctttgcatt aaagccagaa gcacaccagt cacattaagt   1500

aaggatcaac tgagtggtat aaataatatt gcatttagta actaa                    1545
```

<210> SEQ ID NO 4
<211> LENGTH: 1869
<212> TYPE: DNA
<213> ORGANISM: Artificial Sequence
<220> FEATURE:
<223> OTHER INFORMATION: G/F inter-gene - F 5UTR - preF ectodomain-
foldon fusion gene - F 3UTR

<400> SEQUENCE: 4
gtattgttgc aaaaagccat gaccaaatca aacagaatca aaatcaactc tggggcaaat 60
aacaatggag ttgccaatcc tcaaaacaaa tgctattacc acaatccttg ctgcagtcac 120
actctgtttc gcttccagtc aaaacatcac tgaagaattt tatcaatcaa catgcagtgc 180
agtcagcaaa ggctatctta gtgctctaag aactggttgg tatactagtg ttataactat 240
agaattaagt aatatcaagg aaaataagtg taatggtaca gacgctaagg taaaattaat 300
aaaacaagaa ttagataaat ataaaaatgc tgtaacagaa ttgcagttgc tcatgcaaag 360
cacaccagca gccaacaatc gagccagaag agaactacca agatttatga attatacact 420
caacaatacc aaaaacacca atgtaacatt aagtaagaaa aggaaaagaa gatttcttgg 480
atttttgtta ggtgttggat ctgcaatcgc cagtggcatt gccgtatcca aggtcctgca 540
cctagaaggg gaagtgaaca aaatcaaaag tgctctacta tccacaaaca aggctgtagt 600
cagcttatct aatggagtca gtgtcttaac cagcaaggtg ttagacctca aaaactatat 660
agataaacag ttgttaccta ttgttaacaa gcaaagctgc agcatatcaa acattgaaac 720
tgtgatagag ttccaacaaa agaacaacag actactagag attaccagag aatttagtgt 780
taatgcaggt gtaactactc ctgtaagcac ttatatgtta actaatagtg agttattatc 840
attaatcaat gatatgccta taacaaatga tcagaaaaag ttaatgtcca gcaatgttca 900
aatagttaga cagcaaagtt actctatcat gtcaataata aaagaggaag tcttggcata 960
tgtagtacaa ttaccactat atggtgtaat agatactcct tgttggaaac tacacacatc 1020
ccctttatgt acaaccaaca caaaggaagg atccaacatc tgcttaacaa gaaccgacag 1080
aggatggtac tgtgacaatg caggatcagt atcctttttc ccacaagctg aaacatgtaa 1140
agttcaatcg aatcgggtgt tttgtgacac aatgaacagt ttaacattac caagtgaggt 1200
aaatctctgc aacattgaca tattcaaccc caaatatgat tgcaaaatta tgacttcaaa 1260
aacagatgta agcagctccg ttatcacatc tctaggagcc attgtgtcat gctatggcaa 1320
aaccaaatgt acagcatcca ataaaaatcg tgggatcata aagacattct ctaacgggtg 1380
tgattatgta tcaaataagg gggtggatac tgtgtctgta ggtaatacat tatattatgt 1440
aaataagcaa gaaggcaaaa gtctctatgt aaaaggtgaa ccaataataa atttctatga 1500
tccattagtg ttcccctctc tcctgtggga tgcatcaata tctcaagtca atgagaaaat 1560
taatcagagt ctagcattta tccgtaaatc agatgaatta ttaggctctg gcggaagcgg 1620
atacatccct gaggcaccaa gggacggaca ggcctacgtg cgcaaggatg gcgagtgggt 1680
gctgctgtcc acctttctgt gaataaaaat agcacctaat catattctta caatggttcg 1740
ctatttgacc atagataacc catctatcat tagattatcc taaaatttga acttcatcac 1800
aactttcatc tataaaccat ctcacttaca ctttttaagt agatttctat tttatagtta 1860
tataaaaca 1869

<210> SEQ ID NO 5
<211> LENGTH: 1887
<212> TYPE: DNA

-continued

<213> ORGANISM: Artificial Sequence
<220> FEATURE:
<223> OTHER INFORMATION: Single chain PreF

<400> SEQUENCE: 5

```
gtattgttgc aaaaagccat gaccaaatca aacagaatca aaatcaactc tggggcaaat     60

aacaatggag ttgccaatcc tcaaaacaaa tgctattacc acaatccttg ctgcagtcac    120

actctgtttc gcttccagtc aaaacatcac tgaagaattt tatcaatcaa catgcagtgc    180

agtcagcaaa ggctatctta gtgctctaag aactggttgg tatactagtg ttataactat    240

agaattaagt aatatcaagg aaaataagtg taatggtaca gacgctaagg taaaattaat    300

aaaacaagaa ttagataaat ataaaaatgc tgtaacagaa ttgcagttgc tcatgcaaag    360

cacaccagca gccaacaatg gagccagagg ctctggcgga agcggacttg gatttttgtt    420

aggtgttgga tctgcaatcg ccagtggcat tgccgtatcc aaggtcctgc acctagaagg    480

ggaagtgaac aaaatcaaaa gtgctctact atccacaaac aaggctgtag tcagcttatc    540

taatggagtc agtgtcttaa ccagcaaggt gttagacctc aaaaactata tagataaaca    600

gttgttacct attgttaaca agcaaagctg cagcatatca aacattgaaa ctgtgataga    660

gttccaacaa aagaacaaca gactactaga gattaccaga gaatttagtg ttaatgcagg    720

tgtaactact cctgtaagca cttatatgtt aactaatagt gagttattat cattaatcaa    780

tgatatgcct ataacaaatg atcagaaaaa gttaatgtcc agcaatgttc aaatagttag    840

acagcaaagt tactctatca tgtcaataat aaaagaggaa gtcttggcat atgtagtaca    900

attaccacta tatggtgtaa tagatactcc ttgttggaaa ctacacacat cccctttatg    960

tacaaccaac acaaaggaag gatccaacat ctgcttaaca agaaccgaca gaggatggta   1020

ctgtgacaat gcaggatcag tatccttttt cccacaagct gaaacatgta aagttcaatc   1080

gaatcgggtg ttttgtgaca caatgaacag tttaacatta ccaagtgagg taaatctctg   1140

caacattgac atattcaacc ccaaatatga ttgcaaaatt atgacttcaa aaacagatgt   1200

aagcagctcc gttatcacat ctctaggagc cattgtgtca tgctatggca aaaccaaatg   1260

tacagcatcc aataaaaatc gtgggatcat aaagacattc tctaacgggt gtgattatgt   1320

atcaaataag gggtggata ctgtgtctgt aggtaataca ttatattatg taaataagca   1380

agaaggcaaa agtctctatg taaaaggtga accaataata aatttctatg atccattagt   1440

gttcccctct gatgaatttg atgcatcaat atctcaagtc aatgagaaaa ttaatcagag   1500

tctagcattt atccgtaaat cagatgaatt attacataat gtaaatgctg gtaaatccac   1560

cacaaatatc atgataacta ccataattat agtaattata gtaatattgt tagcattaat   1620

tgcagttgga ctgcttctat actgcaaggc cagaagcaca ccagtcacat taagtaagga   1680

tcaactgagt ggtataaata atattgcatt tagtaactga ataaaaatag cacctaatca   1740

tattcttaca atggttcgct atttgaccat agataaccca tctatcatta gattatccta   1800

aaatttgaac ttcatcacaa ctttcatcta taaaccatct cacttacact ttttaagtag   1860

atttctattt tatagttata taaaaca                                       1887
```

<210> SEQ ID NO 6
<211> LENGTH: 16912
<212> TYPE: DNA
<213> ORGANISM: Artificial Sequence
<220> FEATURE:
<223> OTHER INFORMATION: Modified RSV anti-genome with chimeric VSV G
      protein inserted

<400> SEQUENCE: 6

```
acgcgaaaaa atgcgtacaa caaacttgcg taaaccaaaa aaatggggca aataagaatt     60
tgataagtac cacttaaatt taactccttt ggttagaggc gcgccatggg cagcaactca    120
ttgagtatga taaaagttag attgcaaaat ctgtttgaca atgatgaagt agcattgtta    180
aaaataacat gctatactga caaattaata cagttaacta atgctttggc taaggcagtt    240
atacatacaa tcaaattgaa tggcattgta tttgtgcatg ttattacaag tagtgatatt    300
tgccctaata ataatattgt agtgaaatcc aatttcacaa caatgccagt attacaaaat    360
ggaggttata tatgggaaat gatggaatta acacactgct ctcaacctaa tggcctaata    420
gatgacaatt gtgaaattaa attctccaaa aaactaagtg attcaacaat gaccaattat    480
atgaatcaat tatctgaatt acttggattt gacctcaatc cataaatcat aataaatatc    540
aactagcaaa tcaatgtcac taacaccatt agttaatata aaacttgaca gaagataaaa    600
atggggcaaa taaatcaatt cagccgaccc aaccatggac acaacacaca atgataccac    660
accacaaaga ctgatgatca cagacatgag gccattatcg cttgagacta taataacatc    720
tctaaccaga gatatcataa cacataaatt tatatacttg ataaatcatg aatgcatagt    780
aagaaaactt gatgaaagac aggccacatt tacatttctg gtcaactatg aaatgaaact    840
attgcacaaa gtgggaagca ctaaatataa aaaatatact gaatacaaca caaaatatgg    900
cactttccct atgccaatat ttatcaatca tgatgggttc ttagaatgca ttggcattaa    960
gcctaccaag cacacaccca taatatacaa gtatgatctc aatccatgaa tatcaaacca   1020
agattcaaac aatccgaaat aacaacttta tgcataatca cactccatag tccaaatgga   1080
gcctgaaaat tatagttatt taaaattcct gcaggaagga gagacataag atgaaagatg   1140
gggcaaatac aaaaatggct cttagcaaag tcaagttgaa tgatacactc aacaaagatc   1200
aacttctatc atccagcaaa tataccatcc aacggagcac aggagacagc attgacactc   1260
ctaattatga tgtgcagaaa cacattaata agttatgtgg catgttatta atcacagaag   1320
atgctaatca taaattcact gggttaatag gtatgttata tgctatgtct agattaggaa   1380
gagaagacac cataaaaata ctcaaagatg cgggatatca tgttaaggca aatggagtgg   1440
atgtaacaac acatcgtcaa gacattaatg ggaaagaaat gaaatttgaa gtgttaacat   1500
tagcaagctt aacaactgaa attcaaatca acattgagat agaatctaga aaatcctaca   1560
aaaaaatgct aaaagaaatg ggagaggtgg ctccagaata caggcatgac tctcctgatt   1620
gtgggatgat aatattatgt atagcggcat tagtaataac caaattagca gcaggagata   1680
gatcaggtct tacagctgtg attaggagag ctaataatgt cctaaaaaat gaaatgaaac   1740
gttataaagg tttattaccc aaggatatag ccaacagctt ctatgaagtg tttgaaaaat   1800
atcctcactt tatagatgtt tttgttcatt ttggtatagc acaatcttct accagaggtg   1860
gcagtagagt tgaagggatt tttgcaggat tgtttatgaa tgcctatggt gcagggcaag   1920
tgatgttacg gtggggggtc ttagcaaaat cagttaaaaa cattatgtta ggacacgcta   1980
gtgtacaagc agaaatggaa caagttgtgg aggtgtatga gtatgctcag aaattgggtg   2040
gagaagcagg attctaccat atattgaaca acccaaaagc atcactatta tctttgactc   2100
aatttcctca cttctctagt gtagtattgg gcaatgctgc tggcctaggc ataatgggag   2160
aatacagagg tacaccaagg aatcaagatt tatatgatgc tgcaaaagca tatgctgaac   2220
aactcaaaga aaatggtgtg attaactaca gtgtattaga tttgacagca gaagaactag   2280
aggctatcaa acatcagctt aatccaaaag ataatgatgt agagctttga gttaataaaa   2340
```

-continued

```
aagtggggca aataaatcat catggaaaag tttgctcctg aattccatgg agaagatgca   2400
aacaacagag ccaccaaatt cctagaatca ataaagggca aattcacatc acccaaagat   2460
cccaagaaaa aagatagtat catatctgtc aactcaatag atatagaagt aaccaaagaa   2520
agccctataa catcaaattc aaccattata aacccaataa atgagacaga tgatactgta   2580
gggaacaagc ccaattatca aagaaagcct ctagtaagtt tcaaagaaga ccctacgcca   2640
agtgataatc ctttttcaaa actatacaaa gaaaccatag aaacatttga taacaatgaa   2700
gaagaatcta gctattcata tgaagaaata aatgatcaga caaacgataa tataacagca   2760
agattagata ggattgatga gaaattaagt gaaatactag gaatgcttca cacattagta   2820
gtagcgagtg caggacccac atctgctcgg gatggtataa gagatgccat ggttggttta   2880
agagaagaaa tgatagaaaa aatcagaact gaagcattaa tgaccaatga cagactagaa   2940
gctatggcaa gactcaggaa tgaagaaagt gaaaagatgg caaaagacac atcagatgaa   3000
gtgtctctca atccaacatc agagaaactg aacaacctgt tggaagggaa tgatagtgac   3060
aatgatctat cacttgaaga tttctgatta gctaccaaac tgtacatcaa aacacaacac   3120
caatagaaaa ccaacaaaca aaccaactca cccatccaac caaacatcta tctgctgatt   3180
agccaaccag ccaaaaaaca accagccaat ctaaaactag ccacccggaa aaaatcgata   3240
ctatagttac aaaaaaagat ggggcaaata tggaaacata cgtgaataaa cttcacgagg   3300
gctccacata cacagctgct gttcaataca atgtcctaga aaaagacgat gatcctgcat   3360
cacttacaat atgggtgccc atgttccaat catccatgcc agcagatcta ctcataaaag   3420
aactagccaa tgtcaatata ctagtgaaac aaatatccac acccaaggga ccctcattaa   3480
gagtcatgat aaactcaaga agtgcagtgc tagcacaaat gcccagcaaa tttaccatat   3540
gtgccaatgt gtccttggat gaaagaagca agctggcata tgatgtaacc acaccctgtg   3600
aaattaaggc atgcagtcta acatgcctaa aatcaaaaaa tatgttaact acagttaaag   3660
atctcactat gaaaacactc aacccaacac atgacatcat tgctttatgt gaatttgaaa   3720
atatagtaac atcaaaaaaa gtcataatac caacatacct aagatctatc agcgtcagaa   3780
ataaagatct gaacacactt gaaaatataa caaccactga attcaaaaat gccattacaa   3840
atgcaaaaat catcccttac tcaggattat tgttagtcat cacagtgact gacaacaaag   3900
gagcattcaa atacataaag ccacaaagtc aattcatagt agatcttgga gcttacctag   3960
aaaaagaaag tatatattat gttacaacaa attggaagca cacagctaca cgatttgcaa   4020
tcaaacccat ggaagattaa cctttttcct ctacatcaat gagtagattc atacaaactt   4080
tctaactaca ttcttcactt cacaatcata atcaccaacc ctctgtggtt caatcaatca   4140
aacaaaactc atcaagagtt ccagatcatc ccaagtcatt gttcatcaga tccagtactc   4200
aaataagtta ataaaaaatc cacatggggc aaataatcat tgagggaaat ccaactaatc   4260
acaacatctg tcaacataga caagtcaaca cgctagataa aatcaaccaa tggaaaatac   4320
atccataact atagaattct caagcaaatt ctggccttac tttacactaa tacacatgat   4380
aacaacaata atctctttga taatcataat ctccatcatg attgcaatac taaacaaact   4440
ctgcgaatat aatgtattcc ataacaaaac ctttgagcta ccaagagctc gagtcaatac   4500
atagcattca ccaatctgat agctcaaaac agtaaccttg catttgtaaa tgaactaccc   4560
tcacttcttc acaaaaccac atcaacatct caccatgcaa gccatcatct ataccataaa   4620
gtagttaatt aaaaatggcc ggccttgaca gaagataaaa atggggcaaa tgcaaacatg   4680
```

-continued

```
aagtgccttt tgtacttagc ctttttattc attggggtga attgcaagtt caccatagtt   4740
tttccacaca accaaaaagg aaactggaaa aatgttcctt ctaattacca ttattgcccg   4800
tcaagctcag atttaaattg gcataatgac ttaataggca cagccttaca agtcaaaatg   4860
cccaagagtc acaaggctat tcaagcagac ggttggatgt gtcatgcttc caaatgggtc   4920
actacttgtg atttccgctg gtatggaccg aagtatataa cacattccat ccgatccttc   4980
actccatctg tagaacaatg caaggaaagc attgaacaaa cgaaacaagg aacttggctg   5040
aatccaggct tccctcctca aagttgtgga tatgcaactg tgacggatgc cgaagcagtg   5100
attgtccagg tgactcctca ccatgtgctg gttgatgaat acacaggaga atgggttgat   5160
tcacagttca tcaacggaaa atgcagcaat tacatatgcc ccactgtcca taactctaca   5220
acctggcatt ctgactataa ggtcaaaggg ctatgtgatt ctaacctcat ttccatggac   5280
atcaccttct tctcagagga cggagagcta tcatccctgg gaaaggaggg cacagggttc   5340
agaagtaact actttgctta tgaaactgga ggcaaggcct gcaaaatgca atactgcaag   5400
cattggggag tcagactccc atcaggtgtc tggttcgaga tggctgataa ggatctcttt   5460
gctgcagcca gattccctga atgcccagaa gggtcaagta tctctgctcc atctcagacc   5520
tcagtggatg taagtctaat tcaggacgtt gagaggatct tggattattc cctctgccaa   5580
gaaacctgga gcaaaatcag agcgggtctt ccaatctctc cagtggatct cagctatctt   5640
gctcctaaaa acccaggaac cggtcctgct ttcaccataa tcaatggtac cctaaaatac   5700
tttgagacca gatacatcag agtcgatatt gctgctccaa tcctctcaag aatggtcgga   5760
atgatcagtg gaactaccac agaaagggaa ctgtgggatg actgggcacc atatgaagac   5820
gtggaaattg gacccaatgg agttctgagg accagttcag gatataagtt tcctttatac   5880
atgattggac atggtatgtt ggactccgat cttcatctta gctcaaaggc tcaggtgttc   5940
gaacatcctc acattcaaga cgctgcttcg caacttcctg atgatgagag tttatttttt   6000
ggtgatactg ggctatccaa aaatccaatc gagcttgtag aaggttggtt cagtagttgg   6060
aaaagctcta ttgcctcttt tttctttatc atagggttaa tcattggact attcttggtt   6120
ctccgagttg gtatccatct ttgcattaaa gccagaagca caccagtcac attaagtaag   6180
gatcaactga gtggtataaa taatattgca tttagtaact aatagtcatt aaaaagcggc   6240
cggccagtca taacaatgaa ctaggatatt aagaccaaaa acaacgctgg ggcaaatgca   6300
aacatgtcca aaaccgagga ccaacgcacc gccaagacac tagaaaggac ctgggacact   6360
tttaatcatc tattattcat atcatcgtgc ttatacaagt taaatcttaa atctatagca   6420
caaatcacat tatctatttt ggcaattata atctcaacct cacttataat tgcagccatc   6480
atattcatag cctcggcaaa ccacaaagtc acactaacaa ctgcaatcat acaagatgca   6540
acgaaccaga tcaagaacac aaccccaaca tacctcaccc agaatcccca gcatggaatc   6600
agcttctcca atctgtccgg aactacatca caatccacca ccatactagc ttcaacaaca   6660
ccaagtgctg attcaacccc acaatccaca acagtcaaga tcaaaaacac aacaacaacc   6720
caaatattac ctagcaaacc caccacaaaa caacgccaaa ataaaccaca aaacaaaccc   6780
aacaatgatt ttcactttga agtgttcaat tttgtaccct gcagcatatg cagcaacaat   6840
ccaacctgct gggccatctg caagagaata ccaaacaaaa aacctggaaa gaaaaccacc   6900
accaagccca caaaaaaacc aaccctcaag acaaccaaaa aagatcccaa atcccaaacc   6960
acaaaaccaa aggaagtact cactaccaag cctacaggaa agccaaccat caacaccact   7020
aaaacaaaca tcagaactac actgctcacc tccaacacca aaggaaatcc agaacacaca   7080
```

```
agtcaagagg aaaccctcca ctcaaccacc tccgaaggct atccaagccc atcacaagtc   7140
cacacaacat ccggtcaaga ggaaaccctc cactcaacca cctccgaagg ctatccaagc   7200
ccatcacaag tctacacaac atccgagtac ctatcacaat ctctatcttc atccaacaca   7260
acaaaatgat agtcattaaa aagcacgcgt gtattgttgc aaaaagccat gaccaaatca   7320
aacagaatca aaatcaactc tggggcaaat aacaatggag ttgccaatcc tcaaaacaaa   7380
tgctattacc acaatccttg ctgcagtcac actctgtttc gcttccagtc aaaacatcac   7440
tgaagaattt tatcaatcaa catgcagtgc agtcagcaaa ggctatctta gtgctctaag   7500
aactggttgg tatactagtg ttataactat agaattaagt aatatcaagg aaaataagtg   7560
taatggtaca gacgctaagg taaaattaat aaaacaagaa ttagataaat ataaaaatgc   7620
tgtaacagaa ttgcagttgc tcatgcaaag cacaccagca gccaacaatc gagccagaag   7680
agaactacca agatttatga attatacact caacaatacc aaaaacacca atgtaacatt   7740
aagtaagaaa aggaaaagaa gatttcttgg atttttgtta ggtgttggat ctgcaatcgc   7800
cagtggcatt gccgtatcca aggtcctgca cctagaaggg gaagtgaaca aaatcaaaag   7860
tgctctacta tccacaaaca aggctgtagt cagcttatct aatggagtca gtgtcttaac   7920
cagcaaggtg ttagacctca aaaactatat agataaacag ttgttaccta ttgttaacaa   7980
gcaaagctgc agcatatcaa acattgaaac tgtgatagag ttccaacaaa agaacaacag   8040
actactagag attaccagag aatttagtgt taatgcaggt gtaactactc ctgtaagcac   8100
ttatatgtta actaatagtg agttattatc attaatcaat gatatgccta taacaaatga   8160
tcagaaaaag ttaatgtcca gcaatgttca aatagttaga cagcaaagtt actctatcat   8220
gtcaataata aaagaggaag tcttggcata tgtagtacaa ttaccactat atggtgtaat   8280
agatactcct tgttggaaac tacacacatc ccctttatgt acaaccaaca caaaggaagg   8340
atccaacatc tgcttaacaa gaaccgacag aggatggtac tgtgacaatg caggatcagt   8400
atcctttttc ccacaagctg aaacatgtaa agttcaatcg aatcgggtgt tttgtgacac   8460
aatgaacagt ttaacattac caagtgaggt aaatctctgc aacattgaca tattcaaccc   8520
caaatatgat tgcaaaatta tgacttcaaa aacagatgta agcagctccg ttatcacatc   8580
tctaggagcc attgtgtcat gctatggcaa aaccaaatgt acagcatcca ataaaaatcg   8640
tgggatcata aagacattct ctaacgggtg tgattatgta tcaaataagg gggtggatac   8700
tgtgtctgta ggtaatacat tatattatgt aaataagcaa gaaggcaaaa gtctctatgt   8760
aaaaggtgaa ccaataataa atttctatga tccattagtg ttcccctctg atgaatttga   8820
tgcatcaata tctcaagtca atgagaaaat taatcagagt ctagcattta tccgtaaatc   8880
agatgaatta ttacataatg taaatgctgg taaatccacc acaaatatca tgataactac   8940
cataattata gtaattatag taatattgtt agcattaatt gcagttggac tgcttctata   9000
ctgcaaggcc agaagcacac cagtcacatt aagtaaggat caactgagtg gtataaataa   9060
tattgcattt agtaactgaa taaaaatagc acctaatcat attcttacaa tggttcgcta   9120
tttgaccata gataacccat ctatcattag attatcctaa aatttgaact tcatcacaac   9180
tttcatctat aaaccatctc acttacactt tttaagtaga tttctatttt atagttatat   9240
aaaacagggc ccattgaata ccaaattaac ttactatttg taaaaatgag aattggggca   9300
aatatgtcac gaaggaatcc ttgcaaattc gaaattcgag gtcattgctt gaatggtaaa   9360
aggtgtcatt ttagtcataa ttattttgaa tggccacccc atgcactgct tgtaagacaa   9420
```

-continued

```
aactttatgt taaacagaat acttaagtct atggataaaa gcatagatac tttgtcagaa   9480
ataagtggag ctgcagagtt ggacagaaca gaagagtatg ccctcggtgt agttggagtg   9540
ctagagagtt atataggatc aataaaataat ataactaaac aatcagcatg tgttgccatg   9600
agcaaactcc ttactgaact caacagcgat gacatcaaaa aactaaggga caatgaagag   9660
ccaaactcac ccaaagtaag agtgtacaat actgtcatat catatattga aagcaacagg   9720
aagaacaata aacaaactat ccatctgtta aaaagattgc cagcagacgt attgaagaaa   9780
accatcaaaa acacattgga tatccacaag agcataacca tcaataaccc aaaagaatca   9840
actgttagtg atacgaacga ccatgccaaa aataatgata ctacctgaca aatatccttg   9900
tagtataaat tccatactaa taacaagtaa ttgtagagtc actatgtata atcaaaaaaa   9960
cacactatat atcaatcaaa acaaccaaaa tagccatata tacccaccgg atcaaccatt  10020
caatgaaatc cattggacct ctcaagactt gattgatgca actcaaaatt ttctacaaca  10080
tctaggtatt actgatgata tatacacaat atatatatta gtgtcataat actcaatcct  10140
aatacttacc acatcatcaa attattaact caaacaattc aagctatggg acaaaatgga  10200
tcccattatt agtggaaatt ctgctaatgt ttatctaact gatagttatt taaaaggtgt  10260
tatttctttc tcagaatgta acgctttagg aagttacata ttcaatggtc cttatctcaa  10320
aaatgattat accaacttaa ttagtagaca aaatccatta atagaacaca taaatctaaa  10380
gaaactaaat ataacacagt ccttaatatc taagtatcat aaaggtgaaa taaaaataga  10440
agaacctact tactttcagt cattacttat gacatacaag agtatgacct cttcagaaca  10500
gactactact actaatttac ttaaaaagat aataagaaga gctatagaaa tcagtgatgt  10560
caaagtctat gctatattga ataaactggg gctcaaagaa aaagacaaga ttaaatccaa  10620
taatggacaa gatgaagaca actcagtcat tactaccata atcaaagatg atatactttt  10680
agctgtcaag gataatcaat ctcatcttaa agcagacaaa aatcaatcca caaaacaaaa  10740
agatacaatc aaaacaacac ttttgaagaa attaatgtgt tcgatgcaac atcctccatc  10800
atggttaata cattggttta atttatacac aaaattaaac agcatattaa cacaatatcg  10860
atctagtgag gtaaaaaacc atggttttat attgatagat aatcatactc ttagtggatt  10920
ccaatttatt ttgaatcaat atggttgtat agtttatcat aaggaactca aaagaattac  10980
tgtgacaact tataatcaat tcttgacatg gaaagatatt agccttagta gattaaatgt  11040
ttgtttgatt acatggatta gtaactgttt gaacacatta aacaaaagct taggcttaag  11100
atgtggattc aataatgtta tcttgacaca attattcctt tatggagatt gtatactaaa  11160
actattccac aatgaggggt tctacataat aaaagaggta gagggattta ttatgtctct  11220
aattttaaat ataacagaag aagatcaatt cagaaaacgg ttttataata gtatgctcaa  11280
caacatcaca gatgccgcca acaaagctca aaaaaatctg ctatcaagag tatgtcatac  11340
attattagat aagacaatat cagataatat aataaatggc agatggataa ttctattgag  11400
taagttccta aaattaatta agcttgcagg tgacaataac ctcaacaatc tgagtgaatt  11460
atattttttg ttcagaatat ttggacaccc aatggtagat gaaagacaag ccatggatgc  11520
tgttaaagtt aattgcaacg agaccaaatt ttatttgtta agtagtttga gtatgttaag  11580
aggagctttt atatatagaa ttataaaagg gtttgtaaat aattacaaca gatggcctac  11640
tttaagaaat gccattgtct taccettaag atggttaact tactataaac taaacactta  11700
tccttccttg ttggaactta cagaaagaga tttgattgtt ctatcaggac tacgtttcta  11760
tcgagagttt cggttgccta aaaaagtgga tcttgaaatg atcataaatg ataaggctat  11820
```

atcacctcct aaaaatttaa tatggactag tttccctaga aattatatgc cgtcacacat 11880
acaaaattat atagaacatg aaaaattaaa attctctgat agtgataaat caagaagagt 11940
attagagtat tatttaagag ataacaaatt caatgaatgt gatttacaca actgtgtagt 12000
taatcaaagt tatcttaaca acccgaatca tgtggtatca ttgacaggca aagaaagaga 12060
actcagtgta ggtagaatgt ttgcaatgca accaggaatg ttcagacaag ttcaaatatt 12120
agcagagaaa atgatagcag aaaacatatt acaatttttc cctgaaagtc ttacaagata 12180
tggtgatcta gaactacaga aaatattaga attgaaagca ggaataagta acaaatcaaa 12240
tcgttacaat gataattaca acaattacat tagtaagtgc tctatcatca cagatctcag 12300
caaattcaat caagcatttc gatatgaaac atcatgtatt tgtagtgatg tactggatga 12360
actgcatggt gtacaatctc tattttcctg gttacattta actattcctc atgtcacaat 12420
aatatgcaca tataggcatg caccccccta tataaaggat catattgtag atcttaacaa 12480
tgtagatgag caaagtggac tatatagata tcatatgggt ggtatcgaag ggtggtgtca 12540
aaaactatgg accatagaag ctatatcact attagatcta atatctctca aagggaaatt 12600
ctcaattact gctttaatta atggtgacaa tcaatcaata gatataagta aaccagtcag 12660
actcatggaa ggtcaaactc atgctcaagc agattatttg ctagcattaa atagtctcaa 12720
attactgtat aaagagtatg caggaatagg ccacaaatta aaaggaactg agacttatat 12780
atcgagagat atgcaattta tgagtaaaac gatccaacat aacggtgtat attacccagc 12840
tagtataaag aaagtcctaa gagtgggacc gtggataaac actatacttg atgacttcaa 12900
agtgagtcta gaatctatag gtagtttgac acaagaatta gaatatagag gtgaaagtct 12960
attatgcagt ttaatattta gaaatgtatg gttatataat caaattgcat tacaacttaa 13020
aaatcatgca ttatgtaaca acaaattata tttggatata ttaaaagttc taaaacactt 13080
aaaaaccttt tttaatcttg ataacattga tacagcatta acattgtata tgaatttgcc 13140
catgttattt ggtggtggtg atcccaactt gttatatcga agtttctata gaagaactcc 13200
tgatttcctc acagaggcta tagttcactc tgtgttcata cttagttatt atacaaacca 13260
tgatttaaaa gataaacttc aagatctgtc agatgataga ttgaataagt tcttaacatg 13320
cataatcacg tttgataaaa accccaatgc tgaattcgtt acattgatga gagatcctca 13380
agctttagga tctgagaggc aagctaaaat tactagcgaa atcaatagac tggcagttac 13440
cgaggttttg agcacagctc caaacaaaat attttccaaa agtgcacaac actataccac 13500
tacagagata gatcttaatg atattatgca aaatatagaa cctacatatc ctcacgggct 13560
aagagttgtt tatgagagtt taccctttta taaagcagag aaaatagtaa atcttatatc 13620
cggtacaaaa tctataacta acatactgga aaagacttct gccatagact taacagatat 13680
tgatagagcc actgagatga tgaggaaaaa cataactttg cttataagga tattaccatt 13740
agattgtaac agagataaaa gagaaatatt gagtatggaa aacctaagta ttactgaatt 13800
aagcaaatac gttagagaaa gatcttggtc tttatccaat atagttggtg ttacatcacc 13860
cagtatcatg tatacaatgg acataaaata tacaacaagc actatagcta gtggcataat 13920
catagagaaa tataatgtca acagtttaac acgtggtgag agaggaccca ctaaaccatg 13980
ggttggttca tctacacaag agaaaaagac aatgccagtt tataatagac aagttttaac 14040
caaaaaacag agagatcaaa tagatctatt agcaaaattg gattgggtgt atgcatctat 14100
agataacaag gatgaattta tggaggaact tagcatagga actcttgggt taacatatga 14160

-continued

```
gaaggccaaa aaattattcc cacaatattt gagtgttaac tatttgcatc gtcttacagt  14220
cagtagtaga ccatgtgaat tccctgcatc tataccagct tatagaacta caaattatca  14280
ctttgatact agccctatta atcgcatatt aacagaaaag tatggtgatg aagatattga  14340
tatagtattc caaaactgta taagctttgg ccttagctta atgtctgtag tagaacaatt  14400
tactaatgta tgtcctaaca gaattattct catacccaag cttaatgaga tacatttgat  14460
gaaacctccc atattcacag gcgatgttga tattcacaag ttaaaacaag tgatacaaaa  14520
acaacatatg tttttaccag acaaaataag tttgactcaa tatgtggaat tattcttaag  14580
taataaaaca ctcaaatctg gatctaatgt taattctaat ttaatattgg cgcataagat  14640
atctgactat tttcataata cttacatttt gagtactaat ttagctggac attggattct  14700
tattatacaa cttatgaaag attctaaggg tatttttgaa aaagattggg gagagggata  14760
tataactgat catatgttca ttaatttgaa agtttttcttc aatgcttata agacatatct  14820
cttgtgtttt cataaaggtt acggcagagc aaagctggag tgtgatatga atacttcaga  14880
tctcctatgt gtattggaat taatagacag tagttattgg aagtctatgt ctaaggtgtt  14940
tttagaacaa aaagttatca aatacattct tagccaggat gcaagtttac atagagtaaa  15000
aggatgtcat agcttcaaac tatggtttct taaacgtctt aatgtagcag aattcacagt  15060
ttgcccttgg gttgttaaca tagattatca tccaacacat atgaaagcaa tattaactta  15120
tattgatctt gttagaatgg gattgataaa tatagataga atatacatta aaaataaaca  15180
caagttcaat gatgagtttt atacttctaa tctgttttac attaattata acttctcaga  15240
taatactcat ctattaacta aacatataag gattgctaat tccgaattag aaagtaatta  15300
caacaaatta tatcatccta caccagaaac cctagaaaat atactaacca atccggttaa  15360
aagtaatgag aaaaagacac tgagtgacta ttgtataggt aaaaatgttg actcaataat  15420
gttaccatcg ttatctaata agaagcttat taaatcgtct acaatgatta gaaccaatta  15480
cagcagacaa gatttgtata atttatttcc tacggttgtg attgataaaa ttatagatca  15540
ttcaggtaat acagccaaat ctaaccaact ttacactact acttctcatc aaatatcctt  15600
agtgcacaat agcacatcac tttattgcat gcttccttgg catcatatta atagattcaa  15660
ttttgtattt agttctacag gttgtaaaat tagtatagag tatattttaa aagatcttaa  15720
aattaaggat cctaattgta tagcattcat aggtgaagga gcagggaatt tattattgcg  15780
tacagtagtg gaacttcatc ctgatataag atatatttac agaagtctga aagattgcaa  15840
tgatcatagt ttaccaattg agtttttaag gctgtacaat ggacatatca acattgatta  15900
tggtgaaaat ttgaccattc ctgctacaga tgcaaccaac aacattcatt ggtcttattt  15960
acatataaag tttgctgaac ctatcagtct ttttgtctgt gatgctgaat tgcctgtaac  16020
agtcaactgg agtaagatta taatagagtg gagcaagcat gtaagaaaat gcaagtactg  16080
ttcttcagtt aataaatgta cattgatagt aaaatatcat gctcaagatg atatcgattt  16140
caaattagac aacataacta tattaaaaac ttatgtatgc ttaggtagta agttaaaggg  16200
atctgaagtt tacttagtcc ttacaatagg tcctgcaaat gtgttcccag tatttaatgt  16260
agtacaaaat gctaaattga tactatcaag aactaaaaat ttcatcatgc ctaaaaaagc  16320
tgataaagag tctattgatg caaatattaa gagtttgata ccctttcttt gttaccctat  16380
aacaaaaaaa ggaattaata ctgcattgtc taaattaaag agtgttgtta gtggagatat  16440
actatcatat tctatagctg gacgtaatga agttttcagc aataaactta taaatcataa  16500
gcatatgaac atcttaaagt ggttcaatca tgttttaaat ttcagatcaa cagaattaaa  16560
```

ctataatcat ttatatatgg tagaatctac ttatcctcat ctaagtgaat tgttaaacag 16620
cttgacaacc aatgaactta aaaaactgat taaaatcaca ggtagtttgt tatacaactt 16680
ttataatgaa taatgagcaa aaatcttata acaaaaatag ctacacacta acattgtatt 16740
caattatagt tattgaaaat taataattat ataattttta ataacttcta gtgaactaat 16800
cctaaaatta tcattttgat ctaggaagaa taagtttaaa tccaaatcta attggtttat 16860
atgtatatta actaaattac gagatattag tttttgacac tttttttctc gt 16912

<210> SEQ ID NO 7
<211> LENGTH: 16494
<212> TYPE: DNA
<213> ORGANISM: Artificial Sequence
<220> FEATURE:
<223> OTHER INFORMATION: Sequence in which the SH gene is deleted in SEQ ID NO: 6

<400> SEQUENCE: 7
acgcgaaaaa atgcgtacaa caaacttgcg taaaccaaaa aaatggggca aataagaatt 60
tgataagtac cacttaaatt taactccttt ggttagaggc gcgccatggg cagcaactca 120
ttgagtatga taaaagttag attgcaaaat ctgtttgaca atgatgaagt agcattgtta 180
aaaataacat gctatactga caaattaata cagttaacta atgctttggc taaggcagtt 240
atacatacaa tcaaattgaa tggcattgta tttgtgcatg ttattacaag tagtgatatt 300
tgccctaata ataatattgt agtgaaatcc aatttcacaa caatgccagt attacaaaat 360
ggaggttata tatgggaaat gatggaatta acacactgct ctcaacctaa tggcctaata 420
gatgacaatt gtgaaattaa attctccaaa aaactaagtg attcaacaat gaccaattat 480
atgaatcaat tatctgaatt acttggattt gacctcaatc cataaatcat aataaatatc 540
aactagcaaa tcaatgtcac taacaccatt agttaatata aaacttgaca gaagataaaa 600
atggggcaaa taaatcaatt cagccgaccc aaccatggac acaacacaca atgataccac 660
accacaaaga ctgatgatca cagacatgag gccattatcg cttgagacta taataacatc 720
tctaaccaga gatatcataa cacataaatt tatatacttg ataaatcatg aatgcatagt 780
aagaaaactt gatgaaagac aggccacatt tacatttctg gtcaactatg aaatgaaact 840
attgcacaaa gtgggaagca ctaaatataa aaaatatact gaatacaaca caaaatatgg 900
cactttccct atgccaatat ttatcaatca tgatgggttc ttagaatgca ttggcattaa 960
gcctaccaag cacacaccca taatatacaa gtatgatctc aatccatgaa tatcaaacca 1020
agattcaaac aatccgaaat aacaacttta tgcataatca cactccatag tccaaatgga 1080
gcctgaaaat tatagttatt taaaattcct gcaggaagga gagacataag atgaaagatg 1140
gggcaaatac aaaaatggct cttagcaaag tcaagttgaa tgatacactc aacaaagatc 1200
aacttctatc atccagcaaa tataccatcc aacggagcac aggagacagc attgacactc 1260
ctaattatga tgtgcagaaa cacattaata agttatgtgg catgttatta atcacagaag 1320
atgctaatca taaattcact gggttaatag gtatgttata tgctatgtct agattaggaa 1380
gagaagacac cataaaaata ctcaaagatg cgggatatca tgttaaggca aatggagtgg 1440
atgtaacaac acatcgtcaa gacattaatg ggaaagaaat gaaatttgaa gtgttaacat 1500
tagcaagctt aacaactgaa attcaaatca acattgagat agaatctaga aaatcctaca 1560
aaaaaatgct aaaagaaatg ggagaggtgg ctccagaata caggcatgac tctcctgatt 1620
gtgggatgat aatattatgt atagcggcat tagtaataac caaattagca gcaggagata 1680

```
gatcaggtct tacagctgtg attaggagag ctaataatgt cctaaaaaat gaaatgaaac   1740
gttataaagg tttattaccc aaggatatag ccaacagctt ctatgaagtg tttgaaaaat   1800
atcctcactt tatagatgtt tttgttcatt ttggtatagc acaatcttct accagaggtg   1860
gcagtagagt tgaagggatt tttgcaggat tgtttatgaa tgcctatggt gcagggcaag   1920
tgatgttacg gtggggggtc ttagcaaaat cagttaaaaa cattatgtta ggacacgcta   1980
gtgtacaagc agaaatggaa caagttgtgg aggtgtatga gtatgctcag aaattgggtg   2040
gagaagcagg attctaccat atattgaaca acccaaaagc atcactatta tctttgactc   2100
aatttcctca cttctctagt gtagtattgg gcaatgctgc tggcctaggc ataatgggag   2160
aatacagagg tacaccaagg aatcaagatt tatatgatgc tgcaaaagca tatgctgaac   2220
aactcaaaga aaatggtgtg attaactaca gtgtattaga tttgacagca gaagaactag   2280
aggctatcaa acatcagctt aatccaaaag ataatgatgt agagctttga gttaataaaa   2340
aagtggggca aataaatcat catggaaaag tttgctcctg aattccatgg agaagatgca   2400
aacaacagag ccaccaaatt cctagaatca ataaagggca aattcacatc acccaaagat   2460
cccaagaaaa aagatagtat catatctgtc aactcaatag atatagaagt aaccaaagaa   2520
agccctataa catcaaattc aaccattata aacccaataa atgagacaga tgatactgta   2580
gggaacaagc ccaattatca aagaaagcct ctagtaagtt tcaaagaaga ccctacgcca   2640
agtgataatc ctttttcaaa actatacaaa gaaaccatag aaacatttga taacaatgaa   2700
gaagaatcta gctattcata tgaagaaata aatgatcaga caaacgataa tataacagca   2760
agattagata ggattgatga gaaattaagt gaaatactag gaatgcttca cacattagta   2820
gtagcgagtg caggacccac atctgctcgg gatggtataa gagatgccat ggttggttta   2880
agagaagaaa tgatagaaaa aatcagaact gaagcattaa tgaccaatga cagactagaa   2940
gctatggcaa gactcaggaa tgaagaaagt gaaaagatgg caaaagacac atcagatgaa   3000
gtgtctctca atccaacatc agagaaactg aacaacctgt tggaagggaa tgatagtgac   3060
aatgatctat cacttgaaga tttctgatta gctaccaaac tgtacatcaa aacacaacac   3120
caatagaaaa ccaacaaaca aaccaactca cccatccaac caaacatcta tctgctgatt   3180
agccaaccag ccaaaaaaca accagccaat ctaaaactag ccacccggaa aaaatcgata   3240
ctatagttac aaaaaaagat ggggcaaata tggaaacata cgtgaataaa cttcacgagg   3300
gctccacata cacagctgct gttcaataca atgtcctaga aaaagacgat gatcctgcat   3360
cacttacaat atgggtgccc atgttccaat catccatgcc agcagatcta ctcataaaag   3420
aactagccaa tgtcaatata ctagtgaaac aaatatccac acccaaggga ccctcattaa   3480
gagtcatgat aaactcaaga agtgcagtgc tagcacaaat gcccagcaaa tttaccatat   3540
gtgccaatgt gtccttggat gaaagaagca agctggcata tgatgtaacc acaccctgtg   3600
aaattaaggc atgcagtcta acatgcctaa aatcaaaaaa tatgttaact acagttaaag   3660
atctcactat gaaaacactc aacccaacac atgacatcat tgctttatgt gaatttgaaa   3720
atatagtaac atcaaaaaaa gtcataatac caacatacct aagatctatc agcgtcagaa   3780
ataaagatct gaacacactt gaaaatataa caaccactga attcaaaaat gccattacaa   3840
atgcaaaaat catcccttac tcaggattat tgttagtcat cacagtgact gacaacaaag   3900
gagcattcaa atacataaag ccacaaagtc aattcatagt agatcttgga gcttacctag   3960
aaaaagaaag tatatattat gttacaacaa attggaagca cacagctaca cgatttgcaa   4020
```

-continued

```
tcaaacccat ggaagattaa cctttttcct ctacatcaat gagtagattc atacaaactt   4080
tctaactaca ttcttcactt cacaatcata atcaccaacc ctctgtggtt caatcaatca   4140
aacaaaactc atcaagagtt ccagatcatc ccaagtcatt gttcatcaga tccagtactc   4200
aaataagtta ataaaaaatc ggtccgttga cagaagataa aaatggggca aatgcaaaca   4260
tgaagtgcct tttgtactta gcctttttat tcattggggt gaattgcaag ttcaccatag   4320
tttttccaca caaccaaaaa ggaaactgga aaaatgttcc ttctaattac cattattgcc   4380
cgtcaagctc agatttaaat tggcataatg acttaatagg cacagcctta caagtcaaaa   4440
tgcccaagag tcacaaggct attcaagcag acggttggat gtgtcatgct tccaaatggg   4500
tcactacttg tgatttccgc tggtatggac cgaagtatat aacacattcc atccgatcct   4560
tcactccatc tgtagaacaa tgcaaggaaa gcattgaaca aacgaaacaa ggaacttggc   4620
tgaatccagg cttccctcct caaagttgtg gatatgcaac tgtgacggat gccgaagcag   4680
tgattgtcca ggtgactcct caccatgtgc tggttgatga atacacagga gaatgggttg   4740
attcacagtt catcaacgga aaatgcagca attacatatg ccccactgtc cataactcta   4800
caacctggca ttctgactat aaggtcaaag ggctatgtga ttctaacctc atttccatgg   4860
acatcacctt cttctcagag gacggagagc tatcatccct gggaaaggag ggcacagggt   4920
tcagaagtaa ctactttgct tatgaaactg gaggcaaggc ctgcaaaatg caatactgca   4980
agcattgggg agtcagactc ccatcaggtg tctggttcga gatggctgat aaggatctct   5040
ttgctgcagc cagattccct gaatgcccag aagggtcaag tatctctgct ccatctcaga   5100
cctcagtgga tgtaagtcta attcaggacg ttgagaggat cttggattat tccctctgcc   5160
aagaaacctg gagcaaaatc agagcgggtc ttccaatctc tccagtggat ctcagctatc   5220
ttgctcctaa aaacccagga accggtcctg ctttcaccat aatcaatggt accctaaaat   5280
actttgagac cagatacatc agagtcgata ttgctgctcc aatcctctca agaatggtcg   5340
gaatgatcag tggaactacc acagaaaggg aactgtggga tgactgggca ccatatgaag   5400
acgtggaaat tggacccaat ggagttctga ggaccagttc aggatataag tttcctttat   5460
acatgattgg acatggtatg ttggactccg atcttcatct tagctcaaag gctcaggtgt   5520
tcgaacatcc tcacattcaa gacgctgctt cgcaacttcc tgatgatgag agtttatttt   5580
ttggtgatac tgggctatcc aaaaatccaa tcgagcttgt agaaggttgg ttcagtagtt   5640
ggaaaagctc tattgcctct tttttcttta tcatagggtt aatcattgga ctattcttgg   5700
ttctccgagt tggtatccat ctttgcatta aagccagaag cacaccagtc acattaagta   5760
aggatcaact gagtggtata aataatattg catttagtaa ctaatagtca ttaaaaagcg   5820
gccggccagt cataacaatg aactaggata ttaagaccaa aaacaacgct ggggcaaatg   5880
caaacatgtc caaaaccgag gaccaacgca ccgccaagac actagaaagg acctgggaca   5940
cttttaatca tctattattc atatcatcgt gcttatacaa gttaaatctt aaatctatag   6000
cacaaatcac attatctatt ttggcaatta taatctcaac ctcacttata attgcagcca   6060
tcatattcat agcctcggca aaccacaaag tcacactaac aactgcaatc atacaagatg   6120
caacgaacca gatcaagaac acaaccccaa catacctcac ccagaatccc cagcatggaa   6180
tcagcttctc caatctgtcc ggaactacat cacaatccac caccatacta gcttcaacaa   6240
caccaagtgc tgattcaacc ccacaatcca caacagtcaa gatcaaaaac acaacaacaa   6300
cccaaatatt acctagcaaa cccaccacaa aacaacgcca aaataaacca caaaacaaac   6360
ccaacaatga ttttcacttt gaagtgttca attttgtacc ctgcagcata tgcagcaaca   6420
```

-continued

```
atccaacctg ctgggccatc tgcaagagaa taccaaacaa aaaacctgga aagaaaacca   6480
ccaccaagcc cacaaaaaaa ccaaccctca agacaaccaa aaaagatccc aaatcccaaa   6540
ccacaaaacc aaaggaagta ctcactacca agcctacagg aaagccaacc atcaacacca   6600
ctaaaacaaa catcagaact acactgctca cctccaacac caaaggaaat ccagaacaca   6660
caagtcaaga ggaaaccctc cactcaacca cctccgaagg ctatccaagc ccatcacaag   6720
tccacacaac atccggtcaa gaggaaaccc tccactcaac cacctccgaa ggctatccaa   6780
gcccatcaca agtctacaca acatccgagt acctatcaca atctctatct tcatccaaca   6840
caacaaaatg atagtcatta aaaagcacgc gtgtattgtt gcaaaaagcc atgaccaaat   6900
caaacagaat caaaatcaac tctggggcaa ataacaatgg agttgccaat cctcaaaaca   6960
aatgctatta ccacaatcct tgctgcagtc acactctgtt tcgcttccag tcaaaacatc   7020
actgaagaat tttatcaatc aacatgcagt gcagtcagca aaggctatct tagtgctcta   7080
agaactggtt ggtatactag tgttataact atagaattaa gtaatatcaa ggaaaataag   7140
tgtaatggta cagacgctaa ggtaaaatta ataaaacaag aattagataa atataaaaat   7200
gctgtaacag aattgcagtt gctcatgcaa agcacaccag cagccaacaa tcgagccaga   7260
agagaactac caagatttat gaattataca ctcaacaata ccaaaaacac caatgtaaca   7320
ttaagtaaga aaaggaaaag aagatttctt ggatttttgt taggtgttgg atctgcaatc   7380
gccagtggca ttgccgtatc caaggtcctg cacctagaag gggaagtgaa caaaatcaaa   7440
agtgctctac tatccacaaa caaggctgta gtcagcttat ctaatggagt cagtgtctta   7500
accagcaagg tgttagacct caaaaactat atagataaac agttgttacc tattgttaac   7560
aagcaaagct gcagcatatc aaacattgaa actgtgatag agttccaaca aaagaacaac   7620
agactactag agattaccag agaatttagt gttaatgcag gtgtaactac tcctgtaagc   7680
acttatatgt taactaatag tgagttatta tcattaatca atgatatgcc tataacaaat   7740
gatcagaaaa agttaatgtc cagcaatgtt caaatagtta gacagcaaag ttactctatc   7800
atgtcaataa taaaagagga agtcttggca tatgtagtac aattaccact atatggtgta   7860
atagatactc cttgttggaa actacacaca tcccctttat gtacaaccaa cacaaaggaa   7920
ggatccaaca tctgcttaac aagaaccgac agaggatggt actgtgacaa tgcaggatca   7980
gtatcctttt tcccacaagc tgaaacatgt aaagttcaat cgaatcgggt gttttgtgac   8040
acaatgaaca gtttaacatt accaagtgag gtaaatctct gcaacattga catattcaac   8100
cccaaatatg attgcaaaat tatgacttca aaaacagatg taagcagctc cgttatcaca   8160
tctctaggag ccattgtgtc atgctatggc aaaaccaaat gtacagcatc caataaaaat   8220
cgtgggatca taaagacatt ctctaacggg tgtgattatg tatcaaataa gggggtggat   8280
actgtgtctg taggtaatac attatattat gtaaataagc aagaaggcaa aagtctctat   8340
gtaaaaggtg aaccaataat aaatttctat gatccattag tgttcccctc tgatgaattt   8400
gatgcatcaa tatctcaagt caatgagaaa attaatcaga gtctagcatt tatccgtaaa   8460
tcagatgaat tattacataa tgtaaatgct ggtaaatcca ccacaaatat catgataact   8520
accataatta tagtaattat agtaatattg ttagcattaa ttgcagttgg actgcttcta   8580
tactgcaagg ccagaagcac accagtcaca ttaagtaagg atcaactgag tggtataaat   8640
aatattgcat ttagtaactg aataaaaata gcacctaatc atattcttac aatggttcgc   8700
tatttgacca tagataaccc atctatcatt agattatcct aaaatttgaa cttcatcaca   8760
```

actttcatct ataaaccatc tcacttacac tttttaagta gatttctatt ttatagttat 8820
ataaaacagg gcccattgaa taccaaatta acttactatt tgtaaaaatg agaattgggg 8880
caaatatgtc acgaaggaat ccttgcaaat tcgaaattcg aggtcattgc ttgaatggta 8940
aaaggtgtca ttttagtcat aattattttg aatggccacc ccatgcactg cttgtaagac 9000
aaaactttat gttaaacaga atacttaagt ctatggataa aagcatagat actttgtcag 9060
aaataagtgg agctgcagag ttggacagaa cagaagagta tgccctcggt gtagttggag 9120
tgctagagag ttatatagga tcaataaata atataactaa acaatcagca tgtgttgcca 9180
tgagcaaact ccttactgaa ctcaacagcg atgacatcaa aaaactaagg gacaatgaag 9240
agccaaactc acccaaagta agagtgtaca atactgtcat atcatatatt gaaagcaaca 9300
ggaagaacaa taaacaaact atccatctgt taaaaagatt gccagcagac gtattgaaga 9360
aaaccatcaa aaacacattg gatatccaca agagcataac catcaataac ccaaaagaat 9420
caactgttag tgatacgaac gaccatgcca aaaataatga tactacctga caaatatcct 9480
tgtagtataa attccatact aataacaagt aattgtagag tcactatgta taatcaaaaa 9540
aacacactat atatcaatca aaacaaccaa aatagccata tatacccacc ggatcaacca 9600
ttcaatgaaa tccattggac ctctcaagac ttgattgatg caactcaaaa ttttctacaa 9660
catctaggta ttactgatga tatatacaca atatatatat tagtgtcata atactcaatc 9720
ctaatactta ccacatcatc aaattattaa ctcaaacaat tcaagctatg ggacaaaatg 9780
gatcccatta ttagtggaaa ttctgctaat gtttatctaa ctgatagtta tttaaaaggt 9840
gttatttctt tctcagaatg taacgcttta ggaagttaca tattcaatgg tccttatctc 9900
aaaaatgatt ataccaactt aattagtaga caaaatccat taatagaaca cataaatcta 9960
aagaaactaa atataacaca gtccttaata tctaagtatc ataaaggtga aataaaaata 10020
gaagaaccta cttactttca gtcattactt atgacataca agagtatgac ctcttcagaa 10080
cagactacta ctactaattt acttaaaaag ataataagaa gagctataga aatcagtgat 10140
gtcaaagtct atgctatatt gaataaactg gggctcaaag aaaaagacaa gattaaatcc 10200
aataatggac aagatgaaga caactcagtc attactacca taatcaaaga tgatatactt 10260
ttagctgtca aggataatca atctcatctt aaagcagaca aaaatcaatc cacaaaacaa 10320
aaagatacaa tcaaaacaac acttttgaag aaattaatgt gttcgatgca acatcctcca 10380
tcatggttaa tacattggtt taatttatac acaaaattaa acagcatatt aacacaatat 10440
cgatctagtg aggtaaaaaa ccatggtttt atattgatag ataatcatac tcttagtgga 10500
ttccaattta ttttgaatca atatggttgt atagtttatc ataaggaact caaaagaatt 10560
actgtgacaa cttataatca attcttgaca tggaaagata ttagccttag tagattaaat 10620
gtttgtttga ttacatggat tagtaactgt ttgaacacat taaacaaaag cttaggctta 10680
agatgtggat tcaataatgt tatcttgaca caattattcc tttatggaga ttgtatacta 10740
aaactattcc acaatgaggg gttctacata ataaaagagg tagagggatt tattatgtct 10800
ctaattttaa atataacaga agaagatcaa ttcagaaaac ggttttataa tagtatgctc 10860
aacaacatca cagatgccgc caacaaagct caaaaaaatc tgctatcaag agtatgtcat 10920
acattattag ataagacaat atcagataat ataataaatg gcagatggat aattctattg 10980
agtaagttcc taaaattaat taagcttgca ggtgacaata acctcaacaa tctgagtgaa 11040
ttatattttt tgttcagaat atttggacac ccaatggtag atgaaagaca agccatggat 11100
gctgttaaag ttaattgcaa cgagaccaaa ttttatttgt taagtagttt gagtatgtta 11160
agaggagctt ttatatatag aattataaaa gggtttgtaa ataattacaa cagatggcct 11220
actttaagaa atgccattgt cttaccctta agatggttaa cttactataa actaaacact 11280
tatccttcct tgttggaact tacagaaaga gatttgattg ttctatcagg actacgtttc 11340
tatcgagagt ttcggttgcc taaaaaagtg gatcttgaaa tgatcataaa tgataaggct 11400
atatcacctc ctaaaaattt aatatggact agtttcccta gaaattatat gccgtcacac 11460
atacaaaatt atatagaaca tgaaaaatta aaattctctg atagtgataa atcaagaaga 11520
gtattagagt attatttaag agataacaaa ttcaatgaat gtgatttaca caactgtgta 11580
gttaatcaaa gttatcttaa caacccgaat catgtggtat cattgacagg caaagaaaga 11640
gaactcagtg taggtagaat gtttgcaatg caaccaggaa tgttcagaca agttcaaata 11700
ttagcagaga aaatgatagc agaaaacata ttacaatttt tccctgaaag tcttacaaga 11760
tatggtgatc tagaactaca gaaaatatta gaattgaaag caggaataag taacaaatca 11820
aatcgttaca atgataatta caacaattac attagtaagt gctctatcat cacagatctc 11880
agcaaattca atcaagcatt tcgatatgaa acatcatgta tttgtagtga tgtactggat 11940
gaactgcatg gtgtacaatc tctattttcc tggttacatt taactattcc tcatgtcaca 12000
ataaatatgca catataggca tgcacccccc tatataaagg atcatattgt agatcttaac 12060
aatgtagatg agcaaagtgg actatataga tatcatatgg gtggtatcga agggtggtgt 12120
caaaaactat ggaccataga agctatatca ctattagatc taatatctct caaagggaaa 12180
ttctcaatta ctgctttaat taatggtgac aatcaatcaa tagatataag taaaccagtc 12240
agactcatgg aaggtcaaac tcatgctcaa gcagattatt tgctagcatt aaatagtctc 12300
aaattactgt ataaagagta tgcaggaata ggccacaaat taaaaggaac tgagacttat 12360
atatcgagag atatgcaatt tatgagtaaa acgatccaac ataacggtgt atattaccca 12420
gctagtataa agaaagtcct aagagtggga ccgtggataa acactatact tgatgacttc 12480
aaagtgagtc tagaatctat aggtagtttg acacaagaat tagaatatag aggtgaaagt 12540
ctattatgca gtttaatatt tagaaatgta tggttatata atcaaattgc attacaactt 12600
aaaaatcatg cattatgtaa caacaaatta tatttggata tattaaaagt tctaaaacac 12660
ttaaaaacct tttttaatct tgataacatt gatacagcat taacattgta tatgaatttg 12720
cccatgttat ttggtggtgg tgatcccaac ttgttatatc gaagtttcta tagaagaact 12780
cctgatttcc tcacagaggc tatagttcac tctgtgttca tacttagtta ttatacaaac 12840
catgatttaa aagataaact tcaagatctg tcagatgata gattgaataa gttcttaaca 12900
tgcataatca cgtttgataa aaaccccaat gctgaattcg ttacattgat gagagatcct 12960
caagctttag gatctgagag gcaagctaaa attactagcg aaatcaatag actggcagtt 13020
accgaggttt tgagcacagc tccaaacaaa atattttcca aaagtgcaca acactatacc 13080
actacagaga tagatcttaa tgatattatg caaaatatag aacctacata tcctcacggg 13140
ctaagagttg tttatgagag tttacccttt tataaagcag agaaaatagt aaatcttata 13200
tccggtacaa aatctataac taacatactg gaaaagactt ctgccataga cttaacagat 13260
attgatagag ccactgagat gatgaggaaa aacataactt tgcttataag gatattacca 13320
ttagattgta acagagataa aagagaaata ttgagtatgg aaaacctaag tattactgaa 13380
ttaagcaaat acgttagaga aagatcttgg tctttatcca atatagttgg tgttacatca 13440
cccagtatca tgtatacaat ggacataaaa tatacaacaa gcactatagc tagtggcata 13500

-continued

```
atcatagaga aatataatgt caacagttta acacgtggtg agagaggacc cactaaacca  13560
tgggttggtt catctacaca agagaaaaag acaatgccag tttataatag acaagtttta  13620
accaaaaaac agagagatca aatagatcta ttagcaaaat tggattgggt gtatgcatct  13680
atagataaca aggatgaatt tatggaggaa cttagcatag gaactcttgg gttaacatat  13740
gagaaggcca aaaaattatt cccacaatat ttgagtgtta actatttgca tcgtcttaca  13800
gtcagtagta gaccatgtga attccctgca tctataccag cttatagaac tacaaattat  13860
cactttgata ctagccctat taatcgcata ttaacagaaa agtatggtga tgaagatatt  13920
gatatagtat tccaaaactg tataagcttt ggccttagct taatgtctgt agtagaacaa  13980
tttactaatg tatgtcctaa cagaattatt ctcataccca agcttaatga gatacatttg  14040
atgaaacctc ccatattcac aggcgatgtt gatattcaca agttaaaaca agtgatacaa  14100
aaacaacata tgtttttacc agacaaaata agtttgactc aatatgtgga attattctta  14160
agtaataaaa cactcaaatc tggatctaat gttaattcta atttaatatt ggcgcataag  14220
atatctgact attttcataa tacttacatt ttgagtacta atttagctgg acattggatt  14280
cttattatac aacttatgaa agattctaag ggtatttttg aaaaagattg gggagaggga  14340
tatataactg atcatatgtt cattaatttg aaagttttct tcaatgctta taagacatat  14400
ctcttgtgtt ttcataaagg ttacggcaga gcaaagctgg agtgtgatat gaatacttca  14460
gatctcctat gtgtattgga attaatagac agtagttatt ggaagtctat gtctaaggtg  14520
tttttagaac aaaaagttat caaatacatt cttagccagg atgcaagttt acatagagta  14580
aaaggatgtc atagcttcaa actatggttt cttaaacgtc ttaatgtagc agaattcaca  14640
gtttgccctt gggttgttaa catagattat catccaacac atatgaaagc aatattaact  14700
tatattgatc ttgttagaat gggattgata aatatagata gaatatacat taaaaataaa  14760
cacaagttca atgatgagtt ttatacttct aatctgtttt acattaatta taacttctca  14820
gataatactc atctattaac taaacatata aggattgcta attccgaatt agaaagtaat  14880
tacaacaaat tatatcatcc tacaccagaa accctagaaa atatactaac caatccggtt  14940
aaaagtaatg agaaaaagac actgagtgac tattgtatag gtaaaaatgt tgactcaata  15000
atgttaccat cgttatctaa taagaagctt attaaatcgt ctacaatgat tagaaccaat  15060
tacagcagac aagatttgta taatttattt cctacggttg tgattgataa aattatagat  15120
cattcaggta atacagccaa atctaaccaa ctttacacta ctacttctca tcaaatatcc  15180
ttagtgcaca atagcacatc actttattgc atgcttcctt ggcatcatat taatagattc  15240
aattttgtat ttagttctac aggttgtaaa attagtatag agtatatttt aaaagatctt  15300
aaaattaagg atcctaattg tatagcattc ataggtgaag gagcagggaa tttattattg  15360
cgtacagtag tggaacttca tcctgatata agatatattt acagaagtct gaaagattgc  15420
aatgatcata gtttaccaat tgagttttta aggctgtaca atggacatat caacattgat  15480
tatggtgaaa atttgaccat tcctgctaca gatgcaacca acaacattca ttggtcttat  15540
ttacatataa agtttgctga acctatcagt ctttttgtct gtgatgctga attgcctgta  15600
acagtcaact ggagtaagat tataatagag tggagcaagc atgtaagaaa atgcaagtac  15660
tgttcttcag ttaataaatg tacattgata gtaaaatatc atgctcaaga tgatatcgat  15720
ttcaaattag acaacataac tatattaaaa acttatgtat gcttaggtag taagttaaag  15780
ggatctgaag tttacttagt ccttacaata ggtcctgcaa atgtgttccc agtatttaat  15840
gtagtacaaa atgctaaatt gatactatca agaactaaaa atttcatcat gcctaaaaaa  15900
```

-continued gctgataaag agtctattga tgcaaatatt aagagtttga taccctttct ttgttaccct 15960
ataacaaaaa aaggaattaa tactgcattg tctaaattaa agagtgttgt tagtggagat 16020
atactatcat attctatagc tggacgtaat gaagttttca gcaataaact tataaatcat 16080
aagcatatga acatcttaaa gtggttcaat catgttttaa atttcagatc aacagaatta 16140
aactataatc atttatatat ggtagaatct acttatcctc atctaagtga attgttaaac 16200
agcttgacaa ccaatgaact taaaaaactg attaaaatca caggtagttt gttatacaac 16260
ttttataatg aataatgagc aaaaatctta taacaaaaat agctacacac taacattgta 16320
ttcaattata gttattgaaa attaataatt atataatttt taataacttc tagtgaacta 16380
atcctaaaat tatcattttg atctaggaag aataagttta aatccaaatc taattggttt 16440
atatgtatat taactaaatt acgagatatt agtttttgac acttttttc tcgt 16494

<210> SEQ ID NO 8
<211> LENGTH: 15506
<212> TYPE: DNA
<213> ORGANISM: Artificial Sequence
<220> FEATURE:
<223> OTHER INFORMATION: Sequence in which the G gene is deleted in SEQ
ID NO: 7

<400> SEQUENCE: 8
acgcgaaaaa atgcgtacaa caaacttgcg taaaccaaaa aaatggggca aataagaatt 60
tgataagtac cacttaaatt taactccttt ggttagaggc gcgccatggg cagcaactca 120
ttgagtatga taaaagttag attgcaaaat ctgtttgaca atgatgaagt agcattgtta 180
aaaataacat gctatactga caaattaata cagttaacta atgctttggc taaggcagtt 240
atacatacaa tcaaattgaa tggcattgta tttgtgcatg ttattacaag tagtgatatt 300
tgccctaata ataatattgt agtgaaatcc aatttcacaa caatgccagt attacaaaat 360
ggaggttata tatgggaaat gatggaatta acacactgct ctcaacctaa tggcctaata 420
gatgacaatt gtgaaattaa attctccaaa aaactaagtg attcaacaat gaccaattat 480
atgaatcaat tatctgaatt acttggattt gacctcaatc cataaatcat aataaatatc 540
aactagcaaa tcaatgtcac taacaccatt agttaatata aaacttgaca gaagataaaa 600
atggggcaaa taaatcaatt cagccgaccc aaccatggac acaacacaca atgataccac 660
accacaaaga ctgatgatca cagacatgag gccattatcg cttgagacta taataacatc 720
tctaaccaga gatatcataa cacataaatt tatatacttg ataaatcatg aatgcatagt 780
aagaaaactt gatgaaagac aggccacatt tacatttctg gtcaactatg aaatgaaact 840
attgcacaaa gtgggaagca ctaaatataa aaaatatact gaatacaaca caaaatatgg 900
cactttccct atgccaatat ttatcaatca tgatgggttc ttagaatgca ttggcattaa 960
gcctaccaag cacacaccca taatatacaa gtatgatctc aatccatgaa tatcaaacca 1020
agattcaaac aatccgaaat aacaacttta tgcataatca cactccatag tccaaatgga 1080
gcctgaaaat tatagttatt taaaattcct gcaggaagga gagacataag atgaaagatg 1140
gggcaaatac aaaaatggct cttagcaaag tcaagttgaa tgatacactc aacaaagatc 1200
aacttctatc atccagcaaa tataccatcc aacggagcac aggagacagc attgacactc 1260
ctaattatga tgtgcagaaa cacattaata agttatgtgg catgttatta atcacagaag 1320
atgctaatca taaattcact gggttaatag gtatgttata tgctatgtct agattaggaa 1380
gagaagacac cataaaaata ctcaaagatg cgggatatca tgttaaggca aatggagtgg 1440

-continued atgtaacaac acatcgtcaa gacattaatg ggaaagaaat gaaatttgaa gtgttaacat 1500
tagcaagctt aacaactgaa attcaaatca acattgagat agaatctaga aaatcctaca 1560
aaaaaatgct aaaagaaatg ggagaggtgg ctccagaata caggcatgac tctcctgatt 1620
gtgggatgat aatattatgt atagcggcat tagtaataac caaattagca gcaggagata 1680
gatcaggtct tacagctgtg attaggagag ctaataatgt cctaaaaaat gaaatgaaac 1740
gttataaagg tttattaccc aaggatatag ccaacagctt ctatgaagtg tttgaaaaat 1800
atcctcactt tatagatgtt tttgttcatt ttggtatagc acaatcttct accagaggtg 1860
gcagtagagt tgaagggatt tttgcaggat tgtttatgaa tgcctatggt gcagggcaag 1920
tgatgttacg gtgggggtc ttagcaaaat cagttaaaaa cattatgtta ggacacgcta 1980
gtgtacaagc agaaatggaa caagttgtgg aggtgtatga gtatgctcag aaattgggtg 2040
gagaagcagg attctaccat atattgaaca acccaaaagc atcactatta tctttgactc 2100
aatttcctca cttctctagt gtagtattgg gcaatgctgc tggcctaggc ataatgggag 2160
aatacagagg tacaccaagg aatcaagatt tatatgatgc tgcaaaagca tatgctgaac 2220
aactcaaaga aaatggtgtg attaactaca gtgtattaga tttgacagca gaagaactag 2280
aggctatcaa acatcagctt aatccaaaag ataatgatgt agagctttga gttaataaaa 2340
aagtggggca aataaatcat catggaaaag tttgctcctg aattccatgg agaagatgca 2400
aacaacagag ccaccaaatt cctagaatca ataaagggca aattcacatc acccaaagat 2460
cccaagaaaa aagatagtat catatctgtc aactcaatag atatagaagt aaccaaagaa 2520
agccctataa catcaaattc aaccattata aacccaataa atgagacaga tgatactgta 2580
gggaacaagc ccaattatca aagaaagcct ctagtaagtt tcaaagaaga ccctacgcca 2640
agtgataatc ctttttcaaa actatacaaa gaaaccatag aaacatttga taacaatgaa 2700
gaagaatcta gctattcata tgaagaaata aatgatcaga caaacgataa tataacagca 2760
agattagata ggattgatga gaaattaagt gaaatactag gaatgcttca cacattagta 2820
gtagcgagtg caggacccac atctgctcgg gatggtataa gagatgccat ggttggttta 2880
agagaagaaa tgatagaaaa aatcagaact gaagcattaa tgaccaatga cagactagaa 2940
gctatggcaa gactcaggaa tgaagaaagt gaaaagatgg caaaagacac atcagatgaa 3000
gtgtctctca atccaacatc agagaaactg aacaacctgt tggaagggaa tgatagtgac 3060
aatgatctat cacttgaaga tttctgatta gctaccaaac tgtacatcaa aacacaacac 3120
caatagaaaa ccaacaaaca aaccaactca cccatccaac caaacatcta tctgctgatt 3180
agccaaccag ccaaaaaaca accagccaat ctaaaactag ccacccggaa aaaatcgata 3240
ctatagttac aaaaaaagat ggggcaaata tggaaacata cgtgaataaa cttcacgagg 3300
gctccacata cacagctgct gttcaataca atgtcctaga aaaagacgat gatcctgcat 3360
cacttacaat atgggtgccc atgttccaat catccatgcc agcagatcta ctcataaaag 3420
aactagccaa tgtcaatata ctagtgaaac aaatatccac acccaaggga ccctcattaa 3480
gagtcatgat aaactcaaga agtgcagtgc tagcacaaat gcccagcaaa tttaccatat 3540
gtgccaatgt gtccttggat gaaagaagca agctggcata tgatgtaacc acaccctgtg 3600
aaattaaggc atgcagtcta acatgcctaa aatcaaaaaa tatgttaact acagttaaag 3660
atctcactat gaaaacactc aacccaacac atgacatcat tgctttatgt gaatttgaaa 3720
atatagtaac atcaaaaaaa gtcataatac caacatacct aagatctatc agcgtcagaa 3780

-continued

```
ataaagatct gaacacactt gaaaatataa caaccactga attcaaaaat gccattacaa   3840
atgcaaaaat catcccttac tcaggattat tgttagtcat cacagtgact gacaacaaag   3900
gagcattcaa atacataaag ccacaaagtc aattcatagt agatcttgga gcttacctag   3960
aaaaagaaag tatatattat gttacaacaa attggaagca cacagctaca cgatttgcaa   4020
tcaaacccat ggaagattaa ccttttttcct ctacatcaat gagtagattc atacaaactt   4080
tctaactaca ttcttcactt cacaatcata atcaccaacc ctctgtggtt caatcaatca   4140
aacaaaactc atcaagagtt ccagatcatc ccaagtcatt gttcatcaga tccagtactc   4200
aaataagtta ataaaaaatc ggtccgttga cagaagataa aaatggggca aatgcaaaca   4260
tgaagtgcct tttgtactta gcctttttat tcattggggt gaattgcaag ttcaccatag   4320
tttttccaca caaccaaaaa ggaaactgga aaaatgttcc ttctaattac cattattgcc   4380
cgtcaagctc agatttaaat tggcataatg acttaatagg cacagcctta caagtcaaaa   4440
tgcccaagag tcacaaggct attcaagcag acggttggat gtgtcatgct tccaaatggg   4500
tcactacttg tgatttccgc tggtatggac cgaagtatat aacacattcc atccgatcct   4560
tcactccatc tgtagaacaa tgcaaggaaa gcattgaaca aacgaaacaa ggaacttggc   4620
tgaatccagg cttccctcct caaagttgtg gatatgcaac tgtgacggat gccgaagcag   4680
tgattgtcca ggtgactcct caccatgtgc tggttgatga atacacagga gaatgggttg   4740
attcacagtt catcaacgga aaatgcagca attacatatg ccccactgtc cataactcta   4800
caacctggca ttctgactat aaggtcaaag ggctatgtga ttctaacctc atttccatgg   4860
acatcacctt cttctcagag gacggagagc tatcatccct gggaaaggag ggcacagggt   4920
tcagaagtaa ctactttgct tatgaaactg gaggcaaggc ctgcaaaatg caatactgca   4980
agcattgggg agtcagactc ccatcaggtg tctggttcga gatggctgat aaggatctct   5040
ttgctgcagc cagattccct gaatgcccag aagggtcaag tatctctgct ccatctcaga   5100
cctcagtgga tgtaagtcta attcaggacg ttgagaggat cttggattat tccctctgcc   5160
aagaaacctg gagcaaaatc agagcgggtc ttccaatctc tccagtggat ctcagctatc   5220
ttgctcctaa aaacccagga accggtcctg ctttcaccat aatcaatggt accctaaaat   5280
actttgagac cagatacatc agagtcgata ttgctgctcc aatcctctca agaatggtcg   5340
gaatgatcag tggaactacc acagaaaggg aactgtggga tgactgggca ccatatgaag   5400
acgtggaaat tggacccaat ggagttctga ggaccagttc aggatataag tttcctttat   5460
acatgattgg acatggtatg ttggactccg atcttcatct tagctcaaag gctcaggtgt   5520
tcgaacatcc tcacattcaa gacgctgctt cgcaacttcc tgatgatgag agtttatttt   5580
ttggtgatac tgggctatcc aaaaatccaa tcgagcttgt agaaggttgg ttcagtagtt   5640
ggaaaagctc tattgcctct tttttcttta tcatagggtt aatcattgga ctattcttgg   5700
ttctccgagt tggtatccat ctttgcatta aagccagaag cacaccagtc acattaagta   5760
aggatcaact gagtggtata aataatattg catttagtaa ctaatagtca ttaaaaagcg   5820
gccggccgta ttgttgcaaa aagccatgac caaatcaaac agaatcaaaa tcaactctac   5880
gcgtgtattg ttgcaaaaag ccatgaccaa atcaaacaga atcaaaatca actctggggc   5940
aaataacaat ggagttgcca atcctcaaaa caaatgctat taccacaatc cttgctgcag   6000
tcacactctg tttcgcttcc agtcaaaaca tcactgaaga attttatcaa tcaacatgca   6060
gtgcagtcag caaaggctat cttagtgctc taagaactgg ttggtatact agtgttataa   6120
ctatagaatt aagtaatatc aaggaaaata agtgtaatgg tacagacgct aaggtaaaat   6180
```

-continued

```
taataaaaca agaattagat aaatataaaa atgctgtaac agaattgcag ttgctcatgc   6240
aaagcacacc agcagccaac aatcgagcca gaagagaact accaagattt atgaattata   6300
cactcaacaa taccaaaaac accaatgtaa cattaagtaa gaaaaggaaa agaagatttc   6360
ttggattttt gttaggtgtt ggatctgcaa tcgccagtgg cattgccgta tccaaggtcc   6420
tgcacctaga aggggaagtg aacaaaatca aaagtgctct actatccaca aacaaggctg   6480
tagtcagctt atctaatgga gtcagtgtct taaccagcaa ggtgttagac ctcaaaaact   6540
atatagataa acagttgtta cctattgtta acaagcaaag ctgcagcata tcaaacattg   6600
aaactgtgat agagttccaa caaaagaaca acagactact agagattacc agagaattta   6660
gtgttaatgc aggtgtaact actcctgtaa gcacttatat gttaactaat agtgagttat   6720
tatcattaat caatgatatg cctataacaa atgatcagaa aaagttaatg tccagcaatg   6780
ttcaaatagt tagacagcaa agttactcta tcatgtcaat aataaaagag gaagtcttgg   6840
catatgtagt acaattacca ctatatggtg taatagatac tccttgttgg aaactacaca   6900
catccccttt atgtacaacc aacacaaagg aaggatccaa catctgctta acaagaaccg   6960
acagaggatg gtactgtgac aatgcaggat cagtatcctt tttcccacaa gctgaaacat   7020
gtaaagttca atcgaatcgg gtgttttgtg acacaatgaa cagtttaaca ttaccaagtg   7080
aggtaaatct ctgcaacatt gacatattca accccaaata tgattgcaaa attatgactt   7140
caaaaacaga tgtaagcagc tccgttatca catctctagg agccattgtg tcatgctatg   7200
gcaaaaccaa atgtacagca tccaataaaa atcgtgggat cataaagaca ttctctaacg   7260
ggtgtgatta tgtatcaaat aagggggtgg atactgtgtc tgtaggtaat acattatatt   7320
atgtaaataa gcaagaaggc aaaagtctct atgtaaaagg tgaaccaata ataaatttct   7380
atgatccatt agtgttcccc tctgatgaat ttgatgcatc aatatctcaa gtcaatgaga   7440
aaattaatca gagtctagca tttatccgta aatcagatga attattacat aatgtaaatg   7500
ctggtaaatc caccacaaat atcatgataa ctaccataat tatagtaatt atagtaatat   7560
tgttagcatt aattgcagtt ggactgcttc tatactgcaa ggccagaagc acaccagtca   7620
cattaagtaa ggatcaactg agtggtataa ataatattgc atttagtaac tgaataaaaa   7680
tagcacctaa tcatattctt acaatggttc gctatttgac catagataac ccatctatca   7740
ttagattatc ctaaaatttg aacttcatca caactttcat ctataaacca tctcacttac   7800
actttttaag tagatttcta ttttatagtt atataaaaca gggcccattg aataccaaat   7860
taacttacta tttgtaaaaa tgagaattgg ggcaaatatg tcacgaagga atccttgcaa   7920
attcgaaatt cgaggtcatt gcttgaatgg taaaaggtgt cattttagtc ataattattt   7980
tgaatggcca ccccatgcac tgcttgtaag acaaaacttt atgttaaaca gaatacttaa   8040
gtctatggat aaaagcatag atactttgtc agaaataagt ggagctgcag agttggacag   8100
aacagaagag tatgccctcg gtgtagttgg agtgctagag agttatatag gatcaataaa   8160
taatataact aaacaatcag catgtgttgc catgagcaaa ctccttactg aactcaacag   8220
cgatgacatc aaaaaactaa gggacaatga agagccaaac tcacccaaag taagagtgta   8280
caatactgtc atatcatata ttgaaagcaa caggaagaac aataaacaaa ctatccatct   8340
gttaaaaaga ttgccagcag acgtattgaa gaaaaccatc aaaaacacat tggatatcca   8400
caagagcata accatcaata acccaaaaga atcaactgtt agtgatacga acgaccatgc   8460
caaaaataat gatactacct gacaaatatc cttgtagtat aaattccata ctaataacaa   8520
```

-continued

```
gtaattgtag agtcactatg tataatcaaa aaaacacact atatatcaat caaaacaacc   8580
aaaatagcca tatataccca ccggatcaac cattcaatga aatccattgg acctctcaag   8640
acttgattga tgcaactcaa aattttctac aacatctagg tattactgat gatatataca   8700
caatatatat attagtgtca taatactcaa tcctaatact taccacatca tcaaattatt   8760
aactcaaaca attcaagcta tgggacaaaa tggatcccat tattagtgga aattctgcta   8820
atgtttatct aactgatagt tatttaaaag gtgttatttc tttctcagaa tgtaacgctt   8880
taggaagtta catattcaat ggtccttatc tcaaaaatga ttataccaac ttaattagta   8940
gacaaaatcc attaatagaa cacataaatc taaagaaact aaatataaca cagtccttaa   9000
tatctaagta tcataaaggt gaaataaaaa tagaagaacc tacttacttt cagtcattac   9060
ttatgacata caagagtatg acctcttcag aacagactac tactactaat ttacttaaaa   9120
agataataag aagagctata gaaatcagtg atgtcaaagt ctatgctata ttgaataaac   9180
tggggctcaa agaaaaagac aagattaaat ccaataatgg acaagatgaa gacaactcag   9240
tcattactac cataatcaaa gatgatatac ttttagctgt caaggataat caatctcatc   9300
ttaaagcaga caaaaatcaa tccacaaaac aaaaagatac aatcaaaaca acacttttga   9360
agaaattaat gtgttcgatg caacatcctc catcatggtt aatacattgg tttaatttat   9420
acacaaaatt aaacagcata ttaacacaat atcgatctag tgaggtaaaa aaccatggtt   9480
ttatattgat agataatcat actcttagtg gattccaatt tattttgaat caatatggtt   9540
gtatagttta tcataaggaa ctcaaaagaa ttactgtgac aacttataat caattcttga   9600
catggaaaga tattagcctt agtagattaa atgtttgttt gattacatgg attagtaact   9660
gtttgaacac attaaacaaa agcttaggct taagatgtgg attcaataat gttatcttga   9720
cacaattatt cctttatgga gattgtatac taaaactatt ccacaatgag gggttctaca   9780
taataaaaga ggtagaggga tttattatgt ctctaatttt aaatataaca gaagaagatc   9840
aattcagaaa acggttttat aatagtatgc tcaacaacat cacagatgcc gccaacaaag   9900
ctcaaaaaaa tctgctatca agagtatgtc atacattatt agataagaca atatcagata   9960
atataataaa tggcagatgg ataattctat tgagtaagtt cctaaaatta attaagcttg  10020
caggtgacaa taacctcaac aatctgagtg aattatattt tttgttcaga atatttggac  10080
acccaatggt agatgaaaga caagccatgg atgctgttaa agttaattgc aacgagacca  10140
aattttattt gttaagtagt ttgagtatgt taagaggagc ttttatatat agaattataa  10200
aagggtttgt aaataattac aacagatggc ctactttaag aaatgccatt gtcttaccct  10260
taagatggtt aacttactat aaactaaaca cttatccttc cttgttggaa cttacagaaa  10320
gagatttgat tgttctatca ggactacgtt tctatcgaga gtttcggttg cctaaaaaag  10380
tggatcttga aatgatcata aatgataagg ctatatcacc tcctaaaaat ttaatatgga  10440
ctagtttccc tagaaattat atgccgtcac acatacaaaa ttatatagaa catgaaaaat  10500
taaaattctc tgatagtgat aaatcaagaa gagtattaga gtattattta agagataaca  10560
aattcaatga atgtgattta cacaactgtg tagttaatca aagttatctt aacaacccga  10620
atcatgtggt atcattgaca ggcaaagaaa gagaactcag tgtaggtaga atgtttgcaa  10680
tgcaaccagg aatgttcaga caagttcaaa tattagcaga gaaaatgata gcagaaaaca  10740
tattacaatt tttccctgaa agtcttacaa gatatggtga tctagaacta cagaaaatat  10800
tagaattgaa agcaggaata agtaacaaat caaatcgtta caatgataat tacaacaatt  10860
acattagtaa gtgctctatc atcacagatc tcagcaaatt caatcaagca tttcgatatg  10920
```

```
aaacatcatg tatttgtagt gatgtactgg atgaactgca tggtgtacaa tctctatttt   10980

cctggttaca tttaactatt cctcatgtca caataatatg cacatatagg catgcacccc   11040

cctatataaa ggatcatatt gtagatctta acaatgtaga tgagcaaagt ggactatata   11100

gatatcatat gggtggtatc gaagggtggt gtcaaaaact atggaccata gaagctatat   11160

cactattaga tctaatatct ctcaaaggga aattctcaat tactgcttta attaatggtg   11220

acaatcaatc aatagatata agtaaaccag tcagactcat ggaaggtcaa actcatgctc   11280

aagcagatta tttgctagca ttaaatagtc tcaaattact gtataaagag tatgcaggaa   11340

taggccacaa attaaaagga actgagactt atatatcgag agatatgcaa tttatgagta   11400

aaacgatcca acataacggt gtatattacc cagctagtat aaagaaagtc ctaagagtgg   11460

gaccgtggat aaacactata cttgatgact caaagtgag tctagaatct ataggtagtt    11520

tgacacaaga attagaatat agaggtgaaa gtctattatg cagtttaata tttagaaatg   11580

tatggttata taatcaaatt gcattacaac ttaaaaatca tgcattatgt aacaacaaat   11640

tatatttgga tatattaaaa gttctaaaac acttaaaaac cttttttaat cttgataaca   11700

ttgatacagc attaacattg tatatgaatt tgcccatgtt atttggtggt ggtgatccca   11760

acttgttata tcgaagtttc tatagaagaa ctcctgattt cctcacagag gctatagttc   11820

actctgtgtt catacttagt tattatacaa accatgattt aaaagataaa cttcaagatc   11880

tgtcagatga tagattgaat aagttcttaa catgcataat cacgtttgat aaaaacccca   11940

atgctgaatt cgttacattg atgagagatc ctcaagcttt aggatctgag aggcaagcta   12000

aaattactag cgaaatcaat agactggcag ttaccgaggt tttgagcaca gctccaaaca   12060

aaatattttc caaagtgca caacactata ccactacaga gatagatctt aatgatatta    12120

tgcaaaatat agaacctaca tatcctcacg ggctaagagt tgtttatgag agtttaccct   12180

tttataaagc agagaaaata gtaaatctta tatccggtac aaaatctata actaacatac   12240

tggaaaagac ttctgccata gacttaacag atattgatag agccactgag atgatgagga   12300

aaaacataac tttgcttata aggatattac cattagattg taacagagat aaaagagaaa   12360

tattgagtat ggaaaaccta agtattactg aattaagcaa atacgttaga gaaagatctt   12420

ggtctttatc caatatagtt ggtgttacat cacccagtat catgtataca atggacataa   12480

aatatacaac aagcactata gctagtggca taatcataga gaaatataat gtcaacagtt   12540

taacacgtgg tgagagagga cccactaaac catgggttgg ttcatctaca caagagaaaa   12600

agacaatgcc agtttataat agacaagttt taaccaaaaa acagagagat caaatagatc   12660

tattagcaaa attggattgg gtgtatgcat ctatagataa caaggatgaa tttatggagg   12720

aacttagcat aggaactctt gggttaacat atgagaaggc caaaaaatta ttcccacaat   12780

atttgagtgt taactatttg catcgtctta cagtcagtag tagaccatgt gaattccctg   12840

catctatacc agcttataga actacaaatt atcactttga tactagccct attaatcgca   12900

tattaacaga aaagtatggt gatgaagata ttgatatagt attccaaaac tgtataagct   12960

ttggccttag cttaatgtct gtagtagaac aatttactaa tgtatgtcct aacagaatta   13020

ttctcatacc caagcttaat gagatacatt tgatgaaacc tcccatattc acaggcgatg   13080

ttgatattca caagttaaaa caagtgatac aaaaacaaca tatgttttta ccagacaaaa   13140

taagtttgac tcaatatgtg gaattattct taagtaataa aacactcaaa tctggatcta   13200

atgttaattc taatttaata ttggcgcata agatatctga ctattttcat aatacttaca   13260
```

-continued

```
ttttgagtac taatttagct ggacattgga ttcttattat acaacttatg aaagattcta  13320
agggtatttt tgaaaaagat tggggagagg gatatataac tgatcatatg ttcattaatt  13380
tgaaagtttt cttcaatgct tataagacat atctcttgtg ttttcataaa ggttacggca  13440
gagcaaagct ggagtgtgat atgaatactt cagatctcct atgtgtattg gaattaatag  13500
acagtagtta ttggaagtct atgtctaagg tgtttttaga acaaaaagtt atcaaataca  13560
ttcttagcca ggatgcaagt ttacatagag taaaaggatg tcatagcttc aaactatggt  13620
ttcttaaacg tcttaatgta gcagaattca cagtttgccc ttgggttgtt aacatagatt  13680
atcatccaac acatatgaaa gcaatattaa cttatattga tcttgttaga atgggattga  13740
taaatataga tagaatatac attaaaaata aacacaagtt caatgatgag ttttatactt  13800
ctaatctgtt ttacattaat tataacttct cagataatac tcatctatta actaaacata  13860
taaggattgc taattccgaa ttagaaagta attacaacaa attatatcat cctacaccag  13920
aaaccctaga aaatatacta accaatccgg ttaaaagtaa tgagaaaaag acactgagtg  13980
actattgtat aggtaaaaat gttgactcaa taatgttacc atcgttatct aataagaagc  14040
ttattaaatc gtctacaatg attagaacca attacagcag acaagatttg tataatttat  14100
ttcctacggt tgtgattgat aaaattatag atcattcagg taatacagcc aaatctaacc  14160
aactttacac tactacttct catcaaatat ccttagtgca caatagcaca tcactttatt  14220
gcatgcttcc ttggcatcat attaatagat tcaattttgt atttagttct acaggttgta  14280
aaattagtat agagtatatt ttaaaagatc ttaaaattaa ggatcctaat tgtatagcat  14340
tcataggtga aggagcaggg aatttattat tgcgtacagt agtggaactt catcctgata  14400
taagatatat ttacagaagt ctgaaagatt gcaatgatca tagtttacca attgagtttt  14460
taaggctgta caatggacat atcaacattg attatggtga aaatttgacc attcctgcta  14520
cagatgcaac caacaacatt cattggtctt atttacatat aaagtttgct gaacctatca  14580
gtctttttgt ctgtgatgct gaattgcctg taacagtcaa ctggagtaag attataatag  14640
agtggagcaa gcatgtaaga aaatgcaagt actgttcttc agttaataaa tgtacattga  14700
tagtaaaata tcatgctcaa gatgatatcg atttcaaatt agacaacata actatattaa  14760
aaacttatgt atgcttaggt agtaagttaa agggatctga agtttactta gtccttacaa  14820
taggtcctgc aaatgtgttc ccagtattta atgtagtaca aaatgctaaa ttgatactat  14880
caagaactaa aaatttcatc atgcctaaaa aagctgataa agagtctatt gatgcaaata  14940
ttaagagttt gataccccttt ctttgttacc ctataacaaa aaaaggaatt aatactgcat  15000
tgtctaaatt aaagagtgtt gttagtggag atatactatc atattctata gctggacgta  15060
atgaagtttt cagcaataaa cttataaatc ataagcatat gaacatctta aagtggttca  15120
atcatgtttt aaatttcaga tcaacagaat taaactataa tcatttatat atggtagaat  15180
ctacttatcc tcatctaagt gaattgttaa acagcttgac aaccaatgaa cttaaaaaac  15240
tgattaaaat cacaggtagt ttgttataca acttttataa tgaataatga gcaaaaatct  15300
tataacaaaa atagctacac actaacattg tattcaatta tagttattga aaattaataa  15360
ttatataatt tttaataact tctagtgaac taatcctaaa attatcattt tgatctagga  15420
agaataagtt taaatccaaa tctaattggt ttatatgtat attaactaaa ttacgagata  15480
ttagtttttg acactttttt tctcgt                                      15506
```

<210> SEQ ID NO 9
<211> LENGTH: 14589

<212> TYPE: DNA
<213> ORGANISM: Artificial Sequence
<220> FEATURE:
<223> OTHER INFORMATION: Sequence in which the F gene is deleted in SEQ ID NO: 7

<400> SEQUENCE: 9

```
acgcgaaaaa atgcgtacaa caaacttgcg taaaccaaaa aaatggggca aataagaatt     60

tgataagtac cacttaaatt taactccttt ggttagaggc gcgccatggg cagcaactca    120

ttgagtatga taaaagttag attgcaaaat ctgtttgaca atgatgaagt agcattgtta    180

aaaataacat gctatactga caaattaata cagttaacta atgctttggc taaggcagtt    240

atacatacaa tcaaattgaa tggcattgta tttgtgcatg ttattacaag tagtgatatt    300

tgccctaata ataatattgt agtgaaatcc aatttcacaa caatgccagt attacaaaat    360

ggaggttata tatgggaaat gatggaatta acacactgct ctcaacctaa tggcctaata    420

gatgacaatt gtgaaattaa attctccaaa aaactaagtg attcaacaat gaccaattat    480

atgaatcaat tatctgaatt acttggattt gacctcaatc cataaatcat aataaatatc    540

aactagcaaa tcaatgtcac taacaccatt agttaatata aaacttgaca gaagataaaa    600

atggggcaaa taaatcaatt cagccgaccc aaccatggac acaacacaca atgataccac    660

accacaaaga ctgatgatca cagacatgag gccattatcg cttgagacta taataacatc    720

tctaaccaga gatatcataa cacataaatt tatatacttg ataaatcatg aatgcatagt    780

aagaaaactt gatgaaagac aggccacatt tacatttctg gtcaactatg aaatgaaact    840

attgcacaaa gtgggaagca ctaaatataa aaaatatact gaatacaaca caaaatatgg    900

cactttccct atgccaatat ttatcaatca tgatgggttc ttagaatgca ttggcattaa    960

gcctaccaag cacacaccca taatatacaa gtatgatctc aatccatgaa tatcaaacca   1020

agattcaaac aatccgaaat aacaacttta tgcataatca cactccatag tccaaatgga   1080

gcctgaaaat tatagttatt taaaattcct gcaggaagga gagacataag atgaaagatg   1140

gggcaaatac aaaaatggct cttagcaaag tcaagttgaa tgatacactc aacaaagatc   1200

aacttctatc atccagcaaa tataccatcc aacggagcac aggagacagc attgacactc   1260

ctaattatga tgtgcagaaa cacattaata agttatgtgg catgttatta atcacagaag   1320

atgctaatca taaattcact gggttaatag gtatgttata tgctatgtct agattaggaa   1380

gagaagacac cataaaaata ctcaaagatg cgggatatca tgttaaggca aatggagtgg   1440

atgtaacaac acatcgtcaa gacattaatg ggaaagaaat gaaatttgaa gtgttaacat   1500

tagcaagctt aacaactgaa attcaaatca acattgagat agaatctaga aaatcctaca   1560

aaaaaatgct aaaagaaatg ggagaggtgg ctccagaata caggcatgac tctcctgatt   1620

gtgggatgat aatattatgt atagcggcat tagtaataac caaattagca gcaggagata   1680

gatcaggtct tacagctgtg attaggagag ctaataatgt cctaaaaaat gaaatgaaac   1740

gttataaagg tttattaccc aaggatatag ccaacagctt ctatgaagtg tttgaaaaat   1800

atcctcactt tatagatgtt tttgttcatt ttggtatagc acaatcttct accagaggtg   1860

gcagtagagt tgaagggatt tttgcaggat tgtttatgaa tgcctatggt gcagggcaag   1920

tgatgttacg gtggggggtc ttagcaaaat cagttaaaaa cattatgtta ggacacgcta   1980

gtgtacaagc agaaatggaa caagttgtgg aggtgtatga gtatgctcag aaattgggtg   2040

gagaagcagg attctaccat atattgaaca acccaaaagc atcactatta tctttgactc   2100

aatttcctca cttctctagt gtagtattgg gcaatgctgc tggcctaggc ataatgggag   2160
```

-continued

```
aatacagagg tacaccaagg aatcaagatt tatatgatgc tgcaaaagca tatgctgaac   2220
aactcaaaga aaatggtgtg attaactaca gtgtattaga tttgacagca gaagaactag   2280
aggctatcaa acatcagctt aatccaaaag ataatgatgt agagctttga gttaataaaa   2340
aagtggggca aataaatcat catggaaaag tttgctcctg aattccatgg agaagatgca   2400
aacaacagag ccaccaaatt cctagaatca ataaagggca aattcacatc acccaaagat   2460
cccaagaaaa aagatagtat catatctgtc aactcaatag atatagaagt aaccaaagaa   2520
agccctataa catcaaattc aaccattata aacccaataa atgagacaga tgatactgta   2580
gggaacaagc ccaattatca aagaaagcct ctagtaagtt tcaaagaaga ccctacgcca   2640
agtgataatc ctttttcaaa actatacaaa gaaaccatag aaacatttga taacaatgaa   2700
gaagaatcta gctattcata tgaagaaata aatgatcaga caaacgataa tataacagca   2760
agattagata ggattgatga gaaattaagt gaaatactag gaatgcttca cacattagta   2820
gtagcgagtg caggacccac atctgctcgg gatggtataa gagatgccat ggttggttta   2880
agagaagaaa tgatagaaaa aatcagaact gaagcattaa tgaccaatga cagactagaa   2940
gctatggcaa gactcaggaa tgaagaaagt gaaaagatgg caaaagacac atcagatgaa   3000
gtgtctctca atccaacatc agagaaactg aacaacctgt tggaagggaa tgatagtgac   3060
aatgatctat cacttgaaga tttctgatta gctaccaaac tgtacatcaa aacacaacac   3120
caatagaaaa ccaacaaaca aaccaactca cccatccaac caaacatcta tctgctgatt   3180
agccaaccag ccaaaaaaca accagccaat ctaaaactag ccacccggaa aaaatcgata   3240
ctatagttac aaaaaaagat ggggcaaata tggaaacata cgtgaataaa cttcacgagg   3300
gctccacata cacagctgct gttcaataca atgtcctaga aaaagacgat gatcctgcat   3360
cacttacaat atgggtgccc atgttccaat catccatgcc agcagatcta ctcataaaag   3420
aactagccaa tgtcaatata ctagtgaaac aaatatccac acccaaggga ccctcattaa   3480
gagtcatgat aaactcaaga agtgcagtgc tagcacaaat gcccagcaaa tttaccatat   3540
gtgccaatgt gtccttggat gaaagaagca agctggcata tgatgtaacc acaccctgtg   3600
aaattaaggc atgcagtcta acatgcctaa aatcaaaaaa tatgttaact acagttaaag   3660
atctcactat gaaaacactc aacccaacac atgacatcat tgctttatgt gaatttgaaa   3720
atatagtaac atcaaaaaaa gtcataatac caacatacct aagatctatc agcgtcagaa   3780
ataaagatct gaacacactt gaaaatataa caaccactga attcaaaaat gccattacaa   3840
atgcaaaaat catcccttac tcaggattat tgttagtcat cacagtgact gacaacaaag   3900
gagcattcaa atacataaag ccacaaagtc aattcatagt agatcttgga gcttacctag   3960
aaaaagaaag tatatattat gttacaacaa attggaagca cacagctaca cgatttgcaa   4020
tcaaacccat ggaagattaa ccttttttcct ctacatcaat gagtagattc atacaaactt   4080
tctaactaca ttcttcactt cacaatcata atcaccaacc ctctgtggtt caatcaatca   4140
aacaaaactc atcaagagtt ccagatcatc ccaagtcatt gttcatcaga tccagtactc   4200
aaataagtta ataaaaaatc ggtccgttga cagaagataa aaatggggca aatgcaaaca   4260
tgaagtgcct tttgtactta gcctttttat tcattggggt gaattgcaag ttcaccatag   4320
tttttccaca caaccaaaaa ggaaactgga aaaatgttcc ttctaattac cattattgcc   4380
cgtcaagctc agatttaaat tggcataatg acttaatagg cacagcctta caagtcaaaa   4440
tgcccaagag tcacaaggct attcaagcag acggttggat gtgtcatgct tccaaatggg   4500
```

-continued

```
tcactacttg tgatttccgc tggtatggac cgaagtatat aacacattcc atccgatcct   4560
tcactccatc tgtagaacaa tgcaaggaaa gcattgaaca aacgaaacaa ggaacttggc   4620
tgaatccagg cttccctcct caaagttgtg gatatgcaac tgtgacggat gccgaagcag   4680
tgattgtcca ggtgactcct caccatgtgc tggttgatga atacacagga gaatgggttg   4740
attcacagtt catcaacgga aaatgcagca attacatatg ccccactgtc cataactcta   4800
caacctggca ttctgactat aaggtcaaag ggctatgtga ttctaacctc atttccatgg   4860
acatcacctt cttctcagag gacggagagc tatcatccct gggaaaggag ggcacagggt   4920
tcagaagtaa ctactttgct tatgaaactg gaggcaaggc ctgcaaaatg caatactgca   4980
agcattgggg agtcagactc ccatcaggtg tctggttcga gatggctgat aaggatctct   5040
ttgctgcagc cagattccct gaatgcccag aagggtcaag tatctctgct ccatctcaga   5100
cctcagtgga tgtaagtcta attcaggacg ttgagaggat cttggattat tccctctgcc   5160
aagaaacctg gagcaaaatc agagcgggtc ttccaatctc tccagtggat ctcagctatc   5220
ttgctcctaa aaacccagga accggtcctg ctttcaccat aatcaatggt accctaaaat   5280
actttgagac cagatacatc agagtcgata ttgctgctcc aatcctctca agaatggtcg   5340
gaatgatcag tggaactacc acagaaaggg aactgtggga tgactgggca ccatatgaag   5400
acgtggaaat tggacccaat ggagttctga ggaccagttc aggatataag tttcctttat   5460
acatgattgg acatggtatg ttggactccg atcttcatct tagctcaaag gctcaggtgt   5520
tcgaacatcc tcacattcaa gacgctgctt cgcaacttcc tgatgatgag agtttatttt   5580
ttggtgatac tgggctatcc aaaaatccaa tcgagcttgt agaaggttgg ttcagtagtt   5640
ggaaaagctc tattgcctct tttttcttta tcatagggtt aatcattgga ctattcttgg   5700
ttctccgagt tggtatccat ctttgcatta aagccagaag cacaccagtc acattaagta   5760
aggatcaact gagtggtata aataatattg catttagtaa ctaatagtca ttaaaaagcg   5820
gccggccagt cataacaatg aactaggata ttaagaccaa aaacaacgct ggggcaaatg   5880
caaacatgtc caaaaccgag gaccaacgca ccgccaagac actagaaagg acctgggaca   5940
cttttaatca tctattattc atatcatcgt gcttatacaa gttaaatctt aaatctatag   6000
cacaaatcac attatctatt ttggcaatta taatctcaac ctcacttata attgcagcca   6060
tcatattcat agcctcggca aaccacaaag tcacactaac aactgcaatc atacaagatg   6120
caacgaacca gatcaagaac acaaccccaa catacctcac ccagaatccc cagcatggaa   6180
tcagcttctc caatctgtcc ggaactacat cacaatccac caccatacta gcttcaacaa   6240
caccaagtgc tgattcaacc ccacaatcca caacagtcaa gatcaaaaac acaacaacaa   6300
cccaaatatt acctagcaaa cccaccacaa aacaacgcca aaataaacca caaaacaaac   6360
ccaacaatga ttttcacttt gaagtgttca attttgtacc ctgcagcata tgcagcaaca   6420
atccaacctg ctgggccatc tgcaagagaa taccaaacaa aaaacctgga aagaaaacca   6480
ccaccaagcc cacaaaaaaa ccaaccctca agacaaccaa aaaagatccc aaatcccaaa   6540
ccacaaaacc aaaggaagta ctcactacca agcctacagg aaagccaacc atcaacacca   6600
ctaaaacaaa catcagaact acactgctca cctccaacac caaaggaaat ccagaacaca   6660
caagtcaaga ggaaaccctc cactcaacca cctccgaagg ctatccaagc ccatcacaag   6720
tccacacaac atccggtcaa gaggaaaccc tccactcaac cacctccgaa ggctatccaa   6780
gcccatcaca agtctacaca acatccgagt acctatcaca atctctatct tcatccaaca   6840
caacaaaatg atagtcatta aaaagcacgc gtgtattgtt gcaaaaagcc atgaccaaat   6900
```

-continued

```
caaacagaat caaaatcaac tctgggccca ttgaatacca aattaactta ctatttgtaa   6960
aaatgagaat tggggcaaat atgtcacgaa ggaatccttg caaattcgaa attcgaggtc   7020
attgcttgaa tggtaaaagg tgtcatttta gtcataatta ttttgaatgg ccaccccatg   7080
cactgcttgt aagacaaaac tttatgttaa acagaatact taagtctatg gataaaagca   7140
tagatacttt gtcagaaata agtggagctg cagagttgga cagaacagaa gagtatgccc   7200
tcggtgtagt tggagtgcta gagagttata taggatcaat aaataatata actaaacaat   7260
cagcatgtgt tgccatgagc aaactcctta ctgaactcaa cagcgatgac atcaaaaaac   7320
taagggacaa tgaagagcca aactcaccca aagtaagagt gtacaatact gtcatatcat   7380
atattgaaag caacaggaag aacaataaac aaactatcca tctgttaaaa agattgccag   7440
cagacgtatt gaagaaaacc atcaaaaaca cattggatat ccacaagagc ataaccatca   7500
ataacccaaa agaatcaact gttagtgata cgaacgacca tgccaaaaat aatgatacta   7560
cctgacaaat atccttgtag tataaattcc atactaataa caagtaattg tagagtcact   7620
atgtataatc aaaaaaacac actatatatc aatcaaaaca accaaaatag ccatatatac   7680
ccaccggatc aaccattcaa tgaaatccat tggacctctc aagacttgat tgatgcaact   7740
caaaattttc tacaacatct aggtattact gatgatatat acacaatata tatattagtg   7800
tcataatact caatcctaat acttaccaca tcatcaaatt attaactcaa acaattcaag   7860
ctatgggaca aaatggatcc cattattagt ggaaattctg ctaatgttta tctaactgat   7920
agttatttaa aaggtgttat ttctttctca gaatgtaacg ctttaggaag ttacatattc   7980
aatggtcctt atctcaaaaa tgattatacc aacttaatta gtagacaaaa tccattaata   8040
gaacacataa atctaaagaa actaaatata acacagtcct taatatctaa gtatcataaa   8100
ggtgaaataa aaatagaaga acctacttac tttcagtcat tacttatgac atacaagagt   8160
atgacctctt cagaacagac tactactact aatttactta aaaagataat aagaagagct   8220
atagaaatca gtgatgtcaa agtctatgct atattgaata aactggggct caaagaaaaa   8280
gacaagatta aatccaataa tggacaagat gaagacaact cagtcattac taccataatc   8340
aaagatgata tacttttagc tgtcaaggat aatcaatctc atcttaaagc agacaaaaat   8400
caatccacaa aacaaaaaga tacaatcaaa acaacacttt tgaagaaatt aatgtgttcg   8460
atgcaacatc ctccatcatg gttaatacat tggtttaatt tatacacaaa attaaacagc   8520
atattaacac aatatcgatc tagtgaggta aaaaaccatg gttttatatt gatagataat   8580
catactctta gtggattcca atttattttg aatcaatatg gttgtatagt ttatcataag   8640
gaactcaaaa gaattactgt gacaacttat aatcaattct tgacatggaa agatattagc   8700
cttagtagat taaatgtttg tttgattaca tggattagta actgtttgaa cacattaaac   8760
aaaagcttag gcttaagatg tggattcaat aatgttatct tgacacaatt attcctttat   8820
ggagattgta tactaaaact attccacaat gaggggttct acataataaa agaggtagag   8880
ggatttatta tgtctctaat tttaaatata acagaagaag atcaattcag aaaacggttt   8940
tataatagta tgctcaacaa catcacagat gccgccaaca aagctcaaaa aaatctgcta   9000
tcaagagtat gtcatacatt attagataag acaatatcag ataatataat aaatggcaga   9060
tggataattc tattgagtaa gttcctaaaa ttaattaagc ttgcaggtga caataacctc   9120
aacaatctga gtgaattata tttttgttc agaatatttg gacacccaat ggtagatgaa   9180
agacaagcca tggatgctgt taaagttaat tgcaacgaga ccaaatttta tttgttaagt   9240
```

-continued

```
agtttgagta tgttaagagg agcttttata tatagaatta taaaagggtt tgtaaataat   9300
tacaacagat ggcctacttt aagaaatgcc attgtcttac ccttaagatg gttaacttac   9360
tataaactaa acacttatcc ttccttgttg gaacttacag aaagagattt gattgttcta   9420
tcaggactac gtttctatcg agagtttcgg ttgcctaaaa aagtggatct tgaaatgatc   9480
ataaatgata aggctatatc acctcctaaa aatttaatat ggactagttt ccctagaaat   9540
tatatgccgt cacacataca aaattatata gaacatgaaa aattaaaatt ctctgatagt   9600
gataaatcaa gaagagtatt agagtattat ttaagagata acaaattcaa tgaatgtgat   9660
ttacacaact gtgtagttaa tcaaagttat cttaacaacc cgaatcatgt ggtatcattg   9720
acaggcaaag aaagagaact cagtgtaggt agaatgtttg caatgcaacc aggaatgttc   9780
agacaagttc aaatattagc agagaaaatg atagcagaaa acatattaca atttttccct   9840
gaaagtctta caagatatgg tgatctagaa ctacagaaaa tattagaatt gaaagcagga   9900
ataagtaaca aatcaaatcg ttacaatgat aattacaaca attacattag taagtgctct   9960
atcatcacag atctcagcaa attcaatcaa gcatttcgat atgaaacatc atgtatttgt  10020
agtgatgtac tggatgaact gcatggtgta caatctctat tttcctggtt acatttaact  10080
attcctcatg tcacaataat atgcacatat aggcatgcac cccctatat aaaggatcat   10140
attgtagatc ttaacaatgt agatgagcaa agtggactat atagatatca tatgggtggt  10200
atcgaagggt ggtgtcaaaa actatggacc atagaagcta tatcactatt agatctaata  10260
tctctcaaag ggaaattctc aattactgct ttaattaatg gtgacaatca atcaatagat  10320
ataagtaaac cagtcagact catggaaggt caaactcatg ctcaagcaga ttatttgcta  10380
gcattaaata gtctcaaatt actgtataaa gagtatgcag gaataggcca caaattaaaa  10440
ggaactgaga cttatatatc gagagatatg caatttatga gtaaaacgat ccaacataac  10500
ggtgtatatt acccagctag tataaagaaa gtcctaagag tgggaccgtg gataaacact  10560
atacttgatg acttcaaagt gagtctagaa tctataggta gtttgacaca agaattagaa  10620
tatagaggtg aaagtctatt atgcagttta atatttagaa atgtatggtt atataatcaa  10680
attgcattac aacttaaaaa tcatgcatta tgtaacaaca aattatattt ggatatatta  10740
aaagttctaa aacacttaaa aacctttttt aatcttgata acattgatac agcattaaca  10800
ttgtatatga atttgcccat gttatttggt ggtggtgatc ccaacttgtt atatcgaagt  10860
ttctatagaa gaactcctga tttcctcaca gaggctatag ttcactctgt gttcatactt  10920
agttattata caaaccatga tttaaaagat aaacttcaag atctgtcaga tgatagattg  10980
aataagttct taacatgcat aatcacgttt gataaaaacc ccaatgctga attcgttaca  11040
ttgatgagag atcctcaagc tttaggatct gagaggcaag ctaaaattac tagcgaaatc  11100
aatagactgg cagttaccga ggttttgagc acagctccaa acaaaatatt ttccaaaagt  11160
gcacaacact ataccactac agagatagat cttaatgata ttatgcaaaa tatagaacct  11220
acatatcctc acgggctaag agttgtttat gagagtttac ccttttataa agcagagaaa  11280
atagtaaatc ttatatccgg tacaaaatct ataactaaca tactggaaaa gacttctgcc  11340
atagacttaa cagatattga tagagccact gagatgatga ggaaaaacat aactttgctt  11400
ataaggatat taccattaga ttgtaacaga gataaaagag aaatattgag tatggaaaac  11460
ctaagtatta ctgaattaag caaatacgtt agagaaagat cttggtcttt atccaatata  11520
gttggtgtta catcacccag tatcatgtat acaatggaca taaaatatac aacaagcact  11580
atagctagtg gcataatcat agagaaatat aatgtcaaca gtttaacacg tggtgagaga  11640
```

```
ggacccacta aaccatgggt tggttcatct acacaagaga aaaagacaat gccagtttat  11700
aatagacaag ttttaaccaa aaaacagaga gatcaaatag atctattagc aaaattggat  11760
tgggtgtatg catctataga taacaaggat gaatttatgg aggaacttag cataggaact  11820
cttgggttaa catatgagaa ggccaaaaaa ttattcccac aatatttgag tgttaactat  11880
ttgcatcgtc ttacagtcag tagtagacca tgtgaattcc ctgcatctat accagcttat  11940
agaactacaa attatcactt tgatactagc cctattaatc gcatattaac agaaaagtat  12000
ggtgatgaag atattgatat agtattccaa aactgtataa gctttggcct tagcttaatg  12060
tctgtagtag aacaatttac taatgtatgt cctaacagaa ttattctcat acccaagctt  12120
aatgagatac atttgatgaa acctcccata ttcacaggcg atgttgatat tcacaagtta  12180
aaacaagtga tacaaaaaca acatatgttt ttaccagaca aaataagttt gactcaatat  12240
gtggaattat tcttaagtaa taaaacactc aaatctggat ctaatgttaa ttctaattta  12300
atattggcgc ataagatatc tgactatttt cataatactt acattttgag tactaattta  12360
gctggacatt ggattcttat tatacaactt atgaaagatt ctaagggtat tttgaaaaa  12420
gattggggag agggatatat aactgatcat atgttcatta atttgaaagt tttcttcaat  12480
gcttataaga catatctctt gtgttttcat aaaggttacg gcagagcaaa gctggagtgt  12540
gatatgaata cttcagatct cctatgtgta ttggaattaa tagacagtag ttattggaag  12600
tctatgtcta aggtgttttt agaacaaaaa gttatcaaat acattcttag ccaggatgca  12660
agtttacata gagtaaaagg atgtcatagc ttcaaactat ggtttcttaa acgtcttaat  12720
gtagcagaat tcacagtttg cccttgggtt gttaacatag attatcatcc aacacatatg  12780
aaagcaatat taacttatat tgatcttgtt agaatgggat tgataaatat agatagaata  12840
tacattaaaa ataaacacaa gttcaatgat gagttttata cttctaatct gttttacatt  12900
aattataact tctcagataa tactcatcta ttaactaaac atataaggat tgctaattcc  12960
gaattagaaa gtaattacaa caaattatat catcctacac cagaaaccct agaaaatata  13020
ctaaccaatc cggttaaaag taatgagaaa aagacactga gtgactattg tataggtaaa  13080
aatgttgact caataatgtt accatcgtta tctaataaga agcttattaa atcgtctaca  13140
atgattagaa ccaattacag cagacaagat ttgtataatt tatttcctac ggttgtgatt  13200
gataaaatta tagatcattc aggtaataca gccaaatcta accaacttta cactactact  13260
tctcatcaaa tatccttagt gcacaatagc acatcacttt attgcatgct tccttggcat  13320
catattaata gattcaattt tgtatttagt tctacaggtt gtaaaattag tatagagtat  13380
attttaaaag atcttaaaat taaggatcct aattgtatag cattcatagg tgaaggagca  13440
gggaatttat tattgcgtac agtagtggaa cttcatcctg atataagata tatttacaga  13500
agtctgaaag attgcaatga tcatagttta ccaattgagt ttttaaggct gtacaatgga  13560
catatcaaca ttgattatgg tgaaaatttg accattcctg ctacagatgc aaccaacaac  13620
attcattggt cttatttaca tataaagttt gctgaaccta tcagtctttt tgtctgtgat  13680
gctgaattgc ctgtaacagt caactggagt aagattataa tagagtggag caagcatgta  13740
agaaaatgca agtactgttc ttcagttaat aaatgtacat tgatagtaaa atatcatgct  13800
caagatgata tcgatttcaa attagacaac ataactatat taaaaactta tgtatgctta  13860
ggtagtaagt taaagggatc tgaagtttac ttagtcctta caataggtcc tgcaaatgtg  13920
ttcccagtat ttaatgtagt acaaaatgct aaattgatac tatcaagaac taaaaatttc  13980
```

atcatgccta aaaaagctga taaagagtct attgatgcaa atattaagag tttgataccc 14040
tttctttgtt accctataac aaaaaaagga attaatactg cattgtctaa attaaagagt 14100
gttgttagtg gagatatact atcatattct atagctggac gtaatgaagt tttcagcaat 14160
aaacttataa atcataagca tatgaacatc ttaaagtggt tcaatcatgt tttaaatttc 14220
agatcaacag aattaaacta taatcattta tatatggtag aatctactta tcctcatcta 14280
agtgaattgt taaacagctt gacaaccaat gaacttaaaa aactgattaa aatcacaggt 14340
agtttgttat acaactttta taatgaataa tgagcaaaaa tcttataaca aaaatagcta 14400
cacactaaca ttgtattcaa ttatagttat tgaaaattaa taattatata atttttaata 14460
acttctagtg aactaatcct aaaattatca ttttgatcta ggaagaataa gtttaaatcc 14520
aaatctaatt ggtttatatg tatattaact aaattacgag atattagttt ttgacacttt 14580
ttttctcgt 14589

<210> SEQ ID NO 10
<211> LENGTH: 14948
<212> TYPE: DNA
<213> ORGANISM: Artificial Sequence
<220> FEATURE:
<223> OTHER INFORMATION: The sequence in which the F gene of Backbone construct A was replaced with the VSV G gene.

<400> SEQUENCE: 10
acgcgaaaaa atgcgtacaa caaacttgcg taaaccaaaa aaatggggca aataagaatt 60
tgataagtac cacttaaatt taactccttt ggttagaggc gcgccatggg cagcaactca 120
ttgagtatga taaaagttag attgcaaaat ctgtttgaca atgatgaagt agcattgtta 180
aaaataacat gctatactga caaattaata cagttaacta atgctttggc taaggcagtt 240
atacatacaa tcaaattgaa tggcattgta tttgtgcatg ttattacaag tagtgatatt 300
tgccctaata ataatattgt agtgaaatcc aatttcacaa caatgccagt attacaaaat 360
ggaggttata tatgggaaat gatggaatta acacactgct ctcaacctaa tggcctaata 420
gatgacaatt gtgaaattaa attctccaaa aaactaagtg attcaacaat gaccaattat 480
atgaatcaat tatctgaatt acttggattt gacctcaatc cataaatcat aataaatatc 540
aactagcaaa tcaatgtcac taacaccatt agttaatata aaacttgaca gaagataaaa 600
atggggcaaa taaatcaatt cagccgaccc aaccatggac acaacacaca atgataccac 660
accacaaaga ctgatgatca cagacatgag gccattatcg cttgagacta taataacatc 720
tctaaccaga gatatcataa cacataaatt tatatacttg ataaatcatg aatgcatagt 780
aagaaaactt gatgaaagac aggccacatt tacatttctg gtcaactatg aaatgaaact 840
attgcacaaa gtgggaagca ctaaatataa aaaatatact gaatacaaca caaaatatgg 900
cactttccct atgccaatat ttatcaatca tgatgggttc ttagaatgca ttggcattaa 960
gcctaccaag cacacaccca taatatacaa gtatgatctc aatccatgaa tatcaaacca 1020
agattcaaac aatccgaaat aacaacttta tgcataatca cactccatag tccaaatgga 1080
gcctgaaaat tatagttatt taaaattcct gcaggaagga gagacataag atgaaagatg 1140
gggcaaatac aaaaatggct cttagcaaag tcaagttgaa tgatacactc aacaaagatc 1200
aacttctatc atccagcaaa tataccatcc aacggagcac aggagacagc attgacactc 1260
ctaattatga tgtgcagaaa cacattaata agttatgtgg catgttatta atcacagaag 1320
atgctaatca taaattcact gggttaatag gtatgttata tgctatgtct agattaggaa 1380

```
gagaagacac cataaaaata ctcaaagatg cgggatatca tgttaaggca aatggagtgg   1440
atgtaacaac acatcgtcaa gacattaatg ggaaagaaat gaaatttgaa gtgttaacat   1500
tagcaagctt aacaactgaa attcaaatca acattgagat agaatctaga aaatcctaca   1560
aaaaaatgct aaaagaaatg ggagaggtgg ctccagaata caggcatgac tctcctgatt   1620
gtgggatgat aatattatgt atagcggcat tagtaataac caaattagca gcaggagata   1680
gatcaggtct tacagctgtg attaggagag ctaataatgt cctaaaaaat gaaatgaaac   1740
gttataaagg tttattaccc aaggatatag ccaacagctt ctatgaagtg tttgaaaaat   1800
atcctcactt tatagatgtt tttgttcatt ttggtatagc acaatcttct accagaggtg   1860
gcagtagagt tgaagggatt tttgcaggat tgtttatgaa tgcctatggt gcagggcaag   1920
tgatgttacg gtgggggtc ttagcaaaat cagttaaaaa cattatgtta ggacacgcta   1980
gtgtacaagc agaaatggaa caagttgtgg aggtgtatga gtatgctcag aaattgggtg   2040
gagaagcagg attctaccat atattgaaca acccaaaagc atcactatta tctttgactc   2100
aatttcctca cttctctagt gtagtattgg gcaatgctgc tggcctaggc ataatgggag   2160
aatacagagg tacaccaagg aatcaagatt tatatgatgc tgcaaaagca tatgctgaac   2220
aactcaaaga aaatggtgtg attaactaca gtgtattaga tttgacagca gaagaactag   2280
aggctatcaa acatcagctt aatccaaaag ataatgatgt agagctttga gttaataaaa   2340
aagtggggca aataaatcat catggaaaag tttgctcctg aattccatgg agaagatgca   2400
aacaacagag ccaccaaatt cctagaatca ataaagggca aattcacatc acccaaagat   2460
cccaagaaaa aagatagtat catatctgtc aactcaatag atatagaagt aaccaaagaa   2520
agccctataa catcaaattc aaccattata aacccaataa atgagacaga tgatactgta   2580
gggaacaagc ccaattatca aagaaagcct ctagtaagtt tcaaagaaga ccctacgcca   2640
agtgataatc ctttttcaaa actatacaaa gaaaccatag aaacatttga taacaatgaa   2700
gaagaatcta gctattcata tgaagaaata aatgatcaga caaacgataa tataacagca   2760
agattagata ggattgatga gaaattaagt gaaatactag gaatgcttca cacattagta   2820
gtagcgagtg caggacccac atctgctcgg gatggtataa gagatgccat ggttggttta   2880
agagaagaaa tgatagaaaa aatcagaact gaagcattaa tgaccaatga cagactagaa   2940
gctatggcaa gactcaggaa tgaagaaagt gaaaagatgg caaaagacac atcagatgaa   3000
gtgtctctca atccaacatc agagaaactg aacaacctgt tggaagggaa tgatagtgac   3060
aatgatctat cacttgaaga tttctgatta gctaccaaac tgtacatcaa aacacaacac   3120
caatagaaaa ccaacaaaca aaccaactca cccatccaac caaacatcta tctgctgatt   3180
agccaaccag ccaaaaaaca accagccaat ctaaaactag ccacccggaa aaaatcgata   3240
ctatagttac aaaaaaagat ggggcaaata tggaaacata cgtgaataaa cttcacgagg   3300
gctccacata cacagctgct gttcaataca atgtcctaga aaaagacgat gatcctgcat   3360
cacttacaat atgggtgccc atgttccaat catccatgcc agcagatcta ctcataaaag   3420
aactagccaa tgtcaatata ctagtgaaac aaatatccac acccaaggga ccctcattaa   3480
gagtcatgat aaactcaaga agtgcagtgc tagcacaaat gcccagcaaa tttaccatat   3540
gtgccaatgt gtccttggat gaaagaagca agctggcata tgatgtaacc acaccctgtg   3600
aaattaaggc atgcagtcta acatgcctaa aatcaaaaaa tatgttaact acagttaaag   3660
atctcactat gaaaacactc aacccaacac atgacatcat tgctttatgt gaatttgaaa   3720
atatagtaac atcaaaaaaa gtcataatac caacatacct aagatctatc agcgtcagaa   3780
```

-continued

```
ataaagatct gaacacactt gaaaatataa caaccactga attcaaaaat gccattacaa   3840
atgcaaaaat catcccttac tcaggattat tgttagtcat cacagtgact gacaacaaag   3900
gagcattcaa atacataaag ccacaaagtc aattcatagt agatcttgga gcttacctag   3960
aaaaagaaag tatatattat gttacaacaa attggaagca cacagctaca cgatttgcaa   4020
tcaaacccat ggaagattaa ccttttcct ctacatcaat gagtagattc atacaaactt   4080
tctaactaca ttcttcactt cacaatcata atcaccaacc ctctgtggtt caatcaatca   4140
aacaaaactc atcaagagtt ccagatcatc ccaagtcatt gttcatcaga tccagtactc   4200
aaataagtta ataaaaaatc cacatggggc aaataatcat tgagggaaat ccaactaatc   4260
acaacatctg tcaacataga caagtcaaca cgctagataa aatcaaccaa tggaaaatac   4320
atccataact atagaattct caagcaaatt ctggccttac tttacactaa tacacatgat   4380
aacaacaata atctctttga taatcataat ctccatcatg attgcaatac taaacaaact   4440
ctgcgaatat aatgtattcc ataacaaaac ctttgagcta ccaagagctc gagtcaatac   4500
atagcattca ccaatctgat agctcaaaac agtaaccttg catttgtaaa tgaactaccc   4560
tcacttcttc acaaaaccac atcaacatct caccatgcaa gccatcatct ataccataaa   4620
gtagttaatt aaaaatggcc ggccagtcat aacaatgaac taggatatta agaccaaaaa   4680
caacgctggg gcaaatgcaa acatgtccaa aaccgaggac caacgcaccg ccaagacact   4740
agaaaggacc tgggacactt ttaatcatct attattcata tcatcgtgct tatacaagtt   4800
aaatcttaaa tctatagcac aaatcacatt atctattttg gcaattataa tctcaacctc   4860
acttataatt gcagccatca tattcatagc ctcggcaaac cacaaagtca cactaacaac   4920
tgcaatcata caagatgcaa cgaaccagat caagaacaca accccaacat acctcaccca   4980
gaatccccag catggaatca gcttctccaa tctgtccgga actacatcac aatccaccac   5040
catactagct tcaacaacac caagtgctga ttcaacccca caatccacaa cagtcaagat   5100
caaaaacaca acaacaaccc aaatattacc tagcaaaccc accacaaaac aacgccaaaa   5160
taaaccacaa aacaaaccca acaatgattt tcactttgaa gtgttcaatt ttgtaccctg   5220
cagcatatgc agcaacaatc caacctgctg ggccatctgc aagagaatac caaacaaaaa   5280
acctggaaag aaaaccacca ccaagcccac aaaaaaacca accctcaaga caaccaaaaa   5340
agatcccaaa tcccaaacca caaaaccaaa ggaagtactc actaccaagc ctacaggaaa   5400
gccaaccatc aacaccacta aaacaaacat cagaactaca ctgctcacct ccaacaccaa   5460
aggaaatcca gaacacacaa gtcaagagga aaccctccac tcaaccacct ccgaaggcta   5520
tccaagccca tcacaagtcc acacaacatc cggtcaagag gaaaccctcc actcaaccac   5580
ctccgaaggc tatccaagcc catcacaagt ctacacaaca tccgagtacc tatcacaatc   5640
tctatcttca tccaacacaa caaaatgata gtcattaaaa agcacgcgtt tgacagaaga   5700
taaaaatggg gcaaatgcaa acatgaagtg ccttttgtac ttagcctttt tattcattgg   5760
ggtgaattgc aagttcacca tagtttttcc acacaaccaa aaaggaaact ggaaaaatgt   5820
tccttctaat taccattatt gcccgtcaag ctcagattta aattggcata atgacttaat   5880
aggcacagcc ttacaagtca aaatgcccaa gagtcacaag gctattcaag cagacggttg   5940
gatgtgtcat gcttccaaat gggtcactac ttgtgatttc cgctggtatg gaccgaagta   6000
tataacacat tccatccgat ccttcactcc atctgtagaa caatgcaagg aaagcattga   6060
acaaacgaaa caaggaactt ggctgaatcc aggcttccct cctcaaagtt gtggatatgc   6120
```

-continued

```
aactgtgacg gatgccgaag cagtgattgt ccaggtgact cctcaccatg tgctggttga   6180
tgaatacaca ggagaatggg ttgattcaca gttcatcaac ggaaaatgca gcaattacat   6240
atgccccact gtccataact ctacaacctg gcattctgac tataaggtca aagggctatg   6300
tgattctaac ctcatttcca tggacatcac cttcttctca gaggacggag agctatcatc   6360
cctgggaaag gagggcacag ggttcagaag taactacttt gcttatgaaa ctggaggcaa   6420
ggcctgcaaa atgcaatact gcaagcattg gggagtcaga ctcccatcag gtgtctggtt   6480
cgagatggct gataaggatc tctttgctgc agccagattc cctgaatgcc cagaagggtc   6540
aagtatctct gctccatctc agacctcagt ggatgtaagt ctaattcagg acgttgagag   6600
gatcttggat tattccctct gccaagaaac ctggagcaaa atcagagcgg gtcttccaat   6660
ctctccagtg gatctcagct atcttgctcc taaaaaccca ggaaccggtc ctgctttcac   6720
cataatcaat ggtaccctaa aatactttga gaccagatac atcagagtcg atattgctgc   6780
tccaatcctc tcaagaatgg tcggaatgat cagtggaact accacagaaa gggaactgtg   6840
ggatgactgg gcaccatatg aagacgtgga aattggaccc aatggagttc tgaggaccag   6900
ttcaggatat aagtttcctt tatacatgat tggacatggt atgttggact ccgatcttca   6960
tcttagctca aaggctcagg tgttcgaaca tcctcacatt caagacgctg cttcgcaact   7020
tcctgatgat gagagtttat tttttggtga tactgggcta tccaaaaatc caatcgagct   7080
tgtagaaggt tggttcagta gttggaaaag ctctattgcc tctttttttct ttatcatagg   7140
gttaatcatt ggactattct tggttctccg agttggtatc catctttgca ttaaagccag   7200
aagcacacca gtcacattaa gtaaggatca actgagtggt ataaataata ttgcatttag   7260
taactaatag tcattaaaaa gcgggcccat tgaataccaa attaacttac tatttgtaaa   7320
aatgagaatt ggggcaaata tgtcacgaag gaatccttgc aaattcgaaa ttcgaggtca   7380
ttgcttgaat ggtaaaaggt gtcattttag tcataattat tttgaatggc caccccatgc   7440
actgcttgta agacaaaact ttatgttaaa cagaatactt aagtctatgg ataaaagcat   7500
agatactttg tcagaaataa gtggagctgc agagttggac agaacagaag agtatgccct   7560
cggtgtagtt ggagtgctag agagttatat aggatcaata aataatataa ctaaacaatc   7620
agcatgtgtt gccatgagca aactccttac tgaactcaac agcgatgaca tcaaaaaact   7680
aagggacaat gaagagccaa actcacccaa agtaagagtg tacaatactg tcatatcata   7740
tattgaaagc aacaggaaga acaataaaca aactatccat ctgttaaaaa gattgccagc   7800
agacgtattg aagaaaacca tcaaaaacac attggatatc cacaagagca taaccatcaa   7860
taacccaaaa gaatcaactg ttagtgatac gaacgaccat gccaaaaata atgatactac   7920
ctgacaaata tccttgtagt ataaattcca tactaataac aagtaattgt agagtcacta   7980
tgtataatca aaaaaacaca ctatatatca atcaaaacaa ccaaaatagc catatatacc   8040
caccggatca accattcaat gaaatccatt ggacctctca agacttgatt gatgcaactc   8100
aaaatttctt acaacatcta ggtattactg atgatatata cacaatatat atattagtgt   8160
cataatactc aatcctaata cttaccacat catcaaatta ttaactcaaa caattcaagc   8220
tatgggacaa aatggatccc attattagtg gaaattctgc taatgtttat ctaactgata   8280
gttatttaaa aggtgttatt tctttctcag aatgtaacgc tttaggaagt tacatattca   8340
atggtcctta tctcaaaaat gattatacca acttaattag tagacaaaat ccattaatag   8400
aacacataaa tctaaagaaa ctaaatataa cacagtcctt aatatctaag tatcataaag   8460
gtgaaataaa aatagaagaa cctacttact ttcagtcatt acttatgaca tacaagagta   8520
```

```
tgacctcttc agaacagact actactacta atttacttaa aaagataata agaagagcta   8580
tagaaatcag tgatgtcaaa gtctatgcta tattgaataa actggggctc aaagaaaaag   8640
acaagattaa atccaataat ggacaagatg aagacaactc agtcattact accataatca   8700
aagatgatat acttttagct gtcaaggata atcaatctca tcttaaagca gacaaaaatc   8760
aatccacaaa acaaaaagat acaatcaaaa caacactttt gaagaaatta atgtgttcga   8820
tgcaacatcc tccatcatgg ttaatacatt ggtttaattt atacacaaaa ttaaacagca   8880
tattaacaca atatcgatct agtgaggtaa aaaaccatgg ttttatattg atagataatc   8940
atactcttag tggattccaa tttattttga atcaatatgg ttgtatagtt tatcataagg   9000
aactcaaaag aattactgtg acaacttata atcaattctt gacatggaaa gatattagcc   9060
ttagtagatt aaatgtttgt ttgattacat ggattagtaa ctgtttgaac acattaaaca   9120
aaagcttagg cttaagatgt ggattcaata atgttatctt gacacaatta ttcctttatg   9180
gagattgtat actaaaacta ttccacaatg aggggttcta cataataaaa gaggtagagg   9240
gatttattat gtctctaatt ttaaatataa cagaagaaga tcaattcaga aaacggtttt   9300
ataatagtat gctcaacaac atcacagatg ccgccaacaa agctcaaaaa aatctgctat   9360
caagagtatg tcatacatta ttagataaga caatatcaga taatataata aatggcagat   9420
ggataattct attgagtaag ttcctaaaat taattaagct tgcaggtgac aataacctca   9480
acaatctgag tgaattatat tttttgttca gaatatttgg acacccaatg gtagatgaaa   9540
gacaagccat ggatgctgtt aaagttaatt gcaacgagac caaattttat ttgttaagta   9600
gtttgagtat gttaagagga gcttttatat atagaattat aaaagggttt gtaaataatt   9660
acaacagatg gcctacttta agaaatgcca ttgtcttacc cttaagatgg ttaacttact   9720
ataaactaaa cacttatcct tccttgttgg aacttacaga aagagatttg attgttctat   9780
caggactacg tttctatcga gagtttcggt tgcctaaaaa agtggatctt gaaatgatca   9840
taaatgataa ggctatatca cctcctaaaa atttaatatg gactagtttc cctagaaatt   9900
atatgccgtc acacatacaa aattatatag aacatgaaaa attaaaattc tctgatagtg   9960
ataaatcaag aagagtatta gagtattatt taagagataa caaattcaat gaatgtgatt  10020
tacacaactg tgtagttaat caaagttatc ttaacaaccc gaatcatgtg gtatcattga  10080
caggcaaaga aagagaactc agtgtaggta gaatgtttgc aatgcaacca ggaatgttca  10140
gacaagttca aatattagca gagaaaatga tagcagaaaa catattacaa tttttccctg  10200
aaagtcttac aagatatggt gatctagaac tacagaaaat attagaattg aaagcaggaa  10260
taagtaacaa atcaaatcgt tacaatgata attacaacaa ttacattagt aagtgctcta  10320
tcatcacaga tctcagcaaa ttcaatcaag catttcgata tgaaacatca tgtatttgta  10380
gtgatgtact ggatgaactg catggtgtac aatctctatt ttcctggtta catttaacta  10440
ttcctcatgt cacaataata tgcacatata ggcatgcacc cccctatata aaggatcata  10500
ttgtagatct taacaatgta gatgagcaaa gtggactata tagatatcat atgggtggta  10560
tcgaagggtg gtgtcaaaaa ctatggacca tagaagctat atcactatta gatctaatat  10620
ctctcaaagg gaaattctca attactgctt taattaatgg tgacaatcaa tcaatagata  10680
taagtaaacc agtcagactc atggaaggtc aaactcatgc tcaagcagat tatttgctag  10740
cattaaatag tctcaaatta ctgtataaag agtatgcagg aataggccac aaattaaaag  10800
gaactgagac ttatatatcg agagatatgc aatttatgag taaaacgatc caacataacg  10860
```

-continued

```
gtgtatatta cccagctagt ataaagaaag tcctaagagt gggaccgtgg ataaacacta  10920
tacttgatga cttcaaagtg agtctagaat ctataggtag tttgacacaa gaattagaat  10980
atagaggtga aagtctatta tgcagtttaa tatttagaaa tgtatggtta tataatcaaa  11040
ttgcattaca acttaaaaat catgcattat gtaacaacaa attatatttg gatatattaa  11100
aagttctaaa acacttaaaa accttttta atcttgataa cattgataca gcattaacat  11160
tgtatatgaa tttgcccatg ttatttggtg gtggtgatcc caacttgtta tatcgaagtt  11220
tctatagaag aactcctgat ttcctcacag aggctatagt tcactctgtg ttcatactta  11280
gttattatac aaaccatgat ttaaaagata aacttcaaga tctgtcagat gatagattga  11340
ataagttctt aacatgcata atcacgtttg ataaaaaccc caatgctgaa ttcgttacat  11400
tgatgagaga tcctcaagct ttaggatctg agaggcaagc taaaattact agcgaaatca  11460
atagactggc agttaccgag gttttgagca cagctccaaa caaaatattt tccaaaagtg  11520
cacaacacta taccactaca gagatagatc ttaatgatat tatgcaaaat atagaaccta  11580
catatcctca cgggctaaga gttgtttatg agagtttacc cttttataaa gcagagaaaa  11640
tagtaaatct tatatccggt acaaaatcta taactaacat actggaaaag acttctgcca  11700
tagacttaac agatattgat agagccactg agatgatgag gaaaaacata actttgctta  11760
taaggatatt accattagat tgtaacagag ataaaagaga aatattgagt atggaaaacc  11820
taagtattac tgaattaagc aaatacgtta gagaaagatc ttggtcttta tccaatatag  11880
ttggtgttac atcacccagt atcatgtata caatggacat aaaatataca acaagcacta  11940
tagctagtgg cataatcata gagaaatata atgtcaacag tttaacacgt ggtgagagag  12000
gacccactaa accatgggtt ggttcatcta cacaagagaa aaagacaatg ccagtttata  12060
atagacaagt tttaaccaaa aaacagagag atcaaataga tctattagca aaattggatt  12120
gggtgtatgc atctatagat aacaaggatg aatttatgga ggaacttagc ataggaactc  12180
ttgggttaac atatgagaag gccaaaaaat tattcccaca atatttgagt gttaactatt  12240
tgcatcgtct tacagtcagt agtagaccat gtgaattccc tgcatctata ccagcttata  12300
gaactacaaa ttatcacttt gatactagcc ctattaatcg catattaaca gaaaagtatg  12360
gtgatgaaga tattgatata gtattccaaa actgtataag ctttggcctt agcttaatgt  12420
ctgtagtaga acaatttact aatgtatgtc ctaacagaat tattctcata cccaagctta  12480
atgagataca tttgatgaaa cctcccatat tcacaggcga tgttgatatt cacaagttaa  12540
aacaagtgat acaaaaacaa catatgtttt taccagacaa aataagtttg actcaatatg  12600
tggaattatt cttaagtaat aaaacactca aatctggatc taatgttaat tctaatttaa  12660
tattggcgca taagatatct gactattttc ataatactta cattttgagt actaatttag  12720
ctggacattg gattcttatt atacaactta tgaaagattc taagggtatt tttgaaaaag  12780
attggggaga gggatatata actgatcata tgttcattaa tttgaaagtt ttcttcaatg  12840
cttataagac atatctcttg tgttttcata aaggttacgg cagagcaaag ctggagtgtg  12900
atatgaatac ttcagatctc ctatgtgtat tggaattaat agacagtagt tattggaagt  12960
ctatgtctaa ggtgttttta gaacaaaaag ttatcaaata cattcttagc caggatgcaa  13020
gtttacatag agtaaaagga tgtcatagct tcaaactatg gtttcttaaa cgtcttaatg  13080
tagcagaatt cacagtttgc ccttgggttg ttaacataga ttatcatcca acacatatga  13140
aagcaatatt aacttatatt gatcttgtta gaatgggatt gataaatata gatagaatat  13200
acattaaaaa taaacacaag ttcaatgatg agttttatac ttctaatctg ttttacatta  13260
```

attataactt ctcagataat actcatctat taactaaaca tataaggatt gctaattccg 13320
aattagaaag taattacaac aaattatatc atcctacacc agaaacccta gaaaatatac 13380
taaccaatcc ggttaaaagt aatgagaaaa agacactgag tgactattgt ataggtaaaa 13440
atgttgactc aataatgtta ccatcgttat ctaataagaa gcttattaaa tcgtctacaa 13500
tgattagaac caattacagc agacaagatt tgtataattt atttcctacg gttgtgattg 13560
ataaaattat agatcattca ggtaatacag ccaaatctaa ccaactttac actactactt 13620
ctcatcaaat atccttagtg cacaatagca catcacttta ttgcatgctt ccttggcatc 13680
atattaatag attcaatttt gtatttagtt ctacaggttg taaaattagt atagagtata 13740
ttttaaaaga tcttaaaatt aaggatccta attgtatagc attcataggt gaaggagcag 13800
ggaatttatt attgcgtaca gtagtggaac ttcatcctga tataagatat atttacagaa 13860
gtctgaaaga ttgcaatgat catagtttac caattgagtt tttaaggctg tacaatggac 13920
atatcaacat tgattatggt gaaaatttga ccattcctgc tacagatgca accaacaaca 13980
ttcattggtc ttatttacat ataaagtttg ctgaacctat cagtcttttt gtctgtgatg 14040
ctgaattgcc tgtaacagtc aactggagta agattataat agagtggagc aagcatgtaa 14100
gaaaatgcaa gtactgttct tcagttaata aatgtacatt gatagtaaaa tatcatgctc 14160
aagatgatat cgatttcaaa ttagacaaca taactatatt aaaaacttat gtatgcttag 14220
gtagtaagtt aaagggatct gaagtttact tagtccttac aataggtcct gcaaatgtgt 14280
tcccagtatt taatgtagta caaaatgcta aattgatact atcaagaact aaaaatttca 14340
tcatgcctaa aaaagctgat aaagagtcta ttgatgcaaa tattaagagt ttgataccct 14400
ttctttgtta ccctataaca aaaaaaggaa ttaatactgc attgtctaaa ttaaagagtg 14460
ttgttagtgg agatatacta tcatattcta tagctggacg taatgaagtt ttcagcaata 14520
aacttataaa tcataagcat atgaacatct taaagtggtt caatcatgtt ttaaatttca 14580
gatcaacaga attaaactat aatcatttat atatggtaga atctacttat cctcatctaa 14640
gtgaattgtt aaacagcttg acaaccaatg aacttaaaaa actgattaaa atcacaggta 14700
gtttgttata caacttttat aatgaataat gagcaaaaat cttataacaa aaatagctac 14760
acactaacat tgtattcaat tatagttatt gaaaattaat aattatataa tttttaataa 14820
cttctagtga actaatccta aaattatcat tttgatctag gaagaataag tttaaatcca 14880
aatctaattg gtttatatgt atattaacta aattacgaga tattagtttt tgacactttt 14940
tttctcgt 14948

<210> SEQ ID NO 11
<211> LENGTH: 16823
<212> TYPE: DNA
<213> ORGANISM: Artificial Sequence
<220> FEATURE:
<223> OTHER INFORMATION: A sequence in which SEQ ID NO: 10 was digested with ApaI and SEQ ID NO: 4 was inserted.

<400> SEQUENCE: 11
acgcgaaaaa atgcgtacaa caaacttgcg taaaccaaaa aaatggggca aataagaatt 60
tgataagtac cacttaaatt taactccttt ggttagaggc gcgccatggg cagcaactca 120
ttgagtatga taaaagttag attgcaaaat ctgtttgaca atgatgaagt agcattgtta 180
aaaataacat gctatactga caaattaata cagttaacta atgctttggc taaggcagtt 240
atacatacaa tcaaattgaa tggcattgta tttgtgcatg ttattacaag tagtgatatt 300

```
tgccctaata ataatattgt agtgaaatcc aatttcacaa caatgccagt attacaaaat    360
ggaggttata tatgggaaat gatggaatta acacactgct ctcaacctaa tggcctaata    420
gatgacaatt gtgaaattaa attctccaaa aaactaagtg attcaacaat gaccaattat    480
atgaatcaat tatctgaatt acttggattt gacctcaatc cataaatcat aataaatatc    540
aactagcaaa tcaatgtcac taacaccatt agttaatata aaacttgaca gaagataaaa    600
atggggcaaa taaatcaatt cagccgaccc aaccatggac acaacacaca atgataccac    660
accacaaaga ctgatgatca cagacatgag gccattatcg cttgagacta taataacatc    720
tctaaccaga gatatcataa cacataaatt tatatacttg ataaatcatg aatgcatagt    780
aagaaaactt gatgaaagac aggccacatt tacatttctg gtcaactatg aaatgaaact    840
attgcacaaa gtgggaagca ctaaatataa aaaatatact gaatacaaca caaaatatgg    900
cactttccct atgccaatat ttatcaatca tgatgggttc ttagaatgca ttggcattaa    960
gcctaccaag cacacaccca taatatacaa gtatgatctc aatccatgaa tatcaaacca   1020
agattcaaac aatccgaaat aacaacttta tgcataatca cactccatag tccaaatgga   1080
gcctgaaaat tatagttatt taaaattcct gcaggaagga gagacataag atgaaagatg   1140
gggcaaatac aaaaatggct cttagcaaag tcaagttgaa tgatacactc aacaaagatc   1200
aacttctatc atccagcaaa tataccatcc aacggagcac aggagacagc attgacactc   1260
ctaattatga tgtgcagaaa cacattaata agttatgtgg catgttatta atcacagaag   1320
atgctaatca taaattcact gggttaatag gtatgttata tgctatgtct agattaggaa   1380
gagaagacac cataaaaata ctcaaagatg cgggatatca tgttaaggca aatggagtgg   1440
atgtaacaac acatcgtcaa gacattaatg ggaaagaaat gaaatttgaa gtgttaacat   1500
tagcaagctt aacaactgaa attcaaatca acattgagat agaatctaga aaatcctaca   1560
aaaaaatgct aaaagaaatg ggagaggtgg ctccagaata caggcatgac tctcctgatt   1620
gtgggatgat aatattatgt atagcggcat tagtaataac caaattagca gcaggagata   1680
gatcaggtct tacagctgtg attaggagag ctaataatgt cctaaaaaat gaaatgaaac   1740
gttataaagg tttattaccc aaggatatag ccaacagctt ctatgaagtg tttgaaaaat   1800
atcctcactt tatagatgtt tttgttcatt ttggtatagc acaatcttct accagaggtg   1860
gcagtagagt tgaagggatt tttgcaggat tgtttatgaa tgcctatggt gcagggcaag   1920
tgatgttacg gtgggggtc ttagcaaaat cagttaaaaa cattatgtta ggacacgcta    1980
gtgtacaagc agaaatggaa caagttgtgg aggtgtatga gtatgctcag aaattgggtg   2040
gagaagcagg attctaccat atattgaaca acccaaaagc atcactatta tctttgactc   2100
aatttcctca cttctctagt gtagtattgg gcaatgctgc tggcctaggc ataatgggag   2160
aatacagagg tacaccaagg aatcaagatt tatatgatgc tgcaaaagca tatgctgaac   2220
aactcaaaga aaatggtgtg attaactaca gtgtattaga tttgacagca gaagaactag   2280
aggctatcaa acatcagctt aatccaaaag ataatgatgt agagctttga gttaataaaa   2340
aagtggggca aataaatcat catggaaaag tttgctcctg aattccatgg agaagatgca   2400
aacaacagag ccaccaaatt cctagaatca ataaagggca aattcacatc acccaaagat   2460
cccaagaaaa aagatagtat catatctgtc aactcaatag atatagaagt aaccaaagaa   2520
agccctataa catcaaattc aaccattata aacccaataa atgagacaga tgatactgta   2580
gggaacaagc ccaattatca aagaaagcct ctagtaagtt tcaaagaaga ccctacgcca   2640
```

-continued

```
agtgataatc ctttttcaaa actatacaaa gaaaccatag aaacatttga taacaatgaa   2700
gaagaatcta gctattcata tgaagaaata aatgatcaga caaacgataa tataacagca   2760
agattagata ggattgatga gaaattaagt gaaatactag gaatgcttca cacattagta   2820
gtagcgagtg caggacccac atctgctcgg gatggtataa gagatgccat ggttggttta   2880
agagaagaaa tgatagaaaa aatcagaact gaagcattaa tgaccaatga cagactagaa   2940
gctatggcaa gactcaggaa tgaagaaagt gaaaagatgg caaaagacac atcagatgaa   3000
gtgtctctca atccaacatc agagaaactg aacaacctgt tggaagggaa tgatagtgac   3060
aatgatctat cacttgaaga tttctgatta gctaccaaac tgtacatcaa aacacaacac   3120
caatagaaaa ccaacaaaca aaccaactca cccatccaac caaacatcta tctgctgatt   3180
agccaaccag ccaaaaaaca accagccaat ctaaaactag ccacccggaa aaaatcgata   3240
ctatagttac aaaaaaagat ggggcaaata tggaaacata cgtgaataaa cttcacgagg   3300
gctccacata cacagctgct gttcaataca atgtcctaga aaaagacgat gatcctgcat   3360
cacttacaat atgggtgccc atgttccaat catccatgcc agcagatcta ctcataaaag   3420
aactagccaa tgtcaatata ctagtgaaac aaatatccac acccaaggga ccctcattaa   3480
gagtcatgat aaactcaaga agtgcagtgc tagcacaaat gcccagcaaa tttaccatat   3540
gtgccaatgt gtccttggat gaaagaagca agctggcata tgatgtaacc acaccctgtg   3600
aaattaaggc atgcagtcta acatgcctaa aatcaaaaaa tatgttaact acagttaaag   3660
atctcactat gaaaacactc aacccaacac atgacatcat tgctttatgt gaatttgaaa   3720
atatagtaac atcaaaaaaa gtcataatac caacatacct aagatctatc agcgtcagaa   3780
ataaagatct gaacacactt gaaaatataa caaccactga attcaaaaat gccattacaa   3840
atgcaaaaat catcccttac tcaggattat tgttagtcat cacagtgact gacaacaaag   3900
gagcattcaa atacataaag ccacaaagtc aattcatagt agatcttgga gcttacctag   3960
aaaaagaaag tatatattat gttacaacaa attggaagca cacagctaca cgatttgcaa   4020
tcaaacccat ggaagattaa ccttttttcct ctacatcaat gagtagattc atacaaactt   4080
tctaactaca ttcttcactt cacaatcata atcaccaacc ctctgtggtt caatcaatca   4140
aacaaaactc atcaagagtt ccagatcatc ccaagtcatt gttcatcaga tccagtactc   4200
aaataagtta ataaaaaatc cacatggggc aaataatcat tgagggaaat ccaactaatc   4260
acaacatctg tcaacataga caagtcaaca cgctagataa aatcaaccaa tggaaaatac   4320
atccataact atagaattct caagcaaatt ctggccttac tttacactaa tacacatgat   4380
aacaacaata atctctttga taatcataat ctccatcatg attgcaatac taaacaaact   4440
ctgcgaatat aatgtattcc ataacaaaac ctttgagcta ccaagagctc gagtcaatac   4500
atagcattca ccaatctgat agctcaaaac agtaaccttg catttgtaaa tgaactaccc   4560
tcacttcttc acaaaaccac atcaacatct caccatgcaa gccatcatct ataccataaa   4620
gtagttaatt aaaaatggcc ggccagtcat aacaatgaac taggatatta agaccaaaaa   4680
caacgctggg gcaaatgcaa acatgtccaa aaccgaggac caacgcaccg ccaagacact   4740
agaaaggacc tgggacactt ttaatcatct attattcata tcatcgtgct tatacaagtt   4800
aaatcttaaa tctatagcac aaatcacatt atctattttg gcaattataa tctcaacctc   4860
acttataatt gcagccatca tattcatagc ctcggcaaac cacaaagtca cactaacaac   4920
tgcaatcata caagatgcaa cgaaccagat caagaacaca accccaacat acctcaccca   4980
gaatccccag catggaatca gcttctccaa tctgtccgga actacatcac aatccaccac   5040
```

```
catactagct tcaacaacac caagtgctga ttcaacccca caatccacaa cagtcaagat   5100
caaaaacaca acaacaaccc aaatattacc tagcaaaccc accacaaaac aacgccaaaa   5160
taaaccacaa aacaaaccca acaatgattt tcactttgaa gtgttcaatt ttgtaccctg   5220
cagcatatgc agcaacaatc caacctgctg ggccatctgc aagagaatac caaacaaaaa   5280
acctggaaag aaaaccacca ccaagcccac aaaaaaacca accctcaaga caaccaaaaa   5340
agatcccaaa tcccaaacca caaaaccaaa ggaagtactc actaccaagc ctacaggaaa   5400
gccaaccatc aacaccacta aaacaaacat cagaactaca ctgctcacct ccaacaccaa   5460
aggaaatcca gaacacacaa gtcaagagga aaccctccac tcaaccacct ccgaaggcta   5520
tccaagccca tcacaagtcc acacaacatc cggtcaagag gaaaccctcc actcaaccac   5580
ctccgaaggc tatccaagcc catcacaagt ctacacaaca tccgagtacc tatcacaatc   5640
tctatcttca tccaacacaa caaaatgata gtcattaaaa agcacgcgtt tgacagaaga   5700
taaaaatggg gcaaatgcaa acatgaagtg cctttttgtac ttagcctttt tattcattgg   5760
ggtgaattgc aagttcacca tagtttttcc acacaaccaa aaaggaaact ggaaaaatgt   5820
tccttctaat taccattatt gcccgtcaag ctcagattta aattggcata atgacttaat   5880
aggcacagcc ttacaagtca aaatgcccaa gagtcacaag gctattcaag cagacggttg   5940
gatgtgtcat gcttccaaat gggtcactac ttgtgatttc cgctggtatg gaccgaagta   6000
tataacacat tccatccgat ccttcactcc atctgtagaa caatgcaagg aaagcattga   6060
acaaacgaaa caaggaactt ggctgaatcc aggcttccct cctcaaagtt gtggatatgc   6120
aactgtgacg gatgccgaag cagtgattgt ccaggtgact cctcaccatg tgctggttga   6180
tgaatacaca ggagaatggg ttgattcaca gttcatcaac ggaaaatgca gcaattacat   6240
atgccccact gtccataact ctacaacctg gcattctgac tataaggtca aagggctatg   6300
tgattctaac ctcatttcca tggacatcac cttcttctca gaggacggag agctatcatc   6360
cctgggaaag gagggcacag ggttcagaag taactacttt gcttatgaaa ctggaggcaa   6420
ggcctgcaaa atgcaatact gcaagcattg gggagtcaga ctcccatcag gtgtctggtt   6480
cgagatggct gataaggatc tctttgctgc agccagattc cctgaatgcc cagaagggtc   6540
aagtatctct gctccatctc agacctcagt ggatgtaagt ctaattcagg acgttgagag   6600
gatcttggat tattccctct gccaagaaac ctggagcaaa atcagagcgg gtcttccaat   6660
ctctccagtg gatctcagct atcttgctcc taaaaaccca ggaaccggtc ctgctttcac   6720
cataatcaat ggtaccctaa aatactttga gaccagatac atcagagtcg atattgctgc   6780
tccaatcctc tcaagaatgg tcggaatgat cagtggaact accacagaaa gggaactgtg   6840
ggatgactgg gcaccatatg aagacgtgga aattggaccc aatggagttc tgaggaccag   6900
ttcaggatat aagtttcctt tatacatgat tggacatggt atgttggact ccgatcttca   6960
tcttagctca aaggctcagg tgttcgaaca tcctcacatt caagacgctg cttcgcaact   7020
tcctgatgat gagagtttat tttttggtga tactgggcta tccaaaaatc caatcgagct   7080
tgtagaaggt tggttcagta gttggaaaag ctctattgcc tcttttttct ttatcatagg   7140
gttaatcatt ggactattct tggttctccg agttggtatc catctttgca ttaaagccag   7200
aagcacacca gtcacattaa gtaaggatca actgagtggt ataaataata ttgcatttag   7260
taactaatag tcattaaaaa gcgggcccgt attgttgcaa aaagccatga ccaaatcaaa   7320
cagaatcaaa atcaactctg gggcaaataa caatggagtt gccaatcctc aaaacaaatg   7380
```

-continued

```
ctattaccac aatccttgct gcagtcacac tctgtttcgc ttccagtcaa aacatcactg   7440
aagaatttta tcaatcaaca tgcagtgcag tcagcaaagg ctatcttagt gctctaagaa   7500
ctggttggta tactagtgtt ataactatag aattaagtaa tatcaaggaa aataagtgta   7560
atggtacaga cgctaaggta aaattaataa aacaagaatt agataaatat aaaaatgctg   7620
taacagaatt gcagttgctc atgcaaagca caccagcagc caacaatcga gccagaagag   7680
aactaccaag atttatgaat tatacactca acaataccaa aaacaccaat gtaacattaa   7740
gtaagaaaag gaaaagaaga tttcttggat tttgttagg tgttggatct gcaatcgcca   7800
gtggcattgc cgtatccaag gtcctgcacc tagaagggga agtgaacaaa atcaaaagtg   7860
ctctactatc cacaaacaag gctgtagtca gcttatctaa tggagtcagt gtcttaacca   7920
gcaaggtgtt agacctcaaa aactatatag ataaacagtt gttacctatt gttaacaagc   7980
aaagctgcag catatcaaac attgaaactg tgatagagtt ccaacaaaag aacaacagac   8040
tactagagat taccagagaa tttagtgtta atgcaggtgt aactactcct gtaagcactt   8100
atatgttaac taatagtgag ttattatcat taatcaatga tatgcctata acaaatgatc   8160
agaaaaagtt aatgtccagc aatgttcaaa tagttagaca gcaaagttac tctatcatgt   8220
caataataaa agaggaagtc ttggcatatg tagtacaatt accactatat ggtgtaatag   8280
atactccttg ttggaaacta cacacatccc ctttatgtac aaccaacaca aaggaaggat   8340
ccaacatctg cttaacaaga accgacagag gatggtactg tgacaatgca ggatcagtat   8400
cctttttccc acaagctgaa acatgtaaag ttcaatcgaa tcgggtgttt tgtgacacaa   8460
tgaacagttt aacattacca agtgaggtaa atctctgcaa cattgacata ttcaacccca   8520
aatatgattg caaaattatg acttcaaaaa cagatgtaag cagctccgtt atcacatctc   8580
taggagccat tgtgtcatgc tatggcaaaa ccaaatgtac agcatccaat aaaaatcgtg   8640
ggatcataaa gacattctct aacgggtgtg attatgtatc aaataagggg gtggatactg   8700
tgtctgtagg taatacatta tattatgtaa ataagcaaga aggcaaaagt ctctatgtaa   8760
aaggtgaacc aataataaat ttctatgatc cattagtgtt cccctctctc ctgtgggatg   8820
catcaatatc tcaagtcaat gagaaaatta atcagagtct agcatttatc cgtaaatcag   8880
atgaattatt aggctctggc ggaagcggat acatccctga ggcaccaagg gacggacagg   8940
cctacgtgcg caaggatggc gagtgggtgc tgctgtccac ctttctgtga ataaaaatag   9000
cacctaatca tattcttaca atggttcgct atttgaccat agataaccca tctatcatta   9060
gattatccta aaatttgaac ttcatcacaa ctttcatcta taaaccatct cacttacact   9120
ttttaagtag atttctattt tatagttata taaaacaggg cccattgaat accaaattaa   9180
cttactattt gtaaaaatga gaattggggc aaatatgtca cgaaggaatc cttgcaaatt   9240
cgaaattcga ggtcattgct tgaatggtaa aaggtgtcat tttagtcata attattttga   9300
atggccaccc catgcactgc ttgtaagaca aaactttatg ttaaacagaa tacttaagtc   9360
tatggataaa agcatagata ctttgtcaga aataagtgga gctgcagagt tggacagaac   9420
agaagagtat gccctcggtg tagttggagt gctagagagt tatataggat caataaataa   9480
tataactaaa caatcagcat gtgttgccat gagcaaactc cttactgaac tcaacagcga   9540
tgacatcaaa aaactaaggg acaatgaaga gccaaactca cccaaagtaa gagtgtacaa   9600
tactgtcata tcatatattg aaagcaacag gaagaacaat aaacaaacta tccatctgtt   9660
aaaaagattg ccagcagacg tattgaagaa aaccatcaaa aacacattgg atatccacaa   9720
gagcataacc atcaataacc caaaagaatc aactgttagt gatacgaacg accatgccaa   9780
```

-continued

```
aaataatgat actacctgac aaatatcctt gtagtataaa ttccatacta ataacaagta   9840
attgtagagt cactatgtat aatcaaaaaa acacactata tatcaatcaa aacaaccaaa   9900
atagccatat atacccaccg gatcaaccat tcaatgaaat ccattggacc tctcaagact   9960
tgattgatgc aactcaaaat tttctacaac atctaggtat tactgatgat atatacacaa  10020
tatatatatt agtgtcataa tactcaatcc taatacttac cacatcatca aattattaac  10080
tcaaacaatt caagctatgg gacaaaatgg atcccattat tagtggaaat tctgctaatg  10140
tttatctaac tgatagttat ttaaaaggtg ttatttcttt ctcagaatgt aacgctttag  10200
gaagttacat attcaatggt ccttatctca aaaatgatta taccaactta attagtagac  10260
aaaatccatt aatagaacac ataaatctaa agaaactaaa tataacacag tccttaatat  10320
ctaagtatca taaaggtgaa ataaaaatag aagaacctac ttactttcag tcattactta  10380
tgacatacaa gagtatgacc tcttcagaac agactactac tactaattta cttaaaaaga  10440
taataagaag agctatagaa atcagtgatg tcaaagtcta tgctatattg aataaactgg  10500
ggctcaaaga aaaagacaag attaaatcca ataatggaca agatgaagac aactcagtca  10560
ttactaccat aatcaaagat gatatacttt tagctgtcaa ggataatcaa tctcatctta  10620
aagcagacaa aaatcaatcc acaaaacaaa aagatacaat caaaacaaca cttttgaaga  10680
aattaatgtg ttcgatgcaa catcctccat catggttaat acattggttt aatttataca  10740
caaaattaaa cagcatatta acacaatatc gatctagtga ggtaaaaaac catggtttta  10800
tattgataga taatcatact cttagtggat tccaatttat tttgaatcaa tatggttgta  10860
tagtttatca taaggaactc aaaagaatta ctgtgacaac ttataatcaa ttcttgacat  10920
ggaaagatat tagccttagt agattaaatg tttgtttgat tacatggatt agtaactgtt  10980
tgaacacatt aaacaaaagc ttaggcttaa gatgtggatt caataatgtt atcttgacac  11040
aattattcct ttatggagat tgtatactaa aactattcca caatgagggg ttctacataa  11100
taaaagaggt agagggattt attatgtctc taattttaaa tataacagaa gaagatcaat  11160
tcagaaaacg gttttataat agtatgctca acaacatcac agatgccgcc aacaaagctc  11220
aaaaaaatct gctatcaaga gtatgtcata cattattaga taagacaata tcagataata  11280
taataaatgg cagatggata attctattga gtaagttcct aaaattaatt aagcttgcag  11340
gtgacaataa cctcaacaat ctgagtgaat tatatttttt gttcagaata tttggacacc  11400
caatggtaga tgaaagacaa gccatggatg ctgttaaagt taattgcaac gagaccaaat  11460
tttatttgtt aagtagtttg agtatgttaa gaggagcttt tatatataga attataaaag  11520
ggtttgtaaa taattacaac agatggccta ctttaagaaa tgccattgtc ttacccttaa  11580
gatggttaac ttactataaa ctaaacactt atccttcctt gttggaactt acagaaagag  11640
atttgattgt tctatcagga ctacgtttct atcgagagtt tcggttgcct aaaaaagtgg  11700
atcttgaaat gatcataaat gataaggcta tatcacctcc taaaaattta atatggacta  11760
gtttccctag aaattatatg ccgtcacaca tacaaaatta tatagaacat gaaaaattaa  11820
aattctctga tagtgataaa tcaagaagag tattagagta ttatttaaga gataacaaat  11880
tcaatgaatg tgatttacac aactgtgtag ttaatcaaag ttatcttaac aacccgaatc  11940
atgtggtatc attgacaggc aaagaaagag aactcagtgt aggtagaatg tttgcaatgc  12000
aaccaggaat gttcagacaa gttcaaatat tagcagagaa aatgatagca gaaaacatat  12060
tacaattttt ccctgaaagt cttacaagat atggtgatct agaactacag aaaatattag  12120
```

-continued

```
aattgaaagc aggaataagt aacaaatcaa atcgttacaa tgataattac aacaattaca  12180
ttagtaagtg ctctatcatc acagatctca gcaaattcaa tcaagcattt cgatatgaaa  12240
catcatgtat ttgtagtgat gtactggatg aactgcatgg tgtacaatct ctattttcct  12300
ggttacattt aactattcct catgtcacaa taatatgcac atataggcat gcacccccct  12360
atataaagga tcatattgta gatcttaaca atgtagatga gcaaagtgga ctatatagat  12420
atcatatggg tggtatcgaa gggtggtgtc aaaaactatg gaccatagaa gctatatcac  12480
tattagatct aatatctctc aaagggaaat tctcaattac tgctttaatt aatggtgaca  12540
atcaatcaat agatataagt aaaccagtca gactcatgga aggtcaaact catgctcaag  12600
cagattattt gctagcatta aatagtctca aattactgta taaagagtat gcaggaatag  12660
gccacaaatt aaaaggaact gagacttata tatcgagaga tatgcaattt atgagtaaaa  12720
cgatccaaca taacggtgta tattacccag ctagtataaa gaaagtccta agagtgggac  12780
cgtggataaa cactatactt gatgacttca aagtgagtct agaatctata ggtagtttga  12840
cacaagaatt agaatataga ggtgaaagtc tattatgcag tttaatattt agaaatgtat  12900
ggttatataa tcaaattgca ttacaactta aaaatcatgc attatgtaac aacaaattat  12960
atttggatat attaaaagtt ctaaaacact taaaaacctt ttttaatctt gataacattg  13020
atacagcatt aacattgtat atgaatttgc ccatgttatt tggtggtggt gatcccaact  13080
tgttatatcg aagtttctat agaagaactc ctgatttcct cacagaggct atagttcact  13140
ctgtgttcat acttagttat tatacaaacc atgatttaaa agataaactt caagatctgt  13200
cagatgatag attgaataag ttcttaacat gcataatcac gtttgataaa aaccccaatg  13260
ctgaattcgt tacattgatg agagatcctc aagctttagg atctgagagg caagctaaaa  13320
ttactagcga aatcaataga ctggcagtta ccgaggtttt gagcacagct ccaaacaaaa  13380
tattttccaa aagtgcacaa cactatacca ctacagagat agatcttaat gatattatgc  13440
aaaatataga acctacatat cctcacgggc taagagttgt ttatgagagt ttaccctttt  13500
ataaagcaga gaaaatagta aatcttatat ccggtacaaa atctataact aacatactgg  13560
aaaagacttc tgccatagac ttaacagata ttgatagagc cactgagatg atgaggaaaa  13620
acataacttt gcttataagg atattaccat tagattgtaa cagagataaa agagaaatat  13680
tgagtatgga aaacctaagt attactgaat taagcaaata cgttagagaa agatcttggt  13740
ctttatccaa tatagttggt gttacatcac ccagtatcat gtatacaatg gacataaaat  13800
atacaacaag cactatagct agtggcataa tcatagagaa atataatgtc aacagtttaa  13860
cacgtggtga gagaggaccc actaaaccat gggttggttc atctacacaa gagaaaaaga  13920
caatgccagt ttataataga caagttttaa ccaaaaaaca gagagatcaa atagatctat  13980
tagcaaaatt ggattgggtg tatgcatcta tagataacaa ggatgaattt atggaggaac  14040
ttagcatagg aactcttggg ttaacatatg agaaggccaa aaaattattc ccacaatatt  14100
tgagtgttaa ctatttgcat cgtcttacag tcagtagtag accatgtgaa ttccctgcat  14160
ctataccagc ttatagaact acaaattatc actttgatac tagccctatt aatcgcatat  14220
taacagaaaa gtatggtgat gaagatattg atatagtatt ccaaaactgt ataagctttg  14280
gccttagctt aatgtctgta gtagaacaat ttactaatgt atgtcctaac agaattattc  14340
tcatacccaa gcttaatgag atacatttga tgaaacctcc catattcaca ggcgatgttg  14400
atattcacaa gttaaaacaa gtgatacaaa aacaacatat gtttttacca gacaaaataa  14460
gtttgactca atatgtggaa ttattcttaa gtaataaaac actcaaatct ggatctaatg  14520
```

ttaattctaa tttaatattg gcgcataaga tatctgacta ttttcataat acttacattt 14580
tgagtactaa tttagctgga cattggattc ttattataca acttatgaaa gattctaagg 14640
gtatttttga aaaagattgg ggagagggat atataactga tcatatgttc attaatttga 14700
aagttttctt caatgcttat aagacatatc tcttgtgttt tcataaaggt tacggcagag 14760
caaagctgga gtgtgatatg aatacttcag atctcctatg tgtattggaa ttaatagaca 14820
gtagttattg gaagtctatg tctaaggtgt ttttagaaca aaaagttatc aaatacattc 14880
ttagccagga tgcaagttta catagagtaa aaggatgtca tagcttcaaa ctatggtttc 14940
ttaaacgtct taatgtagca gaattcacag tttgcccttg ggttgttaac atagattatc 15000
atccaacaca tatgaaagca atattaactt atattgatct tgttagaatg ggattgataa 15060
atatagatag aatatacatt aaaaataaac acaagttcaa tgatgagttt tatacttcta 15120
atctgtttta cattaattat aacttctcag ataatactca tctattaact aaacatataa 15180
ggattgctaa ttccgaatta gaaagtaatt acaacaaatt atatcatcct acaccagaaa 15240
ccctagaaaa tatactaacc aatccggtta aaagtaatga gaaaaagaca ctgagtgact 15300
attgtatagg taaaaatgtt gactcaataa tgttaccatc gttatctaat aagaagctta 15360
ttaaatcgtc tacaatgatt agaaccaatt acagcagaca agatttgtat aatttatttc 15420
ctacggttgt gattgataaa attatagatc attcaggtaa tacagccaaa tctaaccaac 15480
tttacactac tacttctcat caaatatcct tagtgcacaa tagcacatca ctttattgca 15540
tgcttccttg gcatcatatt aatagattca attttgtatt tagttctaca ggttgtaaaa 15600
ttagtataga gtatatttta aaagatctta aaattaagga tcctaattgt atagcattca 15660
taggtgaagg agcagggaat ttattattgc gtacagtagt ggaacttcat cctgatataa 15720
gatatattta cagaagtctg aaagattgca atgatcatag tttaccaatt gagtttttaa 15780
ggctgtacaa tggacatatc aacattgatt atggtgaaaa tttgaccatt cctgctacag 15840
atgcaaccaa caacattcat tggtcttatt tacatataaa gtttgctgaa cctatcagtc 15900
tttttgtctg tgatgctgaa ttgcctgtaa cagtcaactg gagtaagatt ataatagagt 15960
ggagcaagca tgtaagaaaa tgcaagtact gttcttcagt taataaatgt acattgatag 16020
taaaatatca tgctcaagat gatatcgatt tcaaattaga caacataact atattaaaaa 16080
cttatgtatg cttaggtagt aagttaaagg gatctgaagt ttacttagtc cttacaatag 16140
gtcctgcaaa tgtgttccca gtatttaatg tagtacaaaa tgctaaattg atactatcaa 16200
gaactaaaaa tttcatcatg cctaaaaaag ctgataaaga gtctattgat gcaaatatta 16260
agagtttgat accctttctt tgttacccta taacaaaaaa aggaattaat actgcattgt 16320
ctaaattaaa gagtgttgtt agtggagata tactatcata ttctatagct ggacgtaatg 16380
aagttttcag caataaactt ataaatcata agcatatgaa catcttaaag tggttcaatc 16440
atgttttaaa tttcagatca acagaattaa actataatca tttatatatg gtagaatcta 16500
cttatcctca tctaagtgaa ttgttaaaca gcttgacaac caatgaactt aaaaaactga 16560
ttaaaatcac aggtagtttg ttatacaact tttataatga ataatgagca aaaatcttat 16620
aacaaaaata gctacacact aacattgtat tcaattatag ttattgaaaa ttaataatta 16680
tataattttt aataacttct agtgaactaa tcctaaaatt atcattttga tctaggaaga 16740
ataagtttaa atccaaatct aattggttta tatgtatatt aactaaatta cgagatatta 16800
gtttttgaca cttttttct cgt 16823

<210> SEQ ID NO 12
<211> LENGTH: 15827
<212> TYPE: DNA
<213> ORGANISM: Artificial Sequence
<220> FEATURE:
<223> OTHER INFORMATION: The sequence in which the G gene was removed
from SEQ ID NO: 11.

<400> SEQUENCE: 12

```
acgcgaaaaa atgcgtacaa caaacttgcg taaaccaaaa aaatggggca aataagaatt     60
tgataagtac cacttaaatt taactccttt ggttagaggc gcgccatggg cagcaactca    120
ttgagtatga taaaagttag attgcaaaat ctgtttgaca atgatgaagt agcattgtta    180
aaaataacat gctatactga caaattaata cagttaacta atgctttggc taaggcagtt    240
atacatacaa tcaaattgaa tggcattgta tttgtgcatg ttattacaag tagtgatatt    300
tgccctaata ataatattgt agtgaaatcc aatttcacaa caatgccagt attacaaaat    360
ggaggttata tatgggaaat gatggaatta acacactgct ctcaacctaa tggcctaata    420
gatgacaatt gtgaaattaa attctccaaa aaactaagtg attcaacaat gaccaattat    480
atgaatcaat tatctgaatt acttggattt gacctcaatc cataaatcat aataaatatc    540
aactagcaaa tcaatgtcac taacaccatt agttaatata aaacttgaca gaagataaaa    600
atggggcaaa taaatcaatt cagccgaccc aaccatggac acaacacaca atgataccac    660
accacaaaga ctgatgatca cagacatgag gccattatcg cttgagacta taataacatc    720
tctaaccaga gatatcataa cacataaatt tatatacttg ataaatcatg aatgcatagt    780
aagaaaactt gatgaaagac aggccacatt tacatttctg gtcaactatg aaatgaaact    840
attgcacaaa gtgggaagca ctaaatataa aaaatatact gaatacaaca caaaatatgg    900
cactttccct atgccaatat ttatcaatca tgatgggttc ttagaatgca ttggcattaa    960
gcctaccaag cacacaccca taatatacaa gtatgatctc aatccatgaa tatcaaacca   1020
agattcaaac aatccgaaat aacaacttta tgcataatca cactccatag tccaaatgga   1080
gcctgaaaat tatagttatt taaaattcct gcaggaagga gagacataag atgaaagatg   1140
gggcaaatac aaaaatggct cttagcaaag tcaagttgaa tgatacactc aacaaagatc   1200
aacttctatc atccagcaaa tataccatcc aacggagcac aggagacagc attgacactc   1260
ctaattatga tgtgcagaaa cacattaata agttatgtgg catgttatta atcacagaag   1320
atgctaatca taaattcact gggttaatag gtatgttata tgctatgtct agattaggaa   1380
gagaagacac cataaaaata ctcaaagatg cgggatatca tgttaaggca aatggagtgg   1440
atgtaacaac acatcgtcaa gacattaatg ggaaagaaat gaaatttgaa gtgttaacat   1500
tagcaagctt aacaactgaa attcaaatca acattgagat agaatctaga aaatcctaca   1560
aaaaaatgct aaaagaaatg ggagaggtgg ctccagaata caggcatgac tctcctgatt   1620
gtgggatgat aatattatgt atagcggcat tagtaataac caaattagca gcaggagata   1680
gatcaggtct tacagctgtg attaggagag ctaataatgt cctaaaaaat gaaatgaaac   1740
gttataaagg tttattaccc aaggatatag ccaacagctt ctatgaagtg tttgaaaaat   1800
atcctcactt tatagatgtt tttgttcatt ttggtatagc acaatcttct accagaggtg   1860
gcagtagagt tgaagggatt tttgcaggat tgtttatgaa tgcctatggt gcagggcaag   1920
tgatgttacg gtgggggtc ttagcaaaat cagttaaaaa cattatgtta ggacacgcta   1980
gtgtacaagc agaaatggaa caagttgtgg aggtgtatga gtatgctcag aaattgggtg   2040
```

-continued

```
gagaagcagg attctaccat atattgaaca acccaaaagc atcactatta tctttgactc   2100
aatttcctca cttctctagt gtagtattgg gcaatgctgc tggcctaggc ataatgggag   2160
aatacagagg tacaccaagg aatcaagatt tatatgatgc tgcaaaagca tatgctgaac   2220
aactcaaaga aaatggtgtg attaactaca gtgtattaga tttgacagca gaagaactag   2280
aggctatcaa acatcagctt aatccaaaag ataatgatgt agagctttga gttaataaaa   2340
aagtggggca aataaatcat catggaaaag tttgctcctg aattccatgg agaagatgca   2400
aacaacagag ccaccaaatt cctagaatca ataaagggca aattcacatc acccaaagat   2460
cccaagaaaa aagatagtat catatctgtc aactcaatag atatagaagt aaccaaagaa   2520
agccctataa catcaaattc aaccattata aacccaataa atgagacaga tgatactgta   2580
gggaacaagc ccaattatca aagaaagcct ctagtaagtt tcaaagaaga ccctacgcca   2640
agtgataatc ctttttcaaa actatacaaa gaaaccatag aaacatttga taacaatgaa   2700
gaagaatcta gctattcata tgaagaaata aatgatcaga caaacgataa tataacagca   2760
agattagata ggattgatga gaaattaagt gaaatactag gaatgcttca cacattagta   2820
gtagcgagtg caggacccac atctgctcgg gatggtataa gagatgccat ggttggttta   2880
agagaagaaa tgatagaaaa aatcagaact gaagcattaa tgaccaatga cagactagaa   2940
gctatggcaa gactcaggaa tgaagaaagt gaaaagatgg caaaagacac atcagatgaa   3000
gtgtctctca atccaacatc agagaaactg aacaacctgt tggaagggaa tgatagtgac   3060
aatgatctat cacttgaaga tttctgatta gctaccaaac tgtacatcaa aacacaacac   3120
caatagaaaa ccaacaaaca aaccaactca cccatccaac caaacatcta tctgctgatt   3180
agccaaccag ccaaaaaaca accagccaat ctaaaactag ccacccggaa aaaatcgata   3240
ctatagttac aaaaaaagat ggggcaaata tggaaacata cgtgaataaa cttcacgagg   3300
gctccacata cacagctgct gttcaataca atgtcctaga aaaagacgat gatcctgcat   3360
cacttacaat atgggtgccc atgttccaat catccatgcc agcagatcta ctcataaaag   3420
aactagccaa tgtcaatata ctagtgaaac aaatatccac acccaaggga ccctcattaa   3480
gagtcatgat aaactcaaga agtgcagtgc tagcacaaat gcccagcaaa tttaccatat   3540
gtgccaatgt gtccttggat gaaagaagca agctggcata tgatgtaacc acaccctgtg   3600
aaattaaggc atgcagtcta acatgcctaa aatcaaaaaa tatgttaact acagttaaag   3660
atctcactat gaaaacactc aacccaacac atgacatcat tgctttatgt gaatttgaaa   3720
atatagtaac atcaaaaaaa gtcataatac caacatacct aagatctatc agcgtcagaa   3780
ataaagatct gaacacactt gaaaatataa caaccactga attcaaaaat gccattacaa   3840
atgcaaaaat catcccttac tcaggattat tgttagtcat cacagtgact gacaacaaag   3900
gagcattcaa atacataaag ccacaaagtc aattcatagt agatcttgga gcttacctag   3960
aaaaagaaag tatatattat gttacaacaa attggaagca cacagctaca cgatttgcaa   4020
tcaaacccat ggaagattaa ccttttttcct ctacatcaat gagtagattc atacaaactt   4080
tctaactaca ttcttcactt cacaatcata atcaccaacc ctctgtggtt caatcaatca   4140
aacaaaactc atcaagagtt ccagatcatc ccaagtcatt gttcatcaga tccagtactc   4200
aaataagtta ataaaaaatc cacatggggc aaataatcat tgagggaaat ccaactaatc   4260
acaacatctg tcaacataga caagtcaaca cgctagataa aatcaaccaa tggaaaatac   4320
atccataact atagaattct caagcaaatt ctggccttac tttacactaa tacacatgat   4380
aacaacaata atctctttga taatcataat ctccatcatg attgcaatac taaacaaact   4440
```

-continued

```
ctgcgaatat aatgtattcc ataacaaaac ctttgagcta ccaagagctc gagtcaatac   4500
atagcattca ccaatctgat agctcaaaac agtaaccttg catttgtaaa tgaactaccc   4560
tcacttcttc acaaaaccac atcaacatct caccatgcaa gccatcatct ataccataaa   4620
gtagttaatt aaaaatggcc ggccagtcat aacaatgaac taggatatta agaccaaaaa   4680
caacgctacg cgtttgacag aagataaaaa tggggcaaat gcaaacatga agtgcctttt   4740
gtacttagcc tttttattca ttggggtgaa ttgcaagttc accatagttt ttccacacaa   4800
ccaaaaagga aactggaaaa atgttccttc taattaccat tattgcccgt caagctcaga   4860
tttaaattgg cataatgact taataggcac agccttacaa gtcaaaatgc ccaagagtca   4920
caaggctatt caagcagacg gttggatgtg tcatgcttcc aaatgggtca ctacttgtga   4980
tttccgctgg tatggaccga agtatataac acattccatc cgatccttca ctccatctgt   5040
agaacaatgc aaggaaagca ttgaacaaac gaaacaagga acttggctga atccaggctt   5100
ccctcctcaa agttgtggat atgcaactgt gacggatgcc gaagcagtga ttgtccaggt   5160
gactcctcac catgtgctgg ttgatgaata cacaggagaa tgggttgatt cacagttcat   5220
caacggaaaa tgcagcaatt acatatgccc cactgtccat aactctacaa cctggcattc   5280
tgactataag gtcaaagggc tatgtgattc taacctcatt tccatggaca tcaccttctt   5340
ctcagaggac ggagagctat catccctggg aaaggagggc acagggttca gaagtaacta   5400
ctttgcttat gaaactggag gcaaggcctg caaaatgcaa tactgcaagc attggggagt   5460
cagactccca tcaggtgtct ggttcgagat ggctgataag gatctctttg ctgcagccag   5520
attccctgaa tgcccagaag ggtcaagtat ctctgctcca tctcagacct cagtggatgt   5580
aagtctaatt caggacgttg agaggatctt ggattattcc ctctgccaag aaacctggag   5640
caaaatcaga gcgggtcttc caatctctcc agtggatctc agctatcttg ctcctaaaaa   5700
cccaggaacc ggtcctgctt tcaccataat caatggtacc ctaaaatact ttgagaccag   5760
atacatcaga gtcgatattg ctgctccaat cctctcaaga atggtcggaa tgatcagtgg   5820
aactaccaca gaaagggaac tgtgggatga ctgggcacca tatgaagacg tggaaattgg   5880
acccaatgga gttctgagga ccagttcagg atataagttt cctttataca tgattggaca   5940
tggtatgttg gactccgatc ttcatcttag ctcaaaggct caggtgttcg aacatcctca   6000
cattcaagac gctgcttcgc aacttcctga tgatgagagt ttatttttttg gtgatactgg   6060
gctatccaaa aatccaatcg agcttgtaga aggttggttc agtagttgga aaagctctat   6120
tgcctctttt ttctttatca tagggttaat cattggacta ttcttggttc tccgagttgg   6180
tatccatctt tgcattaaag ccagaagcac accagtcaca ttaagtaagg atcaactgag   6240
tggtataaat aatattgcat ttagtaacta atagtcatta aaaagcgggc ccgtattgtt   6300
gcaaaaagcc atgaccaaat caaacagaat caaaatcaac tctggggcaa ataacaatgg   6360
agttgccaat cctcaaaaca aatgctatta ccacaatcct tgctgcagtc acactctgtt   6420
tcgcttccag tcaaaacatc actgaagaat tttatcaatc aacatgcagt gcagtcagca   6480
aaggctatct tagtgctcta agaactggtt ggtatactag tgttataact atagaattaa   6540
gtaatatcaa ggaaaataag tgtaatggta cagacgctaa ggtaaaatta ataaaacaag   6600
aattagataa atataaaaat gctgtaacag aattgcagtt gctcatgcaa agcacaccag   6660
cagccaacaa tcgagccaga agagaactac caagatttat gaattataca ctcaacaata   6720
ccaaaaacac caatgtaaca ttaagtaaga aaaggaaaag aagatttctt ggatttttgt   6780
```

```
taggtgttgg atctgcaatc gccagtggca ttgccgtatc caaggtcctg cacctagaag   6840
gggaagtgaa caaaatcaaa agtgctctac tatccacaaa caaggctgta gtcagcttat   6900
ctaatggagt cagtgtctta accagcaagg tgttagacct caaaaactat atagataaac   6960
agttgttacc tattgttaac aagcaaagct gcagcatatc aaacattgaa actgtgatag   7020
agttccaaca aaagaacaac agactactag agattaccag agaatttagt gttaatgcag   7080
gtgtaactac tcctgtaagc acttatatgt taactaatag tgagttatta tcattaatca   7140
atgatatgcc tataacaaat gatcagaaaa agttaatgtc cagcaatgtt caaatagtta   7200
gacagcaaag ttactctatc atgtcaataa taaaagagga agtcttggca tatgtagtac   7260
aattaccact atatggtgta atagatactc cttgttggaa actacacaca tcccctttat   7320
gtacaaccaa cacaaaggaa ggatccaaca tctgcttaac aagaaccgac agaggatggt   7380
actgtgacaa tgcaggatca gtatcctttt tcccacaagc tgaaacatgt aaagttcaat   7440
cgaatcgggt gttttgtgac acaatgaaca gtttaacatt accaagtgag gtaaatctct   7500
gcaacattga catattcaac cccaaatatg attgcaaaat tatgacttca aaaacagatg   7560
taagcagctc cgttatcaca tctctaggag ccattgtgtc atgctatggc aaaaccaaat   7620
gtacagcatc caataaaaat cgtgggatca taaagacatt ctctaacggg tgtgattatg   7680
tatcaaataa gggggtggat actgtgtctg taggtaatac attatattat gtaaataagc   7740
aagaaggcaa aagtctctat gtaaaaggtg aaccaataat aaatttctat gatccattag   7800
tgttcccctc tctcctgtgg gatgcatcaa tatctcaagt caatgagaaa attaatcaga   7860
gtctagcatt tatccgtaaa tcagatgaat tattaggctc tggcggaagc ggatacatcc   7920
ctgaggcacc aagggacgga caggcctacg tgcgcaagga tggcgagtgg gtgctgctgt   7980
ccacctttct gtgaataaaa atagcaccta atcatattct tacaatggtt cgctatttga   8040
ccatagataa cccatctatc attagattat cctaaaattt gaacttcatc acaactttca   8100
tctataaacc atctcactta cactttttaa gtagatttct attttatagt tatataaaac   8160
agggcccatt gaataccaaa ttaacttact atttgtaaaa atgagaattg gggcaaatat   8220
gtcacgaagg aatccttgca aattcgaaat tcgaggtcat tgcttgaatg gtaaaaggtg   8280
tcattttagt cataattatt ttgaatggcc accccatgca ctgcttgtaa gacaaaactt   8340
tatgttaaac agaatactta agtctatgga taaaagcata gatactttgt cagaaataag   8400
tggagctgca gagttggaca gaacagaaga gtatgccctc ggtgtagttg gagtgctaga   8460
gagttatata ggatcaataa ataatataac taaacaatca gcatgtgttg ccatgagcaa   8520
actccttact gaactcaaca gcgatgacat caaaaaacta agggacaatg aagagccaaa   8580
ctcacccaaa gtaagagtgt acaatactgt catatcatat attgaaagca acaggaagaa   8640
caataaacaa actatccatc tgttaaaaag attgccagca gacgtattga agaaaaccat   8700
caaaaacaca ttggatatcc acaagagcat aaccatcaat aacccaaaag aatcaactgt   8760
tagtgatacg aacgaccatg ccaaaaataa tgatactacc tgacaaatat ccttgtagta   8820
taaattccat actaataaca agtaattgta gagtcactat gtataatcaa aaaaacacac   8880
tatatatcaa tcaaaacaac caaaatagcc atatataccc accggatcaa ccattcaatg   8940
aaatccattg gacctctcaa gacttgattg atgcaactca aaattttcta caacatctag   9000
gtattactga tgatatatac acaatatata tattagtgtc ataatactca atcctaatac   9060
ttaccacatc atcaaattat taactcaaac aattcaagct atgggacaaa atggatccca   9120
ttattagtgg aaattctgct aatgtttatc taactgatag ttatttaaaa ggtgttattt   9180
```

```
ctttctcaga atgtaacgct ttaggaagtt acatattcaa tggtccttat ctcaaaaatg   9240
attataccaa cttaattagt agacaaaatc cattaataga acacataaat ctaaagaaac   9300
taaatataac acagtcctta atatctaagt atcataaagg tgaaataaaa atagaagaac   9360
ctacttactt tcagtcatta cttatgacat acaagagtat gacctcttca gaacagacta   9420
ctactactaa tttacttaaa aagataataa gaagagctat agaaatcagt gatgtcaaag   9480
tctatgctat attgaataaa ctggggctca aagaaaaaga caagattaaa tccaataatg   9540
gacaagatga agacaactca gtcattacta ccataatcaa agatgatata cttttagctg   9600
tcaaggataa tcaatctcat cttaaagcag acaaaaatca atccacaaaa caaaaagata   9660
caatcaaaac aacacttttg aagaaattaa tgtgttcgat gcaacatcct ccatcatggt   9720
taatacattg gtttaattta tacacaaaat taaacagcat attaacacaa tatcgatcta   9780
gtgaggtaaa aaaccatggt tttatattga tagataatca tactcttagt ggattccaat   9840
ttattttgaa tcaatatggt tgtatagttt atcataagga actcaaaaga attactgtga   9900
caacttataa tcaattcttg acatggaaag atattagcct tagtagatta aatgtttgtt   9960
tgattacatg gattagtaac tgtttgaaca cattaaacaa aagcttaggc ttaagatgtg  10020
gattcaataa tgttatcttg acacaattat tcctttatgg agattgtata ctaaaactat  10080
tccacaatga ggggttctac ataataaaag aggtagaggg atttattatg tctctaattt  10140
taaatataac agaagaagat caattcagaa aacggtttta taatagtatg ctcaacaaca  10200
tcacagatgc cgccaacaaa gctcaaaaaa atctgctatc aagagtatgt catacattat  10260
tagataagac aatatcagat aatataataa atggcagatg gataattcta ttgagtaagt  10320
tcctaaaatt aattaagctt gcaggtgaca ataacctcaa caatctgagt gaattatatt  10380
ttttgttcag aatatttgga cacccaatgg tagatgaaag acaagccatg gatgctgtta  10440
aagttaattg caacgagacc aaattttatt tgttaagtag tttgagtatg ttaagaggag  10500
cttttatata tagaattata aaagggtttg taaataatta caacagatgg cctactttaa  10560
gaaatgccat tgtcttaccc ttaagatggt taacttacta taaactaaac acttatcctt  10620
ccttgttgga acttacagaa agagatttga ttgttctatc aggactacgt ttctatcgag  10680
agtttcggtt gcctaaaaaa gtggatcttg aaatgatcat aaatgataag gctatatcac  10740
ctcctaaaaa tttaatatgg actagtttcc ctagaaatta tatgccgtca cacatacaaa  10800
attatataga acatgaaaaa ttaaaattct ctgatagtga taaatcaaga agagtattag  10860
agtattattt aagagataac aaattcaatg aatgtgattt acacaactgt gtagttaatc  10920
aaagttatct taacaacccg aatcatgtgg tatcattgac aggcaaagaa agagaactca  10980
gtgtaggtag aatgtttgca atgcaaccag gaatgttcag acaagttcaa atattagcag  11040
agaaaatgat agcagaaaac atattacaat tttccctgaa aagtcttaca agatatggtg  11100
atctagaact acagaaaata ttagaattga aagcaggaat aagtaacaaa tcaaatcgtt  11160
acaatgataa ttacaacaat tacattagta agtgctctat catcacagat ctcagcaaat  11220
tcaatcaagc atttcgatat gaaacatcat gtatttgtag tgatgtactg gatgaactgc  11280
atggtgtaca atctctattt tcctggttac atttaactat tcctcatgtc acaataatat  11340
gcacatatag gcatgcaccc ccctatataa aggatcatat tgtagatctt aacaatgtag  11400
atgagcaaag tggactatat agatatcata tgggtggtat cgaagggtgg tgtcaaaaac  11460
tatggaccat agaagctata tcactattag atctaatatc tctcaaaggg aaattctcaa  11520
```

-continued

```
ttactgcttt aattaatggt gacaatcaat caatagatat aagtaaacca gtcagactca  11580
tggaaggtca aactcatgct caagcagatt atttgctagc attaaatagt ctcaaattac  11640
tgtataaaga gtatgcagga ataggccaca aattaaaagg aactgagact tatatatcga  11700
gagatatgca atttatgagt aaaacgatcc aacataacgg tgtatattac ccagctagta  11760
taaagaaagt cctaagagtg ggaccgtgga taaacactat acttgatgac ttcaaagtga  11820
gtctagaatc tataggtagt ttgacacaag aattagaata tagaggtgaa agtctattat  11880
gcagtttaat atttagaaat gtatggttat ataatcaaat tgcattacaa cttaaaaatc  11940
atgcattatg taacaacaaa ttatatttgg atatattaaa agttctaaaa cacttaaaaa  12000
cctttttaa tcttgataac attgatacag cattaacatt gtatatgaat ttgcccatgt  12060
tatttggtgg tggtgatccc aacttgttat atcgaagttt ctatagaaga actcctgatt  12120
tcctcacaga ggctatagtt cactctgtgt tcatacttag ttattataca aaccatgatt  12180
taaaagataa acttcaagat ctgtcagatg atagattgaa taagttctta acatgcataa  12240
tcacgtttga taaaaacccc aatgctgaat tcgttacatt gatgagagat cctcaagctt  12300
taggatctga gaggcaagct aaaattacta gcgaaatcaa tagactggca gttaccgagg  12360
ttttgagcac agctccaaac aaaatatttt ccaaaagtgc acaacactat accactacag  12420
agatagatct taatgatatt atgcaaaata tagaacctac atatcctcac gggctaagag  12480
ttgtttatga gagtttaccc ttttataaag cagagaaaat agtaaatctt atatccggta  12540
caaaatctat aactaacata ctggaaaaga cttctgccat agacttaaca gatattgata  12600
gagccactga gatgatgagg aaaaacataa ctttgcttat aaggatatta ccattagatt  12660
gtaacagaga taaaagagaa atattgagta tggaaaacct aagtattact gaattaagca  12720
aatacgttag agaaagatct tggtctttat ccaatatagt tggtgttaca tcacccagta  12780
tcatgtatac aatggacata aaatatacaa caagcactat agctagtggc ataatcatag  12840
agaaatataa tgtcaacagt ttaacacgtg gtgagagagg acccactaaa ccatgggttg  12900
gttcatctac acaagagaaa aagacaatgc cagtttataa tagacaagtt ttaaccaaaa  12960
aacagagaga tcaaatagat ctattagcaa aattggattg ggtgtatgca tctatagata  13020
acaaggatga atttatggag gaacttagca taggaactct tgggttaaca tatgagaagg  13080
ccaaaaaatt attcccacaa tatttgagtg ttaactattt gcatcgtctt acagtcagta  13140
gtagaccatg tgaattccct gcatctatac cagcttatag aactacaaat tatcactttg  13200
atactagccc tattaatcgc atattaacag aaaagtatgg tgatgaagat attgatatag  13260
tattccaaaa ctgtataagc tttggcctta gcttaatgtc tgtagtagaa caatttacta  13320
atgtatgtcc taacagaatt attctcatac ccaagcttaa tgagatacat ttgatgaaac  13380
ctcccatatt cacaggcgat gttgatattc acaagttaaa acaagtgata caaaaacaac  13440
atatgttttt accagacaaa ataagtttga ctcaatatgt ggaattattc ttaagtaata  13500
aaacactcaa atctggatct aatgttaatt ctaatttaat attggcgcat aagatatctg  13560
actattttca taatacttac attttgagta ctaatttagc tggacattgg attcttatta  13620
tacaacttat gaaagattct aagggtattt ttgaaaaaga ttggggagag ggatatataa  13680
ctgatcatat gttcattaat ttgaaagttt tcttcaatgc ttataagaca tatctcttgt  13740
gttttcataa aggttacggc agagcaaagc tggagtgtga tatgaatact tcagatctcc  13800
tatgtgtatt ggaattaata gacagtagtt attggaagtc tatgtctaag gtgtttttag  13860
aacaaaaagt tatcaaatac attcttagcc aggatgcaag tttacataga gtaaaaggat  13920
```

```
gtcatagctt caaactatgg tttcttaaac gtcttaatgt agcagaattc acagtttgcc  13980

cttgggttgt taacatagat tatcatccaa cacatatgaa agcaatatta acttatattg  14040

atcttgttag aatgggattg ataaatatag atagaatata cattaaaaat aaacacaagt  14100

tcaatgatga gttttatact tctaatctgt tttacattaa ttataacttc tcagataata  14160

ctcatctatt aactaaacat ataaggattg ctaattccga attagaaagt aattacaaca  14220

aattatatca tcctacacca gaaaccctag aaaatatact aaccaatccg gttaaaagta  14280

atgagaaaaa gacactgagt gactattgta taggtaaaaa tgttgactca ataatgttac  14340

catcgttatc taataagaag cttattaaat cgtctacaat gattagaacc aattacagca  14400

gacaagattt gtataattta tttcctacgg ttgtgattga taaaattata gatcattcag  14460

gtaatacagc caaatctaac caactttaca ctactacttc tcatcaaata tccttagtgc  14520

acaatagcac atcactttat tgcatgcttc cttggcatca tattaataga ttcaattttg  14580

tatttagttc tacaggttgt aaaattagta tagagtatat tttaaaagat cttaaaatta  14640

aggatcctaa ttgtatagca ttcataggtg aaggagcagg gaatttatta ttgcgtacag  14700

tagtggaact tcatcctgat ataagatata tttacagaag tctgaaagat tgcaatgatc  14760

atagtttacc aattgagttt ttaaggctgt acaatggaca tatcaacatt gattatggtg  14820

aaaatttgac cattcctgct acagatgcaa ccaacaacat tcattggtct tatttacata  14880

taaagtttgc tgaacctatc agtctttttg tctgtgatgc tgaattgcct gtaacagtca  14940

actggagtaa gattataata gagtggagca agcatgtaag aaaatgcaag tactgttctt  15000

cagttaataa atgtacattg atagtaaaat atcatgctca agatgatatc gatttcaaat  15060

tagacaacat aactatatta aaaacttatg tatgcttagg tagtaagtta aagggatctg  15120

aagtttactt agtccttaca ataggtcctg caaatgtgtt cccagtattt aatgtagtac  15180

aaaatgctaa attgatacta tcaagaacta aaaatttcat catgcctaaa aaagctgata  15240

aagagtctat tgatgcaaat attaagagtt tgataccctt tctttgttac cctataacaa  15300

aaaaaggaat taatactgca ttgtctaaat taaagagtgt tgttagtgga gatatactat  15360

catattctat agctggacgt aatgaagttt tcagcaataa acttataaat cataagcata  15420

tgaacatctt aaagtggttc aatcatgttt taaatttcag atcaacagaa ttaaactata  15480

atcatttata tatggtagaa tctacttatc ctcatctaag tgaattgtta aacagcttga  15540

caaccaatga acttaaaaaa ctgattaaaa tcacaggtag tttgttatac aacttttata  15600

atgaataatg agcaaaaatc ttataacaaa aatagctaca cactaacatt gtattcaatt  15660

atagttattg aaaattaata attatataat ttttaataac ttctagtgaa ctaatcctaa  15720

aattatcatt ttgatctagg aagaataagt ttaaatccaa atctaattgg tttatatgta  15780

tattaactaa attacgagat attagttttt gacacttttt ttctcgt               15827
```

<210> SEQ ID NO 13
<211> LENGTH: 15845
<212> TYPE: DNA
<213> ORGANISM: Artificial Sequence
<220> FEATURE:
<223> OTHER INFORMATION: A sequence in which SEQ ID NO: 12 is cleaved with ApaI and SEQ ID NO: 5 is inserted.

<400> SEQUENCE: 13

```
acgcgaaaaa atgcgtacaa caaacttgcg taaaccaaaa aaatggggca aataagaatt     60

tgataagtac cacttaaatt taactccttt ggttagaggc gcgccatggg cagcaactca    120
```

-continued

```
ttgagtatga taaaagttag attgcaaaat ctgtttgaca atgatgaagt agcattgtta    180
aaaataacat gctatactga caaattaata cagttaacta atgctttggc taaggcagtt    240
atacatacaa tcaaattgaa tggcattgta tttgtgcatg ttattacaag tagtgatatt    300
tgccctaata ataatattgt agtgaaatcc aatttcacaa caatgccagt attacaaaat    360
ggaggttata tatgggaaat gatggaatta acacactgct ctcaacctaa tggcctaata    420
gatgacaatt gtgaaattaa attctccaaa aaactaagtg attcaacaat gaccaattat    480
atgaatcaat tatctgaatt acttggattt gacctcaatc cataaatcat aataaatatc    540
aactagcaaa tcaatgtcac taacaccatt agttaatata aaacttgaca gaagataaaa    600
atggggcaaa taaatcaatt cagccgaccc aaccatggac acaacacaca atgataccac    660
accacaaaga ctgatgatca cagacatgag gccattatcg cttgagacta taataacatc    720
tctaaccaga gatatcataa cacataaatt tatatacttg ataaatcatg aatgcatagt    780
aagaaaactt gatgaaagac aggccacatt tacatttctg gtcaactatg aaatgaaact    840
attgcacaaa gtgggaagca ctaaatataa aaaatatact gaatacaaca caaaatatgg    900
cactttccct atgccaatat ttatcaatca tgatgggttc ttagaatgca ttggcattaa    960
gcctaccaag cacacaccca taatatacaa gtatgatctc aatccatgaa tatcaaacca   1020
agattcaaac aatccgaaat aacaacttta tgcataatca cactccatag tccaaatgga   1080
gcctgaaaat tatagttatt taaaattcct gcaggaagga gagacataag atgaaagatg   1140
gggcaaatac aaaaatggct cttagcaaag tcaagttgaa tgatacactc aacaaagatc   1200
aacttctatc atccagcaaa tataccatcc aacggagcac aggagacagc attgacactc   1260
ctaattatga tgtgcagaaa cacattaata agttatgtgg catgttatta atcacagaag   1320
atgctaatca taaattcact gggttaatag gtatgttata tgctatgtct agattaggaa   1380
gagaagacac cataaaaata ctcaaagatg cgggatatca tgttaaggca aatggagtgg   1440
atgtaacaac acatcgtcaa gacattaatg ggaaagaaat gaaatttgaa gtgttaacat   1500
tagcaagctt aacaactgaa attcaaatca acattgagat agaatctaga aaatcctaca   1560
aaaaaatgct aaaagaaatg ggagaggtgg ctccagaata caggcatgac tctcctgatt   1620
gtgggatgat aatattatgt atagcggcat tagtaataac caaattagca gcaggagata   1680
gatcaggtct tacagctgtg attaggagag ctaataatgt cctaaaaaat gaaatgaaac   1740
gttataaagg tttattaccc aaggatatag ccaacagctt ctatgaagtg tttgaaaaat   1800
atcctcactt tatagatgtt tttgttcatt ttggtatagc acaatcttct accagaggtg   1860
gcagtagagt tgaagggatt tttgcaggat tgtttatgaa tgcctatggt gcagggcaag   1920
tgatgttacg gtgggggggtc ttagcaaaat cagttaaaaa cattatgtta ggacacgcta   1980
gtgtacaagc agaaatggaa caagttgtgg aggtgtatga gtatgctcag aaattgggtg   2040
gagaagcagg attctaccat atattgaaca acccaaaagc atcactatta tctttgactc   2100
aatttcctca cttctctagt gtagtattgg gcaatgctgc tggcctaggc ataatgggag   2160
aatacagagg tacaccaagg aatcaagatt tatatgatgc tgcaaaagca tatgctgaac   2220
aactcaaaga aaatggtgtg attaactaca gtgtattaga tttgacagca gaagaactag   2280
aggctatcaa acatcagctt aatccaaaag ataatgatgt agagctttga gttaataaaa   2340
aagtggggca aataaatcat catggaaaag tttgctcctg aattccatgg agaagatgca   2400
aacaacagag ccaccaaatt cctagaatca ataaagggca aattcacatc acccaaagat   2460
```

-continued

```
cccaagaaaa aagatagtat catatctgtc aactcaatag atatagaagt aaccaaagaa   2520
agccctataa catcaaattc aaccattata aacccaataa atgagacaga tgatactgta   2580
gggaacaagc ccaattatca aagaaagcct ctagtaagtt tcaaagaaga ccctacgcca   2640
agtgataatc ctttttcaaa actatacaaa gaaaccatag aaacatttga taacaatgaa   2700
gaagaatcta gctattcata tgaagaaata aatgatcaga caaacgataa tataacagca   2760
agattagata ggattgatga gaaattaagt gaaatactag gaatgcttca cacattagta   2820
gtagcgagtg caggacccac atctgctcgg gatggtataa gagatgccat ggttggttta   2880
agagaagaaa tgatagaaaa aatcagaact gaagcattaa tgaccaatga cagactagaa   2940
gctatggcaa gactcaggaa tgaagaaagt gaaaagatgg caaaagacac atcagatgaa   3000
gtgtctctca atccaacatc agagaaactg aacaacctgt tggaagggaa tgatagtgac   3060
aatgatctat cacttgaaga tttctgatta gctaccaaac tgtacatcaa aacacaacac   3120
caatagaaaa ccaacaaaca aaccaactca cccatccaac caaacatcta tctgctgatt   3180
agccaaccag ccaaaaaaca accagccaat ctaaaactag ccacccggaa aaaatcgata   3240
ctatagttac aaaaaaagat ggggcaaata tggaaacata cgtgaataaa cttcacgagg   3300
gctccacata cacagctgct gttcaataca atgtcctaga aaaagacgat gatcctgcat   3360
cacttacaat atgggtgccc atgttccaat catccatgcc agcagatcta ctcataaaag   3420
aactagccaa tgtcaatata ctagtgaaac aaatatccac acccaaggga ccctcattaa   3480
gagtcatgat aaactcaaga agtgcagtgc tagcacaaat gcccagcaaa tttaccatat   3540
gtgccaatgt gtccttggat gaaagaagca agctggcata tgatgtaacc acaccctgtg   3600
aaattaaggc atgcagtcta acatgcctaa aatcaaaaaa tatgttaact acagttaaag   3660
atctcactat gaaaacactc aacccaacac atgacatcat tgctttatgt gaatttgaaa   3720
atatagtaac atcaaaaaaa gtcataatac caacatacct aagatctatc agcgtcagaa   3780
ataaagatct gaacacactt gaaaatataa caaccactga attcaaaaat gccattacaa   3840
atgcaaaaat catcccttac tcaggattat tgttagtcat cacagtgact gacaacaaag   3900
gagcattcaa atacataaag ccacaaagtc aattcatagt agatcttgga gcttacctag   3960
aaaaagaaag tatatattat gttacaacaa attggaagca cacagctaca cgatttgcaa   4020
tcaaacccat ggaagattaa ccttttttcct ctacatcaat gagtagattc atacaaactt   4080
tctaactaca ttcttcactt cacaatcata atcaccaacc ctctgtggtt caatcaatca   4140
aacaaaactc atcaagagtt ccagatcatc ccaagtcatt gttcatcaga tccagtactc   4200
aaataagtta ataaaaaatc cacatggggc aaataatcat tgagggaaat ccaactaatc   4260
acaacatctg tcaacataga caagtcaaca cgctagataa aatcaaccaa tggaaaatac   4320
atccataact atagaattct caagcaaatt ctggccttac tttacactaa tacacatgat   4380
aacaacaata atctctttga taatcataat ctccatcatg attgcaatac taaacaaact   4440
ctgcgaatat aatgtattcc ataacaaaac ctttgagcta ccaagagctc gagtcaatac   4500
atagcattca ccaatctgat agctcaaaac agtaaccttg catttgtaaa tgaactaccc   4560
tcacttcttc acaaaaccac atcaacatct caccatgcaa gccatcatct ataccataaa   4620
gtagttaatt aaaaatggcc ggccagtcat aacaatgaac taggatatta agaccaaaaa   4680
caacgctacg cgtttgacag aagataaaaa tggggcaaat gcaaacatga agtgcctttt   4740
gtacttagcc tttttattca ttggggtgaa ttgcaagttc accatagttt ttccacacaa   4800
ccaaaaagga aactggaaaa atgttccttc taattaccat tattgcccgt caagctcaga   4860
```

-continued

```
tttaaattgg cataatgact taataggcac agccttacaa gtcaaaatgc ccaagagtca   4920
caaggctatt caagcagacg gttggatgtg tcatgcttcc aaatgggtca ctacttgtga   4980
tttccgctgg tatggaccga agtatataac acattccatc cgatccttca ctccatctgt   5040
agaacaatgc aaggaaagca ttgaacaaac gaaacaagga acttggctga atccaggctt   5100
ccctcctcaa agttgtggat atgcaactgt gacggatgcc gaagcagtga ttgtccaggt   5160
gactcctcac catgtgctgg ttgatgaata cacaggagaa tgggttgatt cacagttcat   5220
caacggaaaa tgcagcaatt acatatgccc cactgtccat aactctacaa cctggcattc   5280
tgactataag gtcaaagggc tatgtgattc taacctcatt tccatggaca tcaccttctt   5340
ctcagaggac ggagagctat catccctggg aaaggagggc acagggttca gaagtaacta   5400
ctttgcttat gaaactggag gcaaggcctg caaaatgcaa tactgcaagc attggggagt   5460
cagactccca tcaggtgtct ggttcgagat ggctgataag gatctctttg ctgcagccag   5520
attccctgaa tgcccagaag ggtcaagtat ctctgctcca tctcagacct cagtggatgt   5580
aagtctaatt caggacgttg agaggatctt ggattattcc ctctgccaag aaacctggag   5640
caaaatcaga gcgggtcttc caatctctcc agtggatctc agctatcttg ctcctaaaaa   5700
cccaggaacc ggtcctgctt tcaccataat caatggtacc ctaaaatact ttgagaccag   5760
atacatcaga gtcgatattg ctgctccaat cctctcaaga atggtcggaa tgatcagtgg   5820
aactaccaca gaaagggaac tgtgggatga ctgggcacca tatgaagacg tggaaattgg   5880
acccaatgga gttctgagga ccagttcagg atataagttt cctttataca tgattggaca   5940
tggtatgttg gactccgatc ttcatcttag ctcaaaggct caggtgttcg aacatcctca   6000
cattcaagac gctgcttcgc aacttcctga tgatgagagt ttatttttttg gtgatactgg   6060
gctatccaaa aatccaatcg agcttgtaga aggttggttc agtagttgga aaagctctat   6120
tgcctctttt ttctttatca tagggttaat cattggacta ttcttggttc tccgagttgg   6180
tatccatctt tgcattaaag ccagaagcac accagtcaca ttaagtaagg atcaactgag   6240
tggtataaat aatattgcat ttagtaacta atagtcatta aaaagcgggc ccgtattgtt   6300
gcaaaaagcc atgaccaaat caaacagaat caaaatcaac tctggggcaa ataacaatgg   6360
agttgccaat cctcaaaaca aatgctatta ccacaatcct tgctgcagtc acactctgtt   6420
tcgcttccag tcaaaacatc actgaagaat tttatcaatc aacatgcagt gcagtcagca   6480
aaggctatct tagtgctcta agaactggtt ggtatactag tgttataact atagaattaa   6540
gtaatatcaa ggaaaataag tgtaatggta cagacgctaa ggtaaaatta ataaaacaag   6600
aattagataa atataaaaat gctgtaacag aattgcagtt gctcatgcaa agcacaccag   6660
cagccaacaa tggagccaga ggctctggcg gaagcggact tggatttttg ttaggtgttg   6720
gatctgcaat cgccagtggc attgccgtat ccaaggtcct gcacctagaa ggggaagtga   6780
acaaaatcaa aagtgctcta ctatccacaa acaaggctgt agtcagctta tctaatggag   6840
tcagtgtctt aaccagcaag gtgttagacc tcaaaaacta tatagataaa cagttgttac   6900
ctattgttaa caagcaaagc tgcagcatat caaacattga aactgtgata gagttccaac   6960
aaaagaacaa cagactacta gagattacca gagaatttag tgttaatgca ggtgtaacta   7020
ctcctgtaag cacttatatg ttaactaata gtgagttatt atcattaatc aatgatatgc   7080
ctataacaaa tgatcagaaa aagttaatgt ccagcaatgt tcaaatagtt agacagcaaa   7140
gttactctat catgtcaata ataaaagagg aagtcttggc atatgtagta caattaccac   7200
```

-continued

```
tatatggtgt aatagatact ccttgttgga aactacacac atccccttta tgtacaacca   7260
acacaaagga aggatccaac atctgcttaa caagaaccga cagaggatgg tactgtgaca   7320
atgcaggatc agtatccttt ttcccacaag ctgaaacatg taaagttcaa tcgaatcggg   7380
tgttttgtga cacaatgaac agtttaacat taccaagtga ggtaaatctc tgcaacattg   7440
acatattcaa ccccaaatat gattgcaaaa ttatgacttc aaaaacagat gtaagcagct   7500
ccgttatcac atctctagga gccattgtgt catgctatgg caaaaccaaa tgtacagcat   7560
ccaataaaaa tcgtgggatc ataaagacat tctctaacgg gtgtgattat gtatcaaata   7620
agggggtgga tactgtgtct gtaggtaata cattatatta tgtaaataag caagaaggca   7680
aaagtctcta tgtaaaaggt gaaccaataa taaatttcta tgatccatta gtgttcccct   7740
ctgatgaatt tgatgcatca atatctcaag tcaatgagaa aattaatcag agtctagcat   7800
ttatccgtaa atcagatgaa ttattacata atgtaaatgc tggtaaatcc accacaaata   7860
tcatgataac taccataatt atagtaatta tagtaatatt gttagcatta attgcagttg   7920
gactgcttct atactgcaag gccagaagca caccagtcac attaagtaag gatcaactga   7980
gtggtataaa taatattgca tttagtaact gaataaaaat agcacctaat catattctta   8040
caatggttcg ctatttgacc atagataacc catctatcat tagattatcc taaaatttga   8100
acttcatcac aactttcatc tataaaccat ctcacttaca ctttttaagt agatttctat   8160
tttatagtta tataaaacag ggcccattga ataccaaatt aacttactat ttgtaaaaat   8220
gagaattggg gcaaatatgt cacgaaggaa tccttgcaaa ttcgaaattc gaggtcattg   8280
cttgaatggt aaaaggtgtc attttagtca taattatttt gaatggccac cccatgcact   8340
gcttgtaaga caaaacttta tgttaaacag aatacttaag tctatggata aaagcataga   8400
tactttgtca gaaataagtg gagctgcaga gttggacaga acagaagagt atgccctcgg   8460
tgtagttgga gtgctagaga gttatatagg atcaataaat aatataacta aacaatcagc   8520
atgtgttgcc atgagcaaac tccttactga actcaacagc gatgacatca aaaaactaag   8580
ggacaatgaa gagccaaact cacccaaagt aagagtgtac aatactgtca tatcatatat   8640
tgaaagcaac aggaagaaca ataaacaaac tatccatctg ttaaaaagat tgccagcaga   8700
cgtattgaag aaaaccatca aaaacacatt ggatatccac aagagcataa ccatcaataa   8760
cccaaaagaa tcaactgtta gtgatacgaa cgaccatgcc aaaaataatg atactacctg   8820
acaaatatcc ttgtagtata aattccatac taataacaag taattgtaga gtcactatgt   8880
ataatcaaaa aaacacacta tatatcaatc aaaacaacca aaatagccat atatacccac   8940
cggatcaacc attcaatgaa atccattgga cctctcaaga cttgattgat gcaactcaaa   9000
attttctaca acatctaggt attactgatg atatatacac aatatatata ttagtgtcat   9060
aatactcaat cctaatactt accacatcat caaattatta actcaaacaa ttcaagctat   9120
gggacaaaat ggatcccatt attagtggaa attctgctaa tgtttatcta actgatagtt   9180
atttaaaagg tgttatttct ttctcagaat gtaacgcttt aggaagttac atattcaatg   9240
gtccttatct caaaaatgat tataccaact taattagtag acaaaatcca ttaatagaac   9300
acataaatct aaagaaacta aatataacac agtccttaat atctaagtat cataaaggtg   9360
aaataaaaat agaagaacct acttactttc agtcattact tatgacatac aagagtatga   9420
cctcttcaga acagactact actactaatt tacttaaaaa gataataaga agagctatag   9480
aaatcagtga tgtcaaagtc tatgctatat tgaataaact ggggctcaaa gaaaaagaca   9540
agattaaatc caataatgga caagatgaag acaactcagt cattactacc ataatcaaag   9600
```

atgatatact tttagctgtc aaggataatc aatctcatct taaagcagac aaaaatcaat 9660
ccacaaaaca aaaagataca atcaaaacaa cacttttgaa gaaattaatg tgttcgatgc 9720
aacatcctcc atcatggtta atacattggt ttaatttata cacaaaatta aacagcatat 9780
taacacaata tcgatctagt gaggtaaaaa accatggttt tatattgata gataatcata 9840
ctcttagtgg attccaattt attttgaatc aatatggttg tatagtttat cataaggaac 9900
tcaaaagaat tactgtgaca acttataatc aattcttgac atggaaagat attagcctta 9960
gtagattaaa tgtttgtttg attacatgga ttagtaactg tttgaacaca ttaaacaaaa 10020
gcttaggctt aagatgtgga ttcaataatg ttatcttgac acaattattc ctttatggag 10080
attgtatact aaaactattc cacaatgagg ggttctacat aataaaagag gtagagggat 10140
ttattatgtc tctaatttta aatataacag aagaagatca attcagaaaa cggttttata 10200
atagtatgct caacaacatc acagatgccg ccaacaaagc tcaaaaaaat ctgctatcaa 10260
gagtatgtca tacattatta gataagacaa tatcagataa tataataaat ggcagatgga 10320
taattctatt gagtaagttc ctaaaattaa ttaagcttgc aggtgacaat aacctcaaca 10380
atctgagtga attatatttt ttgttcagaa tatttggaca cccaatggta gatgaaagac 10440
aagccatgga tgctgttaaa gttaattgca acgagaccaa attttatttg ttaagtagtt 10500
tgagtatgtt aagaggagct tttatatata gaattataaa agggtttgta aataattaca 10560
acagatggcc tactttaaga aatgccattg tcttaccctt aagatggtta acttactata 10620
aactaaacac ttatccttcc ttgttggaac ttacagaaag agatttgatt gttctatcag 10680
gactacgttt ctatcgagag tttcggttgc ctaaaaaagt ggatcttgaa atgatcataa 10740
atgataaggc tatatcacct cctaaaaatt taatatggac tagtttccct agaaattata 10800
tgccgtcaca catacaaaat tatatagaac atgaaaaatt aaaattctct gatagtgata 10860
aatcaagaag agtattagag tattatttaa gagataacaa attcaatgaa tgtgatttac 10920
acaactgtgt agttaatcaa agttatctta acaacccgaa tcatgtggta tcattgacag 10980
gcaaagaaag agaactcagt gtaggtagaa tgtttgcaat gcaaccagga atgttcagac 11040
aagttcaaat attagcagag aaaatgatag cagaaaacat attacaattt ttccctgaaa 11100
gtcttacaag atatggtgat ctagaactac agaaaatatt agaattgaaa gcaggaataa 11160
gtaacaaatc aaatcgttac aatgataatt acaacaatta cattagtaag tgctctatca 11220
tcacagatct cagcaaattc aatcaagcat ttcgatatga aacatcatgt atttgtagtg 11280
atgtactgga tgaactgcat ggtgtacaat ctctattttc ctggttacat ttaactattc 11340
ctcatgtcac aataatatgc acatataggc atgcaccccc ctatataaag gatcatattg 11400
tagatcttaa caatgtagat gagcaaagtg gactatatag atatcatatg ggtggtatcg 11460
aagggtggtg tcaaaaacta tggaccatag aagctatatc actattagat ctaatatctc 11520
tcaaagggaa attctcaatt actgctttaa ttaatggtga caatcaatca atagatataa 11580
gtaaaccagt cagactcatg gaaggtcaaa ctcatgctca agcagattat ttgctagcat 11640
taaatagtct caaattactg tataaagagt atgcaggaat aggccacaaa ttaaaaggaa 11700
ctgagactta tatatcgaga gatatgcaat ttatgagtaa aacgatccaa cataacggtg 11760
tatattaccc agctagtata aagaaagtcc taagagtggg accgtggata aacactatac 11820
ttgatgactt caaagtgagt ctagaatcta taggtagttt gacacaagaa ttagaatata 11880
gaggtgaaag tctattatgc agtttaatat ttagaaatgt atggttatat aatcaaattg 11940

-continued

```
cattacaact taaaaatcat gcattatgta acaacaaatt atatttggat atattaaaag  12000
ttctaaaaca cttaaaaacc ttttttaatc ttgataacat tgatacagca ttaacattgt  12060
atatgaattt gcccatgtta tttggtggtg gtgatcccaa cttgttatat cgaagtttct  12120
atagaagaac tcctgatttc ctcacagagg ctatagttca ctctgtgttc atacttagtt  12180
attatacaaa ccatgattta aaagataaac ttcaagatct gtcagatgat agattgaata  12240
agttcttaac atgcataatc acgtttgata aaaaccccaa tgctgaattc gttacattga  12300
tgagagatcc tcaagcttta ggatctgaga ggcaagctaa aattactagc gaaatcaata  12360
gactggcagt taccgaggtt ttgagcacag ctccaaacaa aatattttcc aaaagtgcac  12420
aacactatac cactacagag atagatctta atgatattat gcaaaatata gaacctacat  12480
atcctcacgg gctaagagtt gtttatgaga gtttaccctt ttataaagca gagaaaatag  12540
taaatcttat atccggtaca aaatctataa ctaacatact ggaaaagact tctgccatag  12600
acttaacaga tattgataga gccactgaga tgatgaggaa aaacataact ttgcttataa  12660
ggatattacc attagattgt aacagagata aaagagaaat attgagtatg gaaaacctaa  12720
gtattactga attaagcaaa tacgttagag aaagatcttg gtctttatcc aatatagttg  12780
gtgttacatc acccagtatc atgtatacaa tggacataaa atatacaaca agcactatag  12840
ctagtggcat aatcatagag aaatataatg tcaacagttt aacacgtggt gagagaggac  12900
ccactaaacc atgggttggt tcatctacac aagagaaaaa gacaatgcca gtttataata  12960
gacaagtttt aaccaaaaaa cagagagatc aaatagatct attagcaaaa ttggattggg  13020
tgtatgcatc tatagataac aaggatgaat ttatggagga acttagcata ggaactcttg  13080
ggttaacata tgagaaggcc aaaaaattat tcccacaata tttgagtgtt aactatttgc  13140
atcgtcttac agtcagtagt agaccatgtg aattccctgc atctatacca gcttatagaa  13200
ctacaaatta tcactttgat actagcccta ttaatcgcat attaacagaa aagtatggtg  13260
atgaagatat tgatatagta ttccaaaact gtataagctt tggccttagc ttaatgtctg  13320
tagtagaaca atttactaat gtatgtccta acagaattat tctcataccc aagcttaatg  13380
agatacattt gatgaaacct cccatattca caggcgatgt tgatattcac aagttaaaac  13440
aagtgataca aaaacaacat atgtttttac cagacaaaat aagtttgact caatatgtgg  13500
aattattctt aagtaataaa acactcaaat ctggatctaa tgttaattct aatttaatat  13560
tggcgcataa gatatctgac tattttcata atacttacat tttgagtact aatttagctg  13620
gacattggat tcttattata caacttatga aagattctaa gggtattttt gaaaaagatt  13680
ggggagaggg atatataact gatcatatgt tcattaattt gaaagttttc ttcaatgctt  13740
ataagacata tctcttgtgt tttcataaag gttacggcag agcaaagctg gagtgtgata  13800
tgaatacttc agatctccta tgtgtattgg aattaataga cagtagttat tggaagtcta  13860
tgtctaaggt gtttttagaa caaaaagtta tcaaatacat tcttagccag gatgcaagtt  13920
tacatagagt aaaaggatgt catagcttca aactatggtt tcttaaacgt cttaatgtag  13980
cagaattcac agtttgccct tgggttgtta acatagatta tcatccaaca catatgaaag  14040
caatattaac ttatattgat cttgttagaa tgggattgat aaatatagat agaatataca  14100
ttaaaaataa acacaagttc aatgatgagt tttatacttc taatctgttt tacattaatt  14160
ataacttctc agataatact catctattaa ctaaacatat aaggattgct aattccgaat  14220
tagaaagtaa ttacaacaaa ttatatcatc ctacaccaga aaccctagaa aatatactaa  14280
ccaatccggt taaaagtaat gagaaaaaga cactgagtga ctattgtata ggtaaaaatg  14340
```

```
ttgactcaat aatgttacca tcgttatcta ataagaagct tattaaatcg tctacaatga  14400
ttagaaccaa ttacagcaga caagatttgt ataatttatt tcctacggtt gtgattgata  14460
aaattataga tcattcaggt aatacagcca aatctaacca actttacact actacttctc  14520
atcaaatatc cttagtgcac aatagcacat cactttattg catgcttcct tggcatcata  14580
ttaatagatt caattttgta tttagttcta caggttgtaa aattagtata gagtatattt  14640
taaaagatct taaaattaag gatcctaatt gtatagcatt cataggtgaa ggagcaggga  14700
atttattatt gcgtacagta gtggaacttc atcctgatat aagatatatt tacagaagtc  14760
tgaaagattg caatgatcat agtttaccaa ttgagttttt aaggctgtac aatggacata  14820
tcaacattga ttatggtgaa aatttgacca ttcctgctac agatgcaacc aacaacattc  14880
attggtctta tttacatata aagtttgctg aacctatcag tctttttgtc tgtgatgctg  14940
aattgcctgt aacagtcaac tggagtaaga ttataataga gtggagcaag catgtaagaa  15000
aatgcaagta ctgttcttca gttaataaat gtacattgat agtaaaatat catgctcaag  15060
atgatatcga tttcaaatta gacaacataa ctatattaaa aacttatgta tgcttaggta  15120
gtaagttaaa gggatctgaa gtttacttag tccttacaat aggtcctgca aatgtgttcc  15180
cagtatttaa tgtagtacaa aatgctaaat tgatactatc aagaactaaa aatttcatca  15240
tgcctaaaaa agctgataaa gagtctattg atgcaaatat taagagtttg ataccctttc  15300
tttgttaccc tataacaaaa aaaggaatta atactgcatt gtctaaatta aagagtgttg  15360
ttagtggaga tatactatca tattctatag ctggacgtaa tgaagttttc agcaataaac  15420
ttataaatca taagcatatg aacatcttaa agtggttcaa tcatgtttta aatttcagat  15480
caacagaatt aaactataat catttatata tggtagaatc tacttatcct catctaagtg  15540
aattgttaaa cagcttgaca accaatgaac ttaaaaaact gattaaaatc acaggtagtt  15600
tgttatacaa cttttataat gaataatgag caaaaatctt ataacaaaaa tagctacaca  15660
ctaacattgt attcaattat agttattgaa aattaataat tatataattt ttaataactt  15720
ctagtgaact aatcctaaaa ttatcatttt gatctaggaa gaataagttt aaatccaaat  15780
ctaattggtt tatatgtata ttaactaaat tacgagatat tagtttttga cacttttttt  15840
ctcgt                                                             15845
```

<210> SEQ ID NO 14
<211> LENGTH: 16823
<212> TYPE: DNA
<213> ORGANISM: Artificial Sequence
<220> FEATURE:
<223> OTHER INFORMATION: A sequence in which SEQ ID NO: 11 was digested with AscI and Sbfl and replaced with deoptimized NS1 and NS2 coding regions.

<400> SEQUENCE: 14

```
acgcgaaaaa atgcgtacaa caaacttgcg taaaccaaaa aaatggggca aataagaatt     60
tgataagtac cacttaaatt taactccttt ggttagaggc gcgccatggg ttcgaattcg    120
ctatcgatga taaaagtacg tctacaaaat ctatttgata atgatgaagt agcgctacta    180
aaaataacgt gttatacgga taaactaata caactaacga atgcgctagc gaaagcggta    240
atacatacga taaaactaaa tggtatagta tttgtacatg taataacgtc gtcggatata    300
tgtccgaata ataatatagt agtaaaatcg aattttacga cgatgccggt actacaaaat    360
ggtggttata tatgggaaat gatggaacta acgcattgtt cgcaaccgaa tggtctaata    420
```

-continued

```
gatgataatt gtgaaataaa attttcgaaa aaactatcgg attcgacgat gacgaattat    480
atgaatcaac tatcggaact actaggtttt gatctaaatc cgtaaatcat aataaatatc    540
aactagcaaa tcaatgtcac taacaccatt agttaatata aaacttgaca gaagataaaa    600
atggggcaaa taaatcaatt cagccgaccc aaccatggat acgacgcata atgatacgac    660
gccgcaacgt ctaatgataa cggatatgcg tccgctatcg ctagaaacga taataacgtc    720
gctaacgcga gatataataa cgcataaatt tatatatcta ataaatcatg aatgtatagt    780
acgtaaacta gatgaacgtc aagcgacgtt tacgtttcta gtaaattatg aaatgaaact    840
actacataaa gtaggttcga cgaaatataa aaaatatacg gaatataata cgaaatatgg    900
tacgtttccg atgccgatat ttataaatca tgatggtttt ctagaatgta taggtataaa    960
accgacgaaa catacgccga taatatataa atatgatcta aatccgtgaa tatcaaacca   1020
agattcaaac aatccgaaat aacaacttta tgcataatca cactccatag tccaaatgga   1080
gcctgaaaat tatagttatt taaaattcct gcaggaagga gagacataag atgaaagatg   1140
gggcaaatac aaaaatggct cttagcaaag tcaagttgaa tgatacactc aacaaagatc   1200
aacttctatc atccagcaaa tataccatcc aacggagcac aggagacagc attgacactc   1260
ctaattatga tgtgcagaaa cacattaata agttatgtgg catgttatta atcacagaag   1320
atgctaatca taaattcact gggttaatag gtatgttata tgctatgtct agattaggaa   1380
gagaagacac cataaaaata ctcaaagatg cgggatatca tgttaaggca aatggagtgg   1440
atgtaacaac acatcgtcaa gacattaatg ggaaagaaat gaaatttgaa gtgttaacat   1500
tagcaagctt aacaactgaa attcaaatca acattgagat agaatctaga aaatcctaca   1560
aaaaaatgct aaaagaaatg ggagaggtgg ctccagaata caggcatgac tctcctgatt   1620
gtgggatgat aatattatgt atagcggcat tagtaataac caaattagca gcaggagata   1680
gatcaggtct tacagctgtg attaggagag ctaataatgt cctaaaaaat gaaatgaaac   1740
gttataaagg tttattaccc aaggatatag ccaacagctt ctatgaagtg tttgaaaaat   1800
atcctcactt tatagatgtt tttgttcatt ttggtatagc acaatcttct accagaggtg   1860
gcagtagagt tgaagggatt tttgcaggat tgtttatgaa tgcctatggt gcagggcaag   1920
tgatgttacg gtggggggtc ttagcaaaat cagttaaaaa cattatgtta ggacacgcta   1980
gtgtacaagc agaaatggaa caagttgtgg aggtgtatga gtatgctcag aaattgggtg   2040
gagaagcagg attctaccat atattgaaca acccaaaagc atcactatta tctttgactc   2100
aatttcctca cttctctagt gtagtattgg gcaatgctgc tggcctaggc ataatgggag   2160
aatacagagg tacaccaagg aatcaagatt tatatgatgc tgcaaaagca tatgctgaac   2220
aactcaaaga aaatggtgtg attaactaca gtgtattaga tttgacagca gaagaactag   2280
aggctatcaa acatcagctt aatccaaaag ataatgatgt agagctttga gttaataaaa   2340
aagtggggca aataaatcat catggaaaag tttgctcctg aattccatgg agaagatgca   2400
aacaacagag ccaccaaatt cctagaatca ataaagggca aattcacatc acccaaagat   2460
cccaagaaaa aagatagtat catatctgtc aactcaatag atatagaagt aaccaaagaa   2520
agccctataa catcaaattc aaccattata aacccaataa atgagacaga tgatactgta   2580
gggaacaagc ccaattatca aagaaagcct ctagtaagtt tcaaagaaga ccctacgcca   2640
agtgataatc ctttttcaaa actatacaaa gaaaccatag aaacatttga taacaatgaa   2700
gaagaatcta gctattcata tgaagaaata aatgatcaga caaacgataa tataacagca   2760
agattagata ggattgatga gaaattaagt gaaatactag gaatgcttca cacattagta   2820
```

-continued

```
gtagcgagtg caggacccac atctgctcgg gatggtataa gagatgccat ggttggttta   2880
agagaagaaa tgatagaaaa aatcagaact gaagcattaa tgaccaatga cagactagaa   2940
gctatggcaa gactcaggaa tgaagaaagt gaaaagatgg caaaagacac atcagatgaa   3000
gtgtctctca atccaacatc agagaaactg aacaacctgt tggaagggaa tgatagtgac   3060
aatgatctat cacttgaaga tttctgatta gctaccaaac tgtacatcaa aacacaacac   3120
caatagaaaa ccaacaaaca aaccaactca cccatccaac caaacatcta tctgctgatt   3180
agccaaccag ccaaaaaaca accagccaat ctaaaactag ccacccggaa aaaatcgata   3240
ctatagttac aaaaaaagat ggggcaaata tggaaacata cgtgaataaa cttcacgagg   3300
gctccacata cacagctgct gttcaataca atgtcctaga aaaagacgat gatcctgcat   3360
cacttacaat atgggtgccc atgttccaat catccatgcc agcagatcta ctcataaaag   3420
aactagccaa tgtcaatata ctagtgaaac aaatatccac acccaaggga ccctcattaa   3480
gagtcatgat aaactcaaga agtgcagtgc tagcacaaat gcccagcaaa tttaccatat   3540
gtgccaatgt gtccttggat gaaagaagca agctggcata tgatgtaacc acaccctgtg   3600
aaattaaggc atgcagtcta acatgcctaa aatcaaaaaa tatgttaact acagttaaag   3660
atctcactat gaaaacactc aacccaacac atgacatcat tgctttatgt gaatttgaaa   3720
atatagtaac atcaaaaaaa gtcataatac caacatacct aagatctatc agcgtcagaa   3780
ataaagatct gaacacactt gaaaatataa caaccactga attcaaaaat gccattacaa   3840
atgcaaaaat catcccttac tcaggattat tgttagtcat cacagtgact gacaacaaag   3900
gagcattcaa atacataaag ccacaaagtc aattcatagt agatcttgga gcttacctag   3960
aaaaagaaag tatatattat gttacaacaa attggaagca cacagctaca cgatttgcaa   4020
tcaaacccat ggaagattaa ccttttttcct ctacatcaat gagtagattc atacaaactt   4080
tctaactaca ttcttcactt cacaatcata atcaccaacc ctctgtggtt caatcaatca   4140
aacaaaactc atcaagagtt ccagatcatc ccaagtcatt gttcatcaga tccagtactc   4200
aaataagtta ataaaaaatc cacatggggc aaataatcat tgagggaaat ccaactaatc   4260
acaacatctg tcaacataga caagtcaaca cgctagataa aatcaaccaa tggaaaatac   4320
atccataact atagaattct caagcaaatt ctggccttac tttacactaa tacacatgat   4380
aacaacaata atctctttga taatcataat ctccatcatg attgcaatac taaacaaact   4440
ctgcgaatat aatgtattcc ataacaaaac ctttgagcta ccaagagctc gagtcaatac   4500
atagcattca ccaatctgat agctcaaaac agtaaccttg catttgtaaa tgaactaccc   4560
tcacttcttc acaaaaccac atcaacatct caccatgcaa gccatcatct ataccataaa   4620
gtagttaatt aaaaatggcc ggccagtcat aacaatgaac taggatatta agaccaaaaa   4680
caacgctggg gcaaatgcaa acatgtccaa aaccgaggac caacgcaccg ccaagacact   4740
agaaaggacc tgggacactt ttaatcatct attattcata tcatcgtgct tatacaagtt   4800
aaatcttaaa tctatagcac aaatcacatt atctattttg gcaattataa tctcaacctc   4860
acttataatt gcagccatca tattcatagc ctcggcaaac cacaaagtca cactaacaac   4920
tgcaatcata caagatgcaa cgaaccagat caagaacaca accccaacat acctcaccca   4980
gaatccccag catggaatca gcttctccaa tctgtccgga actacatcac aatccaccac   5040
catactagct tcaacaacac caagtgctga ttcaacccca caatccacaa cagtcaagat   5100
caaaaacaca acaacaaccc aaatattacc tagcaaaccc accacaaaac aacgccaaaa   5160
```

```
taaaccacaa aacaaaccca acaatgattt tcactttgaa gtgttcaatt ttgtaccctg   5220

cagcatatgc agcaacaatc caacctgctg ggccatctgc aagagaatac caaacaaaaa   5280

acctggaaag aaaaccacca ccaagcccac aaaaaaacca accctcaaga caaccaaaaa   5340

agatcccaaa tcccaaacca caaaaccaaa ggaagtactc actaccaagc ctacaggaaa   5400

gccaaccatc aacaccacta aaacaaacat cagaactaca ctgctcacct ccaacaccaa   5460

aggaaatcca gaacacacaa gtcaagagga aaccctccac tcaaccacct ccgaaggcta   5520

tccaagccca tcacaagtcc acacaacatc cggtcaagag gaaaccctcc actcaaccac   5580

ctccgaaggc tatccaagcc catcacaagt ctacacaaca tccgagtacc tatcacaatc   5640

tctatcttca tccaacacaa caaaatgata gtcattaaaa agcacgcgtt tgacagaaga   5700

taaaaatggg gcaaatgcaa acatgaagtg ccttttgtac ttagcctttt tattcattgg   5760

ggtgaattgc aagttcacca tagtttttcc acacaaccaa aaaggaaact ggaaaaatgt   5820

tccttctaat taccattatt gcccgtcaag ctcagattta aattggcata atgacttaat   5880

aggcacagcc ttacaagtca aaatgcccaa gagtcacaag gctattcaag cagacggttg   5940

gatgtgtcat gcttccaaat gggtcactac ttgtgatttc cgctggtatg gaccgaagta   6000

tataacacat tccatccgat ccttcactcc atctgtagaa caatgcaagg aaagcattga   6060

acaaacgaaa caaggaactt ggctgaatcc aggcttccct cctcaaagtt gtggatatgc   6120

aactgtgacg gatgccgaag cagtgattgt ccaggtgact cctcaccatg tgctggttga   6180

tgaatacaca ggagaatggg ttgattcaca gttcatcaac ggaaaatgca gcaattacat   6240

atgccccact gtccataact ctacaacctg gcattctgac tataaggtca aagggctatg   6300

tgattctaac ctcatttcca tggacatcac cttcttctca gaggacggag agctatcatc   6360

cctgggaaag gagggcacag ggttcagaag taactacttt gcttatgaaa ctggaggcaa   6420

ggcctgcaaa atgcaatact gcaagcattg gggagtcaga ctcccatcag gtgtctggtt   6480

cgagatggct gataaggatc tctttgctgc agccagattc cctgaatgcc cagaagggtc   6540

aagtatctct gctccatctc agacctcagt ggatgtaagt ctaattcagg acgttgagag   6600

gatcttggat tattccctct gccaagaaac ctggagcaaa atcagagcgg gtcttccaat   6660

ctctccagtg gatctcagct atcttgctcc taaaaaccca ggaaccggtc ctgctttcac   6720

cataatcaat ggtaccctaa aatactttga gaccagatac atcagagtcg atattgctgc   6780

tccaatcctc tcaagaatgg tcggaatgat cagtggaact accacagaaa gggaactgtg   6840

ggatgactgg gcaccatatg aagacgtgga aattggaccc aatggagttc tgaggaccag   6900

ttcaggatat aagtttcctt tatacatgat tggacatggt atgttggact ccgatcttca   6960

tcttagctca aaggctcagg tgttcgaaca tcctcacatt caagacgctg cttcgcaact   7020

tcctgatgat gagagtttat tttttggtga tactgggcta tccaaaaatc caatcgagct   7080

tgtagaaggt tggttcagta gttggaaaag ctctattgcc tctttttttct ttatcatagg   7140

gttaatcatt ggactattct tggttctccg agttggtatc catctttgca ttaaagccag   7200

aagcacacca gtcacattaa gtaaggatca actgagtggt ataaataata ttgcatttag   7260

taactaatag tcattaaaaa gcgggcccgt attgttgcaa aaagccatga ccaaatcaaa   7320

cagaatcaaa atcaactctg ggcaaataa caatggagtt gccaatcctc aaaacaaatg   7380

ctattaccac aatccttgct gcagtcacac tctgtttcgc ttccagtcaa aacatcactg   7440

aagaatttta tcaatcaaca tgcagtgcag tcagcaaagg ctatcttagt gctctaagaa   7500

ctggttggta tactagtgtt ataactatag aattaagtaa tatcaaggaa aataagtgta   7560
```

atggtacaga cgctaaggta aaattaataa aacaagaatt agataaatat aaaaatgctg 7620
taacagaatt gcagttgctc atgcaaagca caccagcagc caacaatcga gccagaagag 7680
aactaccaag atttatgaat tatacactca acaataccaa aaacaccaat gtaacattaa 7740
gtaagaaaag gaaaagaaga tttcttggat ttttgttagg tgttggatct gcaatcgcca 7800
gtggcattgc cgtatccaag gtcctgcacc tagaagggga agtgaacaaa atcaaaagtg 7860
ctctactatc cacaaacaag gctgtagtca gcttatctaa tggagtcagt gtcttaacca 7920
gcaaggtgtt agacctcaaa aactatatag ataaacagtt gttacctatt gttaacaagc 7980
aaagctgcag catatcaaac attgaaactg tgatagagtt ccaacaaaag aacaacagac 8040
tactagagat taccagagaa tttagtgtta atgcaggtgt aactactcct gtaagcactt 8100
atatgttaac taatagtgag ttattatcat taatcaatga tatgcctata acaaatgatc 8160
agaaaaagtt aatgtccagc aatgttcaaa tagttagaca gcaaagttac tctatcatgt 8220
caataataaa agaggaagtc ttggcatatg tagtacaatt accactatat ggtgtaatag 8280
atactccttg ttggaaacta cacacatccc ctttatgtac aaccaacaca aaggaaggat 8340
ccaacatctg cttaacaaga accgacagag gatggtactg tgacaatgca ggatcagtat 8400
cctttttccc acaagctgaa acatgtaaag ttcaatcgaa tcgggtgttt tgtgacacaa 8460
tgaacagttt aacattacca agtgaggtaa atctctgcaa cattgacata ttcaacccca 8520
aatatgattg caaaattatg acttcaaaaa cagatgtaag cagctccgtt atcacatctc 8580
taggagccat tgtgtcatgc tatggcaaaa ccaaatgtac agcatccaat aaaaatcgtg 8640
ggatcataaa gacattctct aacgggtgtg attatgtatc aaataagggg gtggatactg 8700
tgtctgtagg taatacatta tattatgtaa ataagcaaga aggcaaaagt ctctatgtaa 8760
aaggtgaacc aataataaat ttctatgatc cattagtgtt cccctctctc ctgtgggatg 8820
catcaatatc tcaagtcaat gagaaaatta atcagagtct agcatttatc cgtaaatcag 8880
atgaattatt aggctctggc ggaagcggat acatccctga ggcaccaagg gacggacagg 8940
cctacgtgcg caaggatggc gagtgggtgc tgctgtccac ctttctgtga ataaaaatag 9000
cacctaatca tattcttaca atggttcgct atttgaccat agataaccca tctatcatta 9060
gattatccta aaatttgaac ttcatcacaa ctttcatcta taaaccatct cacttacact 9120
ttttaagtag atttctattt tatagttata taaaacaggg cccattgaat accaaattaa 9180
cttactattt gtaaaaatga gaattggggc aaatatgtca cgaaggaatc cttgcaaatt 9240
cgaaattcga ggtcattgct tgaatggtaa aaggtgtcat tttagtcata attattttga 9300
atggccaccc catgcactgc ttgtaagaca aaactttatg ttaaacagaa tacttaagtc 9360
tatggataaa agcatagata ctttgtcaga aataagtgga gctgcagagt tggacagaac 9420
agaagagtat gccctcggtg tagttggagt gctagagagt tatataggat caataaataa 9480
tataactaaa caatcagcat gtgttgccat gagcaaactc cttactgaac tcaacagcga 9540
tgacatcaaa aaactaaggg acaatgaaga gccaaactca cccaaagtaa gagtgtacaa 9600
tactgtcata tcatatattg aaagcaacag gaagaacaat aaacaaacta tccatctgtt 9660
aaaaagattg ccagcagacg tattgaagaa aaccatcaaa aacacattgg atatccacaa 9720
gagcataacc atcaataacc caaaagaatc aactgttagt gatacgaacg accatgccaa 9780
aaataatgat actacctgac aaatatcctt gtagtataaa ttccatacta ataacaagta 9840
attgtagagt cactatgtat aatcaaaaaa acacactata tatcaatcaa aacaaccaaa 9900

```
atagccatat atacccaccg gatcaaccat tcaatgaaat ccattggacc tctcaagact   9960
tgattgatgc aactcaaaat tttctacaac atctaggtat tactgatgat atatacacaa  10020
tatatatatt agtgtcataa tactcaatcc taatacttac cacatcatca aattattaac  10080
tcaaacaatt caagctatgg gacaaaatgg atcccattat tagtggaaat tctgctaatg  10140
tttatctaac tgatagttat ttaaaaggtg ttatttcttt ctcagaatgt aacgctttag  10200
gaagttacat attcaatggt ccttatctca aaaatgatta taccaactta attagtagac  10260
aaaatccatt aatagaacac ataaatctaa agaaactaaa tataacacag tccttaatat  10320
ctaagtatca taaaggtgaa ataaaaatag aagaacctac ttactttcag tcattactta  10380
tgacatacaa gagtatgacc tcttcagaac agactactac tactaattta cttaaaaaga  10440
taataagaag agctatagaa atcagtgatg tcaaagtcta tgctatattg aataaactgg  10500
ggctcaaaga aaaagacaag attaaatcca ataatggaca agatgaagac aactcagtca  10560
ttactaccat aatcaaagat gatatacttt tagctgtcaa ggataatcaa tctcatctta  10620
aagcagacaa aaatcaatcc acaaaacaaa aagatacaat caaaacaaca cttttgaaga  10680
aattaatgtg ttcgatgcaa catcctccat catggttaat acattggttt aatttataca  10740
caaaattaaa cagcatatta acacaatatc gatctagtga ggtaaaaaac catggtttta  10800
tattgataga taatcatact cttagtggat tccaatttat tttgaatcaa tatggttgta  10860
tagtttatca taaggaactc aaaagaatta ctgtgacaac ttataatcaa ttcttgacat  10920
ggaaagatat tagccttagt agattaaatg tttgtttgat tacatggatt agtaactgtt  10980
tgaacacatt aaacaaaagc ttaggcttaa gatgtggatt caataatgtt atcttgacac  11040
aattattcct ttatggagat tgtatactaa aactattcca caatgagggg ttctacataa  11100
taaaagaggt agagggattt attatgtctc taattttaaa tataacagaa gaagatcaat  11160
tcagaaaacg gttttataat agtatgctca acaacatcac agatgccgcc aacaaagctc  11220
aaaaaaatct gctatcaaga gtatgtcata cattattaga taagacaata tcagataata  11280
taataaatgg cagatggata attctattga gtaagttcct aaaattaatt aagcttgcag  11340
gtgacaataa cctcaacaat ctgagtgaat tatatttttt gttcagaata tttggacacc  11400
caatggtaga tgaaagacaa gccatggatg ctgttaaagt taattgcaac gagaccaaat  11460
tttatttgtt aagtagtttg agtatgttaa gaggagcttt tatatataga attataaaag  11520
ggtttgtaaa taattacaac agatggccta ctttaagaaa tgccattgtc ttacccttaa  11580
gatggttaac ttactataaa ctaaacactt atccttcctt gttggaactt acagaaagag  11640
atttgattgt tctatcagga ctacgtttct atcgagagtt tcggttgcct aaaaaagtgg  11700
atcttgaaat gatcataaat gataaggcta tatcacctcc taaaaattta atatggacta  11760
gtttccctag aaattatatg ccgtcacaca tacaaaatta tatagaacat gaaaaattaa  11820
aattctctga tagtgataaa tcaagaagag tattagagta ttatttaaga gataacaaat  11880
tcaatgaatg tgatttacac aactgtgtag ttaatcaaag ttatcttaac aacccgaatc  11940
atgtggtatc attgacaggc aaagaaagag aactcagtgt aggtagaatg tttgcaatgc  12000
aaccaggaat gttcagacaa gttcaaatat tagcagagaa aatgatagca gaaaacatat  12060
tacaattttt ccctgaaagt cttacaagat atggtgatct agaactacag aaaatattag  12120
aattgaaagc aggaataagt aacaaatcaa atcgttacaa tgataattac aacaattaca  12180
ttagtaagtg ctctatcatc acagatctca gcaaattcaa tcaagcattt cgatatgaaa  12240
catcatgtat ttgtagtgat gtactggatg aactgcatgg tgtacaatct ctattttcct  12300
```

```
ggttacattt aactattcct catgtcacaa taatatgcac atataggcat gcaccccccct  12360
atataaagga tcatattgta gatcttaaca atgtagatga gcaaagtgga ctatatagat  12420
atcatatggg tggtatcgaa gggtggtgtc aaaaactatg gaccatagaa gctatatcac  12480
tattagatct aatatctctc aaagggaaat tctcaattac tgctttaatt aatggtgaca  12540
atcaatcaat agatataagt aaaccagtca gactcatgga aggtcaaact catgctcaag  12600
cagattattt gctagcatta aatagtctca aattactgta taaagagtat gcaggaatag  12660
gccacaaatt aaaaggaact gagacttata tatcgagaga tatgcaattt atgagtaaaa  12720
cgatccaaca taacggtgta tattacccag ctagtataaa gaaagtccta agagtgggac  12780
cgtggataaa cactatactt gatgacttca aagtgagtct agaatctata ggtagtttga  12840
cacaagaatt agaatataga ggtgaaagtc tattatgcag tttaatattt agaaatgtat  12900
ggttatataa tcaaattgca ttacaactta aaaatcatgc attatgtaac aacaaattat  12960
atttggatat attaaaagtt ctaaaacact taaaaacctt ttttaatctt gataacattg  13020
atacagcatt aacattgtat atgaatttgc ccatgttatt tggtggtggt gatcccaact  13080
tgttatatcg aagtttctat agaagaactc ctgatttcct cacagaggct atagttcact  13140
ctgtgttcat acttagttat tatacaaacc atgatttaaa agataaactt caagatctgt  13200
cagatgatag attgaataag ttcttaacat gcataatcac gtttgataaa aaccccaatg  13260
ctgaattcgt tacattgatg agagatcctc aagctttagg atctgagagg caagctaaaa  13320
ttactagcga aatcaataga ctggcagtta ccgaggtttt gagcacagct ccaaacaaaa  13380
tattttccaa aagtgcacaa cactatacca ctacagagat agatcttaat gatattatgc  13440
aaaatataga acctacatat cctcacgggc taagagttgt ttatgagagt ttaccctttt  13500
ataaagcaga gaaaatagta aatcttatat ccggtacaaa atctataact aacatactgg  13560
aaaagacttc tgccatagac ttaacagata ttgatagagc cactgagatg atgaggaaaa  13620
acataacttt gcttataagg atattaccat tagattgtaa cagagataaa agagaaatat  13680
tgagtatgga aaacctaagt attactgaat taagcaaata cgttagagaa agatcttggt  13740
ctttatccaa tatagttggt gttacatcac ccagtatcat gtatacaatg gacataaaat  13800
atacaacaag cactatagct agtggcataa tcatagagaa atataatgtc aacagtttaa  13860
cacgtggtga gagaggaccc actaaaccat gggttggttc atctacacaa gagaaaaaga  13920
caatgccagt ttataataga caagttttaa ccaaaaaaca gagagatcaa atagatctat  13980
tagcaaaatt ggattgggtg tatgcatcta tagataacaa ggatgaattt atggaggaac  14040
ttagcatagg aactcttggg ttaacatatg agaaggccaa aaaattattc ccacaatatt  14100
tgagtgttaa ctatttgcat cgtcttacag tcagtagtag accatgtgaa ttccctgcat  14160
ctataccagc ttatagaact acaaattatc actttgatac tagccctatt aatcgcatat  14220
taacagaaaa gtatggtgat gaagatattg atatagtatt ccaaaactgt ataagctttg  14280
gccttagctt aatgtctgta gtagaacaat ttactaatgt atgtcctaac agaattattc  14340
tcatacccaa gcttaatgag atacatttga tgaaacctcc catattcaca ggcgatgttg  14400
atattcacaa gttaaaacaa gtgatacaaa aacaacatat gtttttacca gacaaaataa  14460
gtttgactca atatgtggaa ttattcttaa gtaataaaac actcaaatct ggatctaatg  14520
ttaattctaa tttaatattg gcgcataaga tatctgacta ttttcataat acttacattt  14580
tgagtactaa tttagctgga cattggattc ttattataca acttatgaaa gattctaagg  14640
```

-continued

```
gtatttttga aaaagattgg ggagagggat atataactga tcatatgttc attaatttga  14700
aagttttctt caatgcttat aagacatatc tcttgtgttt tcataaaggt tacggcagag  14760
caaagctgga gtgtgatatg aatacttcag atctcctatg tgtattggaa ttaatagaca  14820
gtagttattg gaagtctatg tctaaggtgt ttttagaaca aaaagttatc aaatacattc  14880
ttagccagga tgcaagttta catagagtaa aaggatgtca tagcttcaaa ctatggtttc  14940
ttaaacgtct taatgtagca gaattcacag tttgcccttg ggttgttaac atagattatc  15000
atccaacaca tatgaaagca atattaactt atattgatct tgttagaatg ggattgataa  15060
atatagatag aatatacatt aaaaataaac acaagttcaa tgatgagttt tatacttcta  15120
atctgtttta cattaattat aacttctcag ataatactca tctattaact aaacatataa  15180
ggattgctaa ttccgaatta gaaagtaatt acaacaaatt atatcatcct acaccagaaa  15240
ccctagaaaa tatactaacc aatccggtta aaagtaatga gaaaaagaca ctgagtgact  15300
attgtatagg taaaaatgtt gactcaataa tgttaccatc gttatctaat aagaagctta  15360
ttaaatcgtc tacaatgatt agaaccaatt acagcagaca agatttgtat aatttatttc  15420
ctacggttgt gattgataaa attatagatc attcaggtaa tacagccaaa tctaaccaac  15480
tttacactac tacttctcat caaatatcct tagtgcacaa tagcacatca ctttattgca  15540
tgcttccttg gcatcatatt aatagattca attttgtatt tagttctaca ggttgtaaaa  15600
ttagtataga gtatatttta aaagatctta aaattaagga tcctaattgt atagcattca  15660
taggtgaagg agcagggaat ttattattgc gtacagtagt ggaacttcat cctgatataa  15720
gatatattta cagaagtctg aaagattgca atgatcatag tttaccaatt gagtttttaa  15780
ggctgtacaa tggacatatc aacattgatt atggtgaaaa tttgaccatt cctgctacag  15840
atgcaaccaa caacattcat tggtcttatt tacatataaa gtttgctgaa cctatcagtc  15900
tttttgtctg tgatgctgaa ttgcctgtaa cagtcaactg gagtaagatt ataatagagt  15960
ggagcaagca tgtaagaaaa tgcaagtact gttcttcagt taataaatgt acattgatag  16020
taaaatatca tgctcaagat gatatcgatt tcaaattaga caacataact atattaaaaa  16080
cttatgtatg cttaggtagt aagttaaagg gatctgaagt ttacttagtc cttacaatag  16140
gtcctgcaaa tgtgttccca gtatttaatg tagtacaaaa tgctaaattg atactatcaa  16200
gaactaaaaa tttcatcatg cctaaaaaag ctgataaaga gtctattgat gcaaatatta  16260
agagtttgat accctttctt tgttacccta taacaaaaaa aggaattaat actgcattgt  16320
ctaaattaaa gagtgttgtt agtggagata tactatcata ttctatagct ggacgtaatg  16380
aagttttcag caataaactt ataaatcata agcatatgaa catcttaaag tggttcaatc  16440
atgttttaaa tttcagatca acagaattaa actataatca tttatatatg gtagaatcta  16500
cttatcctca tctaagtgaa ttgttaaaca gcttgacaac caatgaactt aaaaaactga  16560
ttaaaatcac aggtagtttg ttatacaact tttataatga ataatgagca aaaatcttat  16620
aacaaaaata gctacacact aacattgtat tcaattatag ttattgaaaa ttaataatta  16680
tataattttt aataacttct agtgaactaa tcctaaaatt atcattttga tctaggaaga  16740
ataagtttaa atccaaatct aattggttta tatgtatatt aactaaatta cgagatatta  16800
gtttttgaca cttttttct cgt                                          16823
```

<210> SEQ ID NO 15
<211> LENGTH: 15311
<212> TYPE: DNA
<213> ORGANISM: Artificial Sequence
<220> FEATURE:
<223> OTHER INFORMATION: A sequence modifying the furin cleavage site II
of the F gene included in SEQ ID NO: 1

<400> SEQUENCE: 15
acgcgaaaaa atgcgtacaa caaacttgcg taaaccaaaa aaatggggca aataagaatt 60
tgataagtac cacttaaatt taactccttt ggttagaggc gcgccatggg cagcaactca 120
ttgagtatga taaaagttag attgcaaaat ctgtttgaca atgatgaagt agcattgtta 180
aaaataacat gctatactga caaattaata cagttaacta atgctttggc taaggcagtt 240
atacatacaa tcaaattgaa tggcattgta tttgtgcatg ttattacaag tagtgatatt 300
tgccctaata ataatattgt agtgaaatcc aatttcacaa caatgccagt attacaaaat 360
ggaggttata tatgggaaat gatggaatta acacactgct ctcaacctaa tggcctaata 420
gatgacaatt gtgaaattaa attctccaaa aaactaagtg attcaacaat gaccaattat 480
atgaatcaat tatctgaatt acttggattt gacctcaatc cataaatcat aataaatatc 540
aactagcaaa tcaatgtcac taacaccatt agttaatata aaacttgaca gaagataaaa 600
atggggcaaa taaatcaatt cagccgaccc aaccatggac acaacacaca atgataccac 660
accacaaaga ctgatgatca cagacatgag gccattatcg cttgagacta taataacatc 720
tctaaccaga gatatcataa cacataaatt tatatacttg ataaatcatg aatgcatagt 780
aagaaaactt gatgaaagac aggccacatt tacatttctg gtcaactatg aaatgaaact 840
attgcacaaa gtgggaagca ctaaatataa aaaatatact gaatacaaca caaaatatgg 900
cactttccct atgccaatat ttatcaatca tgatgggttc ttagaatgca ttggcattaa 960
gcctaccaag cacacaccca taatatacaa gtatgatctc aatccatgaa tatcaaacca 1020
agattcaaac aatccgaaat aacaacttta tgcataatca cactccatag tccaaatgga 1080
gcctgaaaat tatagttatt taaaattcct gcaggaagga gagacataag atgaaagatg 1140
gggcaaatac aaaaatggct cttagcaaag tcaagttgaa tgatacactc aacaaagatc 1200
aacttctatc atccagcaaa tataccatcc aacggagcac aggagacagc attgacactc 1260
ctaattatga tgtgcagaaa cacattaata agttatgtgg catgttatta atcacagaag 1320
atgctaatca taaattcact gggttaatag gtatgttata tgctatgtct agattaggaa 1380
gagaagacac cataaaaata ctcaaagatg cgggatatca tgttaaggca aatggagtgg 1440
atgtaacaac acatcgtcaa gacattaatg ggaaagaaat gaaatttgaa gtgttaacat 1500
tagcaagctt aacaactgaa attcaaatca acattgagat agaatctaga aaatcctaca 1560
aaaaaatgct aaaagaaatg ggagaggtgg ctccagaata caggcatgac tctcctgatt 1620
gtgggatgat aatattatgt atagcggcat tagtaataac caaattagca gcaggagata 1680
gatcaggtct tacagctgtg attaggagag ctaataatgt cctaaaaaat gaaatgaaac 1740
gttataaagg tttattaccc aaggatatag ccaacagctt ctatgaagtg tttgaaaaat 1800
atcctcactt tatagatgtt tttgttcatt ttggtatagc acaatcttct accagaggtg 1860
gcagtagagt tgaagggatt tttgcaggat tgtttatgaa tgcctatggt gcagggcaag 1920
tgatgttacg gtgggggg tc ttagcaaaat cagttaaaaa cattatgtta ggacacgcta 1980
gtgtacaagc agaaatggaa caagttgtgg aggtgtatga gtatgctcag aaattgggtg 2040
gagaagcagg attctaccat atattgaaca acccaaaagc atcactatta tctttgactc 2100
aatttcctca cttctctagt gtagtattgg gcaatgctgc tggcctaggc ataatgggag 2160
aatacagagg tacaccaagg aatcaagatt tatatgatgc tgcaaaagca tatgctgaac 2220

```
aactcaaaga aaatggtgtg attaactaca gtgtattaga tttgacagca gaagaactag   2280
aggctatcaa acatcagctt aatccaaaag ataatgatgt agagctttga gttaataaaa   2340
aagtggggca aataaatcat catggaaaag tttgctcctg aattccatgg agaagatgca   2400
aacaacagag ccaccaaatt cctagaatca ataaagggca aattcacatc acccaaagat   2460
cccaagaaaa aagatagtat catatctgtc aactcaatag atatagaagt aaccaaagaa   2520
agccctataa catcaaattc aaccattata aacccaataa atgagacaga tgatactgta   2580
gggaacaagc ccaattatca aagaaagcct ctagtaagtt tcaaagaaga ccctacgcca   2640
agtgataatc ctttttcaaa actatacaaa gaaaccatag aaacatttga taacaatgaa   2700
gaagaatcta gctattcata tgaagaaata aatgatcaga caaacgataa tataacagca   2760
agattagata ggattgatga gaaattaagt gaaatactag gaatgcttca cacattagta   2820
gtagcgagtg caggacccac atctgctcgg gatggtataa gagatgccat ggttggttta   2880
agagaagaaa tgatagaaaa aatcagaact gaagcattaa tgaccaatga cagactagaa   2940
gctatggcaa gactcaggaa tgaagaaagt gaaaagatgg caaaagacac atcagatgaa   3000
gtgtctctca atccaacatc agagaaactg aacaacctgt tggaagggaa tgatagtgac   3060
aatgatctat cacttgaaga tttctgatta gctaccaaac tgtacatcaa aacacaacac   3120
caatagaaaa ccaacaaaca aaccaactca cccatccaac caaacatcta tctgctgatt   3180
agccaaccag ccaaaaaaca accagccaat ctaaaactag ccacccggaa aaaatcgata   3240
ctatagttac aaaaaaagat ggggcaaata tggaaacata cgtgaataaa cttcacgagg   3300
gctccacata cacagctgct gttcaataca atgtcctaga aaaagacgat gatcctgcat   3360
cacttacaat atgggtgccc atgttccaat catccatgcc agcagatcta ctcataaaag   3420
aactagccaa tgtcaatata ctagtgaaac aaatatccac acccaaggga ccctcattaa   3480
gagtcatgat aaactcaaga agtgcagtgc tagcacaaat gcccagcaaa tttaccatat   3540
gtgccaatgt gtccttggat gaaagaagca agctggcata tgatgtaacc acaccctgtg   3600
aaattaaggc atgcagtcta acatgcctaa aatcaaaaaa tatgttaact acagttaaag   3660
atctcactat gaaaacactc aacccaacac atgacatcat tgctttatgt gaatttgaaa   3720
atatagtaac atcaaaaaaa gtcataatac caacatacct aagatctatc agcgtcagaa   3780
ataaagatct gaacacactt gaaaatataa caaccactga attcaaaaat gccattacaa   3840
atgcaaaaat catcccttac tcaggattat tgttagtcat cacagtgact gacaacaaag   3900
gagcattcaa atacataaag ccacaaagtc aattcatagt agatcttgga gcttacctag   3960
aaaaagaaag tatatattat gttacaacaa attggaagca cacagctaca cgatttgcaa   4020
tcaaacccat ggaagattaa ccttttttcct ctacatcaat gagtagattc atacaaactt   4080
tctaactaca ttcttcactt cacaatcata atcaccaacc ctctgtggtt caatcaatca   4140
aacaaaactc atcaagagtt ccagatcatc ccaagtcatt gttcatcaga tccagtactc   4200
aaataagtta ataaaaaatc cacatggggc aaataatcat tgagggaaat ccaactaatc   4260
acaacatctg tcaacataga caagtcaaca cgctagataa aatcaaccaa tggaaaatac   4320
atccataact atagaattct caagcaaatt ctggccttac tttacactaa tacacatgat   4380
aacaacaata atctctttga taatcataat ctccatcatg attgcaatac taaacaaact   4440
ctgcgaatat aatgtattcc ataacaaaac ctttgagcta ccaagagctc gagtcaatac   4500
atagcattca ccaatctgat agctcaaaac agtaaccttg catttgtaaa tgaactaccc   4560
```

-continued

```
tcacttcttc acaaaaccac atcaacatct caccatgcaa gccatcatct ataccataaa   4620
gtagttaatt aaaaatggcc ggccagtcat aacaatgaac taggatatta agaccaaaaa   4680
caacgctggg gcaaatgcaa acatgtccaa aaccgaggac caacgcaccg ccaagacact   4740
agaaaggacc tgggacactt ttaatcatct attattcata tcatcgtgct tatacaagtt   4800
aaatcttaaa tctatagcac aaatcacatt atctattttg gcaattataa tctcaacctc   4860
acttataatt gcagccatca tattcatagc ctcggcaaac cacaaagtca cactaacaac   4920
tgcaatcata caagatgcaa cgaaccagat caagaacaca accccaacat acctcaccca   4980
gaatccccag catggaatca gcttctccaa tctgtccgga actacatcac aatccaccac   5040
catactagct tcaacaacac caagtgctga ttcaacccca caatccacaa cagtcaagat   5100
caaaaacaca acaacaaccc aaatattacc tagcaaaccc accacaaaac aacgccaaaa   5160
taaaccacaa aacaaaccca acaatgattt tcactttgaa gtgttcaatt ttgtaccctg   5220
cagcatatgc agcaacaatc caacctgctg ggccatctgc aagagaatac caaacaaaaa   5280
acctggaaag aaaaccacca ccaagcccac aaaaaaacca accctcaaga caaccaaaaa   5340
agatcccaaa tcccaaacca caaaaccaaa ggaagtactc actaccaagc ctacaggaaa   5400
gccaaccatc aacaccacta aaacaaacat cagaactaca ctgctcacct ccaacaccaa   5460
aggaaatcca gaacacacaa gtcaagagga aaccctccac tcaaccacct ccgaaggcta   5520
tccaagccca tcacaagtcc acacaacatc cggtcaagag gaaaccctcc actcaaccac   5580
ctccgaaggc tatccaagcc catcacaagt ctacacaaca tccgagtacc tatcacaatc   5640
tctatcttca tccaacacaa caaaatgata gtcattaaaa agcacgcgtg tattgttgca   5700
aaaagccatg accaaatcaa acagaatcaa aatcaactct ggggcaaata acaatggagt   5760
tgccaatcct caaaacaaat gctattacca caatccttgc tgcagtcaca ctctgtttcg   5820
cttccagtca aaacatcact gaagaatttt atcaatcaac atgcagtgca gtcagcaaag   5880
gctatcttag tgctctaaga actggttggt atactagtgt tataactata gaattaagta   5940
atatcaagga aaataagtgt aatggtacag acgctaaggt aaaattaata aaacaagaat   6000
tagataaata taaaaatgct gtaacagaat tgcagttgct catgcaaagc acaccagcag   6060
ccaacaatcg accctccaag gaactaccaa gatttatgaa ttatacactc aacaatacca   6120
aaaacaccaa tgtaacatta agtaagaaaa ggaaaagaag atttcttgga tttttgttag   6180
gtgttggatc tgcaatcgcc agtggcattg ccgtatccaa ggtcctgcac ctagaagggg   6240
aagtgaacaa aatcaaaagt gctctactat ccacaaacaa ggctgtagtc agcttatcta   6300
atggagtcag tgtcttaacc agcaaggtgt tagacctcaa aaactatata gataaacagt   6360
tgttacctat tgttaacaag caaagctgca gcatatcaaa cattgaaact gtgatagagt   6420
tccaacaaaa gaacaacaga ctactagaga ttaccagaga atttagtgtt aatgcaggtg   6480
taactactcc tgtaagcact tatatgttaa ctaatagtga gttattatca ttaatcaatg   6540
atatgcctat aacaaatgat cagaaaaagt taatgtccag caatgttcaa atagttagac   6600
agcaaagtta ctctatcatg tcaataataa aagaggaagt cttggcatat gtagtacaat   6660
taccactata tggtgtaata gatactcctt gttggaaact acacacatcc cctttatgta   6720
caaccaacac aaaggaagga tccaacatct gcttaacaag aaccgacaga ggatggtact   6780
gtgacaatgc aggatcagta tccttttttcc cacaagctga aacatgtaaa gttcaatcga   6840
atcgggtgtt ttgtgacaca atgaacagtt taacattacc aagtgaggta aatctctgca   6900
acattgacat attcaacccc aaatatgatt gcaaaattat gacttcaaaa acagatgtaa   6960
```

```
gcagctccgt tatcacatct ctaggagcca ttgtgtcatg ctatggcaaa accaaatgta   7020
cagcatccaa taaaaatcgt gggatcataa agacattctc taacgggtgt gattatgtat   7080
caaataaggg ggtggatact gtgtctgtag gtaatacatt atattatgta aataagcaag   7140
aaggcaaaag tctctatgta aaaggtgaac caataataaa tttctatgat ccattagtgt   7200
tcccctctga tgaatttgat gcatcaatat ctcaagtcaa tgagaaaatt aatcagagtc   7260
tagcatttat ccgtaaatca gatgaattat tacataatgt aaatgctggt aaatccacca   7320
caaatatcat gataactacc ataattatag taattatagt aatattgtta gcattaattg   7380
cagttggact gcttctatac tgcaaggcca gaagcacacc agtcacatta agtaaggatc   7440
aactgagtgg tataaataat attgcattta gtaactgaat aaaaatagca cctaatcata   7500
ttcttacaat ggttcgctat ttgaccatag ataacccatc tatcattaga ttatcctaaa   7560
atttgaactt catcacaact ttcatctata aaccatctca cttacacttt ttaagtagat   7620
ttctatttta tagttatata aaacagggcc cattgaatac caaattaact tactatttgt   7680
aaaaatgaga attggggcaa atatgtcacg aaggaatcct tgcaaattcg aaattcgagg   7740
tcattgcttg aatggtaaaa ggtgtcattt tagtcataat tattttgaat ggccacccca   7800
tgcactgctt gtaagacaaa actttatgtt aaacagaata cttaagtcta tggataaaag   7860
catagatact ttgtcagaaa taagtggagc tgcagagttg gacagaacag aagagtatgc   7920
cctcggtgta gttggagtgc tagagagtta tataggatca ataaataata taactaaaca   7980
atcagcatgt gttgccatga gcaaactcct tactgaactc aacagcgatg acatcaaaaa   8040
actaagggac aatgaagagc caaactcacc caaagtaaga gtgtacaata ctgtcatatc   8100
atatattgaa agcaacagga agaacaataa acaaactatc catctgttaa aaagattgcc   8160
agcagacgta ttgaagaaaa ccatcaaaaa cacattggat atccacaaga gcataaccat   8220
caataaccca aaagaatcaa ctgttagtga tacgaacgac catgccaaaa ataatgatac   8280
tacctgacaa atatccttgt agtataaatt ccatactaat aacaagtaat tgtagagtca   8340
ctatgtataa tcaaaaaaac acactatata tcaatcaaaa caaccaaaat agccatatat   8400
acccaccgga tcaaccattc aatgaaatcc attggacctc tcaagacttg attgatgcaa   8460
ctcaaaattt tctacaacat ctaggtatta ctgatgatat atacacaata tatatattag   8520
tgtcataata ctcaatccta atacttacca catcatcaaa ttattaactc aaacaattca   8580
agctatggga caaaatggat cccattatta gtggaaattc tgctaatgtt tatctaactg   8640
atagttattt aaaaggtgtt atttctttct cagaatgtaa cgctttagga agttacatat   8700
tcaatggtcc ttatctcaaa aatgattata ccaacttaat tagtagacaa aatccattaa   8760
tagaacacat aaatctaaag aaactaaata taacacagtc cttaatatct aagtatcata   8820
aaggtgaaat aaaaatagaa gaacctactt actttcagtc attacttatg acatacaaga   8880
gtatgacctc ttcagaacag actactacta ctaatttact taaaaagata ataagaagag   8940
ctatagaaat cagtgatgtc aaagtctatg ctatattgaa taaactgggg ctcaaagaaa   9000
aagacaagat taaatccaat aatggacaag atgaagacaa ctcagtcatt actaccataa   9060
tcaaagatga tatactttta gctgtcaagg ataatcaatc tcatcttaaa gcagacaaaa   9120
atcaatccac aaaacaaaaa gatacaatca aaacaacact tttgaagaaa ttaatgtgtt   9180
cgatgcaaca tcctccatca tggttaatac attggtttaa tttatacaca aaattaaaca   9240
gcatattaac acaatatcga tctagtgagg taaaaaacca tggttttata ttgatagata   9300
```

-continued

```
atcatactct tagtggattc caatttattt tgaatcaata tggttgtata gtttatcata   9360
aggaactcaa aagaattact gtgacaactt ataatcaatt cttgacatgg aaagatatta   9420
gccttagtag attaaatgtt tgtttgatta catggattag taactgtttg aacacattaa   9480
acaaaagctt aggcttaaga tgtggattca ataatgttat cttgacacaa ttattccttt   9540
atggagattg tatactaaaa ctattccaca atgaggggtt ctacataata aaagaggtag   9600
agggatttat tatgtctcta attttaaata taacagaaga agatcaattc agaaaacggt   9660
tttataatag tatgctcaac aacatcacag atgccgccaa caaagctcaa aaaaatctgc   9720
tatcaagagt atgtcataca ttattagata agacaatatc agataatata ataaatggca   9780
gatggataat tctattgagt aagttcctaa aattaattaa gcttgcaggt gacaataacc   9840
tcaacaatct gagtgaatta tattttttgt tcagaatatt tggacaccca atggtagatg   9900
aaagacaagc catggatgct gttaaagtta attgcaacga gaccaaattt tatttgttaa   9960
gtagtttgag tatgttaaga ggagctttta tatatagaat tataaaaggg tttgtaaata  10020
attacaacag atggcctact ttaagaaatg ccattgtctt acccttaaga tggttaactt  10080
actataaact aaacacttat ccttccttgt tggaacttac agaaagagat ttgattgttc  10140
tatcaggact acgtttctat cgagagtttc ggttgcctaa aaaagtggat cttgaaatga  10200
tcataaatga taaggctata tcacctccta aaaatttaat atggactagt ttccctagaa  10260
attatatgcc gtcacacata caaaattata tagaacatga aaaattaaaa ttctctgata  10320
gtgataaatc aagaagagta ttagagtatt atttaagaga taacaaattc aatgaatgtg  10380
atttacacaa ctgtgtagtt aatcaaagtt atcttaacaa cccgaatcat gtggtatcat  10440
tgacaggcaa agaaagagaa ctcagtgtag gtagaatgtt tgcaatgcaa ccaggaatgt  10500
tcagacaagt tcaaatatta gcagagaaaa tgatagcaga aaacatatta caatttttcc  10560
ctgaaagtct tacaagatat ggtgatctag aactacagaa aatattagaa ttgaaagcag  10620
gaataagtaa caaatcaaat cgttacaatg ataattacaa caattacatt agtaagtgct  10680
ctatcatcac agatctcagc aaattcaatc aagcatttcg atatgaaaca tcatgtattt  10740
gtagtgatgt actggatgaa ctgcatggtg tacaatctct attttcctgg ttacatttaa  10800
ctattcctca tgtcacaata atatgcacat ataggcatgc accccccctat ataaaggatc  10860
atattgtaga tcttaacaat gtagatgagc aaagtggact atatagatat catatgggtg  10920
gtatcgaagg gtggtgtcaa aaactatgga ccatagaagc tatatcacta ttagatctaa  10980
tatctctcaa agggaaattc tcaattactg ctttaattaa tggtgacaat caatcaatag  11040
atataagtaa accagtcaga ctcatggaag gtcaaactca tgctcaagca gattatttgc  11100
tagcattaaa tagtctcaaa ttactgtata aagagtatgc aggaataggc cacaaattaa  11160
aaggaactga gacttatata tcgagagata tgcaatttat gagtaaaacg atccaacata  11220
acggtgtata ttacccagct agtataaaga aagtcctaag agtgggaccg tggataaaca  11280
ctatacttga tgacttcaaa gtgagtctag aatctatagg tagtttgaca caagaattag  11340
aatatagagg tgaaagtcta ttatgcagtt taatatttag aaatgtatgg ttatataatc  11400
aaattgcatt acaacttaaa aatcatgcat tatgtaacaa caaattatat ttggatatat  11460
taaaagttct aaaacactta aaaacctttt ttaatcttga taacattgat acagcattaa  11520
cattgtatat gaatttgccc atgttatttg gtggtggtga tcccaacttg ttatatcgaa  11580
gtttctatag aagaactcct gatttcctca cagaggctat agttcactct gtgttcatac  11640
ttagttatta tacaaaccat gatttaaaag ataaacttca agatctgtca gatgatagat  11700
```

tgaataagtt cttaacatgc ataatcacgt ttgataaaaa ccccaatgct gaattcgtta 11760
cattgatgag agatcctcaa gctttaggat ctgagaggca agctaaaatt actagcgaaa 11820
tcaatagact ggcagttacc gaggttttga gcacagctcc aaacaaaata ttttccaaaa 11880
gtgcacaaca ctataccact acagagatag atcttaatga tattatgcaa aatatagaac 11940
ctacatatcc tcacgggcta agagttgttt atgagagttt accccttttat aaagcagaga 12000 aaatagtaaa tcttatatcc ggtacaaaat ctataactaa catactggaa aagacttctg 12060
ccatagactt aacagatatt gatagagcca ctgagatgat gaggaaaaac ataactttgc 12120
ttataaggat attaccatta gattgtaaca gagataaaag agaaatattg agtatggaaa 12180
acctaagtat tactgaatta agcaaatacg ttagagaaag atcttggtct ttatccaata 12240
tagttggtgt tacatcaccc agtatcatgt atacaatgga cataaaatat acaacaagca 12300
ctatagctag tggcataatc atagagaaat ataatgtcaa cagtttaaca cgtggtgaga 12360
gaggacccac taaaccatgg gttggttcat ctacacaaga gaaaaagaca atgccagttt 12420
ataatagaca agttttaacc aaaaaacaga gagatcaaat agatctatta gcaaaattgg 12480
attgggtgta tgcatctata gataacaagg atgaatttat ggaggaactt agcataggaa 12540
ctcttgggtt aacatatgag aaggccaaaa aattattccc acaatatttg agtgttaact 12600
atttgcatcg tcttacagtc agtagtagac catgtgaatt ccctgcatct ataccagctt 12660
atagaactac aaattatcac tttgatacta gccctattaa tcgcatatta acagaaaagt 12720
atggtgatga agatattgat atagtattcc aaaactgtat aagctttggc cttagcttaa 12780
tgtctgtagt agaacaattt actaatgtat gtcctaacag aattattctc atacccaagc 12840
ttaatgagat acatttgatg aaacctccca tattcacagg cgatgttgat attcacaagt 12900
taaaacaagt gatacaaaaa caacatatgt tttaccaga caaaataagt ttgactcaat 12960
atgtggaatt attcttaagt aataaaacac tcaaatctgg atctaatgtt aattctaatt 13020
taatattggc gcataagata tctgactatt ttcataatac ttacattttg agtactaatt 13080
tagctggaca ttggattctt attatacaac ttatgaaaga ttctaagggt atttttgaaa 13140
aagattgggg agagggatat ataactgatc atatgttcat taatttgaaa gttttcttca 13200
atgcttataa gacatatctc ttgtgttttc ataaaggtta cggcagagca aagctggagt 13260
gtgatatgaa tacttcagat ctcctatgtg tattggaatt aatagacagt agttattgga 13320
agtctatgtc taaggtgttt ttagaacaaa aagttatcaa atacattctt agccaggatg 13380
caagtttaca tagagtaaaa ggatgtcata gcttcaaact atggtttctt aaacgtctta 13440
atgtagcaga attcacagtt tgcccttggg ttgttaacat agattatcat ccaacacata 13500
tgaaagcaat attaacttat attgatcttg ttagaatggg attgataaat atagatagaa 13560
tatacattaa aaataaacac aagttcaatg atgagtttta tacttctaat ctgttttaca 13620
ttaattataa cttctcagat aatactcatc tattaactaa acatataagg attgctaatt 13680
ccgaattaga aagtaattac aacaaattat atcatcctac accagaaacc ctagaaaata 13740
tactaaccaa tccggttaaa agtaatgaga aaaagacact gagtgactat tgtataggta 13800
aaaatgttga ctcaataatg ttaccatcgt tatctaataa gaagcttatt aaatcgtcta 13860
caatgattag aaccaattac agcagacaag atttgtataa tttatttcct acggttgtga 13920
ttgataaaat tatagatcat tcaggtaata cagccaaatc taaccaactt tacactacta 13980
cttctcatca aatatcctta gtgcacaata gcacatcact ttattgcatg cttccttggc 14040
atcatattaa tagattcaat tttgtattta gttctacagg ttgtaaaatt agtatagagt 14100
atattttaaa agatcttaaa attaaggatc ctaattgtat agcattcata ggtgaaggag 14160
cagggaattt attattgcgt acagtagtgg aacttcatcc tgatataaga tatatttaca 14220
gaagtctgaa agattgcaat gatcatagtt taccaattga gtttttaagg ctgtacaatg 14280
gacatatcaa cattgattat ggtgaaaatt tgaccattcc tgctacagat gcaaccaaca 14340
acattcattg gtcttattta catataaagt ttgctgaacc tatcagtctt tttgtctgtg 14400
atgctgaatt gcctgtaaca gtcaactgga gtaagattat aatagagtgg agcaagcatg 14460
taagaaaatg caagtactgt tcttcagtta ataaatgtac attgatagta aaatatcatg 14520
ctcaagatga tatcgatttc aaattagaca acataactat attaaaaact tatgtatgct 14580
taggtagtaa gttaaaggga tctgaagttt acttagtcct tacaataggt cctgcaaatg 14640
tgttcccagt atttaatgta gtacaaaatg ctaaattgat actatcaaga actaaaaatt 14700
tcatcatgcc taaaaaagct gataaagagt ctattgatgc aaatattaag agtttgatac 14760
cctttctttg ttaccctata acaaaaaaag gaattaatac tgcattgtct aaattaaaga 14820
gtgttgttag tggagatata ctatcatatt ctatagctgg acgtaatgaa gttttcagca 14880
ataaacttat aaatcataag catatgaaca tcttaaagtg gttcaatcat gttttaaatt 14940
tcagatcaac agaattaaac tataatcatt tatatatggt agaatctact tatcctcatc 15000
taagtgaatt gttaaacagc ttgacaacca atgaacttaa aaaactgatt aaaatcacag 15060
gtagtttgtt atacaacttt tataatgaat aatgagcaaa aatcttataa caaaaatagc 15120
tacacactaa cattgtattc aattatagtt attgaaaatt aataattata taatttttaa 15180
taacttctag tgaactaatc ctaaaattat cattttgatc taggaagaat aagtttaaat 15240
ccaaatctaa ttggtttata tgtatattaa ctaaattacg agatattagt ttttgacact 15300
ttttttctcg t 15311

<210> SEQ ID NO 16
<211> LENGTH: 15311
<212> TYPE: DNA
<213> ORGANISM: Artificial Sequence
<220> FEATURE:
<223> OTHER INFORMATION: A sequence modifying the furin cleavage site I
of the F gene included in SEQ ID NO: 1

<400> SEQUENCE: 16
acgcgaaaaa atgcgtacaa caaacttgcg taaaccaaaa aaatggggca aataagaatt 60
tgataagtac cacttaaatt taactccttt ggttagaggc gcgccatggg cagcaactca 120
ttgagtatga taaaagttag attgcaaaat ctgtttgaca atgatgaagt agcattgtta 180
aaaataacat gctatactga caaattaata cagttaacta atgctttggc taaggcagtt 240
atacatacaa tcaaattgaa tggcattgta tttgtgcatg ttattacaag tagtgatatt 300
tgccctaata ataatattgt agtgaaatcc aatttcacaa caatgccagt attacaaaat 360
ggaggttata tatgggaaat gatggaatta acacactgct ctcaacctaa tggcctaata 420
gatgacaatt gtgaaattaa attctccaaa aaactaagtg attcaacaat gaccaattat 480
atgaatcaat tatctgaatt acttggattt gacctcaatc cataaatcat aataaatatc 540
aactagcaaa tcaatgtcac taacaccatt agttaatata aaacttgaca gaagataaaa 600
atggggcaaa taaatcaatt cagccgaccc aaccatggac acaacacaca atgataccac 660
accacaaaga ctgatgatca cagacatgag gccattatcg cttgagacta taataacatc 720

-continued

```
tctaaccaga gatatcataa cacataaatt tatatacttg ataaatcatg aatgcatagt    780
aagaaaactt gatgaaagac aggccacatt tacatttctg gtcaactatg aaatgaaact    840
attgcacaaa gtgggaagca ctaaatataa aaaatatact gaatacaaca caaaatatgg    900
cactttccct atgccaatat ttatcaatca tgatgggttc ttagaatgca ttggcattaa    960
gcctaccaag cacacaccca taatatacaa gtatgatctc aatccatgaa tatcaaacca   1020
agattcaaac aatccgaaat aacaacttta tgcataatca cactccatag tccaaatgga   1080
gcctgaaaat tatagttatt taaaattcct gcaggaagga gagacataag atgaaagatg   1140
gggcaaatac aaaaatggct cttagcaaag tcaagttgaa tgatacactc aacaaagatc   1200
aacttctatc atccagcaaa tataccatcc aacggagcac aggagacagc attgacactc   1260
ctaattatga tgtgcagaaa cacattaata agttatgtgg catgttatta atcacagaag   1320
atgctaatca taaattcact gggttaatag gtatgttata tgctatgtct agattaggaa   1380
gagaagacac cataaaaata ctcaaagatg cgggatatca tgttaaggca aatggagtgg   1440
atgtaacaac acatcgtcaa gacattaatg ggaaagaaat gaaatttgaa gtgttaacat   1500
tagcaagctt aacaactgaa attcaaatca acattgagat agaatctaga aaatcctaca   1560
aaaaaatgct aaaagaaatg ggagaggtgg ctccagaata caggcatgac tctcctgatt   1620
gtgggatgat aatattatgt atagcggcat tagtaataac caaattagca gcaggagata   1680
gatcaggtct tacagctgtg attaggagag ctaataatgt cctaaaaaat gaaatgaaac   1740
gttataaagg tttattaccc aaggatatag ccaacagctt ctatgaagtg tttgaaaaat   1800
atcctcactt tatagatgtt tttgttcatt ttggtatagc acaatcttct accagaggtg   1860
gcagtagagt tgaagggatt tttgcaggat tgtttatgaa tgcctatggt gcagggcaag   1920
tgatgttacg gtgggggtc ttagcaaaat cagttaaaaa cattatgtta ggacacgcta   1980
gtgtacaagc agaaatggaa caagttgtgg aggtgtatga gtatgctcag aaattgggtg   2040
gagaagcagg attctaccat atattgaaca acccaaaagc atcactatta tctttgactc   2100
aatttcctca cttctctagt gtagtattgg gcaatgctgc tggcctaggc ataatgggag   2160
aatacagagg tacaccaagg aatcaagatt tatatgatgc tgcaaaagca tatgctgaac   2220
aactcaaaga aaatggtgtg attaactaca gtgtattaga tttgacagca gaagaactag   2280
aggctatcaa acatcagctt aatccaaaag ataatgatgt agagctttga gttaataaaa   2340
aagtggggca aataaatcat catggaaaag tttgctcctg aattccatgg agaagatgca   2400
aacaacagag ccaccaaatt cctagaatca ataaagggca aattcacatc acccaaagat   2460
cccaagaaaa aagatagtat catatctgtc aactcaatag atatagaagt aaccaaagaa   2520
agccctataa catcaaattc aaccattata aacccaataa atgagacaga tgatactgta   2580
gggaacaagc ccaattatca aagaaagcct ctagtaagtt tcaaagaaga ccctacgcca   2640
agtgataatc ctttttcaaa actatacaaa gaaaccatag aaacatttga taacaatgaa   2700
gaagaatcta gctattcata tgaagaaata aatgatcaga caaacgataa tataacagca   2760
agattagata ggattgatga gaaattaagt gaaatactag gaatgcttca cacattagta   2820
gtagcgagtg caggacccac atctgctcgg gatggtataa gagatgccat ggttggttta   2880
agagaagaaa tgatagaaaa aatcagaact gaagcattaa tgaccaatga cagactagaa   2940
gctatggcaa gactcaggaa tgaagaaagt gaaaagatgg caaaagacac atcagatgaa   3000
gtgtctctca atccaacatc agagaaactg aacaacctgt tggaagggaa tgatagtgac   3060
aatgatctat cacttgaaga tttctgatta gctaccaaac tgtacatcaa aacacaacac   3120
```

-continued

```
caatagaaaa ccaacaaaca aaccaactca cccatccaac caaacatcta tctgctgatt   3180
agccaaccag ccaaaaaaca accagccaat ctaaaactag ccacccggaa aaaatcgata   3240
ctatagttac aaaaaaagat ggggcaaata tggaaacata cgtgaataaa cttcacgagg   3300
gctccacata cacagctgct gttcaataca atgtcctaga aaaagacgat gatcctgcat   3360
cacttacaat atgggtgccc atgttccaat catccatgcc agcagatcta ctcataaaag   3420
aactagccaa tgtcaatata ctagtgaaac aaatatccac acccaaggga ccctcattaa   3480
gagtcatgat aaactcaaga agtgcagtgc tagcacaaat gcccagcaaa tttaccatat   3540
gtgccaatgt gtccttggat gaaagaagca agctggcata tgatgtaacc acaccctgtg   3600
aaattaaggc atgcagtcta acatgcctaa aatcaaaaaa tatgttaact acagttaaag   3660
atctcactat gaaaacactc aacccaacac atgacatcat tgctttatgt gaatttgaaa   3720
atatagtaac atcaaaaaaa gtcataatac caacatacct aagatctatc agcgtcagaa   3780
ataaagatct gaacacactt gaaaatataa caaccactga attcaaaaat gccattacaa   3840
atgcaaaaat catcccttac tcaggattat tgttagtcat cacagtgact gacaacaaag   3900
gagcattcaa atacataaag ccacaaagtc aattcatagt agatcttgga gcttacctag   3960
aaaaagaaag tatatattat gttacaacaa attggaagca cacagctaca cgatttgcaa   4020
tcaaacccat ggaagattaa ccttttccct ctacatcaat gagtagattc atacaaactt   4080
tctaactaca ttcttcactt cacaatcata atcaccaacc ctctgtggtt caatcaatca   4140
aacaaaactc atcaagagtt ccagatcatc ccaagtcatt gttcatcaga tccagtactc   4200
aaataagtta ataaaaaatc cacatggggc aaataatcat tgagggaaat ccaactaatc   4260
acaacatctg tcaacataga caagtcaaca cgctagataa aatcaaccaa tggaaaatac   4320
atccataact atagaattct caagcaaatt ctggccttac tttacactaa tacacatgat   4380
aacaacaata atctctttga taatcataat ctccatcatg attgcaatac taaacaaact   4440
ctgcgaatat aatgtattcc ataacaaaac ctttgagcta ccaagagctc gagtcaatac   4500
atagcattca ccaatctgat agctcaaaac agtaaccttg catttgtaaa tgaactaccc   4560
tcacttcttc acaaaaccac atcaacatct caccatgcaa gccatcatct ataccataaa   4620
gtagttaatt aaaaatggcc ggccagtcat aacaatgaac taggatatta agaccaaaaa   4680
caacgctggg gcaaatgcaa acatgtccaa aaccgaggac caacgcaccg ccaagacact   4740
agaaaggacc tgggacactt ttaatcatct attattcata tcatcgtgct tatacaagtt   4800
aaatcttaaa tctatagcac aaatcacatt atctattttg gcaattataa tctcaacctc   4860
acttataatt gcagccatca tattcatagc ctcggcaaac cacaaagtca cactaacaac   4920
tgcaatcata caagatgcaa cgaaccagat caagaacaca accccaacat acctcaccca   4980
gaatccccag catggaatca gcttctccaa tctgtccgga actacatcac aatccaccac   5040
catactagct tcaacaacac caagtgctga ttcaacccca caatccacaa cagtcaagat   5100
caaaaacaca acaacaaccc aaatattacc tagcaaaccc accacaaaac aacgccaaaa   5160
taaaccacaa aacaaaccca acaatgattt tcactttgaa gtgttcaatt ttgtaccctg   5220
cagcatatgc agcaacaatc caacctgctg ggccatctgc aagagaatac caaacaaaaa   5280
acctggaaag aaaaccacca ccaagcccac aaaaaaacca accctcaaga caaccaaaaa   5340
agatcccaaa tcccaaacca caaaaccaaa ggaagtactc actaccaagc ctacaggaaa   5400
gccaaccatc aacaccacta aaacaaacat cagaactaca ctgctcacct ccaacaccaa   5460
```

```
aggaaatcca gaacacacaa gtcaagagga aaccctccac tcaaccacct ccgaaggcta   5520
tccaagccca tcacaagtcc acacaacatc cggtcaagag gaaaccctcc actcaaccac   5580
ctccgaaggc tatccaagcc catcacaagt ctacacaaca tccgagtacc tatcacaatc   5640
tctatcttca tccaacacaa caaaatgata gtcattaaaa agcacgcgtg tattgttgca   5700
aaaagccatg accaaatcaa acagaatcaa aatcaactct ggggcaaata acaatggagt   5760
tgccaatcct caaaacaaat gctattacca caatccttgc tgcagtcaca ctctgtttcg   5820
cttccagtca aaacatcact gaagaatttt atcaatcaac atgcagtgca gtcagcaaag   5880
gctatcttag tgctctaaga actggttggt atactagtgt tataactata gaattaagta   5940
atatcaagga aaataagtgt aatggtacag acgctaaggt aaaattaata aaacaagaat   6000
tagataaata taaaaatgct gtaacagaat tgcagttgct catgcaaagc acaccagcag   6060
ccaacaatcg agccagaaga gaactaccaa gatttatgaa ttatacactc aacaatacca   6120
aaaacaccaa tgtaacatta agtaagaaaa ggaaaagaaa gtttcttgga tttttgttag   6180
gtgttggatc tgcaatcgcc agtggcattg ccgtatccaa ggtcctgcac ctagaagggg   6240
aagtgaacaa aatcaaaagt gctctactat ccacaaacaa ggctgtagtc agcttatcta   6300
atggagtcag tgtcttaacc agcaaggtgt tagacctcaa aaactatata gataaacagt   6360
tgttacctat tgttaacaag caaagctgca gcatatcaaa cattgaaact gtgatagagt   6420
tccaacaaaa gaacaacaga ctactagaga ttaccagaga atttagtgtt aatgcaggtg   6480
taactactcc tgtaagcact tatatgttaa ctaatagtga gttattatca ttaatcaatg   6540
atatgcctat aacaaatgat cagaaaaagt taatgtccag caatgttcaa atagttagac   6600
agcaaagtta ctctatcatg tcaataataa aagaggaagt cttggcatat gtagtacaat   6660
taccactata tggtgtaata gatactcctt gttggaaact acacacatcc cctttatgta   6720
caaccaacac aaaggaagga tccaacatct gcttaacaag aaccgacaga ggatggtact   6780
gtgacaatgc aggatcagta tcctttttcc cacaagctga aacatgtaaa gttcaatcga   6840
atcgggtgtt ttgtgacaca atgaacagtt taacattacc aagtgaggta aatctctgca   6900
acattgacat attcaacccc aaatatgatt gcaaaattat gacttcaaaa acagatgtaa   6960
gcagctccgt tatcacatct ctaggagcca ttgtgtcatg ctatggcaaa accaaatgta   7020
cagcatccaa taaaaatcgt gggatcataa agacattctc taacgggtgt gattatgtat   7080
caaataaggg ggtggatact gtgtctgtag gtaatacatt atattatgta aataagcaag   7140
aaggcaaaag tctctatgta aaaggtgaac caataataaa tttctatgat ccattagtgt   7200
tcccctctga tgaatttgat gcatcaatat ctcaagtcaa tgagaaaatt aatcagagtc   7260
tagcatttat ccgtaaatca gatgaattat tacataatgt aaatgctggt aaatccacca   7320
caaatatcat gataactacc ataattatag taattatagt aatattgtta gcattaattg   7380
cagttggact gcttctatac tgcaaggcca gaagcacacc agtcacatta agtaaggatc   7440
aactgagtgg tataaataat attgcattta gtaactgaat aaaaatagca cctaatcata   7500
ttcttacaat ggttcgctat ttgaccatag ataacccatc tatcattaga ttatcctaaa   7560
atttgaactt catcacaact ttcatctata aaccatctca cttacacttt ttaagtagat   7620
ttctatttta tagttatata aaacagggcc cattgaatac caaattaact tactatttgt   7680
aaaaatgaga attggggcaa atatgtcacg aaggaatcct tgcaaattcg aaattcgagg   7740
tcattgcttg aatggtaaaa ggtgtcattt tagtcataat tattttgaat ggccacccca   7800
tgcactgctt gtaagacaaa actttatgtt aaacagaata cttaagtcta tggataaaag   7860
```

-continued

```
catagatact ttgtcagaaa taagtggagc tgcagagttg gacagaacag aagagtatgc   7920
cctcggtgta gttggagtgc tagagagtta tataggatca ataaataata taactaaaca   7980
atcagcatgt gttgccatga gcaaactcct tactgaactc aacagcgatg acatcaaaaa   8040
actaagggac aatgaagagc caaactcacc caaagtaaga gtgtacaata ctgtcatatc   8100
atatattgaa agcaacagga agaacaataa acaaactatc catctgttaa aaagattgcc   8160
agcagacgta ttgaagaaaa ccatcaaaaa cacattggat atccacaaga gcataaccat   8220
caataaccca aaagaatcaa ctgttagtga tacgaacgac catgccaaaa ataatgatac   8280
tacctgacaa atatccttgt agtataaatt ccatactaat aacaagtaat tgtagagtca   8340
ctatgtataa tcaaaaaaac acactatata tcaatcaaaa caaccaaaat agccatatat   8400
acccaccgga tcaaccattc aatgaaatcc attggacctc tcaagacttg attgatgcaa   8460
ctcaaaattt tctacaacat ctaggtatta ctgatgatat atacacaata tatatattag   8520
tgtcataata ctcaatccta atacttacca catcatcaaa ttattaactc aaacaattca   8580
agctatggga caaaatggat cccattatta gtggaaattc tgctaatgtt tatctaactg   8640
atagttattt aaaaggtgtt atttctttct cagaatgtaa cgctttagga agttacatat   8700
tcaatggtcc ttatctcaaa aatgattata ccaacttaat tagtagacaa aatccattaa   8760
tagaacacat aaatctaaag aaactaaata taacacagtc cttaatatct aagtatcata   8820
aaggtgaaat aaaaatagaa gaacctactt actttcagtc attacttatg acatacaaga   8880
gtatgacctc ttcagaacag actactacta ctaatttact taaaaagata ataagaagag   8940
ctatagaaat cagtgatgtc aaagtctatg ctatattgaa taaactgggg ctcaaagaaa   9000
aagacaagat taaatccaat aatggacaag atgaagacaa ctcagtcatt actaccataa   9060
tcaaagatga tatactttta gctgtcaagg ataatcaatc tcatcttaaa gcagacaaaa   9120
atcaatccac aaaacaaaaa gatacaatca aaacaacact tttgaagaaa ttaatgtgtt   9180
cgatgcaaca tcctccatca tggttaatac attggtttaa tttatacaca aaattaaaca   9240
gcatattaac acaatatcga tctagtgagg taaaaaacca tggttttata ttgatagata   9300
atcatactct tagtggattc caatttattt tgaatcaata tggttgtata gtttatcata   9360
aggaactcaa aagaattact gtgacaactt ataatcaatt cttgacatgg aaagatatta   9420
gccttagtag attaaatgtt tgtttgatta catggattag taactgtttg aacacattaa   9480
acaaaagctt aggcttaaga tgtggattca ataatgttat cttgacacaa ttattccttt   9540
atggagattg tatactaaaa ctattccaca atgaggggtt ctacataata aaagaggtag   9600
agggatttat tatgtctcta attttaaata taacagaaga agatcaattc agaaaacggt   9660
tttataatag tatgctcaac aacatcacag atgccgccaa caaagctcaa aaaaatctgc   9720
tatcaagagt atgtcataca ttattagata agacaatatc agataatata ataaatggca   9780
gatggataat tctattgagt aagttcctaa aattaattaa gcttgcaggt gacaataacc   9840
tcaacaatct gagtgaatta tattttttgt tcagaatatt tggacaccca atggtagatg   9900
aaagacaagc catggatgct gttaaagtta attgcaacga gaccaaattt tatttgttaa   9960
gtagtttgag tatgttaaga ggagctttta tatatagaat tataaaaggg tttgtaaata  10020
attacaacag atggcctact ttaagaaatg ccattgtctt acccttaaga tggttaactt  10080
actataaact aaacacttat ccttccttgt tggaacttac agaaagagat ttgattgttc  10140
tatcaggact acgtttctat cgagagtttc ggttgcctaa aaaagtggat cttgaaatga  10200
```

-continued

```
tcataaatga taaggctata tcacctccta aaaatttaat atggactagt ttccctagaa  10260
attatatgcc gtcacacata caaaattata tagaacatga aaaattaaaa ttctctgata  10320
gtgataaatc aagaagagta ttagagtatt atttaagaga taacaaattc aatgaatgtg  10380
atttacacaa ctgtgtagtt aatcaaagtt atcttaacaa cccgaatcat gtggtatcat  10440
tgacaggcaa agaaagagaa ctcagtgtag gtagaatgtt tgcaatgcaa ccaggaatgt  10500
tcagacaagt tcaaatatta gcagagaaaa tgatagcaga aaacatatta caatttttcc  10560
ctgaaagtct tacaagatat ggtgatctag aactacagaa aatattagaa ttgaaagcag  10620
gaataagtaa caaatcaaat cgttacaatg ataattacaa caattacatt agtaagtgct  10680
ctatcatcac agatctcagc aaattcaatc aagcatttcg atatgaaaca tcatgtattt  10740
gtagtgatgt actggatgaa ctgcatggtg tacaatctct attttcctgg ttacatttaa  10800
ctattcctca tgtcacaata atatgcacat ataggcatgc accccccctat ataaaggatc  10860
atattgtaga tcttaacaat gtagatgagc aaagtggact atatagatat catatgggtg  10920
gtatcgaagg gtggtgtcaa aaactatgga ccatagaagc tatatcacta ttagatctaa  10980
tatctctcaa agggaaattc tcaattactg ctttaattaa tggtgacaat caatcaatag  11040
atataagtaa accagtcaga ctcatggaag gtcaaactca tgctcaagca gattatttgc  11100
tagcattaaa tagtctcaaa ttactgtata aagagtatgc aggaataggc cacaaattaa  11160
aaggaactga gacttatata tcgagagata tgcaatttat gagtaaaacg atccaacata  11220
acggtgtata ttacccagct agtataaaga aagtcctaag agtgggaccg tggataaaca  11280
ctatacttga tgacttcaaa gtgagtctag aatctatagg tagtttgaca caagaattag  11340
aatatagagg tgaaagtcta ttatgcagtt taatatttag aaatgtatgg ttatataatc  11400
aaattgcatt acaacttaaa aatcatgcat tatgtaacaa caaattatat ttggatatat  11460
taaaagttct aaaacactta aaaacctttt ttaatcttga taacattgat acagcattaa  11520
cattgtatat gaatttgccc atgttatttg gtggtggtga tcccaacttg ttatatcgaa  11580
gtttctatag aagaactcct gatttcctca cagaggctat agttcactct gtgttcatac  11640
ttagttatta tacaaaccat gatttaaaag ataaacttca agatctgtca gatgatagat  11700
tgaataagtt cttaacatgc ataatcacgt ttgataaaaa ccccaatgct gaattcgtta  11760
cattgatgag agatcctcaa gctttaggat ctgagaggca agctaaaatt actagcgaaa  11820
tcaatagact ggcagttacc gaggttttga gcacagctcc aaacaaaata ttttccaaaa  11880
gtgcacaaca ctataccact acagagatag atcttaatga tattatgcaa aatatagaac  11940
ctacatatcc tcacgggcta agagttgttt atgagagttt acccttttat aaagcagaga  12000
aaatagtaaa tcttatatcc ggtacaaaat ctataactaa catactggaa aagacttctg  12060
ccatagactt aacagatatt gatagagcca ctgagatgat gaggaaaaac ataactttgc  12120
ttataaggat attaccatta gattgtaaca gagataaaag agaaatattg agtatggaaa  12180
acctaagtat tactgaatta agcaaatacg ttagagaaag atcttggtct ttatccaata  12240
tagttggtgt tacatcaccc agtatcatgt atacaatgga cataaaatat acaacaagca  12300
ctatagctag tggcataatc atagagaaat ataatgtcaa cagtttaaca cgtggtgaga  12360
gaggacccac taaaccatgg gttggttcat ctacacaaga gaaaaagaca atgccagttt  12420
ataatagaca agttttaacc aaaaaacaga gagatcaaat agatctatta gcaaaattgg  12480
attgggtgta tgcatctata gataacaagg atgaatttat ggaggaactt agcataggaa  12540
ctcttgggtt aacatatgag aaggccaaaa aattattccc acaatatttg agtgttaact  12600
```

```
atttgcatcg tcttacagtc agtagtagac catgtgaatt ccctgcatct ataccagctt  12660
atagaactac aaattatcac tttgatacta gccctattaa tcgcatatta acagaaaagt  12720
atggtgatga agatattgat atagtattcc aaaactgtat aagctttggc cttagcttaa  12780
tgtctgtagt agaacaattt actaatgtat gtcctaacag aattattctc atacccaagc  12840
ttaatgagat acatttgatg aaacctccca tattcacagg cgatgttgat attcacaagt  12900
taaaacaagt gatacaaaaa caacatatgt ttttaccaga caaaataagt ttgactcaat  12960
atgtggaatt attcttaagt aataaaacac tcaaatctgg atctaatgtt aattctaatt  13020
taatattggc gcataagata tctgactatt ttcataatac ttacattttg agtactaatt  13080
tagctggaca ttggattctt attatacaac ttatgaaaga ttctaagggt atttttgaaa  13140
aagattgggg agagggatat ataactgatc atatgttcat taatttgaaa gttttcttca  13200
atgcttataa gacatatctc ttgtgttttc ataaaggtta cggcagagca aagctggagt  13260
gtgatatgaa tacttcagat ctcctatgtg tattggaatt aatagacagt agttattgga  13320
agtctatgtc taaggtgttt ttagaacaaa aagttatcaa atacattctt agccaggatg  13380
caagtttaca tagagtaaaa ggatgtcata gcttcaaact atggtttctt aaacgtctta  13440
atgtagcaga attcacagtt tgcccttggg ttgttaacat agattatcat ccaacacata  13500
tgaaagcaat attaacttat attgatcttg ttagaatggg attgataaat atagatagaa  13560
tatacattaa aaataaacac aagttcaatg atgagtttta tacttctaat ctgttttaca  13620
ttaattataa cttctcagat aatactcatc tattaactaa acatataagg attgctaatt  13680
ccgaattaga aagtaattac aacaaattat atcatcctac accagaaacc ctagaaaata  13740
tactaaccaa tccggttaaa agtaatgaga aaaagacact gagtgactat tgtataggta  13800
aaaatgttga ctcaataatg ttaccatcgt tatctaataa gaagcttatt aaatcgtcta  13860
caatgattag aaccaattac agcagacaag atttgtataa tttatttcct acggttgtga  13920
ttgataaaat tatagatcat tcaggtaata cagccaaatc taaccaactt tacactacta  13980
cttctcatca aatatcctta gtgcacaata gcacatcact ttattgcatg cttccttggc  14040
atcatattaa tagattcaat tttgtattta gttctacagg ttgtaaaatt agtatagagt  14100
atattttaaa agatcttaaa attaaggatc ctaattgtat agcattcata ggtgaaggag  14160
cagggaattt attattgcgt acagtagtgg aacttcatcc tgatataaga tatatttaca  14220
gaagtctgaa agattgcaat gatcatagtt taccaattga gtttttaagg ctgtacaatg  14280
gacatatcaa cattgattat ggtgaaaatt tgaccattcc tgctacagat gcaaccaaca  14340
acattcattg gtcttattta catataaagt ttgctgaacc tatcagtctt tttgtctgtg  14400
atgctgaatt gcctgtaaca gtcaactgga gtaagattat aatagagtgg agcaagcatg  14460
taagaaaatg caagtactgt tcttcagtta ataaatgtac attgatagta aaatatcatg  14520
ctcaagatga tatcgatttc aaattagaca acataactat attaaaaact tatgtatgct  14580
taggtagtaa gttaaaggga tctgaagttt acttagtcct tacaataggt cctgcaaatg  14640
tgttcccagt atttaatgta gtacaaaatg ctaaattgat actatcaaga actaaaaatt  14700
tcatcatgcc taaaaaagct gataaagagt ctattgatgc aaatattaag agtttgatac  14760
cctttctttg ttaccctata acaaaaaaag gaattaatac tgcattgtct aaattaaaga  14820
gtgttgttag tggagatata ctatcatatt ctatagctgg acgtaatgaa gttttcagca  14880
ataaacttat aaatcataag catatgaaca tcttaaagtg gttcaatcat gttttaaatt  14940
```

-continued

```
tcagatcaac agaattaaac tataatcatt tatatatggt agaatctact tatcctcatc  15000

taagtgaatt gttaaacagc ttgacaacca atgaacttaa aaaactgatt aaaatcacag  15060

gtagtttgtt atacaacttt tataatgaat aatgagcaaa aatcttataa caaaaatagc  15120

tacacactaa cattgtattc aattatagtt attgaaaatt aataattata taatttttaa  15180

taacttctag tgaactaatc ctaaaattat cattttgatc taggaagaat aagtttaaat  15240

ccaaatctaa ttggtttata tgtatattaa ctaaattacg agatattagt ttttgacact  15300

ttttttctcg t                                                       15311
```

<210> SEQ ID NO 17
<211> LENGTH: 17095
<212> TYPE: DNA
<213> ORGANISM: Artificial Sequence
<220> FEATURE:
<223> OTHER INFORMATION: antigenic cDNA encoding the cRSVA_VSVG_A

<400> SEQUENCE: 17

```
taatacgact cactataggt tttttcgcgt ctgatgaggc cgttaggccg aaactcctct     60

ccggagtcac gcgaaaaaat gcgtacaaca aacttgcgta aaccaaaaaa atggggcaaa    120

taagaatttg ataagtacca cttaaattta actcctttgg ttagaggcgc gccatgggca    180

gcaactcatt gagtatgata aaagttagat tgcaaaatct gtttgacaat gatgaagtag    240

cattgttaaa aataacatgc tatactgaca aattaataca gttaactaat gctttggcta    300

aggcagttat acatacaatc aaattgaatg gcattgtatt tgtgcatgtt attacaagta    360

gtgatatttg ccctaataat aatattgtag tgaaatccaa tttcacaaca atgccagtat    420

tacaaaatgg aggttatata tgggaaatga tggaattaac acactgctct caacctaatg    480

gcctaataga tgacaattgt gaaattaaat tctccaaaaa actaagtgat tcaacaatga    540

ccaattatat gaatcaatta tctgaattac ttggatttga cctcaatcca taaatcataa    600

taaatatcaa ctagcaaatc aatgtcacta acaccattag ttaatataaa acttgacaga    660

agataaaaat ggggcaaata aatcaattca gccgacccaa ccatggacac aacacacaat    720

gataccacac cacaaagact gatgatcaca gacatgaggc cattatcgct tgagactata    780

ataacatctc taaccagaga tatcataaca cataaattta tatacttgat aaatcatgaa    840

tgcatagtaa gaaaacttga tgaaagacag gccacattta catttctggt caactatgaa    900

atgaaactat tgcacaaagt gggaagcact aaatataaaa aatatactga atacaacaca    960

aaatatggca ctttccctat gccaatattt atcaatcatg atgggttctt agaatgcatt   1020

ggcattaagc ctaccaagca cacacccata atatacaagt atgatctcaa tccatgaata   1080

tcaaaccaag attcaaacaa tccgaaataa caactttatg cataatcaca ctccatagtc   1140

caaatggagc ctgaaaatta tagttattta aaattcctgc aggaaggaga gacataagat   1200

gaaagatggg gcaaatacaa aaatggctct tagcaaagtc aagttgaatg atacactcaa   1260

caaagatcaa cttctatcat ccagcaaata taccatccaa cggagcacag gagacagcat   1320

tgacactcct aattatgatg tgcagaaaca cattaataag ttatgtggca tgttattaat   1380

cacagaagat gctaatcata aattcactgg gttaataggt atgttatatg ctatgtctag   1440

attaggaaga gaagacacca taaaaatact caaagatgcg ggatatcatg ttaaggcaaa   1500

tggagtggat gtaacaacac atcgtcaaga cattaatggg aaagaaatga aatttgaagt   1560

gttaacatta gcaagcttaa caactgaaat tcaaatcaac attgagatag aatctagaaa   1620

atcctacaaa aaaatgctaa aagaaatggg agaggtggct ccagaataca ggcatgactc   1680
```

tcctgattgt gggatgataa tattatgtat agcggcatta gtaataacca aattagcagc 1740
aggagataga tcaggtctta cagctgtgat taggagagct aataatgtcc taaaaaatga 1800
aatgaaacgt tataaaggtt tattacccaa ggatatagcc aacagcttct atgaagtgtt 1860
tgaaaaatat cctcacttta tagatgtttt tgttcatttt ggtatagcac aatcttctac 1920
cagaggtggc agtagagttg aagggatttt tgcaggattg tttatgaatg cctatggtgc 1980
agggcaagtg atgttacggt ggggggtctt agcaaaatca gttaaaaaca ttatgttagg 2040
acacgctagt gtacaagcag aaatggaaca agttgtggag gtgtatgagt atgctcagaa 2100
attgggtgga gaagcaggat tctaccatat attgaacaac ccaaaagcat cactattatc 2160
tttgactcaa tttcctcact tctctagtgt agtattgggc aatgctgctg gcctaggcat 2220
aatgggagaa tacagaggta caccaaggaa tcaagattta tatgatgctg caaaagcata 2280
tgctgaacaa ctcaaagaaa atggtgtgat taactacagt gtattagatt tgacagcaga 2340
agaactagag gctatcaaac atcagcttaa tccaaaagat aatgatgtag agctttgagt 2400
taataaaaaa gtggggcaaa taaatcatca tggaaaagtt tgctcctgaa ttccatggag 2460
aagatgcaaa caacagagcc accaaattcc tagaatcaat aaagggcaaa ttcacatcac 2520
ccaaagatcc caagaaaaaa gatagtatca tatctgtcaa ctcaatagat atagaagtaa 2580
ccaaagaaag ccctataaca tcaaattcaa ccattataaa cccaataaat gagacagatg 2640
atactgtagg gaacaagccc aattatcaaa gaaagcctct agtaagtttc aaagaagacc 2700
ctacgccaag tgataatcct ttttcaaaac tatacaaaga aaccatagaa acatttgata 2760
acaatgaaga agaatctagc tattcatatg aagaaataaa tgatcagaca aacgataata 2820
taacagcaag attagatagg attgatgaga aattaagtga aatactagga atgcttcaca 2880
cattagtagt agcgagtgca ggacccacat ctgctcggga tggtataaga gatgccatgg 2940
ttggtttaag agaagaaatg atagaaaaaa tcagaactga agcattaatg accaatgaca 3000
gactagaagc tatggcaaga ctcaggaatg aagaaagtga aaagatggca aaagacacat 3060
cagatgaagt gtctctcaat ccaacatcag agaaactgaa caacctgttg gaagggaatg 3120
atagtgacaa tgatctatca cttgaagatt tctgattagc taccaaactg tacatcaaaa 3180
cacaacacca atagaaaacc aacaaacaaa ccaactcacc catccaacca aacatctatc 3240
tgctgattag ccaaccagcc aaaaaacaac cagccaatct aaaactagcc acccggaaaa 3300
aatcgatact atagttacaa aaaaagatgg ggcaaatatg gaaacatacg tgaataaact 3360
tcacgagggc tccacataca cagctgctgt tcaatacaat gtcctagaaa aagacgatga 3420
tcctgcatca cttacaatat gggtgcccat gttccaatca tccatgccag cagatctact 3480
cataaaagaa ctagccaatg tcaatatact agtgaaacaa atatccacac ccaagggacc 3540
ctcattaaga gtcatgataa actcaagaag tgcagtgcta gcacaaatgc ccagcaaatt 3600
taccatatgt gccaatgtgt ccttggatga aagaagcaag ctggcatatg atgtaaccac 3660
accctgtgaa attaaggcat gcagtctaac atgcctaaaa tcaaaaaata tgttaactac 3720
agttaaagat ctcactatga aaacactcaa cccaacacat gacatcattg ctttatgtga 3780
atttgaaaat atagtaacat caaaaaaagt cataatacca acatacctaa gatctatcag 3840
cgtcagaaat aaagatctga acacacttga aaatataaca accactgaat tcaaaaatgc 3900
cattacaaat gcaaaaatca tcccttactc aggattattg ttagtcatca cagtgactga 3960
caacaaagga gcattcaaat acataaagcc acaaagtcaa ttcatagtag atcttggagc 4020

-continued

```
ttacctagaa aaagaaagta tatattatgt tacaacaaat tggaagcaca cagctacacg   4080
atttgcaatc aaacccatgg aagattaacc tttttcctct acatcaatga gtagattcat   4140
acaaactttc taactacatt cttcacttca caatcataat caccaaccct ctgtggttca   4200
atcaatcaaa caaaactcat caagagttcc agatcatccc aagtcattgt tcatcagatc   4260
cagtactcaa ataagttaat aaaaaatcca catggggcaa ataatcattg agggaaatcc   4320
aactaatcac aacatctgtc aacatagaca agtcaacacg ctagataaaa tcaaccaatg   4380
gaaaatacat ccataactat agaattctca agcaaattct ggccttactt tacactaata   4440
cacatgataa caacaataat ctctttgata atcataatct ccatcatgat tgcaatacta   4500
aacaaactct gcgaatataa tgtattccat aacaaaacct ttgagctacc aagagctcga   4560
gtcaatacat agcattcacc aatctgatag ctcaaaacag taaccttgca tttgtaaatg   4620
aactaccctc acttcttcac aaaaccacat caacatctca ccatgcaagc catcatctat   4680
accataaagt agttaattaa aaatggccgg ccttgacaga agataaaaat ggggcaaatg   4740
caaacatgaa gtgccttttg tacttagcct ttttattcat tggggtgaat tgcaagttca   4800
ccatagtttt tccacacaac caaaaaggaa actggaaaaa tgttccttct aattaccatt   4860
attgcccgtc aagctcagat ttaaattggc ataatgactt aataggcaca gccttacaag   4920
tcaaaatgcc caagagtcac aaggctattc aagcagacgg ttggatgtgt catgcttcca   4980
aatgggtcac tacttgtgat ttccgctggt atggaccgaa gtatataaca cattccatcc   5040
gatccttcac tccatctgta gaacaatgca aggaaagcat tgaacaaacg aaacaaggaa   5100
cttggctgaa tccaggcttc cctcctcaaa gttgtggata tgcaactgtg acggatgccg   5160
aagcagtgat tgtccaggtg actcctcacc atgtgctggt tgatgaatac acaggagaat   5220
gggttgattc acagttcatc aacggaaaat gcagcaatta catatgcccc actgtccata   5280
actctacaac ctggcattct gactataagg tcaaagggct atgtgattct aacctcattt   5340
ccatggacat caccttcttc tcagaggacg gagagctatc atccctggga aaggagggca   5400
cagggttcag aagtaactac tttgcttatg aaactggagg caaggcctgc aaaatgcaat   5460
actgcaagca ttggggagtc agactcccat caggtgtctg gttcgagatg gctgataagg   5520
atctctttgc tgcagccaga ttccctgaat gcccagaagg gtcaagtatc tctgctccat   5580
ctcagacctc agtggatgta agtctaattc aggacgttga gaggatcttg gattattccc   5640
tctgccaaga aacctggagc aaaatcagag cgggtcttcc aatctctcca gtggatctca   5700
gctatcttgc tcctaaaaac ccaggaaccg gtcctgcttt caccataatc aatggtaccc   5760
taaaatactt tgagaccaga tacatcagag tcgatattgc tgctccaatc ctctcaagaa   5820
tggtcggaat gatcagtgga actaccacag aaagggaact gtgggatgac tgggcaccat   5880
atgaagacgt ggaaattgga cccaatggag ttctgaggac cagttcagga tataagtttc   5940
ctttatacat gattggacat ggtatgttgg actccgatct tcatcttagc tcaaaggctc   6000
aggtgttcga acatcctcac attcaagacg ctgcttcgca acttcctgat gatgagagtt   6060
tatttttgg tgatactggg ctatccaaaa atccaatcga gcttgtagaa ggttggttca   6120
gtagttggaa aagctctatt gcctcttttt tctttatcat agggttaatc attggactat   6180
tcttggttct ccgagttggt atccatcttt gcattaaagc cagaagcaca ccagtcacat   6240
taagtaagga tcaactgagt ggtataaata atattgcatt tagtaactaa tagtcattaa   6300
aaagcggccg gccagtcata acaatgaact aggatattaa gaccaaaaac aacgctgggg   6360
caaatgcaaa catgtccaaa accgaggacc aacgcaccgc caagacacta gaaaggacct   6420
```

-continued

```
gggacacttt taatcatcta ttattcatat catcgtgctt atacaagtta aatcttaaat   6480
ctatagcaca aatcacatta tctattttgg caattataat ctcaacctca cttataattg   6540
cagccatcat attcatagcc tcggcaaacc acaaagtcac actaacaact gcaatcatac   6600
aagatgcaac gaaccagatc aagaacacaa ccccaacata cctcacccag aatccccagc   6660
atggaatcag cttctccaat ctgtccggaa ctacatcaca atccaccacc atactagctt   6720
caacaacacc aagtgctgat tcaaccccac aatccacaac agtcaagatc aaaaacacaa   6780
caacaaccca aatattacct agcaaaccca ccacaaaaca acgccaaaat aaaccacaaa   6840
acaaacccaa caatgatttt cactttgaag tgttcaattt tgtaccctgc agcatatgca   6900
gcaacaatcc aacctgctgg gccatctgca agagaatacc aaacaaaaaa cctggaaaga   6960
aaaccaccac caagcccaca aaaaaaccaa ccctcaagac aaccaaaaaa gatcccaaat   7020
cccaaaccac aaaaccaaag gaagtactca ctaccaagcc tacaggaaag ccaaccatca   7080
acaccactaa aacaaacatc agaactacac tgctcacctc caacaccaaa ggaaatccag   7140
aacacacaag tcaagaggaa accctccact caaccacctc cgaaggctat ccaagcccat   7200
cacaagtcca cacaacatcc ggtcaagagg aaaccctcca ctcaaccacc tccgaaggct   7260
atccaagccc atcacaagtc tacacaacat ccgagtacct atcacaatct ctatcttcat   7320
ccaacacaac aaaatgatag tcattaaaaa gcacgcgtgt attgttgcaa aaagccatga   7380
ccaaatcaaa cagaatcaaa atcaactctg ggcaaataa caatggagtt gccaatcctc   7440
aaaacaaatg ctattaccac aatccttgct gcagtcacac tctgtttcgc ttccagtcaa   7500
aacatcactg aagaatttta tcaatcaaca tgcagtgcag tcagcaaagg ctatcttagt   7560
gctctaagaa ctggttggta tactagtgtt ataactatag aattaagtaa tatcaaggaa   7620
aataagtgta atggtacaga cgctaaggta aaattaataa aacaagaatt agataaatat   7680
aaaaatgctg taacagaatt gcagttgctc atgcaaagca caccagcagc caacaatcga   7740
gccagaagag aactaccaag atttatgaat tatacactca acaataccaa aaacaccaat   7800
gtaacattaa gtaagaaaag gaaaagaaga tttcttggat ttttgttagg tgttggatct   7860
gcaatcgcca gtggcattgc cgtatccaag gtcctgcacc tagaagggga agtgaacaaa   7920
atcaaaagtg ctctactatc cacaaacaag gctgtagtca gcttatctaa tggagtcagt   7980
gtcttaacca gcaaggtgtt agacctcaaa aactatatag ataaacagtt gttacctatt   8040
gttaacaagc aaagctgcag catatcaaac attgaaactg tgatagagtt ccaacaaaag   8100
aacaacagac tactagagat taccagagaa tttagtgtta atgcaggtgt aactactcct   8160
gtaagcactt atatgttaac taatagtgag ttattatcat taatcaatga tatgcctata   8220
acaaatgatc agaaaaagtt aatgtccagc aatgttcaaa tagttagaca gcaaagttac   8280
tctatcatgt caataataaa agaggaagtc ttggcatatg tagtacaatt accactatat   8340
ggtgtaatag atactccttg ttggaaacta cacacatccc ctttatgtac aaccaacaca   8400
aaggaaggat ccaacatctg cttaacaaga accgacagag gatggtactg tgacaatgca   8460
ggatcagtat ccttttttccc acaagctgaa acatgtaaag ttcaatcgaa tcgggtgttt   8520
tgtgacacaa tgaacagttt aacattacca agtgaggtaa atctctgcaa cattgacata   8580
ttcaacccca aatatgattg caaaattatg acttcaaaaa cagatgtaag cagctccgtt   8640
atcacatctc taggagccat tgtgtcatgc tatggcaaaa ccaaatgtac agcatccaat   8700
aaaaatcgtg ggatcataaa gacattctct aacgggtgtg attatgtatc aaataagggg   8760
```

-continued

```
gtggatactg tgtctgtagg taatacatta tattatgtaa ataagcaaga aggcaaaagt   8820
ctctatgtaa aaggtgaacc aataataaat ttctatgatc cattagtgtt cccctctgat   8880
gaatttgatg catcaatatc tcaagtcaat gagaaaatta atcagagtct agcatttatc   8940
cgtaaatcag atgaattatt acataatgta aatgctggta aatccaccac aaatatcatg   9000
ataactacca taattatagt aattatagta atattgttag cattaattgc agttggactg   9060
cttctatact gcaaggccag aagcacacca gtcacattaa gtaaggatca actgagtggt   9120
ataaataata ttgcatttag taactgaata aaaatagcac ctaatcatat tcttacaatg   9180
gttcgctatt tgaccataga taacccatct atcattagat tatcctaaaa tttgaacttc   9240
atcacaactt tcatctataa accatctcac ttacactttt taagtagatt tctattttat   9300
agttatataa aacagggccc attgaatacc aaattaactt actatttgta aaaatgagaa   9360
ttggggcaaa tatgtcacga aggaatcctt gcaaattcga aattcgaggt cattgcttga   9420
atggtaaaag gtgtcatttt agtcataatt attttgaatg gccaccccat gcactgcttg   9480
taagacaaaa ctttatgtta aacagaatac ttaagtctat ggataaaagc atagatactt   9540
tgtcagaaat aagtggagct gcagagttgg acagaacaga agagtatgcc ctcggtgtag   9600
ttggagtgct agagagttat ataggatcaa taaataatat aactaaacaa tcagcatgtg   9660
ttgccatgag caaactcctt actgaactca acagcgatga catcaaaaaa ctaagggaca   9720
atgaagagcc aaactcaccc aaagtaagag tgtacaatac tgtcatatca tatattgaaa   9780
gcaacaggaa gaacaataaa caaactatcc atctgttaaa aagattgcca gcagacgtat   9840
tgaagaaaac catcaaaaac acattggata tccacaagag cataaccatc aataacccaa   9900
aagaatcaac tgttagtgat acgaacgacc atgccaaaaa taatgatact acctgacaaa   9960
tatccttgta gtataaattc catactaata acaagtaatt gtagagtcac tatgtataat  10020
caaaaaaaca cactatatat caatcaaaac aaccaaaata gccatatata cccaccggat  10080
caaccattca atgaaatcca ttggacctct caagacttga ttgatgcaac tcaaaatttt  10140
ctacaacatc taggtattac tgatgatata tacacaatat atatattagt gtcataatac  10200
tcaatcctaa tacttaccac atcatcaaat tattaactca aacaattcaa gctatgggac  10260
aaaatggatc ccattattag tggaaattct gctaatgttt atctaactga tagttattta  10320
aaaggtgtta tttctttctc agaatgtaac gctttaggaa gttacatatt caatggtcct  10380
tatctcaaaa atgattatac caacttaatt agtagacaaa atccattaat agaacacata  10440
aatctaaaga aactaaatat aacacagtcc ttaatatcta agtatcataa aggtgaaata  10500
aaaatagaag aacctactta ctttcagtca ttacttatga catacaagag tatgacctct  10560
tcagaacaga ctactactac taatttactt aaaaagataa taagaagagc tatagaaatc  10620
agtgatgtca aagtctatgc tatattgaat aaactggggc tcaaagaaaa agacaagatt  10680
aaatccaata atggacaaga tgaagacaac tcagtcatta ctaccataat caaagatgat  10740
atacttttag ctgtcaagga taatcaatct catcttaaag cagacaaaaa tcaatccaca  10800
aaacaaaaag atacaatcaa aacaacactt ttgaagaaat taatgtgttc gatgcaacat  10860
cctccatcat ggttaataca ttggtttaat ttatacacaa aattaaacag catattaaca  10920
caatatcgat ctagtgaggt aaaaaaccat ggttttatat tgatagataa tcatactctt  10980
agtggattcc aatttatttt gaatcaatat ggttgtatag tttatcataa ggaactcaaa  11040
agaattactg tgacaactta taatcaattc ttgacatgga aagatattag ccttagtaga  11100
ttaaatgttt gtttgattac atggattagt aactgtttga acacattaaa caaaagctta  11160
```

```
ggcttaagat gtggattcaa taatgttatc ttgacacaat tattccttta tggagattgt  11220
atactaaaac tattccacaa tgaggggttc tacataataa aagaggtaga gggatttatt  11280
atgtctctaa ttttaaatat aacagaagaa gatcaattca gaaaacggtt ttataatagt  11340
atgctcaaca acatcacaga tgccgccaac aaagctcaaa aaaatctgct atcaagagta  11400
tgtcatacat tattagataa gacaatatca gataatataa taaatggcag atggataatt  11460
ctattgagta agttcctaaa attaattaag cttgcaggtg acaataacct caacaatctg  11520
agtgaattat atttttgtt cagaatattt ggacacccaa tggtagatga aagacaagcc  11580
atggatgctg ttaaagttaa ttgcaacgag accaaatttt atttgttaag tagtttgagt  11640
atgttaagag gagcttttat atatagaatt ataaaagggt ttgtaaataa ttacaacaga  11700
tggcctactt taagaaatgc cattgtctta cccttaagat ggttaactta ctataaacta  11760
aacacttatc cttccttgtt ggaacttaca gaaagagatt tgattgttct atcaggacta  11820
cgtttctatc gagagtttcg gttgcctaaa aaagtggatc ttgaaatgat cataaatgat  11880
aaggctatat cacctcctaa aaatttaata tggactagtt tccctagaaa ttatatgccg  11940
tcacacatac aaaattatat agaacatgaa aaattaaaat tctctgatag tgataaatca  12000
agaagagtat tagagtatta tttaagagat aacaaattca atgaatgtga tttacacaac  12060
tgtgtagtta atcaaagtta tcttaacaac ccgaatcatg tggtatcatt gacaggcaaa  12120
gaaagagaac tcagtgtagg tagaatgttt gcaatgcaac caggaatgtt cagacaagtt  12180
caaatattag cagagaaaat gatagcagaa aacatattac aatttttccc tgaaagtctt  12240
acaagatatg gtgatctaga actacagaaa atattagaat tgaaagcagg aataagtaac  12300
aaatcaaatc gttacaatga taattacaac aattacatta gtaagtgctc tatcatcaca  12360
gatctcagca aattcaatca agcatttcga tatgaaacat catgtatttg tagtgatgta  12420
ctggatgaac tgcatggtgt acaatctcta ttttcctggt tacatttaac tattcctcat  12480
gtcacaataa tatgcacata taggcatgca ccccccctata taaaggatca tattgtagat  12540
cttaacaatg tagatgagca aagtggacta tatagatatc atatgggtgg tatcgaaggg  12600
tggtgtcaaa aactatggac catagaagct atatcactat tagatctaat atctctcaaa  12660
gggaaattct caattactgc tttaattaat ggtgacaatc aatcaataga tataagtaaa  12720
ccagtcagac tcatggaagg tcaaactcat gctcaagcag attatttgct agcattaaat  12780
agtctcaaat tactgtataa agagtatgca ggaataggcc acaaattaaa aggaactgag  12840
acttatatat cgagagatat gcaatttatg agtaaaacga tccaacataa cggtgtatat  12900
tacccagcta gtataaagaa agtcctaaga gtgggaccgt ggataaacac tatacttgat  12960
gacttcaaag tgagtctaga atctataggt agtttgacac aagaattaga atatagaggt  13020
gaaagtctat tatgcagttt aatatttaga aatgtatggt tatataatca aattgcatta  13080
caacttaaaa atcatgcatt atgtaacaac aaattatatt tggatatatt aaaagttcta  13140
aaacacttaa aaaccttttt taatcttgat aacattgata cagcattaac attgtatatg  13200
aatttgccca tgttatttgg tggtggtgat cccaacttgt tatatcgaag tttctataga  13260
agaactcctg atttcctcac agaggctata gttcactctg tgttcatact tagttattat  13320
acaaaccatg atttaaaaga taaacttcaa gatctgtcag atgatagatt gaataagttc  13380
ttaacatgca taatcacgtt tgataaaaac cccaatgctg aattcgttac attgatgaga  13440
gatcctcaag ctttaggatc tgagaggcaa gctaaaatta ctagcgaaat caatagactg  13500
```

-continued gcagttaccg aggttttgag cacagctcca aacaaaatat tttccaaaag tgcacaacac 13560
tataccacta cagagataga tcttaatgat attatgcaaa atatagaacc tacatatcct 13620
cacgggctaa gagttgttta tgagagttta cccttttata aagcagagaa aatagtaaat 13680
cttatatccg gtacaaaatc tataactaac atactggaaa agacttctgc catagactta 13740
acagatattg atagagccac tgagatgatg aggaaaaaca taactttgct tataaggata 13800
ttaccattag attgtaacag agataaaaga gaaatattga gtatggaaaa cctaagtatt 13860
actgaattaa gcaaatacgt tagagaaaga tcttggtctt tatccaatat agttggtgtt 13920
acatcaccca gtatcatgta tacaatggac ataaaatata caacaagcac tatagctagt 13980
ggcataatca tagagaaata taatgtcaac agtttaacac gtggtgagag aggacccact 14040
aaaccatggg ttggttcatc tacacaagag aaaaagacaa tgccagttta taatagacaa 14100
gttttaacca aaaaacagag agatcaaata gatctattag caaaattgga ttgggtgtat 14160
gcatctatag ataacaagga tgaatttatg gaggaactta gcataggaac tcttgggtta 14220
acatatgaga aggccaaaaa attattccca caatatttga gtgttaacta tttgcatcgt 14280
cttacagtca gtagtagacc atgtgaattc cctgcatcta taccagctta tagaactaca 14340
aattatcact ttgatactag ccctattaat cgcatattaa cagaaaagta tggtgatgaa 14400
gatattgata tagtattcca aaactgtata agctttggcc ttagcttaat gtctgtagta 14460
gaacaattta ctaatgtatg tcctaacaga attattctca tacccaagct taatgagata 14520
catttgatga aacctcccat attcacaggc gatgttgata ttcacaagtt aaaacaagtg 14580
atacaaaaac aacatatgtt tttaccagac aaaataagtt tgactcaata tgtggaatta 14640
ttcttaagta ataaaacact caaatctgga tctaatgtta attctaattt aatattggcg 14700
cataagatat ctgactattt tcataatact tacattttga gtactaattt agctggacat 14760
tggattctta ttatacaact tatgaaagat tctaagggta tttttgaaaa agattgggga 14820
gagggatata taactgatca tatgttcatt aatttgaaag ttttcttcaa tgcttataag 14880
acatatctct tgtgttttca taaaggttac ggcagagcaa agctggagtg tgatatgaat 14940
acttcagatc tcctatgtgt attggaatta atagacagta gttattggaa gtctatgtct 15000
aaggtgtttt tagaacaaaa agttatcaaa tacattctta gccaggatgc aagtttacat 15060
agagtaaaag gatgtcatag cttcaaacta tggtttctta aacgtcttaa tgtagcagaa 15120
ttcacagttt gcccttgggt tgttaacata gattatcatc caacacatat gaaagcaata 15180
ttaacttata ttgatcttgt tagaatggga ttgataaata tagatagaat atacattaaa 15240
aataaacaca agttcaatga tgagttttat acttctaatc tgttttacat taattataac 15300
ttctcagata atactcatct attaactaaa catataagga ttgctaattc cgaattagaa 15360
agtaattaca acaaattata tcatcctaca ccagaaaccc tagaaaatat actaaccaat 15420
ccggttaaaa gtaatgagaa aaagacactg agtgactatt gtataggtaa aaatgttgac 15480
tcaataatgt taccatcgtt atctaataag aagcttatta aatcgtctac aatgattaga 15540
accaattaca gcagacaaga tttgtataat ttatttccta cggttgtgat tgataaaatt 15600
atagatcatt caggtaatac agccaaatct aaccaacttt acactactac ttctcatcaa 15660
atatccttag tgcacaatag cacatcactt tattgcatgc ttccttggca tcatattaat 15720
agattcaatt ttgtatttag ttctacaggt tgtaaaatta gtatagagta tattttaaaa 15780
gatcttaaaa ttaaggatcc taattgtata gcattcatag gtgaaggagc agggaattta 15840
ttattgcgta cagtagtgga acttcatcct gatataagat atatttacag aagtctgaaa 15900

```
gattgcaatg atcatagttt accaattgag tttttaaggc tgtacaatgg acatatcaac  15960

attgattatg gtgaaaattt gaccattcct gctacagatg caaccaacaa cattcattgg  16020

tcttatttac atataaagtt tgctgaacct atcagtcttt ttgtctgtga tgctgaattg  16080

cctgtaacag tcaactggag taagattata atagagtgga gcaagcatgt aagaaaatgc  16140

aagtactgtt cttcagttaa taaatgtaca ttgatagtaa aatatcatgc tcaagatgat  16200

atcgatttca aattagacaa cataactata ttaaaaactt atgtatgctt aggtagtaag  16260

ttaaagggat ctgaagttta cttagtcctt acaataggtc ctgcaaatgt gttcccagta  16320

tttaatgtag tacaaaatgc taaattgata ctatcaagaa ctaaaaattt catcatgcct  16380

aaaaaagctg ataaagagtc tattgatgca aatattaaga gtttgatacc ctttctttgt  16440

taccctataa caaaaaaagg aattaatact gcattgtcta aattaaagag tgttgttagt  16500

ggagatatac tatcatattc tatagctgga cgtaatgaag ttttcagcaa taaacttata  16560

aatcataagc atatgaacat cttaaagtgg ttcaatcatg ttttaaattt cagatcaaca  16620

gaattaaact ataatcattt atatatggta gaatctactt atcctcatct aagtgaattg  16680

ttaaacagct tgacaaccaa tgaacttaaa aaactgatta aatcacagg tagtttgtta  16740

tacaactttt ataatgaata atgagcaaaa atcttataac aaaaatagct acacactaac  16800

attgtattca attatagtta ttgaaaatta ataattatat aatttttaat aacttctagt  16860

gaactaatcc taaaattatc attttgatct aggaagaata agtttaaatc caaatctaat  16920

tggtttatat gtatattaac taaattacga gatattagtt tttgacactt tttttctcgt  16980

ggccggcatg gtcccagcct cctcgctggc gccggctggg caacatgctt cggcatggcg  17040

aatgggacta gcataacccc ttggggcctc taaacgggtc ttgaggggtt ttttg       17095
```

```
<210> SEQ ID NO 18
<211> LENGTH: 16677
<212> TYPE: DNA
<213> ORGANISM: Artificial Sequence
<220> FEATURE:
<223> OTHER INFORMATION: antigenic cDNA encoding cRSVA_VSVG_A_SH
      deletion

<400> SEQUENCE: 18

taatacgact cactataggt tttttcgcgt ctgatgaggc cgttaggccg aaactcctct     60

ccggagtcac gcgaaaaaat gcgtacaaca aacttgcgta aaccaaaaaa atggggcaaa    120

taagaatttg ataagtacca cttaaattta actcctttgg ttagaggcgc gccatgggca    180

gcaactcatt gagtatgata aaagttagat tgcaaaatct gtttgacaat gatgaagtag    240

cattgttaaa aataacatgc tatactgaca aattaataca gttaactaat gctttggcta    300

aggcagttat acatacaatc aaattgaatg gcattgtatt tgtgcatgtt attacaagta    360

gtgatatttg ccctaataat aatattgtag tgaaatccaa tttcacaaca atgccagtat    420

tacaaaatgg aggttatata tgggaaatga tggaattaac acactgctct caacctaatg    480

gcctaataga tgacaattgt gaaattaaat tctccaaaaa actaagtgat tcaacaatga    540

ccaattatat gaatcaatta tctgaattac ttggatttga cctcaatcca taaatcataa    600

taaatatcaa ctagcaaatc aatgtcacta acaccattag ttaatataaa acttgacaga    660

agataaaaat ggggcaaata aatcaattca gccgacccaa ccatggacac aacacacaat    720

gataccacac cacaaagact gatgatcaca gacatgaggc cattatcgct tgagactata    780

ataacatctc taaccagaga tatcataaca cataaattta tatacttgat aaatcatgaa    840
```

```
tgcatagtaa gaaaacttga tgaaagacag gccacattta catttctggt caactatgaa    900
atgaaactat tgcacaaagt gggaagcact aaatataaaa aatatactga atacaacaca    960
aaatatggca ctttccctat gccaatattt atcaatcatg atgggttctt agaatgcatt   1020
ggcattaagc ctaccaagca cacacccata atatacaagt atgatctcaa tccatgaata   1080
tcaaaccaag attcaaacaa tccgaaataa caactttatg cataatcaca ctccatagtc   1140
caaatggagc ctgaaaatta tagttattta aaattcctgc aggaaggaga gacataagat   1200
gaaagatggg gcaaatacaa aaatggctct tagcaaagtc aagttgaatg atacactcaa   1260
caaagatcaa cttctatcat ccagcaaata taccatccaa cggagcacag gagacagcat   1320
tgacactcct aattatgatg tgcagaaaca cattaataag ttatgtggca tgttattaat   1380
cacagaagat gctaatcata aattcactgg gttaataggt atgttatatg ctatgtctag   1440
attaggaaga gaagacacca taaaaatact caaagatgcg ggatatcatg ttaaggcaaa   1500
tggagtggat gtaacaacac atcgtcaaga cattaatggg aaagaaatga aatttgaagt   1560
gttaacatta gcaagcttaa caactgaaat tcaaatcaac attgagatag aatctagaaa   1620
atcctacaaa aaaatgctaa aagaaatggg agaggtggct ccagaataca ggcatgactc   1680
tcctgattgt gggatgataa tattatgtat agcggcatta gtaataacca aattagcagc   1740
aggagataga tcaggtctta cagctgtgat taggagagct aataatgtcc taaaaaatga   1800
aatgaaacgt tataaaggtt tattacccaa ggatatagcc aacagcttct atgaagtgtt   1860
tgaaaaatat cctcacttta tagatgtttt tgttcatttt ggtatagcac aatcttctac   1920
cagaggtggc agtagagttg aagggatttt tgcaggattg tttatgaatg cctatggtgc   1980
agggcaagtg atgttacggt ggggggtctt agcaaaatca gttaaaaaca ttatgttagg   2040
acacgctagt gtacaagcag aaatggaaca agttgtggag gtgtatgagt atgctcagaa   2100
attgggtgga gaagcaggat tctaccatat attgaacaac ccaaaagcat cactattatc   2160
tttgactcaa tttcctcact tctctagtgt agtattgggc aatgctgctg gcctaggcat   2220
aatgggagaa tacagaggta caccaaggaa tcaagattta tatgatgctg caaaagcata   2280
tgctgaacaa ctcaaagaaa atggtgtgat taactacagt gtattagatt tgacagcaga   2340
agaactagag gctatcaaac atcagcttaa tccaaaagat aatgatgtag agctttgagt   2400
taataaaaaa gtggggcaaa taaatcatca tggaaaagtt tgctcctgaa ttccatggag   2460
aagatgcaaa caacagagcc accaaattcc tagaatcaat aaagggcaaa ttcacatcac   2520
ccaaagatcc caagaaaaaa gatagtatca tatctgtcaa ctcaatagat atagaagtaa   2580
ccaaagaaag ccctataaca tcaaattcaa ccattataaa cccaataaat gagacagatg   2640
atactgtagg gaacaagccc aattatcaaa gaaagcctct agtaagtttc aaagaagacc   2700
ctacgccaag tgataatcct tttttcaaaac tatacaaaga aaccatagaa acatttgata   2760
acaatgaaga agaatctagc tattcatatg aagaaataaa tgatcagaca aacgataata   2820
taacagcaag attagatagg attgatgaga aattaagtga aatactagga atgcttcaca   2880
cattagtagt agcgagtgca ggacccacat ctgctcggga tggtataaga gatgccatgg   2940
ttggtttaag agaagaaatg atagaaaaaa tcagaactga agcattaatg accaatgaca   3000
gactagaagc tatggcaaga ctcaggaatg aagaaagtga aaagatggca aaagacacat   3060
cagatgaagt gtctctcaat ccaacatcag agaaactgaa caacctgttg gaagggaatg   3120
atagtgacaa tgatctatca cttgaagatt tctgattagc taccaaactg tacatcaaaa   3180
```

-continued

```
cacaacacca atagaaaacc aacaaacaaa ccaactcacc catccaacca aacatctatc   3240
tgctgattag ccaaccagcc aaaaaacaac cagccaatct aaaactagcc acccggaaaa   3300
aatcgatact atagttacaa aaaaagatgg ggcaaatatg gaaacatacg tgaataaact   3360
tcacgagggc tccacataca cagctgctgt tcaatacaat gtcctagaaa aagacgatga   3420
tcctgcatca cttacaatat gggtgcccat gttccaatca tccatgccag cagatctact   3480
cataaaagaa ctagccaatg tcaatatact agtgaaacaa atatccacac ccaagggacc   3540
ctcattaaga gtcatgataa actcaagaag tgcagtgcta gcacaaatgc ccagcaaatt   3600
taccatatgt gccaatgtgt ccttggatga aagaagcaag ctggcatatg atgtaaccac   3660
accctgtgaa attaaggcat gcagtctaac atgcctaaaa tcaaaaaata tgttaactac   3720
agttaaagat ctcactatga aacactcaa cccaacacat gacatcattg ctttatgtga   3780
atttgaaaat atagtaacat caaaaaaagt cataatacca acatacctaa gatctatcag   3840
cgtcagaaat aaagatctga acacacttga aaatataaca accactgaat tcaaaaatgc   3900
cattacaaat gcaaaaatca tcccttactc aggattattg ttagtcatca cagtgactga   3960
caacaaagga gcattcaaat acataaagcc acaaagtcaa ttcatagtag atcttggagc   4020
ttacctagaa aaagaaagta tatattatgt tacaacaaat tggaagcaca cagctacacg   4080
atttgcaatc aaacccatgg aagattaacc tttttcctct acatcaatga gtagattcat   4140
acaaactttc taactacatt cttcacttca caatcataat caccaaccct ctgtggttca   4200
atcaatcaaa caaaactcat caagagttcc agatcatccc aagtcattgt tcatcagatc   4260
cagtactcaa ataagttaat aaaaaatcgg tccgttgaca gaagataaaa atggggcaaa   4320
tgcaaacatg aagtgccttt tgtacttagc ctttttattc attggggtga attgcaagtt   4380
caccatagtt tttccacaca accaaaaagg aaactggaaa aatgttcctt ctaattacca   4440
ttattgcccg tcaagctcag atttaaattg gcataatgac ttaataggca cagccttaca   4500
agtcaaaatg cccaagagtc acaaggctat tcaagcagac ggttggatgt gtcatgcttc   4560
caaatgggtc actacttgtg atttccgctg gtatggaccg aagtatataa cacattccat   4620
ccgatccttc actccatctg tagaacaatg caaggaaagc attgaacaaa cgaaacaagg   4680
aacttggctg aatccaggct tccctcctca aagttgtgga tatgcaactg tgacggatgc   4740
cgaagcagtg attgtccagg tgactcctca ccatgtgctg gttgatgaat acacaggaga   4800
atgggttgat tcacagttca tcaacggaaa atgcagcaat tacatatgcc ccactgtcca   4860
taactctaca acctggcatt ctgactataa ggtcaaaggg ctatgtgatt ctaacctcat   4920
ttccatggac atcaccttct tctcagagga cggagagcta tcatccctgg gaaaggaggg   4980
cacagggttc agaagtaact actttgctta tgaaactgga ggcaaggcct gcaaaatgca   5040
atactgcaag cattggggag tcagactccc atcaggtgtc tggttcgaga tggctgataa   5100
ggatctcttt gctgcagcca gattccctga atgcccagaa gggtcaagta tctctgctcc   5160
atctcagacc tcagtggatg taagtctaat tcaggacgtt gagaggatct tggattattc   5220
cctctgccaa gaaacctgga gcaaaatcag agcgggtctt ccaatctctc cagtggatct   5280
cagctatctt gctcctaaaa acccaggaac cggtcctgct ttcaccataa tcaatggtac   5340
cctaaaatac tttgagacca gatacatcag agtcgatatt gctgctccaa tcctctcaag   5400
aatggtcgga atgatcagtg gaactaccac agaaagggaa ctgtgggatg actgggcacc   5460
atatgaagac gtggaaattg gacccaatgg agttctgagg accagttcag gatataagtt   5520
tcctttatac atgattggac atggtatgtt ggactccgat cttcatctta gctcaaaggc   5580
```

-continued tcaggtgttc gaacatcctc acattcaaga cgctgcttcg caacttcctg atgatgagag 5640
tttatttttt ggtgatactg ggctatccaa aaatccaatc gagcttgtag aaggttggtt 5700
cagtagttgg aaaagctcta ttgcctcttt tttctttatc atagggttaa tcattggact 5760
attcttggtt ctccgagttg gtatccatct ttgcattaaa gccagaagca caccagtcac 5820
attaagtaag gatcaactga gtggtataaa taatattgca tttagtaact aatagtcatt 5880
aaaaagcggc cggccagtca taacaatgaa ctaggatatt aagaccaaaa acaacgctgg 5940
ggcaaatgca aacatgtcca aaaccgagga ccaacgcacc gccaagacac tagaaaggac 6000
ctgggacact tttaatcatc tattattcat atcatcgtgc ttatacaagt taaatcttaa 6060
atctatagca caaatcacat tatctatttt ggcaattata atctcaacct cacttataat 6120
tgcagccatc atattcatag cctcggcaaa ccacaaagtc acactaacaa ctgcaatcat 6180
acaagatgca acgaaccaga tcaagaacac aaccccaaca tacctcaccc agaatcccca 6240
gcatggaatc agcttctcca atctgtccgg aactacatca caatccacca ccatactagc 6300
ttcaacaaca ccaagtgctg attcaacccc acaatccaca acagtcaaga tcaaaaacac 6360
aacaacaacc caaatattac ctagcaaacc caccacaaaa caacgccaaa ataaaccaca 6420
aaacaaaccc aacaatgatt ttcactttga agtgttcaat tttgtaccct gcagcatatg 6480
cagcaacaat ccaacctgct gggccatctg caagagaata ccaaacaaaa aacctggaaa 6540
gaaaaccacc accaagccca caaaaaaacc aaccctcaag acaaccaaaa aagatcccaa 6600
atcccaaacc acaaaaccaa aggaagtact cactaccaag cctacaggaa agccaaccat 6660
caacaccact aaaacaaaca tcagaactac actgctcacc tccaacacca aaggaaatcc 6720
agaacacaca agtcaagagg aaaccctcca ctcaaccacc tccgaaggct atccaagccc 6780
atcacaagtc cacacaacat ccggtcaaga ggaaaccctc cactcaacca cctccgaagg 6840
ctatccaagc ccatcacaag tctacacaac atccgagtac ctatcacaat ctctatcttc 6900
atccaacaca acaaaatgat agtcattaaa aagcacgcgt gtattgttgc aaaaagccat 6960
gaccaaatca aacagaatca aaatcaactc tggggcaaat aacaatggag ttgccaatcc 7020
tcaaaacaaa tgctattacc acaatccttg ctgcagtcac actctgtttc gcttccagtc 7080
aaaacatcac tgaagaattt tatcaatcaa catgcagtgc agtcagcaaa ggctatctta 7140
gtgctctaag aactggttgg tatactagtg ttataactat agaattaagt aatatcaagg 7200
aaaataagtg taatggtaca gacgctaagg taaaattaat aaaacaagaa ttagataaat 7260
ataaaaatgc tgtaacagaa ttgcagttgc tcatgcaaag cacaccagca gccaacaatc 7320
gagccagaag agaactacca agatttatga attatacact caacaatacc aaaaacacca 7380
atgtaacatt aagtaagaaa aggaaaagaa gatttcttgg atttttgtta ggtgttggat 7440
ctgcaatcgc cagtggcatt gccgtatcca aggtcctgca cctagaaggg gaagtgaaca 7500
aaatcaaaag tgctctacta tccacaaaca aggctgtagt cagcttatct aatggagtca 7560
gtgtcttaac cagcaaggtg ttagacctca aaaactatat agataaacag ttgttaccta 7620
ttgttaacaa gcaaagctgc agcatatcaa acattgaaac tgtgatagag ttccaacaaa 7680
agaacaacag actactagag attaccagag aatttagtgt taatgcaggt gtaactactc 7740
ctgtaagcac ttatatgtta actaatagtg agttattatc attaatcaat gatatgccta 7800
taacaaatga tcagaaaaag ttaatgtcca gcaatgttca aatagttaga cagcaaagtt 7860
actctatcat gtcaataata aaagaggaag tcttggcata tgtagtacaa ttaccactat 7920

-continued

```
atggtgtaat agatactcct tgttggaaac tacacacatc ccctttatgt acaaccaaca   7980
caaaggaagg atccaacatc tgcttaacaa gaaccgacag aggatggtac tgtgacaatg   8040
caggatcagt atcctttttc ccacaagctg aaacatgtaa agttcaatcg aatcgggtgt   8100
tttgtgacac aatgaacagt ttaacattac caagtgaggt aaatctctgc aacattgaca   8160
tattcaaccc caaatatgat tgcaaaatta tgacttcaaa aacagatgta agcagctccg   8220
ttatcacatc tctaggagcc attgtgtcat gctatggcaa aaccaaatgt acagcatcca   8280
ataaaaatcg tgggatcata aagacattct ctaacgggtg tgattatgta tcaaataagg   8340
gggtggatac tgtgtctgta ggtaatacat tatattatgt aaataagcaa gaaggcaaaa   8400
gtctctatgt aaaaggtgaa ccaataataa atttctatga tccattagtg ttcccctctg   8460
atgaatttga tgcatcaata tctcaagtca atgagaaaat taatcagagt ctagcattta   8520
tccgtaaatc agatgaatta ttacataatg taaatgctgg taaatccacc acaaatatca   8580
tgataactac cataattata gtaattatag taatattgtt agcattaatt gcagttggac   8640
tgcttctata ctgcaaggcc agaagcacac cagtcacatt aagtaaggat caactgagtg   8700
gtataaataa tattgcattt agtaactgaa taaaaatagc acctaatcat attcttacaa   8760
tggttcgcta tttgaccata gataacccat ctatcattag attatcctaa aatttgaact   8820
tcatcacaac tttcatctat aaaccatctc acttacactt tttaagtaga tttctatttt   8880
atagttatat aaaacagggc ccattgaata ccaaattaac ttactatttg taaaaatgag   8940
aattggggca aatatgtcac gaaggaatcc ttgcaaattc gaaattcgag gtcattgctt   9000
gaatggtaaa aggtgtcatt ttagtcataa ttattttgaa tggccacccc atgcactgct   9060
tgtaagacaa aactttatgt taaacagaat acttaagtct atggataaaa gcatagatac   9120
tttgtcagaa ataagtggag ctgcagagtt ggacagaaca gaagagtatg ccctcggtgt   9180
agttggagtg ctagagagtt atataggatc aataaataat ataactaaac aatcagcatg   9240
tgttgccatg agcaaactcc ttactgaact caacagcgat gacatcaaaa aactaaggga   9300
caatgaagag ccaaactcac ccaaagtaag agtgtacaat actgtcatat catatattga   9360
aagcaacagg aagaacaata aacaaactat ccatctgtta aaaagattgc cagcagacgt   9420
attgaagaaa accatcaaaa acacattgga tatccacaag agcataacca tcaataaccc   9480
aaaagaatca actgttagtg atacgaacga ccatgccaaa aataatgata ctacctgaca   9540
aatatccttg tagtataaat tccatactaa taacaagtaa ttgtagagtc actatgtata   9600
atcaaaaaaa cacactatat atcaatcaaa acaaccaaaa tagccatata tacccaccgg   9660
atcaaccatt caatgaaatc cattggacct ctcaagactt gattgatgca actcaaaatt   9720
ttctacaaca tctaggtatt actgatgata tatacacaat atatatatta gtgtcataat   9780
actcaatcct aatacttacc acatcatcaa attattaact caaacaattc aagctatggg   9840
acaaaatgga tcccattatt agtggaaatt ctgctaatgt ttatctaact gatagttatt   9900
taaaaggtgt tatttctttc tcagaatgta acgctttagg aagttacata ttcaatggtc   9960
cttatctcaa aaatgattat accaacttaa ttagtagaca aaatccatta atagaacaca  10020
taaatctaaa gaaactaaat ataacacagt ccttaatatc taagtatcat aaaggtgaaa  10080
taaaaataga agaacctact tactttcagt cattacttat gacatacaag agtatgacct  10140
cttcagaaca gactactact actaatttac ttaaaaagat aataagaaga gctatagaaa  10200
tcagtgatgt caaagtctat gctatattga ataaactggg gctcaaagaa aaagacaaga  10260
ttaaatccaa taatggacaa gatgaagaca actcagtcat tactaccata atcaaagatg  10320
```

```
atatactttt agctgtcaag gataatcaat ctcatcttaa agcagacaaa aatcaatcca  10380
caaaacaaaa agatacaatc aaaacaacac ttttgaagaa attaatgtgt tcgatgcaac  10440
atcctccatc atggttaata cattggttta atttatacac aaaattaaac agcatattaa  10500
cacaatatcg atctagtgag gtaaaaaacc atggttttat attgatagat aatcatactc  10560
ttagtggatt ccaatttatt ttgaatcaat atggttgtat agtttatcat aaggaactca  10620
aaagaattac tgtgacaact tataatcaat tcttgacatg gaaagatatt agccttagta  10680
gattaaatgt ttgtttgatt acatggatta gtaactgttt gaacacatta aacaaaagct  10740
taggcttaag atgtggattc aataatgtta tcttgacaca attattcctt tatggagatt  10800
gtatactaaa actattccac aatgaggggt tctacataat aaaagaggta gagggattta  10860
ttatgtctct aattttaaat ataacagaag aagatcaatt cagaaaacgg ttttataata  10920
gtatgctcaa caacatcaca gatgccgcca acaaagctca aaaaaatctg ctatcaagag  10980
tatgtcatac attattagat aagacaatat cagataatat aataaatggc agatggataa  11040
ttctattgag taagttccta aaattaatta agcttgcagg tgacaataac ctcaacaatc  11100
tgagtgaatt atatttttg ttcagaatat ttggacaccc aatggtagat gaaagacaag  11160
ccatggatgc tgttaaagtt aattgcaacg agaccaaatt ttatttgtta agtagtttga  11220
gtatgttaag aggagctttt atatatagaa ttataaaagg gtttgtaaat aattacaaca  11280
gatggcctac tttaagaaat gccattgtct taccottaag atggttaact tactataaac  11340
taaacactta tccttccttg ttggaactta cagaaagaga tttgattgtt ctatcaggac  11400
tacgtttcta tcgagagttt cggttgccta aaaaagtgga tcttgaaatg atcataaatg  11460
ataaggctat atcacctcct aaaaatttaa tatggactag tttccctaga aattatatgc  11520
cgtcacacat acaaaattat atagaacatg aaaaattaaa attctctgat agtgataaat  11580
caagaagagt attagagtat tatttaagag ataacaaatt caatgaatgt gatttacaca  11640
actgtgtagt taatcaaagt tatcttaaca acccgaatca tgtggtatca ttgacaggca  11700
aagaaagaga actcagtgta ggtagaatgt ttgcaatgca accaggaatg ttcagacaag  11760
ttcaaatatt agcagagaaa atgatagcag aaaacatatt acaatttttc cctgaaagtc  11820
ttacaagata tggtgatcta gaactacaga aaatattaga attgaaagca ggaataagta  11880
acaaatcaaa tcgttacaat gataattaca acaattacat tagtaagtgc tctatcatca  11940
cagatctcag caaattcaat caagcatttc gatatgaaac atcatgtatt tgtagtgatg  12000
tactggatga actgcatggt gtacaatctc tattttcctg gttacattta actattcctc  12060
atgtcacaat aatatgcaca tataggcatg cacccccta tataaaggat catattgtag  12120
atcttaacaa tgtagatgag caaagtggac tatatagata tcatatgggt ggtatcgaag  12180
ggtggtgtca aaaactatgg accatagaag ctatatcact attagatcta atatctctca  12240
aagggaaatt ctcaattact gctttaatta atggtgacaa tcaatcaata gatataagta  12300
aaccagtcag actcatggaa ggtcaaactc atgctcaagc agattatttg ctagcattaa  12360
atagtctcaa attactgtat aaagagtatg caggaatagg ccacaaatta aaaggaactg  12420
agacttatat atcgagagat atgcaattta tgagtaaaac gatccaacat aacggtgtat  12480
attacccagc tagtataaag aaagtcctaa gagtgggacc gtggataaac actatacttg  12540
atgacttcaa agtgagtcta gaatctatag gtagtttgac acaagaatta gaatatagag  12600
gtgaaagtct attatgcagt ttaatattta gaaatgtatg gttatataat caaattgcat  12660
```

-continued tacaacttaa aaatcatgca ttatgtaaca acaaattata tttggatata ttaaaagttc 12720
taaaacactt aaaaaccttt tttaatcttg ataacattga tacagcatta acattgtata 12780
tgaatttgcc catgttattt ggtggtggtg atcccaactt gttatatcga agtttctata 12840
gaagaactcc tgatttcctc acagaggcta tagttcactc tgtgttcata cttagttatt 12900
atacaaacca tgatttaaaa gataaacttc aagatctgtc agatgataga ttgaataagt 12960
tcttaacatg cataatcacg tttgataaaa accccaatgc tgaattcgtt acattgatga 13020
gagatcctca agctttagga tctgagaggc aagctaaaat tactagcgaa atcaatagac 13080
tggcagttac cgaggttttg agcacagctc caaacaaaat attttccaaa agtgcacaac 13140
actataccac tacagagata gatcttaatg atattatgca aaatatagaa cctacatatc 13200
ctcacgggct aagagttgtt tatgagagtt taccctttta taaagcagag aaaatagtaa 13260
atcttatatc cggtacaaaa tctataacta acatactgga aaagacttct gccatagact 13320
taacagatat tgatagagcc actgagatga tgaggaaaaa cataactttg cttataagga 13380
tattaccatt agattgtaac agagataaaa gagaaatatt gagtatggaa aacctaagta 13440
ttactgaatt aagcaaatac gttagagaaa gatcttggtc tttatccaat atagttggtg 13500
ttacatcacc cagtatcatg tatacaatgg acataaaata tacaacaagc actatagcta 13560
gtggcataat catagagaaa tataatgtca acagtttaac acgtggtgag agaggaccca 13620
ctaaaccatg ggttggttca tctacacaag agaaaaagac aatgccagtt tataatagac 13680
aagttttaac caaaaaacag agagatcaaa tagatctatt agcaaaattg gattgggtgt 13740
atgcatctat agataacaag gatgaattta tggaggaact tagcatagga actcttgggt 13800
taacatatga gaaggccaaa aaattattcc cacaatattt gagtgttaac tatttgcatc 13860
gtcttacagt cagtagtaga ccatgtgaat tccctgcatc tataccagct tatagaacta 13920
caaattatca ctttgatact agccctatta atcgcatatt aacagaaaag tatggtgatg 13980
aagatattga tatagtattc caaaactgta taagctttgg ccttagctta atgtctgtag 14040
tagaacaatt tactaatgta tgtcctaaca gaattattct catacccaag cttaatgaga 14100
tacatttgat gaaacctccc atattcacag gcgatgttga tattcacaag ttaaaacaag 14160
tgatacaaaa acaacatatg tttttaccag acaaaataag tttgactcaa tatgtggaat 14220
tattcttaag taataaaaca ctcaaatctg gatctaatgt taattctaat ttaatattgg 14280
cgcataagat atctgactat tttcataata cttacatttt gagtactaat ttagctggac 14340
attggattct tattatacaa cttatgaaag attctaaggg tatttttgaa aaagattggg 14400
gagagggata tataactgat catatgttca ttaatttgaa agttttcttc aatgcttata 14460
agacatatct cttgtgtttt cataaaggtt acggcagagc aaagctggag tgtgatatga 14520
atacttcaga tctcctatgt gtattggaat taatagacag tagttattgg aagtctatgt 14580
ctaaggtgtt tttagaacaa aaagttatca aatacattct tagccaggat gcaagtttac 14640
atagagtaaa aggatgtcat agcttcaaac tatggtttct taaacgtctt aatgtagcag 14700
aattcacagt ttgcccttgg gttgttaaca tagattatca tccaacacat atgaaagcaa 14760
tattaactta tattgatctt gttagaatgg gattgataaa tatagataga atatacatta 14820
aaaataaaca caagttcaat gatgagtttt atacttctaa tctgttttac attaattata 14880
acttctcaga taatactcat ctattaacta aacatataag gattgctaat tccgaattag 14940
aaagtaatta caacaaatta tatcatccta caccagaaac cctagaaaat atactaacca 15000
atccggttaa aagtaatgag aaaaagacac tgagtgacta ttgtataggt aaaaatgttg 15060

-continued actcaataat gttaccatcg ttatctaata agaagcttat taaatcgtct acaatgatta 15120
gaaccaatta cagcagacaa gatttgtata atttatttcc tacggttgtg attgataaaa 15180
ttatagatca ttcaggtaat acagccaaat ctaaccaact ttacactact acttctcatc 15240
aaatatcctt agtgcacaat agcacatcac tttattgcat gcttccttgg catcatatta 15300
atagattcaa ttttgtattt agttctacag gttgtaaaat tagtatagag tatattttaa 15360
aagatcttaa aattaaggat cctaattgta tagcattcat aggtgaagga gcagggaatt 15420
tattattgcg tacagtagtg gaacttcatc ctgatataag atatatttac agaagtctga 15480
aagattgcaa tgatcatagt ttaccaattg agtttttaag gctgtacaat ggacatatca 15540
acattgatta tggtgaaaat ttgaccattc ctgctacaga tgcaaccaac aacattcatt 15600
ggtcttattt acatataaag tttgctgaac ctatcagtct ttttgtctgt gatgctgaat 15660
tgcctgtaac agtcaactgg agtaagatta taatagagtg gagcaagcat gtaagaaaat 15720
gcaagtactg ttcttcagtt aataaatgta cattgatagt aaaatatcat gctcaagatg 15780
atatcgattt caaattagac aacataacta tattaaaaac ttatgtatgc ttaggtagta 15840
agttaaaggg atctgaagtt tacttagtcc ttacaatagg tcctgcaaat gtgttcccag 15900
tatttaatgt agtacaaaat gctaaattga tactatcaag aactaaaaat ttcatcatgc 15960
ctaaaaaagc tgataaagag tctattgatg caaatattaa gagtttgata ccctttcttt 16020
gttaccctat aacaaaaaaa ggaattaata ctgcattgtc taaattaaag agtgttgtta 16080
gtggagatat actatcatat tctatagctg gacgtaatga agttttcagc aataaactta 16140
taaatcataa gcatatgaac atcttaaagt ggttcaatca tgttttaaat ttcagatcaa 16200
cagaattaaa ctataatcat ttatatatgg tagaatctac ttatcctcat ctaagtgaat 16260
tgttaaacag cttgacaacc aatgaactta aaaaactgat taaaatcaca ggtagtttgt 16320
tatacaactt ttataatgaa taatgagcaa aaatcttata acaaaaatag ctacacacta 16380
acattgtatt caattatagt tattgaaaat taataattat ataattttta ataacttcta 16440
gtgaactaat cctaaaatta tcattttgat ctaggaagaa taagtttaaa tccaaatcta 16500
attggtttat atgtatatta actaaattac gagatattag tttttgacac tttttttctc 16560
gtggccggca tggtcccagc ctcctcgctg gcgccggctg ggcaacatgc ttcggcatgg 16620
cgaatgggac tagcataacc ccttggggcc tctaaacggg tcttgagggg ttttttg 16677

<210> SEQ ID NO 19
<211> LENGTH: 15689
<212> TYPE: DNA
<213> ORGANISM: Artificial Sequence
<220> FEATURE:
<223> OTHER INFORMATION: antigenic cDNA encoding cRSVA_VSVG_A_SH deletion_G deletion

<400> SEQUENCE: 19
taatacgact cactataggt tttttcgcgt ctgatgaggc cgttaggccg aaactcctct 60
ccggagtcac gcgaaaaaat gcgtacaaca aacttgcgta aaccaaaaaa atggggcaaa 120
taagaatttg ataagtacca cttaaattta actcctttgg ttagaggcgc gccatgggca 180
gcaactcatt gagtatgata aaagttagat tgcaaaatct gtttgacaat gatgaagtag 240
cattgttaaa aataacatgc tatactgaca aattaataca gttaactaat gctttggcta 300
aggcagttat acatacaatc aaattgaatg gcattgtatt tgtgcatgtt attacaagta 360
gtgatatttg ccctaataat aatattgtag tgaaatccaa tttcacaaca atgccagtat 420

```
tacaaaatgg aggttatata tgggaaatga tggaattaac acactgctct caacctaatg    480
gcctaataga tgacaattgt gaaattaaat tctccaaaaa actaagtgat tcaacaatga    540
ccaattatat gaatcaatta tctgaattac ttggatttga cctcaatcca taaatcataa    600
taaatatcaa ctagcaaatc aatgtcacta acaccattag ttaatataaa acttgacaga    660
agataaaaat ggggcaaata aatcaattca gccgacccaa ccatggacac aacacacaat    720
gataccacac cacaaagact gatgatcaca gacatgaggc cattatcgct tgagactata    780
ataacatctc taaccagaga tatcataaca cataaattta tatacttgat aaatcatgaa    840
tgcatagtaa gaaaacttga tgaaagacag gccacattta catttctggt caactatgaa    900
atgaaactat tgcacaaagt gggaagcact aaatataaaa aatatactga atacaacaca    960
aaatatggca ctttccctat gccaatattt atcaatcatg atgggttctt agaatgcatt   1020
ggcattaagc ctaccaagca cacacccata atatacaagt atgatctcaa tccatgaata   1080
tcaaaccaag attcaaacaa tccgaaataa caactttatg cataatcaca ctccatagtc   1140
caaatggagc ctgaaaatta tagttattta aaattcctgc aggaaggaga gacataagat   1200
gaaagatggg gcaaatacaa aaatggctct tagcaaagtc aagttgaatg atacactcaa   1260
caaagatcaa cttctatcat ccagcaaata taccatccaa cggagcacag gagacagcat   1320
tgacactcct aattatgatg tgcagaaaca cattaataag ttatgtggca tgttattaat   1380
cacagaagat gctaatcata aattcactgg gttaataggt atgttatatg ctatgtctag   1440
attaggaaga gaagacacca taaaaatact caaagatgcg ggatatcatg ttaaggcaaa   1500
tggagtggat gtaacaacac atcgtcaaga cattaatggg aaagaaatga aatttgaagt   1560
gttaacatta gcaagcttaa caactgaaat tcaaatcaac attgagatag aatctagaaa   1620
atcctacaaa aaaatgctaa aagaaatggg agaggtggct ccagaataca ggcatgactc   1680
tcctgattgt gggatgataa tattatgtat agcggcatta gtaataacca aattagcagc   1740
aggagataga tcaggtctta cagctgtgat taggagagct aataatgtcc taaaaaatga   1800
aatgaaacgt tataaaggtt tattacccaa ggatatagcc aacagcttct atgaagtgtt   1860
tgaaaaatat cctcacttta tagatgtttt tgttcatttt ggtatagcac aatcttctac   1920
cagaggtggc agtagagttg aagggatttt tgcaggattg tttatgaatg cctatggtgc   1980
agggcaagtg atgttacggt ggggggtctt agcaaaatca gttaaaaaca ttatgttagg   2040
acacgctagt gtacaagcag aaatggaaca agttgtggag gtgtatgagt atgctcagaa   2100
attgggtgga gaagcaggat tctaccatat attgaacaac ccaaaagcat cactattatc   2160
tttgactcaa tttcctcact tctctagtgt agtattgggc aatgctgctg gcctaggcat   2220
aatgggagaa tacagaggta caccaaggaa tcaagattta tatgatgctg caaaagcata   2280
tgctgaacaa ctcaaagaaa atggtgtgat taactacagt gtattagatt tgacagcaga   2340
agaactagag gctatcaaac atcagcttaa tccaaaagat aatgatgtag agctttgagt   2400
taataaaaaa gtggggcaaa taaatcatca tggaaaagtt tgctcctgaa ttccatggag   2460
aagatgcaaa caacagagcc accaaattcc tagaatcaat aaagggcaaa ttcacatcac   2520
ccaaagatcc caagaaaaaa gatagtatca tatctgtcaa ctcaatagat atagaagtaa   2580
ccaaagaaag ccctataaca tcaaattcaa ccattataaa cccaataaat gagacagatg   2640
atactgtagg gaacaagccc aattatcaaa gaaagcctct agtaagtttc aaagaagacc   2700
ctacgccaag tgataatcct tttcaaaac tatacaaaga aaccatagaa acatttgata   2760
```

-continued

```
acaatgaaga agaatctagc tattcatatg aagaaataaa tgatcagaca aacgataata   2820
taacagcaag attagatagg attgatgaga aattaagtga aatactagga atgcttcaca   2880
cattagtagt agcgagtgca ggacccacat ctgctcggga tggtataaga gatgccatgg   2940
ttggtttaag agaagaaatg atagaaaaaa tcagaactga agcattaatg accaatgaca   3000
gactagaagc tatggcaaga ctcaggaatg aagaaagtga aaagatggca aaagacacat   3060
cagatgaagt gtctctcaat ccaacatcag agaaactgaa caacctgttg gaagggaatg   3120
atagtgacaa tgatctatca cttgaagatt tctgattagc taccaaactg tacatcaaaa   3180
cacaacacca atagaaaacc aacaaacaaa ccaactcacc catccaacca aacatctatc   3240
tgctgattag ccaaccagcc aaaaaacaac cagccaatct aaaactagcc acccggaaaa   3300
aatcgatact atagttacaa aaaaagatgg ggcaaatatg gaaacatacg tgaataaact   3360
tcacgagggc tccacataca cagctgctgt tcaatacaat gtcctagaaa aagacgatga   3420
tcctgcatca cttacaatat gggtgcccat gttccaatca tccatgccag cagatctact   3480
cataaaagaa ctagccaatg tcaatatact agtgaaacaa atatccacac ccaagggacc   3540
ctcattaaga gtcatgataa actcaagaag tgcagtgcta gcacaaatgc ccagcaaatt   3600
taccatatgt gccaatgtgt ccttggatga aagaagcaag ctggcatatg atgtaaccac   3660
accctgtgaa attaaggcat gcagtctaac atgcctaaaa tcaaaaaata tgttaactac   3720
agttaaagat ctcactatga aacactcaa cccaacacat gacatcattg ctttatgtga    3780
atttgaaaat atagtaacat caaaaaaagt cataatacca acatacctaa gatctatcag   3840
cgtcagaaat aaagatctga acacacttga aaatataaca accactgaat tcaaaaatgc   3900
cattacaaat gcaaaaatca tcccttactc aggattattg ttagtcatca cagtgactga   3960
caacaaagga gcattcaaat acataaagcc acaaagtcaa ttcatagtag atcttggagc   4020
ttacctagaa aaagaaagta tatattatgt tacaacaaat tggaagcaca cagctacacg   4080
atttgcaatc aaacccatgg aagattaacc tttttcctct acatcaatga gtagattcat   4140
acaaactttc taactacatt cttcacttca caatcataat caccaaccct ctgtggttca   4200
atcaatcaaa caaaactcat caagagttcc agatcatccc aagtcattgt tcatcagatc   4260
cagtactcaa ataagttaat aaaaaatcgg tccgttgaca gaagataaaa atggggcaaa   4320
tgcaaacatg aagtgccttt tgtacttagc ctttttattc attggggtga attgcaagtt   4380
caccatagtt tttccacaca accaaaaagg aaactggaaa aatgttcctt ctaattacca   4440
ttattgcccg tcaagctcag atttaaattg gcataatgac ttaataggca cagccttaca   4500
agtcaaaatg cccaagagtc acaaggctat tcaagcagac ggttggatgt gtcatgcttc   4560
caaatgggtc actacttgtg atttccgctg gtatggaccg aagtatataa cacattccat   4620
ccgatccttc actccatctg tagaacaatg caaggaaagc attgaacaaa cgaaacaagg   4680
aacttggctg aatccaggct tccctcctca aagttgtgga tatgcaactg tgacggatgc   4740
cgaagcagtg attgtccagg tgactcctca ccatgtgctg gttgatgaat acacaggaga   4800
atgggttgat tcacagttca tcaacggaaa atgcagcaat tacatatgcc ccactgtcca   4860
taactctaca acctggcatt ctgactataa ggtcaaaggg ctatgtgatt ctaacctcat   4920
ttccatggac atcaccttct tctcagagga cggagagcta tcatccctgg gaaaggaggg   4980
cacagggttc agaagtaact actttgctta tgaaactgga ggcaaggcct gcaaaatgca   5040
atactgcaag cattggggag tcagactccc atcaggtgtc tggttcgaga tggctgataa   5100
ggatctcttt gctgcagcca gattccctga atgcccagaa gggtcaagta tctctgctcc   5160
```

atctcagacc tcagtggatg taagtctaat tcaggacgtt gagaggatct tggattattc 5220
cctctgccaa gaaacctgga gcaaaatcag agcgggtctt ccaatctctc cagtggatct 5280
cagctatctt gctcctaaaa acccaggaac cggtcctgct ttcaccataa tcaatggtac 5340
cctaaaatac tttgagacca gatacatcag agtcgatatt gctgctccaa tcctctcaag 5400
aatggtcgga atgatcagtg gaactaccac agaaagggaa ctgtgggatg actgggcacc 5460
atatgaagac gtggaaattg gacccaatgg agttctgagg accagttcag gatataagtt 5520
tcctttatac atgattggac atggtatgtt ggactccgat cttcatctta gctcaaaggc 5580
tcaggtgttc gaacatcctc acattcaaga cgctgcttcg caacttcctg atgatgagag 5640
tttatttttt ggtgatactg ggctatccaa aaatccaatc gagcttgtag aaggttggtt 5700
cagtagttgg aaaagctcta ttgcctcttt tttctttatc atagggttaa tcattggact 5760
attcttggtt ctccgagttg gtatccatct ttgcattaaa gccagaagca caccagtcac 5820
attaagtaag gatcaactga gtggtataaa taatattgca tttagtaact aatagtcatt 5880
aaaaagcggc cggccgtatt gttgcaaaaa gccatgacca aatcaaacag aatcaaaatc 5940
aactctacgc gtgtattgtt gcaaaaagcc atgaccaaat caaacagaat caaaatcaac 6000
tctggggcaa ataacaatgg agttgccaat cctcaaaaca aatgctatta ccacaatcct 6060
tgctgcagtc acactctgtt tcgcttccag tcaaaacatc actgaagaat tttatcaatc 6120
aacatgcagt gcagtcagca aaggctatct tagtgctcta agaactggtt ggtatactag 6180
tgttataact atagaattaa gtaatatcaa ggaaaataag tgtaatggta cagacgctaa 6240
ggtaaaatta ataaaacaag aattagataa atataaaaat gctgtaacag aattgcagtt 6300
gctcatgcaa agcacaccag cagccaacaa tcgagccaga agagaactac caagatttat 6360
gaattataca ctcaacaata ccaaaaacac caatgtaaca ttaagtaaga aaaggaaaag 6420
aagatttctt ggatttttgt taggtgttgg atctgcaatc gccagtggca ttgccgtatc 6480
caaggtcctg cacctagaag gggaagtgaa caaaatcaaa agtgctctac tatccacaaa 6540
caaggctgta gtcagcttat ctaatggagt cagtgtctta accagcaagg tgttagacct 6600
caaaaactat atagataaac agttgttacc tattgttaac aagcaaagct gcagcatatc 6660
aaacattgaa actgtgatag agttccaaca aaagaacaac agactactag agattaccag 6720
agaatttagt gttaatgcag gtgtaactac tcctgtaagc acttatatgt taactaatag 6780
tgagttatta tcattaatca atgatatgcc tataacaaat gatcagaaaa agttaatgtc 6840
cagcaatgtt caaatagtta gacagcaaag ttactctatc atgtcaataa taaaagagga 6900
agtcttggca tatgtagtac aattaccact atatggtgta atagatactc cttgttggaa 6960
actacacaca tcccctttat gtacaaccaa cacaaaggaa ggatccaaca tctgcttaac 7020
aagaaccgac agaggatggt actgtgacaa tgcaggatca gtatcctttt tcccacaagc 7080
tgaaacatgt aaagttcaat cgaatcgggt gttttgtgac acaatgaaca gtttaacatt 7140
accaagtgag gtaaatctct gcaacattga catattcaac cccaaatatg attgcaaaat 7200
tatgacttca aaaacagatg taagcagctc cgttatcaca tctctaggag ccattgtgtc 7260
atgctatggc aaaaccaaat gtacagcatc caataaaaat cgtgggatca taaagacatt 7320
ctctaacggg tgtgattatg tatcaaataa gggggtggat actgtgtctg taggtaatac 7380
attatattat gtaaataagc aagaaggcaa aagtctctat gtaaaaggtg aaccaataat 7440
aaatttctat gatccattag tgttcccctc tgatgaattt gatgcatcaa tatctcaagt 7500

```
caatgagaaa attaatcaga gtctagcatt tatccgtaaa tcagatgaat tattacataa   7560
tgtaaatgct ggtaaatcca ccacaaatat catgataact accataatta tagtaattat   7620
agtaatattg ttagcattaa ttgcagttgg actgcttcta tactgcaagg ccagaagcac   7680
accagtcaca ttaagtaagg atcaactgag tggtataaat aatattgcat ttagtaactg   7740
aataaaaata gcacctaatc atattcttac aatggttcgc tatttgacca tagataaccc   7800
atctatcatt agattatcct aaaatttgaa cttcatcaca actttcatct ataaaccatc   7860
tcacttacac tttttaagta gatttctatt ttatagttat ataaaacagg gcccattgaa   7920
taccaaatta acttactatt tgtaaaaatg agaattgggg caaatatgtc acgaaggaat   7980
ccttgcaaat tcgaaattcg aggtcattgc ttgaatggta aaaggtgtca ttttagtcat   8040
aattattttg aatggccacc ccatgcactg cttgtaagac aaaactttat gttaaacaga   8100
atacttaagt ctatggataa aagcatagat actttgtcag aaataagtgg agctgcagag   8160
ttggacagaa cagaagagta tgccctcggt gtagttggag tgctagagag ttatatagga   8220
tcaataaata atataactaa acaatcagca tgtgttgcca tgagcaaact ccttactgaa   8280
ctcaacagcg atgacatcaa aaaactaagg gacaatgaag agccaaactc acccaaagta   8340
agagtgtaca atactgtcat atcatatatt gaaagcaaca ggaagaacaa taaacaaact   8400
atccatctgt taaaaagatt gccagcagac gtattgaaga aaaccatcaa aaacacattg   8460
gatatccaca agagcataac catcaataac ccaaaagaat caactgttag tgatacgaac   8520
gaccatgcca aaaataatga tactacctga caaatatcct tgtagtataa attccatact   8580
aataacaagt aattgtagag tcactatgta taatcaaaaa aacacactat atatcaatca   8640
aaacaaccaa aatagccata tatacccacc ggatcaacca ttcaatgaaa tccattggac   8700
ctctcaagac ttgattgatg caactcaaaa ttttctacaa catctaggta ttactgatga   8760
tatatacaca atatatatat tagtgtcata atactcaatc ctaatactta ccacatcatc   8820
aaattattaa ctcaaacaat tcaagctatg ggacaaaatg gatcccatta ttagtggaaa   8880
ttctgctaat gtttatctaa ctgatagtta tttaaaaggt gttatttctt tctcagaatg   8940
taacgcttta ggaagttaca tattcaatgg tccttatctc aaaaatgatt ataccaactt   9000
aattagtaga caaaatccat taatagaaca cataaatcta aagaaactaa atataacaca   9060
gtccttaata tctaagtatc ataaaggtga aataaaaata gaagaaccta cttactttca   9120
gtcattactt atgacataca agagtatgac ctcttcagaa cagactacta ctactaattt   9180
acttaaaaag ataataagaa gagctataga aatcagtgat gtcaaagtct atgctatatt   9240
gaataaactg gggctcaaag aaaaagacaa gattaaatcc aataatggac aagatgaaga   9300
caactcagtc attactacca taatcaaaga tgatatactt ttagctgtca aggataatca   9360
atctcatctt aaagcagaca aaaatcaatc cacaaaacaa aaagatacaa tcaaaacaac   9420
acttttgaag aaattaatgt gttcgatgca acatcctcca tcatggttaa tacattggtt   9480
taatttatac acaaaattaa acagcatatt aacacaatat cgatctagtg aggtaaaaaa   9540
ccatggtttt atattgatag ataatcatac tcttagtgga ttccaattta ttttgaatca   9600
atatggttgt atagtttatc ataaggaact caaaagaatt actgtgacaa cttataatca   9660
attcttgaca tggaaagata ttagccttag tagattaaat gtttgtttga ttacatggat   9720
tagtaactgt ttgaacacat taaacaaaag cttaggctta agatgtggat tcaataatgt   9780
tatcttgaca caattattcc tttatggaga ttgtatacta aaactattcc acaatgaggg   9840
gttctacata ataaaagagg tagagggatt tattatgtct ctaattttaa atataacaga   9900
```

```
agaagatcaa ttcagaaaac ggttttataa tagtatgctc aacaacatca cagatgccgc   9960
caacaaagct caaaaaaatc tgctatcaag agtatgtcat acattattag ataagacaat  10020
atcagataat ataataaatg gcagatggat aattctattg agtaagttcc taaaattaat  10080
taagcttgca ggtgacaata acctcaacaa tctgagtgaa ttatattttt tgttcagaat  10140
atttggacac ccaatggtag atgaaagaca agccatggat gctgttaaag ttaattgcaa  10200
cgagaccaaa ttttatttgt taagtagttt gagtatgtta agaggagctt ttatatatag  10260
aattataaaa gggtttgtaa ataattacaa cagatggcct actttaagaa atgccattgt  10320
cttaccctta agatggttaa cttactataa actaaacact tatccttcct tgttggaact  10380
tacagaaaga gatttgattg ttctatcagg actacgtttc tatcgagagt ttcggttgcc  10440
taaaaaagtg gatcttgaaa tgatcataaa tgataaggct atatcacctc ctaaaaattt  10500
aatatggact agtttcccta gaaattatat gccgtcacac atacaaaatt atatagaaca  10560
tgaaaaatta aaattctctg atagtgataa atcaagaaga gtattagagt attatttaag  10620
agataacaaa ttcaatgaat gtgatttaca caactgtgta gttaatcaaa gttatcttaa  10680
caacccgaat catgtggtat cattgacagg caaagaaaga gaactcagtg taggtagaat  10740
gtttgcaatg caaccaggaa tgttcagaca agttcaaata ttagcagaga aaatgatagc  10800
agaaaacata ttacaatttt tccctgaaag tcttacaaga tatggtgatc tagaactaca  10860
gaaaatatta gaattgaaag caggaataag taacaaatca aatcgttaca atgataatta  10920
caacaattac attagtaagt gctctatcat cacagatctc agcaaattca atcaagcatt  10980
tcgatatgaa acatcatgta tttgtagtga tgtactggat gaactgcatg gtgtacaatc  11040
tctattttcc tggttacatt taactattcc tcatgtcaca ataaatatgca catataggca  11100
tgcacccccc tatataaagg atcatattgt agatcttaac aatgtagatg agcaaagtgg  11160
actatataga tatcatatgg gtggtatcga agggtggtgt caaaaactat ggaccataga  11220
agctatatca ctattagatc taatatctct caaagggaaa ttctcaatta ctgctttaat  11280
taatggtgac aatcaatcaa tagatataag taaaccagtc agactcatgg aaggtcaaac  11340
tcatgctcaa gcagattatt tgctagcatt aaatagtctc aaattactgt ataaagagta  11400
tgcaggaata ggccacaaat taaaaggaac tgagacttat atatcgagag atatgcaatt  11460
tatgagtaaa acgatccaac ataacggtgt atattaccca gctagtataa agaaagtcct  11520
aagagtggga ccgtggataa acactatact tgatgacttc aaagtgagtc tagaatctat  11580
aggtagtttg acacaagaat tagaatatag aggtgaaagt ctattatgca gtttaatatt  11640
tagaaatgta tggttatata atcaaattgc attacaactt aaaaatcatg cattatgtaa  11700
caacaaatta tatttggata tattaaaagt tctaaaacac ttaaaaacct tttttaatct  11760
tgataacatt gatacagcat taacattgta tatgaatttg cccatgttat ttggtggtgg  11820
tgatcccaac ttgttatatc gaagtttcta tagaagaact cctgatttcc tcacagaggc  11880
tatagttcac tctgtgttca tacttagtta ttatacaaac catgatttaa aagataaact  11940
tcaagatctg tcagatgata gattgaataa gttcttaaca tgcataatca cgtttgataa  12000
aaaccccaat gctgaattcg ttacattgat gagagatcct caagctttag gatctgagag  12060
gcaagctaaa attactagcg aaatcaatag actggcagtt accgaggttt tgagcacagc  12120
tccaaacaaa atattttcca aaagtgcaca acactatacc actacagaga tagatcttaa  12180
tgatattatg caaaatatag aacctacata tcctcacggg ctaagagttg tttatgagag  12240
```

-continued

```
tttaccettt tataaagcag agaaaatagt aaatcttata tccggtacaa aatctataac  12300
taacatactg gaaaagactt ctgccataga cttaacagat attgatagag ccactgagat  12360
gatgaggaaa aacataactt tgcttataag gatattacca ttagattgta acagagataa  12420
aagagaaata ttgagtatgg aaaacctaag tattactgaa ttaagcaaat acgttagaga  12480
aagatcttgg tctttatcca atatagttgg tgttacatca cccagtatca tgtatacaat  12540
ggacataaaa tatacaacaa gcactatagc tagtggcata atcatagaga aatataatgt  12600
caacagttta acacgtggtg agagaggacc cactaaacca tgggttggtt catctacaca  12660
agagaaaaag acaatgccag tttataatag acaagtttta accaaaaaac agagagatca  12720
aatagatcta ttagcaaaat tggattgggt gtatgcatct atagataaca aggatgaatt  12780
tatggaggaa cttagcatag gaactcttgg gttaacatat gagaaggcca aaaaattatt  12840
cccacaatat ttgagtgtta actatttgca tcgtcttaca gtcagtagta gaccatgtga  12900
attccctgca tctataccag cttatagaac tacaaattat cactttgata ctagccctat  12960
taatcgcata ttaacagaaa agtatggtga tgaagatatt gatatagtat tccaaaactg  13020
tataagcttt ggccttagct taatgtctgt agtagaacaa tttactaatg tatgtcctaa  13080
cagaattatt ctcataccca agcttaatga gatacatttg atgaaacctc ccatattcac  13140
aggcgatgtt gatattcaca agttaaaaca agtgatacaa aaacaacata tgtttttacc  13200
agacaaaata agtttgactc aatatgtgga attattctta agtaataaaa cactcaaatc  13260
tggatctaat gttaattcta atttaatatt ggcgcataag atatctgact attttcataa  13320
tacttacatt ttgagtacta atttagctgg acattggatt cttattatac aacttatgaa  13380
agattctaag ggtatttttg aaaaagattg ggagagagga tatataactg atcatatgtt  13440
cattaatttg aaagttttct tcaatgctta taagacatat ctcttgtgtt ttcataaagg  13500
ttacggcaga gcaaagctgg agtgtgatat gaatacttca gatctcctat gtgtattgga  13560
attaatagac agtagttatt ggaagtctat gtctaaggtg tttttagaac aaaaagttat  13620
caaatacatt cttagccagg atgcaagttt acatagagta aaaggatgtc atagcttcaa  13680
actatggttt cttaaacgtc ttaatgtagc agaattcaca gtttgccctt gggttgttaa  13740
catagattat catccaacac atatgaaagc aatattaact tatattgatc ttgttagaat  13800
gggattgata aatatagata gaatatacat taaaaataaa cacaagttca atgatgagtt  13860
ttatacttct aatctgtttt acattaatta taacttctca gataatactc atctattaac  13920
taaacatata aggattgcta attccgaatt agaaagtaat tacaacaaat tatatcatcc  13980
tacaccagaa accctagaaa atatactaac caatccggtt aaaagtaatg agaaaaagac  14040
actgagtgac tattgtatag gtaaaaatgt tgactcaata atgttaccat cgttatctaa  14100
taagaagctt attaaatcgt ctacaatgat tagaaccaat tacagcagac aagatttgta  14160
taatttattt cctacggttg tgattgataa aattatagat cattcaggta atacagccaa  14220
atctaaccaa ctttacacta ctacttctca tcaaatatcc ttagtgcaca atagcacatc  14280
actttattgc atgcttcctt ggcatcatat taatagattc aattttgtat ttagttctac  14340
aggttgtaaa attagtatag agtatatttt aaaagatctt aaaattaagg atcctaattg  14400
tatagcattc ataggtgaag gagcagggaa tttattattg cgtacagtag tggaacttca  14460
tcctgatata agatatattt acagaagtct gaaagattgc aatgatcata gtttaccaat  14520
tgagttttta aggctgtaca atggacatat caacattgat tatggtgaaa atttgaccat  14580
tcctgctaca gatgcaacca acaacattca ttggtcttat ttacatataa agtttgctga  14640
```

acctatcagt ctttttgtct gtgatgctga attgcctgta acagtcaact ggagtaagat 14700
tataatagag tggagcaagc atgtaagaaa atgcaagtac tgttcttcag ttaataaatg 14760
tacattgata gtaaaatatc atgctcaaga tgatatcgat ttcaaattag acaacataac 14820
tatattaaaa acttatgtat gcttaggtag taagttaaag ggatctgaag tttacttagt 14880
ccttacaata ggtcctgcaa atgtgttccc agtatttaat gtagtacaaa atgctaaatt 14940
gatactatca agaactaaaa atttcatcat gcctaaaaaa gctgataaag agtctattga 15000
tgcaaatatt aagagtttga taccctttct ttgttaccct ataacaaaaa aaggaattaa 15060
tactgcattg tctaaattaa agagtgttgt tagtggagat atactatcat attctatagc 15120
tggacgtaat gaagttttca gcaataaact tataaatcat aagcatatga acatcttaaa 15180
gtggttcaat catgttttaa atttcagatc aacagaatta aactataatc atttatatat 15240
ggtagaatct acttatcctc atctaagtga attgttaaac agcttgacaa ccaatgaact 15300
taaaaaactg attaaaatca caggtagttt gttatacaac ttttataatg aataatgagc 15360
aaaaatctta taacaaaaat agctacacac taacattgta ttcaattata gttattgaaa 15420
attaataatt atataatttt taataacttc tagtgaacta atcctaaaat tatcattttg 15480
atctaggaag aataagttta aatccaaatc taattggttt atatgtatat taactaaatt 15540
acgagatatt agtttttgac acttttttc tcgtggccgg catggtccca gcctcctcgc 15600
tggcgccggc tgggcaacat gcttcggcat ggcgaatggg actagcataa ccccttgggg 15660
cctctaaacg ggtcttgagg ggtttttg 15689

<210> SEQ ID NO 20
<211> LENGTH: 14772
<212> TYPE: DNA
<213> ORGANISM: Artificial Sequence
<220> FEATURE:
<223> OTHER INFORMATION: antigenic cDNA encoding cRSVA_VSVG_A_SH deletion_F deletion

<400> SEQUENCE: 20
taatacgact cactataggt tttttcgcgt ctgatgaggc cgttaggccg aaactcctct 60
ccggagtcac gcgaaaaaat gcgtacaaca aacttgcgta aaccaaaaaa atggggcaaa 120
taagaatttg ataagtacca cttaaattta actcctttgg ttagaggcgc gccatgggca 180
gcaactcatt gagtatgata aaagttagat tgcaaaatct gtttgacaat gatgaagtag 240
cattgttaaa aataacatgc tatactgaca aattaataca gttaactaat gctttggcta 300
aggcagttat acatacaatc aaattgaatg gcattgtatt tgtgcatgtt attacaagta 360
gtgatatttg ccctaataat aatattgtag tgaaatccaa tttcacaaca atgccagtat 420
tacaaaatgg aggttatata tgggaaatga tggaattaac acactgctct caacctaatg 480
gcctaataga tgacaattgt gaaattaaat tctccaaaaa actaagtgat tcaacaatga 540
ccaattatat gaatcaatta tctgaattac ttggatttga cctcaatcca taaatcataa 600
taaatatcaa ctagcaaatc aatgtcacta acaccattag ttaatataaa acttgacaga 660
agataaaaat ggggcaaata aatcaattca gccgacccaa ccatggacac aacacacaat 720
gataccacac cacaaagact gatgatcaca gacatgaggc cattatcgct tgagactata 780
ataacatctc taaccagaga tatcataaca cataaattta tatacttgat aaatcatgaa 840
tgcatagtaa gaaaacttga tgaaagacag gccacattta catttctggt caactatgaa 900
atgaaactat tgcacaaagt gggaagcact aaatataaaa aatatactga atacaacaca 960
aaatatggca ctttccctat gccaatattt atcaatcatg atgggttctt agaatgcatt 1020
ggcattaagc ctaccaagca cacacccata atatacaagt atgatctcaa tccatgaata 1080
tcaaaccaag attcaaacaa tccgaaataa caactttatg cataatcaca ctccatagtc 1140
caaatggagc ctgaaaatta tagttattta aaattcctgc aggaaggaga gacataagat 1200
gaaagatggg gcaaatacaa aaatggctct tagcaaagtc aagttgaatg atacactcaa 1260
caaagatcaa cttctatcat ccagcaaata taccatccaa cggagcacag gagacagcat 1320
tgacactcct aattatgatg tgcagaaaca cattaataag ttatgtggca tgttattaat 1380
cacagaagat gctaatcata aattcactgg gttaataggt atgttatatg ctatgtctag 1440
attaggaaga gaagacacca taaaaatact caaagatgcg ggatatcatg ttaaggcaaa 1500
tggagtggat gtaacaacac atcgtcaaga cattaatggg aaagaaatga aatttgaagt 1560
gttaacatta gcaagcttaa caactgaaat tcaaatcaac attgagatag aatctagaaa 1620
atcctacaaa aaaatgctaa aagaaatggg agaggtggct ccagaataca ggcatgactc 1680
tcctgattgt gggatgataa tattatgtat agcggcatta gtaataacca aattagcagc 1740
aggagataga tcaggtctta cagctgtgat taggagagct aataatgtcc taaaaaatga 1800
aatgaaacgt tataaaggtt tattacccaa ggatatagcc aacagcttct atgaagtgtt 1860
tgaaaaatat cctcacttta tagatgtttt tgttcatttt ggtatagcac aatcttctac 1920
cagaggtggc agtagagttg aagggatttt tgcaggattg tttatgaatg cctatggtgc 1980
agggcaagtg atgttacggt ggggggtctt agcaaaatca gttaaaaaca ttatgttagg 2040
acacgctagt gtacaagcag aaatggaaca agttgtggag gtgtatgagt atgctcagaa 2100
attgggtgga gaagcaggat tctaccatat attgaacaac ccaaaagcat cactattatc 2160
tttgactcaa tttcctcact tctctagtgt agtattgggc aatgctgctg gcctaggcat 2220
aatgggagaa tacagaggta caccaaggaa tcaagattta tatgatgctg caaaagcata 2280
tgctgaacaa ctcaaagaaa atggtgtgat taactacagt gtattagatt tgacagcaga 2340
agaactagag gctatcaaac atcagcttaa tccaaaagat aatgatgtag agctttgagt 2400
taataaaaaa gtggggcaaa taaatcatca tggaaaagtt tgctcctgaa ttccatggag 2460
aagatgcaaa caacagagcc accaaattcc tagaatcaat aaagggcaaa ttcacatcac 2520
ccaaagatcc caagaaaaaa gatagtatca tatctgtcaa ctcaatagat atagaagtaa 2580
ccaaagaaag ccctataaca tcaaattcaa ccattataaa cccaataaat gagacagatg 2640
atactgtagg gaacaagccc aattatcaaa gaaagcctct agtaagtttc aaagaagacc 2700
ctacgccaag tgataatcct ttttcaaaac tatacaaaga aaccatagaa acatttgata 2760
acaatgaaga agaatctagc tattcatatg aagaaataaa tgatcagaca aacgataata 2820
taacagcaag attagatagg attgatgaga aattaagtga aatactagga atgcttcaca 2880
cattagtagt agcgagtgca ggacccacat ctgctcggga tggtataaga gatgccatgg 2940
ttggtttaag agaagaaatg atagaaaaaa tcagaactga agcattaatg accaatgaca 3000
gactagaagc tatggcaaga ctcaggaatg aagaaagtga aaagatggca aaagacacat 3060
cagatgaagt gtctctcaat ccaacatcag agaaactgaa caacctgttg gaagggaatg 3120
atagtgacaa tgatctatca cttgaagatt tctgattagc taccaaactg tacatcaaaa 3180
cacaacacca atagaaaacc aacaaacaaa ccaactcacc catccaacca aacatctatc 3240
tgctgattag ccaaccagcc aaaaaacaac cagccaatct aaaactagcc acccggaaaa 3300

-continued

```
aatcgatact atagttacaa aaaaagatgg ggcaaatatg gaaacatacg tgaataaact   3360
tcacgagggc tccacataca cagctgctgt tcaatacaat gtcctagaaa aagacgatga   3420
tcctgcatca cttacaatat gggtgcccat gttccaatca tccatgccag cagatctact   3480
cataaaagaa ctagccaatg tcaatatact agtgaaacaa atatccacac ccaagggacc   3540
ctcattaaga gtcatgataa actcaagaag tgcagtgcta gcacaaatgc ccagcaaatt   3600
taccatatgt gccaatgtgt ccttggatga aagaagcaag ctggcatatg atgtaaccac   3660
accctgtgaa attaaggcat gcagtctaac atgcctaaaa tcaaaaaata tgttaactac   3720
agttaaagat ctcactatga aacactcaa cccaacacat gacatcattg ctttatgtga   3780
atttgaaaat atagtaacat caaaaaaagt cataatacca acatacctaa gatctatcag   3840
cgtcagaaat aaagatctga acacacttga aaatataaca accactgaat tcaaaaatgc   3900
cattacaaat gcaaaaatca tcccttactc aggattattg ttagtcatca cagtgactga   3960
caacaaagga gcattcaaat acataaagcc acaaagtcaa ttcatagtag atcttggagc   4020
ttacctagaa aaagaaagta tatattatgt tacaacaaat tggaagcaca cagctacacg   4080
atttgcaatc aaacccatgg aagattaacc tttttcctct acatcaatga gtagattcat   4140
acaaactttc taactacatt cttcacttca caatcataat caccaaccct ctgtggttca   4200
atcaatcaaa caaaactcat caagagttcc agatcatccc aagtcattgt tcatcagatc   4260
cagtactcaa ataagttaat aaaaaatcgg tccgttgaca gaagataaaa atggggcaaa   4320
tgcaaacatg aagtgccttt tgtacttagc ctttttattc attggggtga attgcaagtt   4380
caccatagtt tttccacaca accaaaaagg aaactggaaa aatgttcctt ctaattacca   4440
ttattgcccg tcaagctcag atttaaattg gcataatgac ttaataggca cagccttaca   4500
agtcaaaatg cccaagagtc acaaggctat tcaagcagac ggttggatgt gtcatgcttc   4560
caaatgggtc actacttgtg atttccgctg gtatggaccg aagtatataa cacattccat   4620
ccgatccttc actccatctg tagaacaatg caaggaaagc attgaacaaa cgaaacaagg   4680
aacttggctg aatccaggct tccctcctca aagttgtgga tatgcaactg tgacggatgc   4740
cgaagcagtg attgtccagg tgactcctca ccatgtgctg gttgatgaat acacaggaga   4800
atgggttgat tcacagttca tcaacggaaa atgcagcaat tacatatgcc ccactgtcca   4860
taactctaca acctggcatt ctgactataa ggtcaaaggg ctatgtgatt ctaacctcat   4920
ttccatggac atcaccttct tctcagagga cggagagcta tcatccctgg gaaaggaggg   4980
cacagggttc agaagtaact actttgctta tgaaactgga ggcaaggcct gcaaaatgca   5040
atactgcaag cattggggag tcagactccc atcaggtgtc tggttcgaga tggctgataa   5100
ggatctcttt gctgcagcca gattccctga atgcccagaa gggtcaagta tctctgctcc   5160
atctcagacc tcagtggatg taagtctaat tcaggacgtt gagaggatct tggattattc   5220
cctctgccaa gaaacctgga gcaaaatcag agcgggtctt ccaatctctc cagtggatct   5280
cagctatctt gctcctaaaa acccaggaac cggtcctgct ttcaccataa tcaatggtac   5340
cctaaaatac tttgagacca gatacatcag agtcgatatt gctgctccaa tcctctcaag   5400
aatggtcgga atgatcagtg gaactaccac agaaagggaa ctgtgggatg actgggcacc   5460
atatgaagac gtggaaattg gacccaatgg agttctgagg accagttcag gatataagtt   5520
tcctttatac atgattggac atggtatgtt ggactccgat cttcatctta gctcaaaggc   5580
tcaggtgttc gaacatcctc acattcaaga cgctgcttcg caacttcctg atgatgagag   5640
tttatttttt ggtgatactg ggctatccaa aaatccaatc gagcttgtag aaggttggtt   5700
```

-continued

```
cagtagttgg aaaagctcta ttgcctcttt tttctttatc atagggttaa tcattggact   5760
attcttggtt ctccgagttg gtatccatct ttgcattaaa gccagaagca caccagtcac   5820
attaagtaag gatcaactga gtggtataaa taatattgca tttagtaact aatagtcatt   5880
aaaaagcggc cggccagtca taacaatgaa ctaggatatt aagaccaaaa acaacgctgg   5940
ggcaaatgca aacatgtcca aaaccgagga ccaacgcacc gccaagacac tagaaaggac   6000
ctgggacact tttaatcatc tattattcat atcatcgtgc ttatacaagt taaatcttaa   6060
atctatagca caaatcacat tatctatttt ggcaattata atctcaacct cacttataat   6120
tgcagccatc atattcatag cctcggcaaa ccacaaagtc acactaacaa ctgcaatcat   6180
acaagatgca acgaaccaga tcaagaacac aaccccaaca tacctcaccc agaatcccca   6240
gcatggaatc agcttctcca atctgtccgg aactacatca caatccacca ccatactagc   6300
ttcaacaaca ccaagtgctg attcaacccc acaatccaca acagtcaaga tcaaaaacac   6360
aacaacaacc caaatattac ctagcaaacc caccacaaaa caacgccaaa ataaaccaca   6420
aaacaaaccc aacaatgatt ttcactttga agtgttcaat tttgtaccct gcagcatatg   6480
cagcaacaat ccaacctgct gggccatctg caagagaata ccaaacaaaa aacctggaaa   6540
gaaaaccacc accaagccca caaaaaaacc aaccctcaag acaaccaaaa aagatcccaa   6600
atcccaaacc acaaaaccaa aggaagtact cactaccaag cctacaggaa agccaaccat   6660
caacaccact aaaacaaaca tcagaactac actgctcacc tccaacacca aaggaaatcc   6720
agaacacaca agtcaagagg aaaccctcca ctcaaccacc tccgaaggct atccaagccc   6780
atcacaagtc cacacaacat ccggtcaaga ggaaaccctc cactcaacca cctccgaagg   6840
ctatccaagc ccatcacaag tctacacaac atccgagtac ctatcacaat ctctatcttc   6900
atccaacaca acaaaatgat agtcattaaa aagcacgcgt gtattgttgc aaaaagccat   6960
gaccaaatca aacagaatca aaatcaactc tgggcccatt gaataccaaa ttaacttact   7020
atttgtaaaa atgagaattg gggcaaatat gtcacgaagg aatccttgca aattcgaaat   7080
tcgaggtcat tgcttgaatg gtaaaaggtg tcattttagt cataattatt ttgaatggcc   7140
accccatgca ctgcttgtaa gacaaaactt tatgttaaac agaatactta agtctatgga   7200
taaaagcata gatactttgt cagaaataag tggagctgca gagttggaca gaacagaaga   7260
gtatgccctc ggtgtagttg gagtgctaga gagttatata ggatcaataa ataatataac   7320
taaacaatca gcatgtgttg ccatgagcaa actccttact gaactcaaca gcgatgacat   7380
caaaaaacta agggacaatg aagagccaaa ctcacccaaa gtaagagtgt acaatactgt   7440
catatcatat attgaaagca acaggaagaa caataaacaa actatccatc tgttaaaaag   7500
attgccagca gacgtattga agaaaaccat caaaaacaca ttggatatcc acaagagcat   7560
aaccatcaat aacccaaaag aatcaactgt tagtgatacg aacgaccatg ccaaaaataa   7620
tgatactacc tgacaaatat ccttgtagta taaattccat actaataaca agtaattgta   7680
gagtcactat gtataatcaa aaaaacacac tatatatcaa tcaaaacaac caaaatagcc   7740
atatataccc accggatcaa ccattcaatg aaatccattg gacctctcaa gacttgattg   7800
atgcaactca aaattttcta caacatctag gtattactga tgatatatac acaatatata   7860
tattagtgtc ataatactca atcctaatac ttaccacatc atcaaattat taactcaaac   7920
aattcaagct atgggacaaa atggatccca ttattagtgg aaattctgct aatgtttatc   7980
taactgatag ttatttaaaa ggtgttattt ctttctcaga atgtaacgct ttaggaagtt   8040
```

acatattcaa tggtccttat ctcaaaaatg attataccaa cttaattagt agacaaaatc 8100
cattaataga acacataaat ctaaagaaac taaatataac acagtcctta atatctaagt 8160
atcataaagg tgaaataaaa atagaagaac ctacttactt tcagtcatta cttatgacat 8220
acaagagtat gacctcttca gaacagacta ctactactaa tttacttaaa aagataataa 8280
gaagagctat agaaatcagt gatgtcaaag tctatgctat attgaataaa ctggggctca 8340
aagaaaaaga caagattaaa tccaataatg gacaagatga agacaactca gtcattacta 8400
ccataatcaa agatgatata cttttagctg tcaaggataa tcaatctcat cttaaagcag 8460
acaaaaatca atccacaaaa caaaaagata caatcaaaac aacacttttg aagaaattaa 8520
tgtgttcgat gcaacatcct ccatcatggt taatacattg gtttaattta tacacaaaat 8580
taaacagcat attaacacaa tatcgatcta gtgaggtaaa aaaccatggt tttatattga 8640
tagataatca tactcttagt ggattccaat ttattttgaa tcaatatggt tgtatagttt 8700
atcataagga actcaaaaga attactgtga caacttataa tcaattcttg acatggaaag 8760
atattagcct tagtagatta aatgtttgtt tgattacatg gattagtaac tgtttgaaca 8820
cattaaacaa aagcttaggc ttaagatgtg gattcaataa tgttatcttg acacaattat 8880
tcctttatgg agattgtata ctaaaactat tccacaatga ggggttctac ataataaaag 8940
aggtagaggg atttattatg tctctaattt taaatataac agaagaagat caattcagaa 9000
aacggtttta taatagtatg ctcaacaaca tcacagatgc cgccaacaaa gctcaaaaaa 9060
atctgctatc aagagtatgt catacattat tagataagac aatatcagat aatataataa 9120
atggcagatg gataattcta ttgagtaagt tcctaaaatt aattaagctt gcaggtgaca 9180
ataacctcaa caatctgagt gaattatatt ttttgttcag aatatttgga cacccaatgg 9240
tagatgaaag acaagccatg gatgctgtta aagttaattg caacgagacc aaattttatt 9300
tgttaagtag tttgagtatg ttaagaggag cttttatata tagaattata aaagggtttg 9360
taaataatta caacagatgg cctactttaa gaaatgccat tgtcttaccc ttaagatggt 9420
taacttacta taaactaaac acttatcctt ccttgttgga acttacagaa agagatttga 9480
ttgttctatc aggactacgt ttctatcgag agtttcggtt gcctaaaaaa gtggatcttg 9540
aaatgatcat aaatgataag gctatatcac ctcctaaaaa tttaatatgg actagtttcc 9600
ctagaaatta tatgccgtca cacatacaaa attatataga acatgaaaaa ttaaaattct 9660
ctgatagtga taaatcaaga agagtattag agtattattt aagagataac aaattcaatg 9720
aatgtgattt acacaactgt gtagttaatc aaagttatct taacaacccg aatcatgtgg 9780
tatcattgac aggcaaagaa agagaactca gtgtaggtag aatgtttgca atgcaaccag 9840
gaatgttcag acaagttcaa atattagcag agaaaatgat agcagaaaac atattacaat 9900
ttttccctga aagtcttaca agatatggtg atctagaact acagaaaata ttagaattga 9960
aagcaggaat aagtaacaaa tcaaatcgtt acaatgataa ttacaacaat tacattagta 10020
agtgctctat catcacagat ctcagcaaat tcaatcaagc atttcgatat gaaacatcat 10080
gtatttgtag tgatgtactg gatgaactgc atggtgtaca atctctattt tcctggttac 10140
atttaactat tcctcatgtc acaataatat gcacatatag gcatgcaccc ccctatataa 10200
aggatcatat tgtagatctt aacaatgtag atgagcaaag tggactatat agatatcata 10260
tgggtggtat cgaagggtgg tgtcaaaaac tatggaccat agaagctata tcactattag 10320
atctaatatc tctcaaaggg aaattctcaa ttactgcttt aattaatggt gacaatcaat 10380
caatagatat aagtaaacca gtcagactca tggaaggtca aactcatgct caagcagatt 10440
atttgctagc attaaatagt ctcaaattac tgtataaaga gtatgcagga ataggccaca 10500
aattaaaagg aactgagact tatatatcga gagatatgca atttatgagt aaaacgatcc 10560
aacataacgg tgtatattac ccagctagta taaagaaagt cctaagagtg ggaccgtgga 10620
taaacactat acttgatgac ttcaaagtga gtctagaatc tataggtagt ttgacacaag 10680
aattagaata tagaggtgaa agtctattat gcagtttaat atttagaaat gtatggttat 10740
ataatcaaat tgcattacaa cttaaaaatc atgcattatg taacaacaaa ttatatttgg 10800
atatattaaa agttctaaaa cacttaaaaa cctttttaa tcttgataac attgatacag 10860
cattaacatt gtatatgaat ttgcccatgt tatttggtgg tggtgatccc aacttgttat 10920
atcgaagttt ctatagaaga actcctgatt tcctcacaga ggctatagtt cactctgtgt 10980
tcatacttag ttattataca aaccatgatt taaaagataa acttcaagat ctgtcagatg 11040
atagattgaa taagttctta acatgcataa tcacgtttga taaaaacccc aatgctgaat 11100
tcgttacatt gatgagagat cctcaagctt taggatctga gaggcaagct aaaattacta 11160
gcgaaatcaa tagactggca gttaccgagg ttttgagcac agctccaaac aaaatatttt 11220
ccaaaagtgc acaacactat accactacag agatagatct taatgatatt atgcaaaata 11280
tagaacctac atatcctcac gggctaagag ttgtttatga gagtttaccc ttttataaag 11340
cagagaaaat agtaaatctt atatccggta caaaatctat aactaacata ctggaaaaga 11400
cttctgccat agacttaaca gatattgata gagccactga gatgatgagg aaaaacataa 11460
ctttgcttat aaggatatta ccattagatt gtaacagaga taaaagagaa atattgagta 11520
tggaaaacct aagtattact gaattaagca aatacgttag agaaagatct tggtctttat 11580
ccaatatagt tggtgttaca tcacccagta tcatgtatac aatggacata aaatatacaa 11640
caagcactat agctagtggc ataatcatag agaaatataa tgtcaacagt ttaacacgtg 11700
gtgagagagg acccactaaa ccatgggttg gttcatctac acaagagaaa aagacaatgc 11760
cagtttataa tagacaagtt ttaaccaaaa aacagagaga tcaaatagat ctattagcaa 11820
aattggattg ggtgtatgca tctatagata acaaggatga atttatggag gaacttagca 11880
taggaactct tgggttaaca tatgagaagg ccaaaaaatt attcccacaa tatttgagtg 11940
ttaactattt gcatcgtctt acagtcagta gtagaccatg tgaattccct gcatctatac 12000
cagcttatag aactacaaat tatcactttg atactagccc tattaatcgc atattaacag 12060
aaaagtatgg tgatgaagat attgatatag tattccaaaa ctgtataagc tttggcctta 12120
gcttaatgtc tgtagtagaa caatttacta atgtatgtcc taacagaatt attctcatac 12180
ccaagcttaa tgagatacat ttgatgaaac ctcccatatt cacaggcgat gttgatattc 12240
acaagttaaa acaagtgata caaaaacaac atatgttttt accagacaaa ataagtttga 12300
ctcaatatgt ggaattattc ttaagtaata aaacactcaa atctggatct aatgttaatt 12360
ctaatttaat attggcgcat aagatatctg actattttca taatacttac attttgagta 12420
ctaatttagc tggacattgg attcttatta tacaacttat gaaagattct aagggtattt 12480
ttgaaaaaga ttggggagag ggatatataa ctgatcatat gttcattaat ttgaaagttt 12540
tcttcaatgc ttataagaca tatctcttgt gttttcataa aggttacggc agagcaaagc 12600
tggagtgtga tatgaatact tcagatctcc tatgtgtatt ggaattaata gacagtagtt 12660
attggaagtc tatgtctaag gtgtttttag aacaaaaagt tatcaaatac attcttagcc 12720
aggatgcaag tttacataga gtaaaaggat gtcatagctt caaactatgg tttcttaaac 12780

-continued

```
gtcttaatgt agcagaattc acagtttgcc cttgggttgt taacatagat tatcatccaa  12840
cacatatgaa agcaatatta acttatattg atcttgttag aatgggattg ataaatatag  12900
atagaatata cattaaaaat aaacacaagt tcaatgatga gttttatact tctaatctgt  12960
tttacattaa ttataacttc tcagataata ctcatctatt aactaaacat ataaggattg  13020
ctaattccga attagaaagt aattacaaca aattatatca tcctacacca gaaaccctag  13080
aaaatatact aaccaatccg gttaaaagta atgagaaaaa gacactgagt gactattgta  13140
taggtaaaaa tgttgactca ataatgttac catcgttatc taataagaag cttattaaat  13200
cgtctacaat gattagaacc aattacagca gacaagattt gtataattta tttcctacgg  13260
ttgtgattga taaaattata gatcattcag gtaatacagc caaatctaac caactttaca  13320
ctactacttc tcatcaaata tccttagtgc acaatagcac atcactttat tgcatgcttc  13380
cttggcatca tattaataga ttcaattttg tatttagttc tacaggttgt aaaattagta  13440
tagagtatat tttaaaagat cttaaaatta aggatcctaa ttgtatagca ttcataggtg  13500
aaggagcagg gaatttatta ttgcgtacag tagtggaact tcatcctgat ataagatata  13560
tttacagaag tctgaaagat tgcaatgatc atagtttacc aattgagttt ttaaggctgt  13620
acaatggaca tatcaacatt gattatggtg aaaatttgac cattcctgct acagatgcaa  13680
ccaacaacat tcattggtct tatttacata taaagtttgc tgaacctatc agtctttttg  13740
tctgtgatgc tgaattgcct gtaacagtca actggagtaa gattataata gagtggagca  13800
agcatgtaag aaaatgcaag tactgttctt cagttaataa atgtacattg atagtaaaat  13860
atcatgctca agatgatatc gatttcaaat tagacaacat aactatatta aaaacttatg  13920
tatgcttagg tagtaagtta aagggatctg aagtttactt agtccttaca ataggtcctg  13980
caaatgtgtt cccagtattt aatgtagtac aaaatgctaa attgatacta tcaagaacta  14040
aaaatttcat catgcctaaa aaagctgata aagagtctat tgatgcaaat attaagagtt  14100
tgataccctt tctttgttac cctataacaa aaaaaggaat taatactgca ttgtctaaat  14160
taaagagtgt tgttagtgga gatatactat catattctat agctggacgt aatgaagttt  14220
tcagcaataa acttataaat cataagcata tgaacatctt aaagtggttc aatcatgttt  14280
taaatttcag atcaacagaa ttaaactata atcatttata tatggtagaa tctacttatc  14340
ctcatctaag tgaattgtta aacagcttga caaccaatga acttaaaaaa ctgattaaaa  14400
tcacaggtag tttgttatac aacttttata atgaataatg agcaaaaatc ttataacaaa  14460
aatagctaca cactaacatt gtattcaatt atagttattg aaaattaata attatataat  14520
ttttaataac ttctagtgaa ctaatcctaa aattatcatt ttgatctagg aagaataagt  14580
ttaaatccaa atctaattgg tttatatgta tattaactaa attacgagat attagttttt  14640
gacacttttt ttctcgtggc cggcatggtc ccagcctcct cgctggcgcc ggctgggcaa  14700
catgcttcgg catggcgaat gggactagca taaccccttg gggcctctaa acgggtcttg  14760
aggggttttt tg                                                      14772
```

<210> SEQ ID NO 21
<211> LENGTH: 15131
<212> TYPE: DNA
<213> ORGANISM: Artificial Sequence
<220> FEATURE:
<223> OTHER INFORMATION: antigenic cDNA encoding cRSVA_VSVG_S

<400> SEQUENCE: 21

```
taatacgact cactataggt tttttcgcgt ctgatgaggc cgttaggccg aaactcctct     60
```

```
ccggagtcac gcgaaaaaat gcgtacaaca aacttgcgta aaccaaaaaa atggggcaaa    120
taagaatttg ataagtacca cttaaattta actcctttgg ttagaggcgc gccatgggca    180
gcaactcatt gagtatgata aaagttagat tgcaaaatct gtttgacaat gatgaagtag    240
cattgttaaa aataacatgc tatactgaca aattaataca gttaactaat gctttggcta    300
aggcagttat acatacaatc aaattgaatg gcattgtatt tgtgcatgtt attacaagta    360
gtgatatttg ccctaataat aatattgtag tgaaatccaa tttcacaaca atgccagtat    420
tacaaaatgg aggttatata tgggaaatga tggaattaac acactgctct caacctaatg    480
gcctaataga tgacaattgt gaaattaaat tctccaaaaa actaagtgat tcaacaatga    540
ccaattatat gaatcaatta tctgaattac ttggatttga cctcaatcca taaatcataa    600
taaatatcaa ctagcaaatc aatgtcacta acaccattag ttaatataaa acttgacaga    660
agataaaaat ggggcaaata aatcaattca gccgacccaa ccatggacac aacacacaat    720
gataccacac cacaaagact gatgatcaca gacatgaggc cattatcgct tgagactata    780
ataacatctc taaccagaga tatcataaca cataaattta tatacttgat aaatcatgaa    840
tgcatagtaa gaaaacttga tgaaagacag gccacattta catttctggt caactatgaa    900
atgaaactat tgcacaaagt gggaagcact aaatataaaa aatatactga atacaacaca    960
aaatatggca ctttccctat gccaatattt atcaatcatg atgggttctt agaatgcatt   1020
ggcattaagc ctaccaagca cacacccata atatacaagt atgatctcaa tccatgaata   1080
tcaaaccaag attcaaacaa tccgaaataa caactttatg cataatcaca ctccatagtc   1140
caaatggagc ctgaaaatta tagttattta aaattcctgc aggaaggaga gacataagat   1200
gaaagatggg gcaaatacaa aaatggctct tagcaaagtc aagttgaatg atacactcaa   1260
caaagatcaa cttctatcat ccagcaaata taccatccaa cggagcacag gagacagcat   1320
tgacactcct aattatgatg tgcagaaaca cattaataag ttatgtggca tgttattaat   1380
cacagaagat gctaatcata aattcactgg gttaataggt atgttatatg ctatgtctag   1440
attaggaaga gaagacacca taaaaatact caaagatgcg ggatatcatg ttaaggcaaa   1500
tggagtggat gtaacaacac atcgtcaaga cattaatggg aaagaaatga aatttgaagt   1560
gttaacatta gcaagcttaa caactgaaat tcaaatcaac attgagatag aatctagaaa   1620
atcctacaaa aaaatgctaa aagaaatggg agaggtggct ccagaataca ggcatgactc   1680
tcctgattgt gggatgataa tattatgtat agcggcatta gtaataacca aattagcagc   1740
aggagataga tcaggtctta cagctgtgat taggagagct aataatgtcc taaaaaatga   1800
aatgaaacgt tataaaggtt tattacccaa ggatatagcc aacagcttct atgaagtgtt   1860
tgaaaaatat cctcacttta tagatgtttt tgttcatttt ggtatagcac aatcttctac   1920
cagaggtggc agtagagttg aagggatttt tgcaggattg tttatgaatg cctatggtgc   1980
agggcaagtg atgttacggt gggggtctt agcaaaatca gttaaaaaca ttatgttagg    2040
acacgctagt gtacaagcag aaatggaaca agttgtggag gtgtatgagt atgctcagaa   2100
attgggtgga gaagcaggat tctaccatat attgaacaac ccaaaagcat cactattatc   2160
tttgactcaa tttcctcact tctctagtgt agtattgggc aatgctgctg gcctaggcat   2220
aatgggagaa tacagaggta caccaaggaa tcaagattta tatgatgctg caaaagcata   2280
tgctgaacaa ctcaaagaaa atggtgtgat taactacagt gtattagatt tgacagcaga   2340
agaactagag gctatcaaac atcagcttaa tccaaaagat aatgatgtag agctttgagt   2400
```

-continued

```
taataaaaaa gtggggcaaa taaatcatca tggaaaagtt tgctcctgaa ttccatggag   2460
aagatgcaaa caacagagcc accaaattcc tagaatcaat aaagggcaaa ttcacatcac   2520
ccaaagatcc caagaaaaaa gatagtatca tatctgtcaa ctcaatagat atagaagtaa   2580
ccaaagaaag ccctataaca tcaaattcaa ccattataaa cccaataaat gagacagatg   2640
atactgtagg gaacaagccc aattatcaaa gaaagcctct agtaagtttc aaagaagacc   2700
ctacgccaag tgataatcct ttttcaaaac tatacaaaga aaccatagaa acatttgata   2760
acaatgaaga agaatctagc tattcatatg aagaaataaa tgatcagaca aacgataata   2820
taacagcaag attagatagg attgatgaga aattaagtga aatactagga atgcttcaca   2880
cattagtagt agcgagtgca ggacccacat ctgctcggga tggtataaga gatgccatgg   2940
ttggtttaag agaagaaatg atagaaaaaa tcagaactga agcattaatg accaatgaca   3000
gactagaagc tatggcaaga ctcaggaatg aagaaagtga aaagatggca aaagacacat   3060
cagatgaagt gtctctcaat ccaacatcag agaaactgaa caacctgttg gaagggaatg   3120
atagtgacaa tgatctatca cttgaagatt tctgattagc taccaaactg tacatcaaaa   3180
cacaacacca atagaaaacc aacaaacaaa ccaactcacc catccaacca aacatctatc   3240
tgctgattag ccaaccagcc aaaaaacaac cagccaatct aaaactagcc acccggaaaa   3300
aatcgatact atagttacaa aaaaagatgg ggcaaatatg gaaacatacg tgaataaact   3360
tcacgagggc tccacataca cagctgctgt tcaatacaat gtcctagaaa aagacgatga   3420
tcctgcatca cttacaatat gggtgcccat gttccaatca tccatgccag cagatctact   3480
cataaaagaa ctagccaatg tcaatatact agtgaaacaa atatccacac ccaagggacc   3540
ctcattaaga gtcatgataa actcaagaag tgcagtgcta gcacaaatgc ccagcaaatt   3600
taccatatgt gccaatgtgt ccttggatga aagaagcaag ctggcatatg atgtaaccac   3660
accctgtgaa attaaggcat gcagtctaac atgcctaaaa tcaaaaaata tgttaactac   3720
agttaaagat ctcactatga aaacactcaa cccaacacat gacatcattg ctttatgtga   3780
atttgaaaat atagtaacat caaaaaaagt cataatacca acatacctaa gatctatcag   3840
cgtcagaaat aaagatctga acacacttga aaatataaca accactgaat tcaaaaatgc   3900
cattacaaat gcaaaaatca tcccttactc aggattattg ttagtcatca cagtgactga   3960
caacaaagga gcattcaaat acataaagcc acaaagtcaa ttcatagtag atcttggagc   4020
ttacctagaa aaagaaagta tatattatgt tacaacaaat tggaagcaca cagctacacg   4080
atttgcaatc aaacccatgg aagattaacc tttttcctct acatcaatga gtagattcat   4140
acaaactttc taactacatt cttcacttca caatcataat caccaaccct ctgtggttca   4200
atcaatcaaa caaaactcat caagagttcc agatcatccc aagtcattgt tcatcagatc   4260
cagtactcaa ataagttaat aaaaaatcca catggggcaa ataatcattg agggaaatcc   4320
aactaatcac aacatctgtc aacatagaca agtcaacacg ctagataaaa tcaaccaatg   4380
gaaaatacat ccataactat agaattctca agcaaattct ggccttactt tacactaata   4440
cacatgataa caacaataat ctctttgata atcataatct ccatcatgat tgcaatacta   4500
aacaaactct gcgaatataa tgtattccat aacaaaacct ttgagctacc aagagctcga   4560
gtcaatacat agcattcacc aatctgatag ctcaaaacag taaccttgca tttgtaaatg   4620
aactaccctc acttcttcac aaaaccacat caacatctca ccatgcaagc catcatctat   4680
accataaagt agttaattaa aaatggccgg ccagtcataa caatgaacta ggatattaag   4740
accaaaaaca acgctggggc aaatgcaaac atgtccaaaa ccgaggacca acgcaccgcc   4800
```

```
aagacactag aaaggacctg ggacactttt aatcatctat tattcatatc atcgtgctta   4860
tacaagttaa atcttaaatc tatagcacaa atcacattat ctattttggc aattataatc   4920
tcaacctcac ttataattgc agccatcata ttcatagcct cggcaaacca caaagtcaca   4980
ctaacaactg caatcataca agatgcaacg aaccagatca agaacacaac cccaacatac   5040
ctcacccaga atccccagca tggaatcagc ttctccaatc tgtccggaac tacatcacaa   5100
tccaccacca tactagcttc aacaacacca agtgctgatt caaccccaca atccacaaca   5160
gtcaagatca aaaacacaac aacaacccaa atattaccta gcaaacccac cacaaaacaa   5220
cgccaaaata aaccacaaaa caaacccaac aatgattttc actttgaagt gttcaatttt   5280
gtaccctgca gcatatgcag caacaatcca acctgctggg ccatctgcaa gagaatacca   5340
aacaaaaaac ctggaaagaa aaccaccacc aagcccacaa aaaaaccaac cctcaagaca   5400
accaaaaaag atcccaaatc ccaaaccaca aaaccaaagg aagtactcac taccaagcct   5460
acaggaaagc caaccatcaa caccactaaa acaaacatca gaactacact gctcacctcc   5520
aacaccaaag gaaatccaga acacacaagt caagaggaaa ccctccactc aaccacctcc   5580
gaaggctatc caagcccatc acaagtccac acaacatccg gtcaagagga aaccctccac   5640
tcaaccacct ccgaaggcta tccaagccca tcacaagtct acacaacatc cgagtaccta   5700
tcacaatctc tatcttcatc caacacaaca aaatgatagt cattaaaaag cacgcgtttg   5760
acagaagata aaaatggggc aaatgcaaac atgaagtgcc ttttgtactt agccttttta   5820
ttcattgggg tgaattgcaa gttcaccata gtttttccac acaaccaaaa aggaaactgg   5880
aaaaatgttc cttctaatta ccattattgc ccgtcaagct cagatttaaa ttggcataat   5940
gacttaatag gcacagcctt acaagtcaaa atgcccaaga gtcacaaggc tattcaagca   6000
gacggttgga tgtgtcatgc ttccaaatgg gtcactactt gtgatttccg ctggtatgga   6060
ccgaagtata taacacattc catccgatcc ttcactccat ctgtagaaca atgcaaggaa   6120
agcattgaac aaacgaaaca aggaacttgg ctgaatccag gcttccctcc tcaaagttgt   6180
ggatatgcaa ctgtgacgga tgccgaagca gtgattgtcc aggtgactcc tcaccatgtg   6240
ctggttgatg aatacacagg agaatgggtt gattcacagt tcatcaacgg aaaatgcagc   6300
aattacatat gccccactgt ccataactct acaacctggc attctgacta taaggtcaaa   6360
gggctatgtg attctaacct catttccatg gacatcacct tcttctcaga ggacggagag   6420
ctatcatccc tgggaaagga gggcacaggg ttcagaagta actactttgc ttatgaaact   6480
ggaggcaagg cctgcaaaat gcaatactgc aagcattggg gagtcagact cccatcaggt   6540
gtctggttcg agatggctga taaggatctc tttgctgcag ccagattccc tgaatgccca   6600
gaagggtcaa gtatctctgc tccatctcag acctcagtgg atgtaagtct aattcaggac   6660
gttgagagga tcttggatta ttccctctgc caagaaacct ggagcaaaat cagagcgggt   6720
cttccaatct ctccagtgga tctcagctat cttgctccta aaaacccagg aaccggtcct   6780
gctttcacca taatcaatgg taccctaaaa tactttgaga ccagatacat cagagtcgat   6840
attgctgctc caatcctctc aagaatggtc ggaatgatca gtggaactac cacagaaagg   6900
gaactgtggg atgactgggc accatatgaa gacgtggaaa ttggacccaa tggagttctg   6960
aggaccagtt caggatataa gtttccttta tacatgattg gacatggtat gttggactcc   7020
gatcttcatc ttagctcaaa ggctcaggtg ttcgaacatc ctcacattca agacgctgct   7080
tcgcaacttc ctgatgatga gagtttattt tttggtgata ctgggctatc caaaaatcca   7140
```

-continued

```
atcgagcttg tagaaggttg gttcagtagt tggaaaagct ctattgcctc tttttctttt   7200
atcatagggt taatcattgg actattcttg gttctccgag ttggtatcca tctttgcatt   7260
aaagccagaa gcacaccagt cacattaagt aaggatcaac tgagtggtat aaataatatt   7320
gcatttagta actaatagtc attaaaaagc gggcccattg aataccaaat taacttacta   7380
tttgtaaaaa tgagaattgg ggcaaatatg tcacgaagga atccttgcaa attcgaaatt   7440
cgaggtcatt gcttgaatgg taaaaggtgt catttttagtc ataattattt tgaatggcca   7500
ccccatgcac tgcttgtaag acaaaacttt atgttaaaca gaatacttaa gtctatggat   7560
aaaagcatag atactttgtc agaaataagt ggagctgcag agttggacag aacagaagag   7620
tatgccctcg gtgtagttgg agtgctagag agttatatag gatcaataaa taatataact   7680
aaacaatcag catgtgttgc catgagcaaa ctccttactg aactcaacag cgatgacatc   7740
aaaaaactaa gggacaatga agagccaaac tcacccaaag taagagtgta caatactgtc   7800
atatcatata ttgaaagcaa caggaagaac aataaacaaa ctatccatct gttaaaaaga   7860
ttgccagcag acgtattgaa gaaaaccatc aaaaacacat tggatatcca caagagcata   7920
accatcaata acccaaaaga atcaactgtt agtgatacga acgaccatgc caaaaataat   7980
gatactacct gacaaatatc cttgtagtat aaattccata ctaataacaa gtaattgtag   8040
agtcactatg tataatcaaa aaaacacact atatatcaat caaaacaacc aaaatagcca   8100
tatataccca ccggatcaac cattcaatga aatccattgg acctctcaag acttgattga   8160
tgcaactcaa aattttctac aacatctagg tattactgat gatatataca caatatatat   8220
attagtgtca taatactcaa tcctaatact taccacatca tcaaattatt aactcaaaca   8280
attcaagcta tgggacaaaa tggatcccat tattagtgga aattctgcta atgtttatct   8340
aactgatagt tatttaaaag gtgttatttc tttctcagaa tgtaacgctt taggaagtta   8400
catattcaat ggtccttatc tcaaaaatga ttataccaac ttaattagta gacaaaatcc   8460
attaatagaa cacataaatc taaagaaact aaatataaca cagtccttaa tatctaagta   8520
tcataaaggt gaaataaaaa tagaagaacc tacttacttt cagtcattac ttatgacata   8580
caagagtatg acctcttcag aacagactac tactactaat ttacttaaaa agataataag   8640
aagagctata gaaatcagtg atgtcaaagt ctatgctata ttgaataaac tggggctcaa   8700
agaaaaagac aagattaaat ccaataatgg acaagatgaa gacaactcag tcattactac   8760
cataatcaaa gatgatatac ttttagctgt caaggataat caatctcatc ttaaagcaga   8820
caaaaatcaa tccacaaaac aaaaagatac aatcaaaaca acacttttga agaaattaat   8880
gtgttcgatg caacatcctc catcatggtt aatacattgg tttaatttat acacaaaatt   8940
aaacagcata ttaacacaat atcgatctag tgaggtaaaa aaccatggtt ttatattgat   9000
agataatcat actcttagtg gattccaatt tattttgaat caatatggtt gtatagttta   9060
tcataaggaa ctcaaaagaa ttactgtgac aacttataat caattcttga catggaaaga   9120
tattagcctt agtagattaa atgtttgttt gattacatgg attagtaact gtttgaacac   9180
attaaacaaa agcttaggct taagatgtgg attcaataat gttatcttga cacaattatt   9240
cctttatgga gattgtatac taaaactatt ccacaatgag ggttctaca taataaaaga   9300
ggtagaggga tttattatgt ctctaatttt aaatataaca gaagaagatc aattcagaaa   9360
acggttttat aatagtatgc tcaacaacat cacagatgcc gccaacaaag ctcaaaaaaa   9420
tctgctatca agagtatgtc atacattatt agataagaca atatcagata atataataaa   9480
tggcagatgg ataattctat tgagtaagtt cctaaaatta attaagcttg caggtgacaa   9540
```

```
taacctcaac aatctgagtg aattatattt tttgttcaga atatttggac acccaatggt   9600
agatgaaaga caagccatgg atgctgttaa agttaattgc aacgagacca aattttattt   9660
gttaagtagt ttgagtatgt taagaggagc ttttatatat agaattataa aagggtttgt   9720
aaataattac aacagatggc ctactttaag aaatgccatt gtcttaccct taagatggtt   9780
aacttactat aaactaaaca cttatccttc cttgttggaa cttacagaaa gagatttgat   9840
tgttctatca ggactacgtt tctatcgaga gtttcggttg cctaaaaaag tggatcttga   9900
aatgatcata aatgataagg ctatatcacc tcctaaaaat ttaatatgga ctagtttccc   9960
tagaaattat atgccgtcac acatacaaaa ttatatagaa catgaaaaat taaaattctc  10020
tgatagtgat aaatcaagaa gagtattaga gtattattta agagataaca aattcaatga  10080
atgtgattta cacaactgtg tagttaatca aagttatctt aacaacccga atcatgtggt  10140
atcattgaca ggcaaagaaa gagaactcag tgtaggtaga atgtttgcaa tgcaaccagg  10200
aatgttcaga caagttcaaa tattagcaga gaaaatgata gcagaaaaca tattacaatt  10260
tttccctgaa agtcttacaa gatatggtga tctagaacta cagaaaatat tagaattgaa  10320
agcaggaata agtaacaaat caaatcgtta caatgataat tacaacaatt acattagtaa  10380
gtgctctatc atcacagatc tcagcaaatt caatcaagca tttcgatatg aaacatcatg  10440
tatttgtagt gatgtactgg atgaactgca tggtgtacaa tctctatttt cctggttaca  10500
tttaactatt cctcatgtca caataaatatg cacatatagg catgcacccc cctatataaa  10560
ggatcatatt gtagatctta acaatgtaga tgagcaaagt ggactatata gatatcatat  10620
gggtggtatc gaagggtggt gtcaaaaact atggaccata gaagctatat cactattaga  10680
tctaatatct ctcaaaggga aattctcaat tactgcttta attaatggtg acaatcaatc  10740
aatagatata agtaaaccag tcagactcat ggaaggtcaa actcatgctc aagcagatta  10800
tttgctagca ttaaatagtc tcaaattact gtataaagag tatgcaggaa taggccacaa  10860
attaaaagga actgagactt atatatcgag agatatgcaa tttatgagta aaacgatcca  10920
acataacggt gtatattacc cagctagtat aaagaaagtc ctaagagtgg gaccgtggat  10980
aaacactata cttgatgact tcaaagtgag tctagaatct ataggtagtt tgacacaaga  11040
attagaatat agaggtgaaa gtctattatg cagtttaata tttagaaatg tatggttata  11100
taatcaaatt gcattacaac ttaaaaatca tgcattatgt aacaacaaat tatatttgga  11160
tatattaaaa gttctaaaac acttaaaaac ctttttaat cttgataaca ttgatacagc  11220
attaacattg tatatgaatt tgcccatgtt atttggtggt ggtgatccca acttgttata  11280
tcgaagtttc tatagaagaa ctcctgattt cctcacagag gctatagttc actctgtgtt  11340
catacttagt tattatacaa accatgattt aaaagataaa cttcaagatc tgtcagatga  11400
tagattgaat aagttcttaa catgcataat cacgtttgat aaaaaacccca atgctgaatt  11460
cgttacattg atgagagatc ctcaagcttt aggatctgag aggcaagcta aaattactag  11520
cgaaatcaat agactggcag ttaccgaggt tttgagcaca gctccaaaca aaatattttc  11580
caaaagtgca caacactata ccactacaga gatagatctt aatgatatta tgcaaaatat  11640
agaacctaca tatcctcacg ggctaagagt tgtttatgag agtttaccct tttataaagc  11700
agagaaaata gtaaatctta tatccggtac aaaatctata actaacatac tggaaaagac  11760
ttctgccata gacttaacag atattgatag agccactgag atgatgagga aaaacataac  11820
tttgcttata aggatattac cattagattg taacagagat aaaagagaaa tattgagtat  11880
```

-continued

```
ggaaaaccta agtattactg aattaagcaa atacgttaga gaaagatctt ggtctttatc  11940
caatatagtt ggtgttacat cacccagtat catgtataca atggacataa aatatacaac  12000
aagcactata gctagtggca taatcataga gaaatataat gtcaacagtt taacacgtgg  12060
tgagagagga cccactaaac catgggttgg ttcatctaca caagagaaaa agacaatgcc  12120
agtttataat agacaagttt taaccaaaaa acagagagat caaatagatc tattagcaaa  12180
attggattgg gtgtatgcat ctatagataa caaggatgaa tttatggagg aacttagcat  12240
aggaactctt gggttaacat atgagaaggc caaaaaatta ttcccacaat atttgagtgt  12300
taactatttg catcgtctta cagtcagtag tagaccatgt gaattccctg catctatacc  12360
agcttataga actacaaatt atcactttga tactagccct attaatcgca tattaacaga  12420
aaagtatggt gatgaagata ttgatatagt attccaaaac tgtataagct ttggccttag  12480
cttaatgtct gtagtagaac aatttactaa tgtatgtcct aacagaatta ttctcatacc  12540
caagcttaat gagatacatt tgatgaaacc tcccatattc acaggcgatg ttgatattca  12600
caagttaaaa caagtgatac aaaaacaaca tatgttttta ccagacaaaa taagtttgac  12660
tcaatatgtg gaattattct taagtaataa aacactcaaa tctggatcta atgttaattc  12720
taatttaata ttggcgcata agatatctga ctattttcat aatacttaca ttttgagtac  12780
taatttagct ggacattgga ttcttattat acaacttatg aaagattcta agggtatttt  12840
tgaaaaagat tggggagagg gatatataac tgatcatatg ttcattaatt tgaaagtttt  12900
cttcaatgct tataagacat atctcttgtg ttttcataaa ggttacggca gagcaaagct  12960
ggagtgtgat atgaatactt cagatctcct atgtgtattg gaattaatag acagtagtta  13020
ttggaagtct atgtctaagg tgtttttaga acaaaaagtt atcaaataca ttcttagcca  13080
ggatgcaagt ttacatagag taaaaggatg tcatagcttc aaactatggt ttcttaaacg  13140
tcttaatgta gcagaattca cagtttgccc ttgggttgtt aacatagatt atcatccaac  13200
acatatgaaa gcaatattaa cttatattga tcttgttaga atgggattga taaatataga  13260
tagaatatac attaaaaata aacacaagtt caatgatgag ttttatactt ctaatctgtt  13320
ttacattaat tataacttct cagataatac tcatctatta actaaacata taaggattgc  13380
taattccgaa ttagaaagta attacaacaa attatatcat cctacaccag aaaccctaga  13440
aaatatacta accaatccgg ttaaaagtaa tgagaaaaag acactgagtg actattgtat  13500
aggtaaaaat gttgactcaa taatgttacc atcgttatct aataagaagc ttattaaatc  13560
gtctacaatg attagaacca attacagcag acaagatttg tataatttat ttcctacggt  13620
tgtgattgat aaaattatag atcattcagg taatacagcc aaatctaacc aactttacac  13680
tactacttct catcaaatat ccttagtgca caatagcaca tcactttatt gcatgcttcc  13740
ttggcatcat attaatagat tcaattttgt atttagttct acaggttgta aaattagtat  13800
agagtatatt ttaaaagatc ttaaaattaa ggatcctaat tgtatagcat tcataggtga  13860
aggagcaggg aatttattat tgcgtacagt agtggaactt catcctgata taagatatat  13920
ttacagaagt ctgaaagatt gcaatgatca tagtttacca attgagtttt taaggctgta  13980
caatggacat atcaacattg attatggtga aaatttgacc attcctgcta cagatgcaac  14040
caacaacatt cattggtctt atttacatat aaagtttgct gaacctatca gtctttttgt  14100
ctgtgatgct gaattgcctg taacagtcaa ctggagtaag attataatag agtggagcaa  14160
gcatgtaaga aaatgcaagt actgttcttc agttaataaa tgtacattga tagtaaaata  14220
tcatgctcaa gatgatatcg atttcaaatt agacaacata actatattaa aaacttatgt  14280
```

atgcttaggt agtaagttaa agggatctga agtttactta gtccttacaa taggtcctgc 14340
aaatgtgttc ccagtattta atgtagtaca aaatgctaaa ttgatactat caagaactaa 14400
aaatttcatc atgcctaaaa aagctgataa agagtctatt gatgcaaata ttaagagttt 14460
gatacccttt ctttgttacc ctataacaaa aaaaggaatt aatactgcat tgtctaaatt 14520
aaagagtgtt gttagtggag atatactatc atattctata gctggacgta atgaagtttt 14580
cagcaataaa cttataaatc ataagcatat gaacatctta aagtggttca atcatgtttt 14640
aaatttcaga tcaacagaat taaactataa tcatttatat atggtagaat ctacttatcc 14700
tcatctaagt gaattgttaa acagcttgac aaccaatgaa cttaaaaaac tgattaaaat 14760
cacaggtagt ttgttataca acttttataa tgaataatga gcaaaaatct tataacaaaa 14820
atagctacac actaacattg tattcaatta tagttattga aaattaataa ttatataatt 14880
tttaataact tctagtgaac taatcctaaa attatcattt tgatctagga agaataagtt 14940
taaatccaaa tctaattggt ttatatgtat attaactaaa ttacgagata ttagtttttg 15000
acactttttt tctcgtggcc ggcatggtcc cagcctcctc gctggcgccg gctgggcaac 15060
atgcttcggc atggcgaatg ggactagcat aaccccttgg ggcctctaaa cgggtcttga 15120
ggggtttttt g 15131

<210> SEQ ID NO 22
<211> LENGTH: 17006
<212> TYPE: DNA
<213> ORGANISM: Artificial Sequence
<220> FEATURE:
<223> OTHER INFORMATION: antigenic cDNA encoding cRSVA_VSVG_A_preF_ef

<400> SEQUENCE: 22
taatacgact cactataggt tttttcgcgt ctgatgaggc cgttaggccg aaactcctct 60
ccggagtcac gcgaaaaaat gcgtacaaca aacttgcgta aaccaaaaaa atggggcaaa 120
taagaatttg ataagtacca cttaaattta actcctttgg ttagaggcgc gccatgggca 180
gcaactcatt gagtatgata aaagttagat tgcaaaatct gtttgacaat gatgaagtag 240
cattgttaaa aataacatgc tatactgaca aattaataca gttaactaat gctttggcta 300
aggcagttat acatacaatc aaattgaatg gcattgtatt tgtgcatgtt attacaagta 360
gtgatatttg ccctaataat aatattgtag tgaaatccaa tttcacaaca atgccagtat 420
tacaaaatgg aggttatata tgggaaatga tggaattaac acactgctct caacctaatg 480
gcctaataga tgacaattgt gaaattaaat tctccaaaaa actaagtgat tcaacaatga 540
ccaattatat gaatcaatta tctgaattac ttggatttga cctcaatcca taaatcataa 600
taaatatcaa ctagcaaatc aatgtcacta acaccattag ttaatataaa acttgacaga 660
agataaaaat ggggcaaata aatcaattca gccgacccaa ccatggacac aacacacaat 720
gataccacac cacaaagact gatgatcaca gacatgaggc cattatcgct tgagactata 780
ataacatctc taaccagaga tatcataaca cataaattta tatacttgat aaatcatgaa 840
tgcatagtaa gaaaacttga tgaaagacag gccacattta catttctggt caactatgaa 900
atgaaactat tgcacaaagt gggaagcact aaatataaaa aatatactga atacaacaca 960
aaatatggca ctttccctat gccaatattt atcaatcatg atgggttctt agaatgcatt 1020
ggcattaagc ctaccaagca cacacccata atatacaagt atgatctcaa tccatgaata 1080
tcaaaccaag attcaaacaa tccgaaataa caactttatg cataatcaca ctccatagtc 1140
caaatggagc ctgaaaatta tagttattta aaattcctgc aggaaggaga gacataagat 1200
gaaagatggg gcaaatacaa aaatggctct tagcaaagtc aagttgaatg atacactcaa 1260
caaagatcaa cttctatcat ccagcaaata taccatccaa cggagcacag gagacagcat 1320
tgacactcct aattatgatg tgcagaaaca cattaataag ttatgtggca tgttattaat 1380
cacagaagat gctaatcata aattcactgg gttaataggt atgttatatg ctatgtctag 1440
attaggaaga gaagacacca taaaaatact caaagatgcg ggatatcatg ttaaggcaaa 1500
tggagtggat gtaacaacac atcgtcaaga cattaatggg aaagaaatga aatttgaagt 1560
gttaacatta gcaagcttaa caactgaaat tcaaatcaac attgagatag aatctagaaa 1620
atcctacaaa aaaatgctaa aagaaatggg agaggtggct ccagaataca ggcatgactc 1680
tcctgattgt gggatgataa tattatgtat agcggcatta gtaataacca aattagcagc 1740
aggagataga tcaggtctta cagctgtgat taggagagct aataatgtcc taaaaaatga 1800
aatgaaacgt tataaaggtt tattacccaa ggatatagcc aacagcttct atgaagtgtt 1860
tgaaaaatat cctcacttta tagatgtttt tgttcatttt ggtatagcac aatcttctac 1920
cagaggtggc agtagagttg aagggatttt tgcaggattg tttatgaatg cctatggtgc 1980
agggcaagtg atgttacggt ggggggtctt agcaaaatca gttaaaaaca ttatgttagg 2040
acacgctagt gtacaagcag aaatggaaca agttgtggag gtgtatgagt atgctcagaa 2100
attgggtgga gaagcaggat tctaccatat attgaacaac ccaaaagcat cactattatc 2160
tttgactcaa tttcctcact tctctagtgt agtattgggc aatgctgctg gcctaggcat 2220
aatgggagaa tacagaggta caccaaggaa tcaagattta tatgatgctg caaaagcata 2280
tgctgaacaa ctcaaagaaa atggtgtgat taactacagt gtattagatt tgacagcaga 2340
agaactagag gctatcaaac atcagcttaa tccaaaagat aatgatgtag agctttgagt 2400
taataaaaaa gtggggcaaa taaatcatca tggaaaagtt tgctcctgaa ttccatggag 2460
aagatgcaaa caacagagcc accaaattcc tagaatcaat aaagggcaaa ttcacatcac 2520
ccaaagatcc caagaaaaaa gatagtatca tatctgtcaa ctcaatagat atagaagtaa 2580
ccaaagaaag ccctataaca tcaaattcaa ccattataaa cccaataaat gagacagatg 2640
atactgtagg gaacaagccc aattatcaaa gaaagcctct agtaagtttc aaagaagacc 2700
ctacgccaag tgataatcct ttttcaaaac tatacaaaga aaccatagaa acatttgata 2760
acaatgaaga agaatctagc tattcatatg aagaaataaa tgatcagaca aacgataata 2820
taacagcaag attagatagg attgatgaga aattaagtga aatactagga atgcttcaca 2880
cattagtagt agcgagtgca ggacccacat ctgctcggga tggtataaga gatgccatgg 2940
ttggtttaag agaagaaatg atagaaaaaa tcagaactga agcattaatg accaatgaca 3000
gactagaagc tatggcaaga ctcaggaatg aagaaagtga aaagatggca aaagacacat 3060
cagatgaagt gtctctcaat ccaacatcag agaaactgaa caacctgttg gaagggaatg 3120
atagtgacaa tgatctatca cttgaagatt tctgattagc taccaaactg tacatcaaaa 3180
cacaacacca atagaaaacc aacaaacaaa ccaactcacc catccaacca aacatctatc 3240
tgctgattag ccaaccagcc aaaaaacaac cagccaatct aaaactagcc acccggaaaa 3300
aatcgatact atagttacaa aaaaagatgg ggcaaatatg gaaacatacg tgaataaact 3360
tcacgagggc tccacataca cagctgctgt tcaatacaat gtcctagaaa aagacgatga 3420
tcctgcatca cttacaatat gggtgcccat gttccaatca tccatgccag cagatctact 3480
cataaaagaa ctagccaatg tcaatatact agtgaaacaa atatccacac ccaagggacc 3540

-continued

```
ctcattaaga gtcatgataa actcaagaag tgcagtgcta gcacaaatgc ccagcaaatt   3600
taccatatgt gccaatgtgt ccttggatga aagaagcaag ctggcatatg atgtaaccac   3660
accctgtgaa attaaggcat gcagtctaac atgcctaaaa tcaaaaaata tgttaactac   3720
agttaaagat ctcactatga aaacactcaa cccaacacat gacatcattg ctttatgtga   3780
atttgaaaat atagtaacat caaaaaaagt cataatacca acatacctaa gatctatcag   3840
cgtcagaaat aaagatctga acacacttga aaatataaca accactgaat tcaaaaatgc   3900
cattacaaat gcaaaaatca tcccttactc aggattattg ttagtcatca cagtgactga   3960
caacaaagga gcattcaaat acataaagcc acaaagtcaa ttcatagtag atcttggagc   4020
ttacctagaa aaagaaagta tatattatgt tacaacaaat tggaagcaca cagctacacg   4080
atttgcaatc aaacccatgg aagattaacc tttttcctct acatcaatga gtagattcat   4140
acaaactttc taactacatt cttcacttca caatcataat caccaaccct ctgtggttca   4200
atcaatcaaa caaaactcat caagagttcc agatcatccc aagtcattgt tcatcagatc   4260
cagtactcaa ataagttaat aaaaaatcca catggggcaa ataatcattg agggaaatcc   4320
aactaatcac aacatctgtc aacatagaca agtcaacacg ctagataaaa tcaaccaatg   4380
gaaaatacat ccataactat agaattctca agcaaattct ggccttactt tacactaata   4440
cacatgataa caacaataat ctctttgata atcataatct ccatcatgat tgcaatacta   4500
aacaaactct gcgaatataa tgtattccat aacaaaacct ttgagctacc aagagctcga   4560
gtcaatacat agcattcacc aatctgatag ctcaaaacag taaccttgca tttgtaaatg   4620
aactaccctc acttcttcac aaaaccacat caacatctca ccatgcaagc catcatctat   4680
accataaagt agttaattaa aaatggccgg ccagtcataa caatgaacta ggatattaag   4740
accaaaaaca acgctggggc aaatgcaaac atgtccaaaa ccgaggacca acgcaccgcc   4800
aagacactag aaaggacctg ggacactttt aatcatctat tattcatatc atcgtgctta   4860
tacaagttaa atcttaaatc tatagcacaa atcacattat ctattttggc aattataatc   4920
tcaacctcac ttataattgc agccatcata ttcatagcct cggcaaacca caaagtcaca   4980
ctaacaactg caatcataca agatgcaacg aaccagatca agaacacaac cccaacatac   5040
ctcacccaga atccccagca tggaatcagc ttctccaatc tgtccggaac tacatcacaa   5100
tccaccacca tactagcttc aacaacacca agtgctgatt caaccccaca atccacaaca   5160
gtcaagatca aaaacacaac aacaacccaa atattaccta gcaaacccac cacaaaacaa   5220
cgccaaaata aaccacaaaa caaacccaac aatgattttc actttgaagt gttcaatttt   5280
gtaccctgca gcatatgcag caacaatcca acctgctggg ccatctgcaa gagaatacca   5340
aacaaaaaac ctggaaagaa aaccaccacc aagcccacaa aaaaaccaac cctcaagaca   5400
accaaaaaag atcccaaatc ccaaaccaca aaaccaaagg aagtactcac taccaagcct   5460
acaggaaagc caaccatcaa caccactaaa acaaacatca gaactacact gctcacctcc   5520
aacaccaaag gaaatccaga acacacaagt caagaggaaa ccctccactc aaccacctcc   5580
gaaggctatc caagcccatc acaagtccac acaacatccg gtcaagagga aaccctccac   5640
tcaaccacct ccgaaggcta tccaagccca tcacaagtct acacaacatc cgagtaccta   5700
tcacaatctc tatcttcatc caacacaaca aaatgatagt cattaaaaag cacgcgtttg   5760
acagaagata aaaatggggc aaatgcaaac atgaagtgcc ttttgtactt agccttttta   5820
ttcattgggg tgaattgcaa gttcaccata gtttttccac acaaccaaaa aggaaactgg   5880
```

-continued

```
aaaaatgttc cttctaatta ccattattgc ccgtcaagct cagatttaaa ttggcataat   5940
gacttaatag gcacagcctt acaagtcaaa atgcccaaga gtcacaaggc tattcaagca   6000
gacggttgga tgtgtcatgc ttccaaatgg gtcactactt gtgatttccg ctggtatgga   6060
ccgaagtata taacacattc catccgatcc ttcactccat ctgtagaaca atgcaaggaa   6120
agcattgaac aaacgaaaca aggaacttgg ctgaatccag gcttccctcc tcaaagttgt   6180
ggatatgcaa ctgtgacgga tgccgaagca gtgattgtcc aggtgactcc tcaccatgtg   6240
ctggttgatg aatacacagg agaatgggtt gattcacagt tcatcaacgg aaaatgcagc   6300
aattacatat gccccactgt ccataactct acaacctggc attctgacta taaggtcaaa   6360
gggctatgtg attctaacct catttccatg gacatcacct tcttctcaga ggacggagag   6420
ctatcatccc tgggaaagga gggcacaggg ttcagaagta actactttgc ttatgaaact   6480
ggaggcaagg cctgcaaaat gcaatactgc aagcattggg gagtcagact cccatcaggt   6540
gtctggttcg agatggctga taaggatctc tttgctgcag ccagattccc tgaatgccca   6600
gaagggtcaa gtatctctgc tccatctcag acctcagtgg atgtaagtct aattcaggac   6660
gttgagagga tcttggatta ttccctctgc caagaaacct ggagcaaaat cagagcgggt   6720
cttccaatct ctccagtgga tctcagctat cttgctccta aaaacccagg aaccggtcct   6780
gctttcacca taatcaatgg taccctaaaa tactttgaga ccagatacat cagagtcgat   6840
attgctgctc caatcctctc aagaatggtc ggaatgatca gtggaactac cacagaaagg   6900
gaactgtggg atgactgggc accatatgaa gacgtggaaa ttggacccaa tggagttctg   6960
aggaccagtt caggatataa gtttccttta tacatgattg gacatggtat gttggactcc   7020
gatcttcatc ttagctcaaa ggctcaggtg ttcgaacatc ctcacattca agacgctgct   7080
tcgcaacttc ctgatgatga gagtttattt tttggtgata ctgggctatc caaaaatcca   7140
atcgagcttg tagaaggttg gttcagtagt tggaaaagct ctattgcctc tttttttctt   7200
atcatagggt taatcattgg actattcttg gttctccgag ttggtatcca tctttgcatt   7260
aaagccagaa gcacaccagt cacattaagt aaggatcaac tgagtggtat aaataatatt   7320
gcatttagta actaatagtc attaaaaagc gggcccgtat tgttgcaaaa agccatgacc   7380
aaatcaaaca gaatcaaaat caactctggg gcaaataaca atggagttgc caatcctcaa   7440
aacaaatgct attaccacaa tccttgctgc agtcacactc tgtttcgctt ccagtcaaaa   7500
catcactgaa gaattttatc aatcaacatg cagtgcagtc agcaaaggct atcttagtgc   7560
tctaagaact ggttggtata ctagtgttat aactatagaa ttaagtaata tcaaggaaaa   7620
taagtgtaat ggtacagacg ctaaggtaaa attaataaaa caagaattag ataaatataa   7680
aaatgctgta acagaattgc agttgctcat gcaaagcaca ccagcagcca acaatcgagc   7740
cagaagagaa ctaccaagat ttatgaatta tacactcaac aataccaaaa acaccaatgt   7800
aacattaagt aagaaaagga aaagaagatt tcttggattt ttgttaggtg ttggatctgc   7860
aatcgccagt ggcattgccg tatccaaggt cctgcaccta gaaggggaag tgaacaaaat   7920
caaaagtgct ctactatcca caaacaaggc tgtagtcagc ttatctaatg gagtcagtgt   7980
cttaaccagc aaggtgttag acctcaaaaa ctatatagat aaacagttgt tacctattgt   8040
taacaagcaa agctgcagca tatcaaacat tgaaactgtg atagagttcc aacaaaagaa   8100
caacagacta ctagagatta ccagagaatt tagtgttaat gcaggtgtaa ctactcctgt   8160
aagcacttat atgttaacta atagtgagtt attatcatta atcaatgata tgcctataac   8220
aaatgatcag aaaaagttaa tgtccagcaa tgttcaaata gttagacagc aaagttactc   8280
```

```
tatcatgtca ataataaaag aggaagtctt ggcatatgta gtacaattac cactatatgg   8340
tgtaatagat actccttgtt ggaaactaca cacatcccct ttatgtacaa ccaacacaaa   8400
ggaaggatcc aacatctgct taacaagaac cgacagagga tggtactgtg acaatgcagg   8460
atcagtatcc tttttcccac aagctgaaac atgtaaagtt caatcgaatc gggtgttttg   8520
tgacacaatg aacagtttaa cattaccaag tgaggtaaat ctctgcaaca ttgacatatt   8580
caaccccaaa tatgattgca aaattatgac ttcaaaaaca gatgtaagca gctccgttat   8640
cacatctcta ggagccattg tgtcatgcta tggcaaaacc aaatgtacag catccaataa   8700
aaatcgtggg atcataaaga cattctctaa cgggtgtgat tatgtatcaa ataagggggt   8760
ggatactgtg tctgtaggta atacattata ttatgtaaat aagcaagaag gcaaaagtct   8820
ctatgtaaaa ggtgaaccaa taataaattt ctatgatcca ttagtgttcc cctctctcct   8880
gtgggatgca tcaatatctc aagtcaatga gaaaattaat cagagtctag catttatccg   8940
taaatcagat gaattattag gctctggcgg aagcggatac atccctgagg caccaaggga   9000
cggacaggcc tacgtgcgca aggatggcga gtgggtgctg ctgtccacct ttctgtgaat   9060
aaaaatagca cctaatcata ttcttacaat ggttcgctat ttgaccatag ataacccatc   9120
tatcattaga ttatcctaaa atttgaactt catcacaact ttcatctata aaccatctca   9180
cttacacttt ttaagtagat ttctatttta tagttatata aaacagggcc cattgaatac   9240
caaattaact tactatttgt aaaaatgaga attggggcaa atatgtcacg aaggaatcct   9300
tgcaaattcg aaattcgagg tcattgcttg aatggtaaaa ggtgtcattt tagtcataat   9360
tattttgaat ggccacccca tgcactgctt gtaagacaaa actttatgtt aaacagaata   9420
cttaagtcta tggataaaag catagatact ttgtcagaaa taagtggagc tgcagagttg   9480
gacagaacag aagagtatgc cctcggtgta gttggagtgc tagagagtta tataggatca   9540
ataaataata taactaaaca atcagcatgt gttgccatga gcaaactcct tactgaactc   9600
aacagcgatg acatcaaaaa actaagggac aatgaagagc caaactcacc caaagtaaga   9660
gtgtacaata ctgtcatatc atatattgaa agcaacagga agaacaataa acaaactatc   9720
catctgttaa aaagattgcc agcagacgta ttgaagaaaa ccatcaaaaa cacattggat   9780
atccacaaga gcataaccat caataaccca aaagaatcaa ctgttagtga tacgaacgac   9840
catgccaaaa ataatgatac tacctgacaa atatccttgt agtataaatt ccatactaat   9900
aacaagtaat tgtagagtca ctatgtataa tcaaaaaaac acactatata tcaatcaaaa   9960
caaccaaaat agccatatat acccaccgga tcaaccattc aatgaaatcc attggacctc  10020
tcaagacttg attgatgcaa ctcaaaattt tctacaacat ctaggtatta ctgatgatat  10080
atacacaata tatatattag tgtcataata ctcaatccta atacttacca catcatcaaa  10140
ttattaactc aaacaattca agctatggga caaaatggat cccattatta gtggaaattc  10200
tgctaatgtt tatctaactg atagttattt aaaaggtgtt atttctttct cagaatgtaa  10260
cgctttagga agttacatat tcaatggtcc ttatctcaaa aatgattata ccaacttaat  10320
tagtagacaa aatccattaa tagaacacat aaatctaaag aaactaaata taacacagtc  10380
cttaatatct aagtatcata aaggtgaaat aaaaatagaa gaacctactt actttcagtc  10440
attacttatg acatacaaga gtatgacctc ttcagaacag actactacta ctaatttact  10500
taaaaagata ataagaagag ctatagaaat cagtgatgtc aaagtctatg ctatattgaa  10560
taaactgggg ctcaaagaaa aagacaagat taaatccaat aatggacaag atgaagacaa  10620
```

-continued

```
ctcagtcatt actaccataa tcaaagatga tatactttta gctgtcaagg ataatcaatc  10680
tcatcttaaa gcagacaaaa atcaatccac aaaacaaaaa gatacaatca aaacaacact  10740
tttgaagaaa ttaatgtgtt cgatgcaaca tcctccatca tggttaatac attggtttaa  10800
tttatacaca aaattaaaca gcatattaac acaatatcga tctagtgagg taaaaaacca  10860
tggttttata ttgatagata atcatactct tagtggattc caatttattt tgaatcaata  10920
tggttgtata gtttatcata aggaactcaa aagaattact gtgacaactt ataatcaatt  10980
cttgacatgg aaagatatta gccttagtag attaaatgtt tgtttgatta catggattag  11040
taactgtttg aacacattaa acaaaagctt aggcttaaga tgtggattca ataatgttat  11100
cttgacacaa ttattccttt atggagattg tatactaaaa ctattccaca atgaggggtt  11160
ctacataata aaagaggtag agggatttat tatgtctcta attttaaata taacagaaga  11220
agatcaattc agaaaacggt tttataatag tatgctcaac aacatcacag atgccgccaa  11280
caaagctcaa aaaaatctgc tatcaagagt atgtcataca ttattagata agacaatatc  11340
agataatata ataaatggca gatggataat tctattgagt aagttcctaa aattaattaa  11400
gcttgcaggt gacaataacc tcaacaatct gagtgaatta tattttttgt tcagaatatt  11460
tggacaccca atggtagatg aaagacaagc catggatgct gttaaagtta attgcaacga  11520
gaccaaattt tatttgttaa gtagtttgag tatgttaaga ggagctttta tatatagaat  11580
tataaaaggg tttgtaaata attacaacag atggcctact ttaagaaatg ccattgtctt  11640
acccttaaga tggttaactt actataaact aaacacttat ccttccttgt tggaacttac  11700
agaaagagat ttgattgttc tatcaggact acgtttctat cgagagtttc ggttgcctaa  11760
aaaagtggat cttgaaatga tcataaatga taaggctata tcacctccta aaaatttaat  11820
atggactagt ttccctagaa attatatgcc gtcacacata caaaattata tagaacatga  11880
aaaattaaaa ttctctgata gtgataaatc aagaagagta ttagagtatt atttaagaga  11940
taacaaattc aatgaatgtg atttacacaa ctgtgtagtt aatcaaagtt atcttaacaa  12000
cccgaatcat gtggtatcat tgacaggcaa agaaagagaa ctcagtgtag gtagaatgtt  12060
tgcaatgcaa ccaggaatgt tcagacaagt tcaaatatta gcagagaaaa tgatagcaga  12120
aaacatatta caatttttcc ctgaaagtct tacaagatat ggtgatctag aactacagaa  12180
aatattagaa ttgaaagcag gaataagtaa caaatcaaat cgttacaatg ataattacaa  12240
caattacatt agtaagtgct ctatcatcac agatctcagc aaattcaatc aagcatttcg  12300
atatgaaaca tcatgtattt gtagtgatgt actggatgaa ctgcatggtg tacaatctct  12360
attttcctgg ttacatttaa ctattcctca tgtcacaata atatgcacat ataggcatgc  12420
accccccctat ataaaggatc atattgtaga tcttaacaat gtagatgagc aaagtggact  12480
atatagatat catatgggtg gtatcgaagg gtggtgtcaa aaactatgga ccatagaagc  12540
tatatcacta ttagatctaa tatctctcaa agggaaattc tcaattactg ctttaattaa  12600
tggtgacaat caatcaatag atataagtaa accagtcaga ctcatggaag gtcaaactca  12660
tgctcaagca gattatttgc tagcattaaa tagtctcaaa ttactgtata aagagtatgc  12720
aggaataggc cacaaattaa aaggaactga gacttatata tcgagagata tgcaatttat  12780
gagtaaaacg atccaacata acggtgtata ttacccagct agtataaaga aagtcctaag  12840
agtgggaccg tggataaaca ctatacttga tgacttcaaa gtgagtctag aatctatagg  12900
tagtttgaca caagaattag aatatagagg tgaaagtcta ttatgcagtt taatatttag  12960
aaatgtatgg ttatataatc aaattgcatt acaacttaaa aatcatgcat tatgtaacaa  13020
```

```
caaattatat ttggatatat taaaagttct aaaacactta aaaacctttt ttaatcttga  13080
taacattgat acagcattaa cattgtatat gaatttgccc atgttatttg gtggtggtga  13140
tcccaacttg ttatatcgaa gtttctatag aagaactcct gatttcctca cagaggctat  13200
agttcactct gtgttcatac ttagttatta tacaaaccat gatttaaaag ataaacttca  13260
agatctgtca gatgatagat tgaataagtt cttaacatgc ataatcacgt ttgataaaaa  13320
ccccaatgct gaattcgtta cattgatgag agatcctcaa gctttaggat ctgagaggca  13380
agctaaaatt actagcgaaa tcaatagact ggcagttacc gaggttttga gcacagctcc  13440
aaacaaaata ttttccaaaa gtgcacaaca ctataccact acagagatag atcttaatga  13500
tattatgcaa aatatagaac ctacatatcc tcacgggcta agagttgttt atgagagttt  13560
accccttttat aaagcagaga aaatagtaaa tcttatatcc ggtacaaaat ctataactaa  13620
catactggaa aagacttctg ccatagactt aacagatatt gatagagcca ctgagatgat  13680
gaggaaaaac ataactttgc ttataaggat attaccatta gattgtaaca gagataaaag  13740
agaaatattg agtatggaaa acctaagtat tactgaatta agcaaatacg ttagagaaag  13800
atcttggtct ttatccaata tagttggtgt tacatcaccc agtatcatgt atacaatgga  13860
cataaaatat acaacaagca ctatagctag tggcataatc atagagaaat ataatgtcaa  13920
cagtttaaca cgtggtgaga gaggacccac taaaccatgg gttggttcat ctacacaaga  13980
gaaaaagaca atgccagttt ataatagaca agttttaacc aaaaaacaga gagatcaaat  14040
agatctatta gcaaaattgg attgggtgta tgcatctata gataacaagg atgaatttat  14100
ggaggaactt agcataggaa ctcttgggtt aacatatgag aaggccaaaa aattattccc  14160
acaatatttg agtgttaact atttgcatcg tcttacagtc agtagtagac catgtgaatt  14220
ccctgcatct ataccagctt atagaactac aaattatcac tttgatacta gccctattaa  14280
tcgcatatta acagaaaagt atggtgatga agatattgat atagtattcc aaaactgtat  14340
aagctttggc cttagcttaa tgtctgtagt agaacaattt actaatgtat gtcctaacag  14400
aattattctc atacccaagc ttaatgagat acatttgatg aaacctccca tattcacagg  14460
cgatgttgat attcacaagt taaaacaagt gatacaaaaa caacatatgt tttaccaga  14520
caaaaataagt ttgactcaat atgtggaatt attcttaagt aataaaacac tcaaatctgg  14580
atctaatgtt aattctaatt taatattggc gcataagata tctgactatt ttcataatac  14640
ttacattttg agtactaatt tagctggaca ttggattctt attatacaac ttatgaaaga  14700
ttctaagggt atttttgaaa aagattgggg agagggatat ataactgatc atatgttcat  14760
taatttgaaa gttttcttca atgcttataa gacatatctc ttgtgttttc ataaaggtta  14820
cggcagagca aagctggagt gtgatatgaa tacttcagat ctcctatgtg tattggaatt  14880
aatagacagt agttattgga agtctatgtc taaggtgttt ttagaacaaa aagttatcaa  14940
atacattctt agccaggatg caagtttaca tagagtaaaa ggatgtcata gcttcaaact  15000
atggtttctt aaacgtctta atgtagcaga attcacagtt tgcccttggg ttgttaacat  15060
agattatcat ccaacacata tgaaagcaat attaacttat attgatcttg ttagaatggg  15120
attgataaat atagatagaa tatacattaa aaataaacac aagttcaatg atgagtttta  15180
tacttctaat ctgttttaca ttaattataa cttctcagat aatactcatc tattaactaa  15240
acatataagg attgctaatt ccgaattaga aagtaattac aacaaattat atcatcctac  15300
accagaaacc ctagaaaata tactaaccaa tccggttaaa agtaatgaga aaaagacact  15360
```

gagtgactat tgtataggta aaaatgttga ctcaataatg ttaccatcgt tatctaataa 15420
gaagcttatt aaatcgtcta caatgattag aaccaattac agcagacaag atttgtataa 15480
tttatttcct acggttgtga ttgataaaat tatagatcat tcaggtaata cagccaaatc 15540
taaccaactt tacactacta cttctcatca aatatcctta gtgcacaata gcacatcact 15600
ttattgcatg cttccttggc atcatattaa tagattcaat tttgtattta gttctacagg 15660
ttgtaaaatt agtatagagt atattttaaa agatcttaaa attaaggatc ctaattgtat 15720
agcattcata ggtgaaggag cagggaattt attattgcgt acagtagtgg aacttcatcc 15780
tgatataaga tatatttaca gaagtctgaa agattgcaat gatcatagtt taccaattga 15840
gtttttaagg ctgtacaatg gacatatcaa cattgattat ggtgaaaatt tgaccattcc 15900
tgctacagat gcaaccaaca acattcattg gtcttattta catataaagt ttgctgaacc 15960
tatcagtctt tttgtctgtg atgctgaatt gcctgtaaca gtcaactgga gtaagattat 16020
aatagagtgg agcaagcatg taagaaaatg caagtactgt tcttcagtta ataaatgtac 16080
attgatagta aaatatcatg ctcaagatga tatcgatttc aaattagaca acataactat 16140
attaaaaact tatgtatgct taggtagtaa gttaaaggga tctgaagttt acttagtcct 16200
tacaataggt cctgcaaatg tgttcccagt atttaatgta gtacaaaatg ctaaattgat 16260
actatcaaga actaaaaatt tcatcatgcc taaaaaagct gataaagagt ctattgatgc 16320
aaatattaag agtttgatac cctttctttg ttaccctata acaaaaaaag gaattaatac 16380
tgcattgtct aaattaaaga gtgttgttag tggagatata ctatcatatt ctatagctgg 16440
acgtaatgaa gttttcagca ataaacttat aaatcataag catatgaaca tcttaaagtg 16500
gttcaatcat gttttaaatt tcagatcaac agaattaaac tataatcatt tatatatggt 16560
agaatctact tatcctcatc taagtgaatt gttaaacagc ttgacaacca atgaacttaa 16620
aaaactgatt aaaatcacag gtagtttgtt atacaacttt tataatgaat aatgagcaaa 16680
aatcttataa caaaaatagc tacacactaa cattgtattc aattatagtt attgaaaatt 16740
aataattata taatttttaa taacttctag tgaactaatc ctaaaattat cattttgatc 16800
taggaagaat aagtttaaat ccaaatctaa ttggtttata tgtatattaa ctaaattacg 16860
agatattagt ttttgacact ttttttctcg tggccggcat ggtcccagcc tcctcgctgg 16920
cgccggctgg gcaacatgct tcggcatggc gaatgggact agcataaccc cttggggcct 16980
ctaaacgggt cttgaggggt tttttg 17006

<210> SEQ ID NO 23
<211> LENGTH: 16010
<212> TYPE: DNA
<213> ORGANISM: Artificial Sequence
<220> FEATURE:
<223> OTHER INFORMATION: antigenic cDNA encoding cRSVA_VSVG_S_preF_ef

<400> SEQUENCE: 23
taatacgact cactataggt tttttcgcgt ctgatgaggc cgttaggccg aaactcctct 60
ccggagtcac gcgaaaaaat gcgtacaaca aacttgcgta aaccaaaaaa atggggcaaa 120
taagaatttg ataagtacca cttaaattta actcctttgg ttagaggcgc gccatgggca 180
gcaactcatt gagtatgata aaagttagat tgcaaaatct gtttgacaat gatgaagtag 240
cattgttaaa aataacatgc tatactgaca aattaataca gttaactaat gctttggcta 300
aggcagttat acatacaatc aaattgaatg gcattgtatt tgtgcatgtt attacaagta 360
gtgatatttg ccctaataat aatattgtag tgaaatccaa tttcacaaca atgccagtat 420

```
tacaaaatgg aggttatata tgggaaatga tggaattaac acactgctct caacctaatg    480
gcctaataga tgacaattgt gaaattaaat tctccaaaaa actaagtgat tcaacaatga    540
ccaattatat gaatcaatta tctgaattac ttggatttga cctcaatcca taaatcataa    600
taaatatcaa ctagcaaatc aatgtcacta acaccattag ttaatataaa acttgacaga    660
agataaaaat ggggcaaata aatcaattca gccgacccaa ccatggacac aacacacaat    720
gataccacac cacaaagact gatgatcaca gacatgaggc cattatcgct tgagactata    780
ataacatctc taaccagaga tatcataaca cataaattta tatacttgat aaatcatgaa    840
tgcatagtaa gaaaacttga tgaaagacag gccacattta catttctggt caactatgaa    900
atgaaactat tgcacaaagt gggaagcact aaatataaaa aatatactga atacaacaca    960
aaatatggca ctttccctat gccaatattt atcaatcatg atgggttctt agaatgcatt   1020
ggcattaagc ctaccaagca cacacccata atatacaagt atgatctcaa tccatgaata   1080
tcaaaccaag attcaaacaa tccgaaataa caactttatg cataatcaca ctccatagtc   1140
caaatggagc ctgaaaatta tagttattta aaattcctgc aggaaggaga gacataagat   1200
gaaagatggg gcaaatacaa aaatggctct tagcaaagtc aagttgaatg atacactcaa   1260
caaagatcaa cttctatcat ccagcaaata taccatccaa cggagcacag gagacagcat   1320
tgacactcct aattatgatg tgcagaaaca cattaataag ttatgtggca tgttattaat   1380
cacagaagat gctaatcata aattcactgg gttaataggt atgttatatg ctatgtctag   1440
attaggaaga gaagacacca taaaaatact caaagatgcg ggatatcatg ttaaggcaaa   1500
tggagtggat gtaacaacac atcgtcaaga cattaatggg aaagaaatga aatttgaagt   1560
gttaacatta gcaagcttaa caactgaaat tcaaatcaac attgagatag aatctagaaa   1620
atcctacaaa aaaatgctaa aagaaatggg agaggtggct ccagaataca ggcatgactc   1680
tcctgattgt gggatgataa tattatgtat agcggcatta gtaataacca aattagcagc   1740
aggagataga tcaggtctta cagctgtgat taggagagct aataatgtcc taaaaaatga   1800
aatgaaacgt tataaaggtt tattacccaa ggatatagcc aacagcttct atgaagtgtt   1860
tgaaaaatat cctcacttta tagatgtttt tgttcatttt ggtatagcac aatcttctac   1920
cagaggtggc agtagagttg aagggatttt tgcaggattg tttatgaatg cctatggtgc   1980
agggcaagtg atgttacggt ggggggtctt agcaaaatca gttaaaaaca ttatgttagg   2040
acacgctagt gtacaagcag aaatggaaca agttgtggag gtgtatgagt atgctcagaa   2100
attgggtgga gaagcaggat tctaccatat attgaacaac ccaaaagcat cactattatc   2160
tttgactcaa tttcctcact tctctagtgt agtattgggc aatgctgctg gcctaggcat   2220
aatgggagaa tacagaggta caccaaggaa tcaagattta tatgatgctg caaaagcata   2280
tgctgaacaa ctcaaagaaa atggtgtgat taactacagt gtattagatt tgacagcaga   2340
agaactagag gctatcaaac atcagcttaa tccaaaagat aatgatgtag agctttgagt   2400
taataaaaaa gtggggcaaa taaatcatca tggaaaagtt tgctcctgaa ttccatggag   2460
aagatgcaaa caacagagcc accaaattcc tagaatcaat aaagggcaaa ttcacatcac   2520
ccaaagatcc caagaaaaaa gatagtatca tatctgtcaa ctcaatagat atagaagtaa   2580
ccaaagaaag ccctataaca tcaaattcaa ccattataaa cccaataaat gagacagatg   2640
atactgtagg gaacaagccc aattatcaaa gaaagcctct agtaagtttc aaagaagacc   2700
ctacgccaag tgataatcct tttcaaaac tatacaaaga aaccatagaa acatttgata   2760
```

```
acaatgaaga agaatctagc tattcatatg aagaaataaa tgatcagaca aacgataata   2820
taacagcaag attagatagg attgatgaga aattaagtga aatactagga atgcttcaca   2880
cattagtagt agcgagtgca ggacccacat ctgctcggga tggtataaga gatgccatgg   2940
ttggtttaag agaagaaatg atagaaaaaa tcagaactga agcattaatg accaatgaca   3000
gactagaagc tatggcaaga ctcaggaatg aagaaagtga aaagatggca aaagacacat   3060
cagatgaagt gtctctcaat ccaacatcag agaaactgaa caacctgttg gaagggaatg   3120
atagtgacaa tgatctatca cttgaagatt tctgattagc taccaaactg tacatcaaaa   3180
cacaacacca atagaaaacc aacaaacaaa ccaactcacc catccaacca aacatctatc   3240
tgctgattag ccaaccagcc aaaaaacaac cagccaatct aaaactagcc acccggaaaa   3300
aatcgatact atagttacaa aaaaagatgg ggcaaatatg gaaacatacg tgaataaact   3360
tcacgagggc tccacataca cagctgctgt tcaatacaat gtcctagaaa aagacgatga   3420
tcctgcatca cttacaatat gggtgcccat gttccaatca tccatgccag cagatctact   3480
cataaaagaa ctagccaatg tcaatatact agtgaaacaa atatccacac ccaagggacc   3540
ctcattaaga gtcatgataa actcaagaag tgcagtgcta gcacaaatgc ccagcaaatt   3600
taccatatgt gccaatgtgt ccttggatga aagaagcaag ctggcatatg atgtaaccac   3660
accctgtgaa attaaggcat gcagtctaac atgcctaaaa tcaaaaaata tgttaactac   3720
agttaaagat ctcactatga aacactcaa cccaacacat gacatcattg ctttatgtga   3780
atttgaaaat atagtaacat caaaaaaagt cataatacca acatacctaa gatctatcag   3840
cgtcagaaat aaagatctga acacacttga aaatataaca accactgaat tcaaaaatgc   3900
cattacaaat gcaaaaatca tcccttactc aggattattg ttagtcatca cagtgactga   3960
caacaaagga gcattcaaat acataaagcc acaaagtcaa ttcatagtag atcttggagc   4020
ttacctagaa aaagaaagta tatattatgt tacaacaaat tggaagcaca cagctacacg   4080
atttgcaatc aaacccatgg aagattaacc tttttcctct acatcaatga gtagattcat   4140
acaaactttc taactacatt cttcacttca caatcataat caccaaccct ctgtggttca   4200
atcaatcaaa caaaactcat caagagttcc agatcatccc aagtcattgt tcatcagatc   4260
cagtactcaa ataagttaat aaaaaatcca catggggcaa ataatcattg agggaaatcc   4320
aactaatcac aacatctgtc aacatagaca agtcaacacg ctagataaaa tcaaccaatg   4380
gaaaatacat ccataactat agaattctca agcaaattct ggccttactt tacactaata   4440
cacatgataa caacaataat ctctttgata atcataatct ccatcatgat tgcaatacta   4500
aacaaactct gcgaatataa tgtattccat aacaaaacct ttgagctacc aagagctcga   4560
gtcaatacat agcattcacc aatctgatag ctcaaaacag taaccttgca tttgtaaatg   4620
aactaccctc acttcttcac aaaaccacat caacatctca ccatgcaagc catcatctat   4680
accataaagt agttaattaa aaatggccgg ccagtcataa caatgaacta ggatattaag   4740
accaaaaaca acgctacgcg tttgacagaa gataaaaatg gggcaaatgc aaacatgaag   4800
tgccttttgt acttagcctt tttattcatt ggggtgaatt gcaagttcac catagttttt   4860
ccacacaacc aaaaaggaaa ctggaaaaat gttccttcta attaccatta ttgcccgtca   4920
agctcagatt taaattggca taatgactta ataggcacag ccttacaagt caaaatgccc   4980
aagagtcaca aggctattca agcagacggt tggatgtgtc atgcttccaa atgggtcact   5040
acttgtgatt tccgctggta tggaccgaag tatataacac attccatccg atccttcact   5100
ccatctgtag aacaatgcaa ggaaagcatt gaacaaacga aacaaggaac ttggctgaat   5160
```

```
ccaggcttcc ctcctcaaag ttgtggatat gcaactgtga cggatgccga agcagtgatt   5220
gtccaggtga ctcctcacca tgtgctggtt gatgaataca caggagaatg ggttgattca   5280
cagttcatca acggaaaatg cagcaattac atatgcccca ctgtccataa ctctacaacc   5340
tggcattctg actataaggt caaagggcta tgtgattcta acctcatttc catggacatc   5400
accttcttct cagaggacgg agagctatca tccctgggaa aggagggcac agggttcaga   5460
agtaactact ttgcttatga aactggaggc aaggcctgca aaatgcaata ctgcaagcat   5520
tggggagtca gactcccatc aggtgtctgg ttcgagatgg ctgataagga tctctttgct   5580
gcagccagat tccctgaatg cccagaaggg tcaagtatct ctgctccatc tcagacctca   5640
gtggatgtaa gtctaattca ggacgttgag aggatcttgg attattccct ctgccaagaa   5700
acctggagca aaatcagagc gggtcttcca atctctccag tggatctcag ctatcttgct   5760
cctaaaaacc caggaaccgg tcctgctttc accataatca atggtaccct aaaatacttt   5820
gagaccagat acatcagagt cgatattgct gctccaatcc tctcaagaat ggtcggaatg   5880
atcagtggaa ctaccacaga aagggaactg tgggatgact gggcaccata tgaagacgtg   5940
gaaattggac ccaatggagt tctgaggacc agttcaggat ataagtttcc tttatacatg   6000
attggacatg gtatgttgga ctccgatctt catcttagct caaaggctca ggtgttcgaa   6060
catcctcaca ttcaagacgc tgcttcgcaa cttcctgatg atgagagttt attttttggt   6120
gatactgggc tatccaaaaa tccaatcgag cttgtagaag gttggttcag tagttggaaa   6180
agctctattg cctctttttt ctttatcata gggttaatca ttggactatt cttggttctc   6240
cgagttggta tccatctttg cattaaagcc agaagcacac cagtcacatt aagtaaggat   6300
caactgagtg gtataaataa tattgcattt agtaactaat agtcattaaa aagcgggccc   6360
gtattgttgc aaaaagccat gaccaaatca aacagaatca aaatcaactc tggggcaaat   6420
aacaatggag ttgccaatcc tcaaaacaaa tgctattacc acaatccttg ctgcagtcac   6480
actctgtttc gcttccagtc aaaacatcac tgaagaattt tatcaatcaa catgcagtgc   6540
agtcagcaaa ggctatctta gtgctctaag aactggttgg tatactagtg ttataactat   6600
agaattaagt aatatcaagg aaaataagtg taatggtaca gacgctaagg taaaattaat   6660
aaaacaagaa ttagataaat ataaaaatgc tgtaacagaa ttgcagttgc tcatgcaaag   6720
cacaccagca gccaacaatc gagccagaag agaactacca agatttatga attatacact   6780
caacaatacc aaaaacacca atgtaacatt aagtaagaaa aggaaaagaa gatttcttgg   6840
atttttgtta ggtgttggat ctgcaatcgc cagtggcatt gccgtatcca aggtcctgca   6900
cctagaaggg gaagtgaaca aaatcaaaag tgctctacta tccacaaaca aggctgtagt   6960
cagcttatct aatggagtca gtgtcttaac cagcaaggtg ttagacctca aaaactatat   7020
agataaacag ttgttaccta ttgttaacaa gcaaagctgc agcatatcaa acattgaaac   7080
tgtgatagag ttccaacaaa agaacaacag actactagag attaccagag aatttagtgt   7140
taatgcaggt gtaactactc ctgtaagcac ttatatgtta actaatagtg agttattatc   7200
attaatcaat gatatgccta taacaaatga tcagaaaaag ttaatgtcca gcaatgttca   7260
aatagttaga cagcaaagtt actctatcat gtcaataata aaagaggaag tcttggcata   7320
tgtagtacaa ttaccactat atggtgtaat agatactcct tgttggaaac tacacacatc   7380
ccctttatgt acaaccaaca caaaggaagg atccaacatc tgcttaacaa gaaccgacag   7440
aggatggtac tgtgacaatg caggatcagt atcctttttc ccacaagctg aaacatgtaa   7500
```

-continued

```
agttcaatcg aatcgggtgt tttgtgacac aatgaacagt ttaacattac caagtgaggt   7560
aaatctctgc aacattgaca tattcaaccc caaatatgat tgcaaaatta tgacttcaaa   7620
aacagatgta agcagctccg ttatcacatc tctaggagcc attgtgtcat gctatggcaa   7680
aaccaaatgt acagcatcca ataaaaatcg tgggatcata aagacattct ctaacgggtg   7740
tgattatgta tcaaataagg gggtggatac tgtgtctgta ggtaatacat tatattatgt   7800
aaataagcaa gaaggcaaaa gtctctatgt aaaaggtgaa ccaataataa atttctatga   7860
tccattagtg ttcccctctc tcctgtggga tgcatcaata tctcaagtca atgagaaaat   7920
taatcagagt ctagcattta tccgtaaatc agatgaatta ttaggctctg gcggaagcgg   7980
atacatccct gaggcaccaa gggacggaca ggcctacgtg cgcaaggatg gcgagtgggt   8040
gctgctgtcc acctttctgt gaataaaaat agcacctaat catattctta caatggttcg   8100
ctatttgacc atagataacc catctatcat tagattatcc taaaatttga acttcatcac   8160
aactttcatc tataaaccat ctcacttaca ctttttaagt agatttctat tttatagtta   8220
tataaaacag ggcccattga ataccaaatt aacttactat ttgtaaaaat gagaattggg   8280
gcaaatatgt cacgaaggaa tccttgcaaa ttcgaaattc gaggtcattg cttgaatggt   8340
aaaaggtgtc attttagtca taattatttt gaatggccac cccatgcact gcttgtaaga   8400
caaaacttta tgttaaacag aatacttaag tctatggata aaagcataga tactttgtca   8460
gaaataagtg gagctgcaga gttggacaga acagaagagt atgccctcgg tgtagttgga   8520
gtgctagaga gttatatagg atcaataaat aatataacta aacaatcagc atgtgttgcc   8580
atgagcaaac tccttactga actcaacagc gatgacatca aaaaactaag ggacaatgaa   8640
gagccaaact cacccaaagt aagagtgtac aatactgtca tatcatatat tgaaagcaac   8700
aggaagaaca ataaacaaac tatccatctg ttaaaaagat tgccagcaga cgtattgaag   8760
aaaaccatca aaaacacatt ggatatccac aagagcataa ccatcaataa cccaaaagaa   8820
tcaactgtta gtgatacgaa cgaccatgcc aaaaataatg atactacctg acaaatatcc   8880
ttgtagtata aattccatac taataacaag taattgtaga gtcactatgt ataatcaaaa   8940
aaacacacta tatatcaatc aaaacaacca aaatagccat atatacccac cggatcaacc   9000
attcaatgaa atccattgga cctctcaaga cttgattgat gcaactcaaa attttctaca   9060
acatctaggt attactgatg atatatacac aatatatata ttagtgtcat aatactcaat   9120
cctaatactt accacatcat caaattatta actcaaacaa ttcaagctat gggacaaaat   9180
ggatcccatt attagtggaa attctgctaa tgtttatcta actgatagtt atttaaaagg   9240
tgttatttct ttctcagaat gtaacgcttt aggaagttac atattcaatg gtccttatct   9300
caaaaatgat tataccaact taattagtag acaaaatcca ttaatagaac acataaatct   9360
aaagaaacta aatataacac agtccttaat atctaagtat cataaaggtg aaataaaaat   9420
agaagaacct acttactttc agtcattact tatgacatac aagagtatga cctcttcaga   9480
acagactact actactaatt tacttaaaaa gataataaga agagctatag aaatcagtga   9540
tgtcaaagtc tatgctatat tgaataaact ggggctcaaa gaaaaagaca agattaaatc   9600
caataatgga caagatgaag acaactcagt cattactacc ataatcaaag atgatatact   9660
tttagctgtc aaggataatc aatctcatct taaagcagac aaaaatcaat ccacaaaaca   9720
aaaagataca atcaaaacaa cacttttgaa gaaattaatg tgttcgatgc aacatcctcc   9780
atcatggtta atacattggt ttaatttata cacaaaatta aacagcatat taacacaata   9840
tcgatctagt gaggtaaaaa accatggttt tatattgata gataatcata ctcttagtgg   9900
```

attccaattt attttgaatc aatatggttg tatagtttat cataaggaac tcaaaagaat 9960
tactgtgaca acttataatc aattcttgac atggaaagat attagcctta gtagattaaa 10020
tgtttgtttg attacatgga ttagtaactg tttgaacaca ttaaacaaaa gcttaggctt 10080
aagatgtgga ttcaataatg ttatcttgac acaattattc ctttatggag attgtatact 10140
aaaactattc cacaatgagg ggttctacat aataaaagag gtagagggat ttattatgtc 10200
tctaatttta aatataacag aagaagatca attcagaaaa cggttttata atagtatgct 10260
caacaacatc acagatgccg ccaacaaagc tcaaaaaaat ctgctatcaa gagtatgtca 10320
tacattatta gataagacaa tatcagataa tataataaat ggcagatgga taattctatt 10380
gagtaagttc ctaaaattaa ttaagcttgc aggtgacaat aacctcaaca atctgagtga 10440
attatatttt ttgttcagaa tatttggaca cccaatggta gatgaaagac aagccatgga 10500
tgctgttaaa gttaattgca acgagaccaa attttatttg ttaagtagtt tgagtatgtt 10560
aagaggagct tttatatata gaattataaa agggtttgta aataattaca acagatggcc 10620
tactttaaga aatgccattg tcttaccctt aagatggtta acttactata aactaaacac 10680
ttatccttcc ttgttggaac ttacagaaag agatttgatt gttctatcag gactacgttt 10740
ctatcgagag tttcggttgc ctaaaaaagt ggatcttgaa atgatcataa atgataaggc 10800
tatatcacct cctaaaaatt taatatggac tagtttccct agaaattata tgccgtcaca 10860
catacaaaat tatatagaac atgaaaaatt aaaattctct gatagtgata aatcaagaag 10920
agtattagag tattatttaa gagataacaa attcaatgaa tgtgatttac acaactgtgt 10980
agttaatcaa agttatctta acaacccgaa tcatgtggta tcattgacag gcaaagaaag 11040
agaactcagt gtaggtagaa tgtttgcaat gcaaccagga atgttcagac aagttcaaat 11100
attagcagag aaaatgatag cagaaaacat attacaattt ttccctgaaa gtcttacaag 11160
atatggtgat ctagaactac agaaaatatt agaattgaaa gcaggaataa gtaacaaatc 11220
aaatcgttac aatgataatt acaacaatta cattagtaag tgctctatca tcacagatct 11280
cagcaaattc aatcaagcat ttcgatatga aacatcatgt atttgtagtg atgtactgga 11340
tgaactgcat ggtgtacaat ctctattttc ctggttacat ttaactattc ctcatgtcac 11400
aataatatgc acatataggc atgcaccccc ctatataaag gatcatattg tagatcttaa 11460
caatgtagat gagcaaagtg gactatatag atatcatatg ggtggtatcg aagggtggtg 11520
tcaaaaacta tggaccatag aagctatatc actattagat ctaatatctc tcaaagggaa 11580
attctcaatt actgctttaa ttaatggtga caatcaatca atagatataa gtaaaccagt 11640
cagactcatg gaaggtcaaa ctcatgctca agcagattat ttgctagcat taaatagtct 11700
caaattactg tataaagagt atgcaggaat aggccacaaa ttaaaaggaa ctgagactta 11760
tatatcgaga gatatgcaat ttatgagtaa aacgatccaa cataacggtg tatattaccc 11820
agctagtata aagaaagtcc taagagtggg accgtggata aacactatac ttgatgactt 11880
caaagtgagt ctagaatcta taggtagttt gacacaagaa ttagaatata gaggtgaaag 11940
tctattatgc agtttaatat ttagaaatgt atggttatat aatcaaattg cattacaact 12000
taaaaatcat gcattatgta acaacaaatt atatttggat atattaaaag ttctaaaaca 12060
cttaaaaacc ttttttaatc ttgataacat tgatacagca ttaacattgt atatgaattt 12120
gcccatgtta tttggtggtg gtgatcccaa cttgttatat cgaagtttct atagaagaac 12180
tcctgatttc ctcacagagg ctatagttca ctctgtgttc atacttagtt attatacaaa 12240

```
ccatgattta aaagataaac ttcaagatct gtcagatgat agattgaata agttcttaac  12300
atgcataatc acgtttgata aaaaccccaa tgctgaattc gttacattga tgagagatcc  12360
tcaagcttta ggatctgaga ggcaagctaa aattactagc gaaatcaata gactggcagt  12420
taccgaggtt ttgagcacag ctccaaacaa aatattttcc aaaagtgcac aacactatac  12480
cactacagag atagatctta atgatattat gcaaaatata gaacctacat atcctcacgg  12540
gctaagagtt gtttatgaga gtttaccctt ttataaagca gagaaaatag taaatcttat  12600
atccggtaca aaatctataa ctaacatact ggaaaagact tctgccatag acttaacaga  12660
tattgataga gccactgaga tgatgaggaa aaacataact ttgcttataa ggatattacc  12720
attagattgt aacagagata aaagagaaat attgagtatg gaaaacctaa gtattactga  12780
attaagcaaa tacgttagag aaagatcttg gtctttatcc aatatagttg gtgttacatc  12840
acccagtatc atgtatacaa tggacataaa atatacaaca agcactatag ctagtggcat  12900
aatcatagag aaatataatg tcaacagttt aacacgtggt gagagaggac ccactaaacc  12960
atgggttggt tcatctacac aagagaaaaa gacaatgcca gtttataata gacaagtttt  13020
aaccaaaaaa cagagagatc aaatagatct attagcaaaa ttggattggg tgtatgcatc  13080
tatagataac aaggatgaat ttatggagga acttagcata ggaactcttg ggttaacata  13140
tgagaaggcc aaaaaattat tcccacaata tttgagtgtt aactatttgc atcgtcttac  13200
agtcagtagt agaccatgtg aattccctgc atctatacca gcttatagaa ctacaaatta  13260
tcactttgat actagcccta ttaatcgcat attaacagaa aagtatggtg atgaagatat  13320
tgatatagta ttccaaaact gtataagctt tggccttagc ttaatgtctg tagtagaaca  13380
atttactaat gtatgtccta acagaattat tctcataccc aagcttaatg agatacattt  13440
gatgaaacct cccatattca caggcgatgt tgatattcac aagttaaaac aagtgataca  13500
aaaacaacat atgtttttac cagacaaaat aagtttgact caatatgtgg aattattctt  13560
aagtaataaa acactcaaat ctggatctaa tgttaattct aatttaatat tggcgcataa  13620
gatatctgac tattttcata atacttacat tttgagtact aatttagctg gacattggat  13680
tcttattata caacttatga aagattctaa gggtattttt gaaaaagatt ggggagaggg  13740
atatataact gatcatatgt tcattaattt gaaagttttc ttcaatgctt ataagacata  13800
tctcttgtgt tttcataaag gttacggcag agcaaagctg gagtgtgata tgaatacttc  13860
agatctccta tgtgtattgg aattaataga cagtagttat tggaagtcta tgtctaaggt  13920
gtttttagaa caaaaagtta tcaaatacat tcttagccag gatgcaagtt tacatagagt  13980
aaaaggatgt catagcttca aactatggtt tcttaaacgt cttaatgtag cagaattcac  14040
agtttgccct tgggttgtta acatagatta tcatccaaca catatgaaag caatattaac  14100
ttatattgat cttgttagaa tgggattgat aaatatagat agaatataca ttaaaaataa  14160
acacaagttc aatgatgagt tttatacttc taatctgttt tacattaatt ataacttctc  14220
agataatact catctattaa ctaaacatat aaggattgct aattccgaat tagaaagtaa  14280
ttacaacaaa ttatatcatc ctacaccaga aaccctagaa aatatactaa ccaatccggt  14340
taaaagtaat gagaaaaaga cactgagtga ctattgtata ggtaaaaatg ttgactcaat  14400
aatgttacca tcgttatcta ataagaagct tattaaatcg tctacaatga ttagaaccaa  14460
ttacagcaga caagatttgt ataatttatt tcctacggtt gtgattgata aaattataga  14520
tcattcaggt aatacagcca aatctaacca actttacact actacttctc atcaaatatc  14580
cttagtgcac aatagcacat cactttattg catgcttcct tggcatcata ttaatagatt  14640
```

caattttgta tttagttcta caggttgtaa aattagtata gagtatattt taaaagatct 14700
taaaattaag gatcctaatt gtatagcatt cataggtgaa ggagcaggga atttattatt 14760
gcgtacagta gtggaacttc atcctgatat aagatatatt tacagaagtc tgaaagattg 14820
caatgatcat agtttaccaa ttgagttttt aaggctgtac aatggacata tcaacattga 14880
ttatggtgaa aatttgacca ttcctgctac agatgcaacc aacaacattc attggtctta 14940
tttacatata aagtttgctg aacctatcag tctttttgtc tgtgatgctg aattgcctgt 15000
aacagtcaac tggagtaaga ttataataga gtggagcaag catgtaagaa aatgcaagta 15060
ctgttcttca gttaataaat gtacattgat agtaaaatat catgctcaag atgatatcga 15120
tttcaaatta gacaacataa ctatattaaa aacttatgta tgcttaggta gtaagttaaa 15180
gggatctgaa gtttacttag tccttacaat aggtcctgca aatgtgttcc cagtatttaa 15240
tgtagtacaa aatgctaaat tgatactatc aagaactaaa aatttcatca tgcctaaaaa 15300
agctgataaa gagtctattg atgcaaatat taagagtttg ataccctttc tttgttaccc 15360
tataacaaaa aaaggaatta atactgcatt gtctaaatta aagagtgttg ttagtggaga 15420
tatactatca tattctatag ctggacgtaa tgaagttttc agcaataaac ttataaatca 15480
taagcatatg aacatcttaa agtggttcaa tcatgtttta aatttcagat caacagaatt 15540
aaactataat catttatata tggtagaatc tacttatcct catctaagtg aattgttaaa 15600
cagcttgaca accaatgaac ttaaaaaact gattaaaatc acaggtagtt tgttatacaa 15660
cttttataat gaataatgag caaaaatctt ataacaaaaa tagctacaca ctaacattgt 15720
attcaattat agttattgaa aattaataat tatataattt ttaataactt ctagtgaact 15780
aatcctaaaa ttatcatttt gatctaggaa gaataagttt aaatccaaat ctaattggtt 15840
tatatgtata ttaactaaat tacgagatat tagtttttga cacttttttt ctcgtggccg 15900
gcatggtccc agcctcctcg ctggcgccgg ctgggcaaca tgcttcggca tggcgaatgg 15960
gactagcata accccttggg gcctctaaac gggtcttgag gggttttttg 16010

<210> SEQ ID NO 24
<211> LENGTH: 16028
<212> TYPE: DNA
<213> ORGANISM: Artificial Sequence
<220> FEATURE:
<223> OTHER INFORMATION: antigenic cDNA encoding cRSVA_VSVG_S_preF_sc

<400> SEQUENCE: 24
taatacgact cactataggt tttttcgcgt ctgatgaggc cgttaggccg aaactcctct 60
ccggagtcac gcgaaaaaat gcgtacaaca aacttgcgta aaccaaaaaa atggggcaaa 120
taagaatttg ataagtacca cttaaattta actcctttgg ttagaggcgc gccatgggca 180
gcaactcatt gagtatgata aaagttagat tgcaaaatct gtttgacaat gatgaagtag 240
cattgttaaa aataacatgc tatactgaca aattaataca gttaactaat gctttggcta 300
aggcagttat acatacaatc aaattgaatg gcattgtatt tgtgcatgtt attacaagta 360
gtgatatttg ccctaataat aatattgtag tgaaatccaa tttcacaaca atgccagtat 420
tacaaaatgg aggttatata tgggaaatga tggaattaac acactgctct caacctaatg 480
gcctaataga tgacaattgt gaaattaaat tctccaaaaa actaagtgat tcaacaatga 540
ccaattatat gaatcaatta tctgaattac ttggatttga cctcaatcca taaatcataa 600
taaatatcaa ctagcaaatc aatgtcacta acaccattag ttaatataaa acttgacaga 660

-continued

```
agataaaaat ggggcaaata aatcaattca gccgacccaa ccatggacac aacacacaat    720
gataccacac cacaaagact gatgatcaca gacatgaggc cattatcgct tgagactata    780
ataacatctc taaccagaga tatcataaca cataaattta tatacttgat aaatcatgaa    840
tgcatagtaa gaaaacttga tgaaagacag gccacattta catttctggt caactatgaa    900
atgaaactat tgcacaaagt gggaagcact aaatataaaa aatatactga atacaacaca    960
aaatatggca ctttccctat gccaatattt atcaatcatg atgggttctt agaatgcatt   1020
ggcattaagc ctaccaagca cacacccata atatacaagt atgatctcaa tccatgaata   1080
tcaaaccaag attcaaacaa tccgaaataa caactttatg cataatcaca ctccatagtc   1140
caaatggagc ctgaaaatta tagttattta aaattcctgc aggaaggaga gacataagat   1200
gaaagatggg gcaaatacaa aaatggctct tagcaaagtc aagttgaatg atacactcaa   1260
caaagatcaa cttctatcat ccagcaaata taccatccaa cggagcacag gagacagcat   1320
tgacactcct aattatgatg tgcagaaaca cattaataag ttatgtggca tgttattaat   1380
cacagaagat gctaatcata aattcactgg gttaataggt atgttatatg ctatgtctag   1440
attaggaaga gaagacacca taaaaatact caaagatgcg ggatatcatg ttaaggcaaa   1500
tggagtggat gtaacaacac atcgtcaaga cattaatggg aaagaaatga aatttgaagt   1560
gttaacatta gcaagcttaa caactgaaat tcaaatcaac attgagatag aatctagaaa   1620
atcctacaaa aaaatgctaa aagaaatggg agaggtggct ccagaataca ggcatgactc   1680
tcctgattgt gggatgataa tattatgtat agcggcatta gtaataacca aattagcagc   1740
aggagataga tcaggtctta cagctgtgat taggagagct aataatgtcc taaaaaatga   1800
aatgaaacgt tataaaggtt tattacccaa ggatatagcc aacagcttct atgaagtgtt   1860
tgaaaaatat cctcacttta tagatgtttt tgttcatttt ggtatagcac aatcttctac   1920
cagaggtggc agtagagttg aagggatttt tgcaggattg tttatgaatg cctatggtgc   1980
agggcaagtg atgttacggt ggggggtctt agcaaaatca gttaaaaaca ttatgttagg   2040
acacgctagt gtacaagcag aaatggaaca agttgtggag gtgtatgagt atgctcagaa   2100
attgggtgga gaagcaggat tctaccatat attgaacaac ccaaaagcat cactattatc   2160
tttgactcaa tttcctcact tctctagtgt agtattgggc aatgctgctg gcctaggcat   2220
aatgggagaa tacagaggta caccaaggaa tcaagattta tatgatgctg caaaagcata   2280
tgctgaacaa ctcaaagaaa atggtgtgat taactacagt gtattagatt tgacagcaga   2340
agaactagag gctatcaaac atcagcttaa tccaaaagat aatgatgtag agctttgagt   2400
taataaaaaa gtggggcaaa taaatcatca tggaaaagtt tgctcctgaa ttccatggag   2460
aagatgcaaa caacagagcc accaaattcc tagaatcaat aaagggcaaa ttcacatcac   2520
ccaaagatcc caagaaaaaa gatagtatca tatctgtcaa ctcaatagat atagaagtaa   2580
ccaaagaaag ccctataaca tcaaattcaa ccattataaa cccaataaat gagacagatg   2640
atactgtagg gaacaagccc aattatcaaa gaaagcctct agtaagtttc aaagaagacc   2700
ctacgccaag tgataatcct tttcaaaac tatacaaaga aaccatagaa acatttgata   2760
acaatgaaga agaatctagc tattcatatg aagaaataaa tgatcagaca aacgataata   2820
taacagcaag attagatagg attgatgaga aattaagtga aatactagga atgcttcaca   2880
cattagtagt agcgagtgca ggacccacat ctgctcggga tggtataaga gatgccatgg   2940
ttggtttaag agaagaaatg atagaaaaaa tcagaactga agcattaatg accaatgaca   3000
gactagaagc tatggcaaga ctcaggaatg aagaaagtga aaagatggca aaagacacat   3060
```

```
cagatgaagt gtctctcaat ccaacatcag agaaactgaa caacctgttg gaagggaatg   3120
atagtgacaa tgatctatca cttgaagatt tctgattagc taccaaactg tacatcaaaa   3180
cacaacacca atagaaaacc aacaaacaaa ccaactcacc catccaacca aacatctatc   3240
tgctgattag ccaaccagcc aaaaaacaac cagccaatct aaaactagcc acccggaaaa   3300
aatcgatact atagttacaa aaaaagatgg ggcaaatatg gaaacatacg tgaataaact   3360
tcacgagggc tccacataca cagctgctgt tcaatacaat gtcctagaaa aagacgatga   3420
tcctgcatca cttacaatat gggtgcccat gttccaatca tccatgccag cagatctact   3480
cataaaagaa ctagccaatg tcaatatact agtgaaacaa atatccacac ccaagggacc   3540
ctcattaaga gtcatgataa actcaagaag tgcagtgcta gcacaaatgc ccagcaaatt   3600
taccatatgt gccaatgtgt ccttggatga aagaagcaag ctggcatatg atgtaaccac   3660
accctgtgaa attaaggcat gcagtctaac atgcctaaaa tcaaaaaata tgttaactac   3720
agttaaagat ctcactatga aacactcaa cccaacacat gacatcattg ctttatgtga   3780
atttgaaaat atagtaacat caaaaaaagt cataatacca acatacctaa gatctatcag   3840
cgtcagaaat aaagatctga acacacttga aaatataaca accactgaat tcaaaaatgc   3900
cattacaaat gcaaaaatca tcccttactc aggattattg ttagtcatca cagtgactga   3960
caacaaagga gcattcaaat acataaagcc acaaagtcaa ttcatagtag atcttggagc   4020
ttacctagaa aaagaaagta tatattatgt tacaacaaat tggaagcaca cagctacacg   4080
atttgcaatc aaacccatgg aagattaacc tttttcctct acatcaatga gtagattcat   4140
acaaactttc taactacatt cttcacttca caatcataat caccaaccct ctgtggttca   4200
atcaatcaaa caaaactcat caagagttcc agatcatccc aagtcattgt tcatcagatc   4260
cagtactcaa ataagttaat aaaaaatcca catggggcaa ataatcattg agggaaatcc   4320
aactaatcac aacatctgtc aacatagaca agtcaacacg ctagataaaa tcaaccaatg   4380
gaaaatacat ccataactat agaattctca agcaaattct ggccttactt tacactaata   4440
cacatgataa caacaataat ctctttgata atcataatct ccatcatgat tgcaatacta   4500
aacaaactct gcgaatataa tgtattccat aacaaaacct ttgagctacc aagagctcga   4560
gtcaatacat agcattcacc aatctgatag ctcaaaacag taaccttgca tttgtaaatg   4620
aactaccctc acttcttcac aaaaccacat caacatctca ccatgcaagc catcatctat   4680
accataaagt agttaattaa aaatggccgg ccagtcataa caatgaacta ggatattaag   4740
accaaaaaca acgctacgcg tttgacagaa gataaaaatg gggcaaatgc aaacatgaag   4800
tgcctttttgt acttagcctt tttattcatt ggggtgaatt gcaagttcac catagttttt   4860
ccacacaacc aaaaaggaaa ctggaaaaat gttccttcta attaccatta ttgcccgtca   4920
agctcagatt taaattggca taatgactta ataggcacag ccttacaagt caaaatgccc   4980
aagagtcaca aggctattca agcagacggt tggatgtgtc atgcttccaa atgggtcact   5040
acttgtgatt tccgctggta tggaccgaag tatataacac attccatccg atccttcact   5100
ccatctgtag aacaatgcaa ggaaagcatt gaacaaacga aacaaggaac ttggctgaat   5160
ccaggcttcc ctcctcaaag ttgtggatat gcaactgtga cggatgccga agcagtgatt   5220
gtccaggtga ctcctcacca tgtgctggtt gatgaataca caggagaatg ggttgattca   5280
cagttcatca acggaaaatg cagcaattac atatgcccca ctgtccataa ctctacaacc   5340
tggcattctg actataaggt caaagggcta tgtgattcta acctcatttc catggacatc   5400
```

-continued

```
accttcttct cagaggacgg agagctatca tccctgggaa aggagggcac agggttcaga   5460
agtaactact ttgcttatga aactggaggc aaggcctgca aaatgcaata ctgcaagcat   5520
tggggagtca gactcccatc aggtgtctgg ttcgagatgg ctgataagga tctctttgct   5580
gcagccagat tccctgaatg cccagaaggg tcaagtatct ctgctccatc tcagacctca   5640
gtggatgtaa gtctaattca ggacgttgag aggatcttgg attattccct ctgccaagaa   5700
acctggagca aaatcagagc gggtcttcca atctctccag tggatctcag ctatcttgct   5760
cctaaaaacc caggaaccgg tcctgctttc accataatca atggtaccct aaaatacttt   5820
gagaccagat acatcagagt cgatattgct gctccaatcc tctcaagaat ggtcggaatg   5880
atcagtggaa ctaccacaga aagggaactg tgggatgact gggcaccata tgaagacgtg   5940
gaaattggac ccaatggagt tctgaggacc agttcaggat ataagtttcc tttatacatg   6000
attggacatg gtatgttgga ctccgatctt catcttagct caaaggctca ggtgttcgaa   6060
catcctcaca ttcaagacgc tgcttcgcaa cttcctgatg atgagagttt attttttggt   6120
gatactgggc tatccaaaaa tccaatcgag cttgtagaag gttggttcag tagttggaaa   6180
agctctattg cctctttttt ctttatcata gggttaatca ttggactatt cttggttctc   6240
cgagttggta tccatctttg cattaaagcc agaagcacac cagtcacatt aagtaaggat   6300
caactgagtg gtataaataa tattgcattt agtaactaat agtcattaaa aagcgggccc   6360
gtattgttgc aaaaagccat gaccaaatca aacagaatca aaatcaactc tggggcaaat   6420
aacaatggag ttgccaatcc tcaaaacaaa tgctattacc acaatccttg ctgcagtcac   6480
actctgtttc gcttccagtc aaaacatcac tgaagaattt tatcaatcaa catgcagtgc   6540
agtcagcaaa ggctatctta gtgctctaag aactggttgg tatactagtg ttataactat   6600
agaattaagt aatatcaagg aaaataagtg taatggtaca gacgctaagg taaaattaat   6660
aaaacaagaa ttagataaat ataaaaatgc tgtaacagaa ttgcagttgc tcatgcaaag   6720
cacaccagca gccaacaatg gagccagagg ctctggcgga agcggacttg gatttttgtt   6780
aggtgttgga tctgcaatcg ccagtggcat tgccgtatcc aaggtcctgc acctagaagg   6840
ggaagtgaac aaaatcaaaa gtgctctact atccacaaac aaggctgtag tcagcttatc   6900
taatggagtc agtgtcttaa ccagcaaggt gttagacctc aaaaactata tagataaaca   6960
gttgttacct attgttaaca agcaaagctg cagcatatca aacattgaaa ctgtgataga   7020
gttccaacaa aagaacaaca gactactaga gattaccaga gaatttagtg ttaatgcagg   7080
tgtaactact cctgtaagca cttatatgtt aactaatagt gagttattat cattaatcaa   7140
tgatatgcct ataacaaatg atcagaaaaa gttaatgtcc agcaatgttc aaatagttag   7200
acagcaaagt tactctatca tgtcaataat aaaagaggaa gtcttggcat atgtagtaca   7260
attaccacta tatggtgtaa tagatactcc ttgttggaaa ctacacacat cccctttatg   7320
tacaaccaac acaaaggaag gatccaacat ctgcttaaca agaaccgaca gaggatggta   7380
ctgtgacaat gcaggatcag tatccttttt cccacaagct gaaacatgta aagttcaatc   7440
gaatcgggtg ttttgtgaca caatgaacag tttaacatta ccaagtgagg taaatctctg   7500
caacattgac atattcaacc ccaaatatga ttgcaaaatt atgacttcaa aaacagatgt   7560
aagcagctcc gttatcacat ctctaggagc cattgtgtca tgctatggca aaaccaaatg   7620
tacagcatcc aataaaaatc gtgggatcat aaagacattc tctaacgggt gtgattatgt   7680
atcaaataag gggtggata ctgtgtctgt aggtaataca ttatattatg taaataagca   7740
agaaggcaaa agtctctatg taaaaggtga accaataata aatttctatg atccattagt   7800
```

```
gttcccctct gatgaatttg atgcatcaat atctcaagtc aatgagaaaa ttaatcagag   7860
tctagcattt atccgtaaat cagatgaatt attacataat gtaaatgctg gtaaatccac   7920
cacaaatatc atgataacta ccataattat agtaattata gtaatattgt tagcattaat   7980
tgcagttgga ctgcttctat actgcaaggc cagaagcaca ccagtcacat taagtaagga   8040
tcaactgagt ggtataaata atattgcatt tagtaactga ataaaaatag cacctaatca   8100
tattcttaca atggttcgct atttgaccat agataaccca tctatcatta gattatccta   8160
aaatttgaac ttcatcacaa ctttcatcta taaaccatct cacttacact ttttaagtag   8220
atttctattt tatagttata taaaacaggg cccattgaat accaaattaa cttactattt   8280
gtaaaaatga gaattggggc aaatatgtca cgaaggaatc cttgcaaatt cgaaattcga   8340
ggtcattgct tgaatggtaa aaggtgtcat tttagtcata attattttga atggccaccc   8400
catgcactgc ttgtaagaca aaactttatg ttaaacagaa tacttaagtc tatggataaa   8460
agcatagata ctttgtcaga aataagtgga gctgcagagt tggacagaac agaagagtat   8520
gccctcggtg tagttggagt gctagagagt tatataggat caataaataa tataactaaa   8580
caatcagcat gtgttgccat gagcaaactc cttactgaac tcaacagcga tgacatcaaa   8640
aaactaaggg acaatgaaga gccaaactca cccaaagtaa gagtgtacaa tactgtcata   8700
tcatatattg aaagcaacag gaagaacaat aaacaaacta tccatctgtt aaaaagattg   8760
ccagcagacg tattgaagaa aaccatcaaa aacacattgg atatccacaa gagcataacc   8820
atcaataacc caaaagaatc aactgttagt gatacgaacg accatgccaa aaataatgat   8880
actacctgac aaatatcctt gtagtataaa ttccatacta ataacaagta attgtagagt   8940
cactatgtat aatcaaaaaa acacactata tatcaatcaa aacaaccaaa atagccatat   9000
atacccaccg gatcaaccat tcaatgaaat ccattggacc tctcaagact tgattgatgc   9060
aactcaaaat tttctacaac atctaggtat tactgatgat atatacacaa tatatatatt   9120
agtgtcataa tactcaatcc taatacttac cacatcatca aattattaac tcaaacaatt   9180
caagctatgg gacaaaatgg atcccattat tagtggaaat tctgctaatg tttatctaac   9240
tgatagttat ttaaaaggtg ttatttcttt ctcagaatgt aacgctttag gaagttacat   9300
attcaatggt ccttatctca aaaatgatta taccaactta attagtagac aaaatccatt   9360
aatagaacac ataaatctaa agaaactaaa tataacacag tccttaatat ctaagtatca   9420
taaaggtgaa ataaaaatag aagaacctac ttactttcag tcattactta tgacatacaa   9480
gagtatgacc tcttcagaac agactactac tactaattta cttaaaaaga taataagaag   9540
agctatagaa atcagtgatg tcaaagtcta tgctatattg aataaactgg ggctcaaaga   9600
aaaagacaag attaaatcca ataatggaca agatgaagac aactcagtca ttactaccat   9660
aatcaaagat gatatacttt tagctgtcaa ggataatcaa tctcatctta aagcagacaa   9720
aaatcaatcc acaaaacaaa aagatacaat caaaacaaca cttttgaaga aattaatgtg   9780
ttcgatgcaa catcctccat catggttaat acattggttt aatttataca caaaattaaa   9840
cagcatatta acacaatatc gatctagtga ggtaaaaaac catggtttta tattgataga   9900
taatcatact cttagtggat tccaatttat tttgaatcaa tatggttgta tagtttatca   9960
taaggaactc aaaagaatta ctgtgacaac ttataatcaa ttcttgacat ggaaagatat  10020
tagccttagt agattaaatg tttgtttgat tacatggatt agtaactgtt tgaacacatt  10080
aaacaaaagc ttaggcttaa gatgtggatt caataatgtt atcttgacac aattattcct  10140
```

```
ttatggagat tgtatactaa aactattcca caatgagggg ttctacataa taaaagaggt  10200
agagggattt attatgtctc taattttaaa tataacagaa gaagatcaat tcagaaaacg  10260
gttttataat agtatgctca acaacatcac agatgccgcc aacaaagctc aaaaaaatct  10320
gctatcaaga gtatgtcata cattattaga taagacaata tcagataata taataaatgg  10380
cagatggata attctattga gtaagttcct aaaattaatt aagcttgcag gtgacaataa  10440
cctcaacaat ctgagtgaat tatatttttt gttcagaata tttggacacc caatggtaga  10500
tgaaagacaa gccatggatg ctgttaaagt taattgcaac gagaccaaat tttatttgtt  10560
aagtagtttg agtatgttaa gaggagcttt tatatataga attataaaag ggtttgtaaa  10620
taattacaac agatggccta ctttaagaaa tgccattgtc ttacccttaa gatggttaac  10680
ttactataaa ctaaacactt atccttcctt gttggaactt acagaaagag atttgattgt  10740
tctatcagga ctacgtttct atcgagagtt tcggttgcct aaaaaagtgg atcttgaaat  10800
gatcataaat gataaggcta tatcacctcc taaaaattta atatggacta gtttccctag  10860
aaattatatg ccgtcacaca tacaaaatta tatagaacat gaaaaattaa aattctctga  10920
tagtgataaa tcaagaagag tattagagta ttatttaaga gataacaaat tcaatgaatg  10980
tgatttacac aactgtgtag ttaatcaaag ttatcttaac aacccgaatc atgtggtatc  11040
attgacaggc aaagaaagag aactcagtgt aggtagaatg tttgcaatgc aaccaggaat  11100
gttcagacaa gttcaaatat tagcagagaa aatgatagca gaaaacatat tacaattttt  11160
ccctgaaagt cttacaagat atggtgatct agaactacag aaaatattag aattgaaagc  11220
aggaataagt aacaaatcaa atcgttacaa tgataattac aacaattaca ttagtaagtg  11280
ctctatcatc acagatctca gcaaattcaa tcaagcattt cgatatgaaa catcatgtat  11340
ttgtagtgat gtactggatg aactgcatgg tgtacaatct ctattttcct ggttacattt  11400
aactattcct catgtcacaa taatatgcac atataggcat gcaccccccct atataaagga  11460
tcatattgta gatcttaaca atgtagatga gcaaagtgga ctatatagat atcatatggg  11520
tggtatcgaa gggtggtgtc aaaaactatg gaccatagaa gctatatcac tattagatct  11580
aatatctctc aaagggaaat tctcaattac tgctttaatt aatggtgaca atcaatcaat  11640
agatataagt aaaccagtca gactcatgga aggtcaaact catgctcaag cagattattt  11700
gctagcatta aatagtctca aattactgta taaagagtat gcaggaatag gccacaaatt  11760
aaaaggaact gagacttata tatcgagaga tatgcaattt atgagtaaaa cgatccaaca  11820
taacggtgta tattacccag ctagtataaa gaaagtccta agagtgggac cgtggataaa  11880
cactatactt gatgacttca aagtgagtct agaatctata ggtagtttga cacaagaatt  11940
agaatataga ggtgaaagtc tattatgcag tttaatattt agaaatgtat ggttatataa  12000
tcaaattgca ttacaactta aaaatcatgc attatgtaac aacaaattat atttggatat  12060
attaaaagtt ctaaaacact taaaaacctt ttttaatctt gataacattg atacagcatt  12120
aacattgtat atgaatttgc ccatgttatt tggtggtggt gatcccaact tgttatatcg  12180
aagtttctat agaagaactc ctgatttcct cacagaggct atagttcact ctgtgttcat  12240
acttagttat tatacaaacc atgatttaaa agataaactt caagatctgt cagatgatag  12300
attgaataag ttcttaacat gcataatcac gtttgataaa aaccccaatg ctgaattcgt  12360
tacattgatg agagatcctc aagctttagg atctgagagg caagctaaaa ttactagcga  12420
aatcaataga ctggcagtta ccgaggtttt gagcacagct ccaaacaaaa tattttccaa  12480
aagtgcacaa cactatacca ctacagagat agatcttaat gatattatgc aaaatataga  12540
```

-continued

```
acctacatat cctcacgggc taagagttgt ttatgagagt ttacccttt ataaagcaga  12600
gaaaatagta aatcttatat ccggtacaaa atctataact aacatactgg aaaagacttc  12660
tgccatagac ttaacagata ttgatagagc cactgagatg atgaggaaaa acataacttt  12720
gcttataagg atattaccat tagattgtaa cagagataaa agagaaatat tgagtatgga  12780
aaacctaagt attactgaat taagcaaata cgttagagaa agatcttggt ctttatccaa  12840
tatagttggt gttacatcac ccagtatcat gtatacaatg gacataaaat atacaacaag  12900
cactatagct agtggcataa tcatagagaa atataatgtc aacagtttaa cacgtggtga  12960
gagaggaccc actaaaccat gggttggttc atctacacaa gagaaaaaga caatgccagt  13020
ttataataga caagttttaa ccaaaaaaca gagagatcaa atagatctat tagcaaaatt  13080
ggattgggtg tatgcatcta tagataacaa ggatgaattt atggaggaac ttagcatagg  13140
aactcttggg ttaacatatg agaaggccaa aaaattattc ccacaatatt tgagtgttaa  13200
ctatttgcat cgtcttacag tcagtagtag accatgtgaa ttccctgcat ctataccagc  13260
ttatagaact acaaattatc actttgatac tagccctatt aatcgcatat taacagaaaa  13320
gtatggtgat gaagatattg atatagtatt ccaaaactgt ataagctttg gccttagctt  13380
aatgtctgta gtagaacaat ttactaatgt atgtcctaac agaattattc tcatacccaa  13440
gcttaatgag atacatttga tgaaacctcc catattcaca ggcgatgttg atattcacaa  13500
gttaaaacaa gtgatacaaa aacaacatat gtttttacca gacaaaataa gtttgactca  13560
atatgtggaa ttattcttaa gtaataaaac actcaaatct ggatctaatg ttaattctaa  13620
tttaatattg gcgcataaga tatctgacta ttttcataat acttacattt tgagtactaa  13680
tttagctgga cattggattc ttattataca acttatgaaa gattctaagg gtatttttga  13740
aaaagattgg ggagagggat atataactga tcatatgttc attaatttga aagttttctt  13800
caatgcttat aagacatatc tcttgtgttt tcataaaggt tacggcagag caaagctgga  13860
gtgtgatatg aatacttcag atctcctatg tgtattggaa ttaatagaca gtagttattg  13920
gaagtctatg tctaaggtgt ttttagaaca aaaagttatc aaatacattc ttagccagga  13980
tgcaagttta catagagtaa aaggatgtca tagcttcaaa ctatggtttc ttaaacgtct  14040
taatgtagca gaattcacag tttgcccttg ggttgttaac atagattatc atccaacaca  14100
tatgaaagca atattaactt atattgatct tgttagaatg ggattgataa atatagatag  14160
aatatacatt aaaaataaac acaagttcaa tgatgagttt tatacttcta atctgtttta  14220
cattaattat aacttctcag ataatactca tctattaact aaacatataa ggattgctaa  14280
ttccgaatta gaaagtaatt acaacaaatt atatcatcct acaccagaaa ccctagaaaa  14340
tatactaacc aatccggtta aaagtaatga gaaaaagaca ctgagtgact attgtatagg  14400
taaaaatgtt gactcaataa tgttaccatc gttatctaat aagaagctta ttaaatcgtc  14460
tacaatgatt agaaccaatt acagcagaca agatttgtat aatttatttc ctacggttgt  14520
gattgataaa attatagatc attcaggtaa tacagccaaa tctaaccaac tttacactac  14580
tacttctcat caaatatcct tagtgcacaa tagcacatca ctttattgca tgcttccttg  14640
gcatcatatt aatagattca attttgtatt tagttctaca ggttgtaaaa ttagtataga  14700
gtatatttta aaagatctta aaattaagga tcctaattgt atagcattca taggtgaagg  14760
agcagggaat ttattattgc gtacagtagt ggaacttcat cctgatataa gatatattta  14820
cagaagtctg aaagattgca atgatcatag tttaccaatt gagtttttaa ggctgtacaa  14880
```

tggacatatc aacattgatt atggtgaaaa tttgaccatt cctgctacag atgcaaccaa 14940
caacattcat tggtcttatt tacatataaa gtttgctgaa cctatcagtc tttttgtctg 15000
tgatgctgaa ttgcctgtaa cagtcaactg gagtaagatt ataatagagt ggagcaagca 15060
tgtaagaaaa tgcaagtact gttcttcagt taataaatgt acattgatag taaaatatca 15120
tgctcaagat gatatcgatt tcaaattaga caacataact atattaaaaa cttatgtatg 15180
cttaggtagt aagttaaagg gatctgaagt ttacttagtc cttacaatag gtcctgcaaa 15240
tgtgttccca gtatttaatg tagtacaaaa tgctaaattg atactatcaa gaactaaaaa 15300
tttcatcatg cctaaaaaag ctgataaaga gtctattgat gcaaatatta agagtttgat 15360
accctttctt tgttacccta taacaaaaaa aggaattaat actgcattgt ctaaattaaa 15420
gagtgttgtt agtggagata tactatcata ttctatagct ggacgtaatg aagttttcag 15480
caataaactt ataaatcata agcatatgaa catcttaaag tggttcaatc atgttttaaa 15540
tttcagatca acagaattaa actataatca tttatatatg gtagaatcta cttatcctca 15600
tctaagtgaa ttgttaaaca gcttgacaac caatgaactt aaaaaactga ttaaaatcac 15660
aggtagtttg ttatacaact tttataatga ataatgagca aaaatcttat aacaaaaata 15720
gctacacact aacattgtat tcaattatag ttattgaaaa ttaataatta tataattttt 15780
aataacttct agtgaactaa tcctaaaatt atcattttga tctaggaaga ataagtttaa 15840
atccaaatct aattggttta tatgtatatt aactaaatta cgagatatta gtttttgaca 15900
ctttttttct cgtggccggc atggtcccag cctcctcgct ggcgccggct gggcaacatg 15960
cttcggcatg gcgaatggga ctagcataac cccttggggc ctctaaacgg gtcttgaggg 16020
gttttttg 16028

<210> SEQ ID NO 25
<211> LENGTH: 17006
<212> TYPE: DNA
<213> ORGANISM: Artificial Sequence
<220> FEATURE:
<223> OTHER INFORMATION: antigenic cDNA encoding cRSVA_VSVG_A_preF_ef_NS1/NS2deop

<400> SEQUENCE: 25
taatacgact cactataggt tttttcgcgt ctgatgaggc cgttaggccg aaactcctct 60
ccggagtcac gcgaaaaaat gcgtacaaca aacttgcgta aaccaaaaaa atggggcaaa 120
taagaatttg ataagtacca cttaaattta actcctttgg ttagaggcgc gccatgggtt 180
cgaattcgct atcgatgata aaagtacgtc tacaaaatct atttgataat gatgaagtag 240
cgctactaaa aataacgtgt tatacggata aactaataca actaacgaat gcgctagcga 300
aagcggtaat acatacgata aaactaaatg gtatagtatt tgtacatgta ataacgtcgt 360
cggatatatg tccgaataat aatatagtag taaaatcgaa ttttacgacg atgccggtac 420
tacaaaatgg tggttatata tgggaaatga tggaactaac gcattgttcg caaccgaatg 480
gtctaataga tgataattgt gaaataaaat tttcgaaaaa actatcggat tcgacgatga 540
cgaattatat gaatcaacta tcggaactac taggttttga tctaaatccg taaatcataa 600
taaatatcaa ctagcaaatc aatgtcacta acaccattag ttaatataaa acttgacaga 660
agataaaaat ggggcaaata aatcaattca gccgacccaa ccatggatac gacgcataat 720
gatacgacgc cgcaacgtct aatgataacg gatatgcgtc cgctatcgct agaaacgata 780
ataacgtcgc taacgcgaga tataataacg cataaattta tatatctaat aaatcatgaa 840

-continued

```
tgtatagtac gtaaactaga tgaacgtcaa gcgacgttta cgtttctagt aaattatgaa    900
atgaaactac tacataaagt aggttcgacg aaatataaaa aatatacgga atataatacg    960
aaatatggta cgtttccgat gccgatattt ataaatcatg atggttttct agaatgtata   1020
ggtataaaac cgacgaaaca tacgccgata atatataaat atgatctaaa tccgtgaata   1080
tcaaaccaag attcaaacaa tccgaaataa caactttatg cataatcaca ctccatagtc   1140
caaatggagc ctgaaaatta tagttattta aaattcctgc aggaaggaga gacataagat   1200
gaaagatggg gcaaatacaa aaatggctct tagcaaagtc aagttgaatg atacactcaa   1260
caaagatcaa cttctatcat ccagcaaata taccatccaa cggagcacag gagacagcat   1320
tgacactcct aattatgatg tgcagaaaca cattaataag ttatgtggca tgttattaat   1380
cacagaagat gctaatcata aattcactgg gttaataggt atgttatatg ctatgtctag   1440
attaggaaga gaagacacca taaaaatact caaagatgcg ggatatcatg ttaaggcaaa   1500
tggagtggat gtaacaacac atcgtcaaga cattaatggg aaagaaatga aatttgaagt   1560
gttaacatta gcaagcttaa caactgaaat tcaaatcaac attgagatag aatctagaaa   1620
atcctacaaa aaaatgctaa aagaaatggg agaggtggct ccagaataca ggcatgactc   1680
tcctgattgt gggatgataa tattatgtat agcggcatta gtaataacca aattagcagc   1740
aggagataga tcaggtctta cagctgtgat taggagagct aataatgtcc taaaaaatga   1800
aatgaaacgt tataaaggtt tattacccaa ggatatagcc aacagcttct atgaagtgtt   1860
tgaaaaatat cctcacttta tagatgtttt tgttcatttt ggtatagcac aatcttctac   1920
cagaggtggc agtagagttg aagggatttt tgcaggattg tttatgaatg cctatggtgc   1980
agggcaagtg atgttacggt ggggggtctt agcaaaatca gttaaaaaca ttatgttagg   2040
acacgctagt gtacaagcag aaatggaaca agttgtggag gtgtatgagt atgctcagaa   2100
attgggtgga gaagcaggat tctaccatat attgaacaac ccaaaagcat cactattatc   2160
tttgactcaa tttcctcact tctctagtgt agtattgggc aatgctgctg gcctaggcat   2220
aatgggagaa tacagaggta caccaaggaa tcaagattta tatgatgctg caaaagcata   2280
tgctgaacaa ctcaaagaaa atggtgtgat taactacagt gtattagatt tgacagcaga   2340
agaactagag gctatcaaac atcagcttaa tccaaaagat aatgatgtag agctttgagt   2400
taataaaaaa gtggggcaaa taaatcatca tggaaaagtt tgctcctgaa ttccatggag   2460
aagatgcaaa caacagagcc accaaattcc tagaatcaat aaagggcaaa ttcacatcac   2520
ccaaagatcc caagaaaaaa gatagtatca tatctgtcaa ctcaatagat atagaagtaa   2580
ccaaagaaag ccctataaca tcaaattcaa ccattataaa cccaataaat gagacagatg   2640
atactgtagg gaacaagccc aattatcaaa gaaagcctct agtaagtttc aaagaagacc   2700
ctacgccaag tgataatcct tttcaaaac tatacaaaga aaccatagaa acatttgata    2760
acaatgaaga agaatctagc tattcatatg aagaaataaa tgatcagaca aacgataata   2820
taacagcaag attagatagg attgatgaga aattaagtga aatactagga atgcttcaca   2880
cattagtagt agcgagtgca ggacccacat ctgctcggga tggtataaga gatgccatgg   2940
ttggtttaag agaagaaatg atagaaaaaa tcagaactga agcattaatg accaatgaca   3000
gactagaagc tatggcaaga ctcaggaatg aagaaagtga aaagatggca aaagacacat   3060
cagatgaagt gtctctcaat ccaacatcag agaaactgaa caacctgttg gaagggaatg   3120
atagtgacaa tgatctatca cttgaagatt tctgattagc taccaaactg tacatcaaaa   3180
cacaacacca atagaaaacc aacaaacaaa ccaactcacc catccaacca aacatctatc   3240
```

-continued

```
tgctgattag ccaaccagcc aaaaaacaac cagccaatct aaaactagcc acccggaaaa   3300
aatcgatact atagttacaa aaaaagatgg ggcaaatatg gaaacatacg tgaataaact   3360
tcacgagggc tccacataca cagctgctgt tcaatacaat gtcctagaaa aagacgatga   3420
tcctgcatca cttacaatat gggtgcccat gttccaatca tccatgccag cagatctact   3480
cataaaagaa ctagccaatg tcaatatact agtgaaacaa atatccacac ccaagggacc   3540
ctcattaaga gtcatgataa actcaagaag tgcagtgcta gcacaaatgc ccagcaaatt   3600
taccatatgt gccaatgtgt ccttggatga aagaagcaag ctggcatatg atgtaaccac   3660
accctgtgaa attaaggcat gcagtctaac atgcctaaaa tcaaaaaata tgttaactac   3720
agttaaagat ctcactatga aaacactcaa cccaacacat gacatcattg ctttatgtga   3780
atttgaaaat atagtaacat caaaaaaagt cataatacca acatacctaa gatctatcag   3840
cgtcagaaat aaagatctga acacacttga aaatataaca accactgaat tcaaaaatgc   3900
cattacaaat gcaaaaatca tcccttactc aggattattg ttagtcatca cagtgactga   3960
caacaaagga gcattcaaat acataaagcc acaaagtcaa ttcatagtag atcttggagc   4020
ttacctagaa aaagaaagta tatattatgt tacaacaaat tggaagcaca cagctacacg   4080
atttgcaatc aaacccatgg aagattaacc tttttcctct acatcaatga gtagattcat   4140
acaaactttc taactacatt cttcacttca caatcataat caccaaccct ctgtggttca   4200
atcaatcaaa caaaactcat caagagttcc agatcatccc aagtcattgt tcatcagatc   4260
cagtactcaa ataagttaat aaaaaatcca catggggcaa ataatcattg agggaaatcc   4320
aactaatcac aacatctgtc aacatagaca agtcaacacg ctagataaaa tcaaccaatg   4380
gaaaatacat ccataactat agaattctca agcaaattct ggccttactt tacactaata   4440
cacatgataa caacaataat ctctttgata atcataatct ccatcatgat tgcaatacta   4500
aacaaactct gcgaatataa tgtattccat aacaaaacct ttgagctacc aagagctcga   4560
gtcaatacat agcattcacc aatctgatag ctcaaaacag taaccttgca tttgtaaatg   4620
aactaccctc acttcttcac aaaaccacat caacatctca ccatgcaagc catcatctat   4680
accataaagt agttaattaa aaatggccgg ccagtcataa caatgaacta ggatattaag   4740
accaaaaaca acgctggggc aaatgcaaac atgtccaaaa ccgaggacca acgcaccgcc   4800
aagacactag aaaggacctg ggacactttt aatcatctat tattcatatc atcgtgctta   4860
tacaagttaa atcttaaatc tatagcacaa atcacattat ctattttggc aattataatc   4920
tcaacctcac ttataattgc agccatcata ttcatagcct cggcaaacca caaagtcaca   4980
ctaacaactg caatcataca agatgcaacg aaccagatca agaacacaac cccaacatac   5040
ctcacccaga atccccagca tggaatcagc ttctccaatc tgtccggaac tacatcacaa   5100
tccaccacca tactagcttc aacaacacca agtgctgatt caaccccaca atccacaaca   5160
gtcaagatca aaaacacaac aacaacccaa atattaccta gcaaacccac cacaaaacaa   5220
cgccaaaata aaccacaaaa caaacccaac aatgattttc actttgaagt gttcaatttt   5280
gtaccctgca gcatatgcag caacaatcca acctgctggg ccatctgcaa gagaatacca   5340
aacaaaaaac ctggaaagaa aaccaccacc aagcccacaa aaaaaccaac cctcaagaca   5400
accaaaaaag atcccaaatc ccaaaccaca aaaccaaagg aagtactcac taccaagcct   5460
acaggaaagc caaccatcaa caccactaaa acaaacatca gaactacact gctcacctcc   5520
aacaccaaag gaaatccaga acacacaagt caagaggaaa ccctccactc aaccacctcc   5580
```

-continued

```
gaaggctatc caagcccatc acaagtccac acaacatccg gtcaagagga aaccctccac   5640
tcaaccacct ccgaaggcta tccaagccca tcacaagtct acacaacatc cgagtaccta   5700
tcacaatctc tatcttcatc caacacaaca aaatgatagt cattaaaaag cacgcgtttg   5760
acagaagata aaaatggggc aaatgcaaac atgaagtgcc ttttgtactt agccttttta   5820
ttcattgggg tgaattgcaa gttcaccata gtttttccac acaaccaaaa aggaaactgg   5880
aaaaatgttc cttctaatta ccattattgc ccgtcaagct cagatttaaa ttggcataat   5940
gacttaatag gcacagcctt acaagtcaaa atgcccaaga gtcacaaggc tattcaagca   6000
gacggttgga tgtgtcatgc ttccaaatgg gtcactactt gtgatttccg ctggtatgga   6060
ccgaagtata taacacattc catccgatcc ttcactccat ctgtagaaca atgcaaggaa   6120
agcattgaac aaacgaaaca aggaacttgg ctgaatccag gcttccctcc tcaaagttgt   6180
ggatatgcaa ctgtgacgga tgccgaagca gtgattgtcc aggtgactcc tcaccatgtg   6240
ctggttgatg aatacacagg agaatgggtt gattcacagt tcatcaacgg aaaatgcagc   6300
aattacatat gccccactgt ccataactct acaacctggc attctgacta taaggtcaaa   6360
gggctatgtg attctaacct catttccatg gacatcacct tcttctcaga ggacggagag   6420
ctatcatccc tgggaaagga gggcacaggg ttcagaagta actactttgc ttatgaaact   6480
ggaggcaagg cctgcaaaat gcaatactgc aagcattggg gagtcagact cccatcaggt   6540
gtctggttcg agatggctga taaggatctc tttgctgcag ccagattccc tgaatgccca   6600
gaagggtcaa gtatctctgc tccatctcag acctcagtgg atgtaagtct aattcaggac   6660
gttgagagga tcttggatta ttccctctgc caagaaacct ggagcaaaat cagagcgggt   6720
cttccaatct ctccagtgga tctcagctat cttgctccta aaaacccagg aaccggtcct   6780
gctttcacca taatcaatgg taccctaaaa tactttgaga ccagatacat cagagtcgat   6840
attgctgctc caatcctctc aagaatggtc ggaatgatca gtggaactac cacagaaagg   6900
gaactgtggg atgactgggc accatatgaa gacgtggaaa ttggacccaa tggagttctg   6960
aggaccagtt caggatataa gtttccttta tacatgattg gacatggtat gttggactcc   7020
gatcttcatc ttagctcaaa ggctcaggtg ttcgaacatc ctcacattca agacgctgct   7080
tcgcaacttc ctgatgatga gagtttattt tttggtgata ctgggctatc caaaaatcca   7140
atcgagcttg tagaaggttg gttcagtagt tggaaaagct ctattgcctc tttttcttt    7200
atcatagggt taatcattgg actattcttg gttctccgag ttggtatcca tctttgcatt   7260
aaagccagaa gcacaccagt cacattaagt aaggatcaac tgagtggtat aaataatatt   7320
gcatttagta actaatagtc attaaaaagc gggcccgtat tgttgcaaaa agccatgacc   7380
aaatcaaaca gaatcaaaat caactctggg gcaaataaca atggagttgc caatcctcaa   7440
aacaaatgct attaccacaa tccttgctgc agtcacactc tgtttcgctt ccagtcaaaa   7500
catcactgaa gaattttatc aatcaacatg cagtgcagtc agcaaaggct atcttagtgc   7560
tctaagaact ggttggtata ctagtgttat aactatagaa ttaagtaata tcaaggaaaa   7620
taagtgtaat ggtacagacg ctaaggtaaa attaataaaa caagaattag ataaatataa   7680
aaatgctgta acagaattgc agttgctcat gcaaagcaca ccagcagcca acaatcgagc   7740
cagaagagaa ctaccaagat ttatgaatta tacactcaac aataccaaaa acaccaatgt   7800
aacattaagt aagaaaagga aaagaagatt tcttggattt ttgttaggtg ttggatctgc   7860
aatcgccagt ggcattgccg tatccaaggt cctgcaccta gaaggggaag tgaacaaaat   7920
caaaagtgct ctactatcca caaacaaggc tgtagtcagc ttatctaatg gagtcagtgt   7980
```

```
cttaaccagc aaggtgttag acctcaaaaa ctatatagat aaacagttgt tacctattgt   8040
taacaagcaa agctgcagca tatcaaacat tgaaactgtg atagagttcc aacaaaagaa   8100
caacagacta ctagagatta ccagagaatt tagtgttaat gcaggtgtaa ctactcctgt   8160
aagcacttat atgttaacta atagtgagtt attatcatta atcaatgata tgcctataac   8220
aaatgatcag aaaaagttaa tgtccagcaa tgttcaaata gttagacagc aaagttactc   8280
tatcatgtca ataataaaag aggaagtctt ggcatatgta gtacaattac cactatatgg   8340
tgtaatagat actccttgtt ggaaactaca cacatcccct ttatgtacaa ccaacacaaa   8400
ggaaggatcc aacatctgct taacaagaac cgacagagga tggtactgtg acaatgcagg   8460
atcagtatcc tttttcccac aagctgaaac atgtaaagtt caatcgaatc gggtgttttg   8520
tgacacaatg aacagtttaa cattaccaag tgaggtaaat ctctgcaaca ttgacatatt   8580
caaccccaaa tatgattgca aaattatgac ttcaaaaaca gatgtaagca gctccgttat   8640
cacatctcta ggagccattg tgtcatgcta tggcaaaacc aaatgtacag catccaataa   8700
aaatcgtggg atcataaaga cattctctaa cgggtgtgat tatgtatcaa ataagggggt   8760
ggatactgtg tctgtaggta atacattata ttatgtaaat aagcaagaag gcaaaagtct   8820
ctatgtaaaa ggtgaaccaa taataaattt ctatgatcca ttagtgttcc cctctctcct   8880
gtgggatgca tcaatatctc aagtcaatga gaaaattaat cagagtctag catttatccg   8940
taaatcagat gaattattag gctctggcgg aagcggatac atccctgagg caccaaggga   9000
cggacaggcc tacgtgcgca aggatggcga gtgggtgctg ctgtccacct ttctgtgaat   9060
aaaaatagca cctaatcata ttcttacaat ggttcgctat ttgaccatag ataacccatc   9120
tatcattaga ttatcctaaa atttgaactt catcacaact ttcatctata aaccatctca   9180
cttacacttt ttaagtagat ttctatttta tagttatata aaacagggcc cattgaatac   9240
caaattaact tactatttgt aaaaatgaga attggggcaa atatgtcacg aaggaatcct   9300
tgcaaattcg aaattcgagg tcattgcttg aatggtaaaa ggtgtcattt tagtcataat   9360
tattttgaat ggccacccca tgcactgctt gtaagacaaa actttatgtt aaacagaata   9420
cttaagtcta tggataaaag catagatact ttgtcagaaa taagtggagc tgcagagttg   9480
gacagaacag aagagtatgc cctcggtgta gttggagtgc tagagagtta tataggatca   9540
ataaataata taactaaaca atcagcatgt gttgccatga gcaaactcct tactgaactc   9600
aacagcgatg acatcaaaaa actaagggac aatgaagagc caaactcacc caaagtaaga   9660
gtgtacaata ctgtcatatc atatattgaa agcaacagga agaacaataa acaaactatc   9720
catctgttaa aaagattgcc agcagacgta ttgaagaaaa ccatcaaaaa cacattggat   9780
atccacaaga gcataaccat caataaccca aaagaatcaa ctgttagtga tacgaacgac   9840
catgccaaaa ataatgatac tacctgacaa atatccttgt agtataaatt ccatactaat   9900
aacaagtaat tgtagagtca ctatgtataa tcaaaaaaac acactatata tcaatcaaaa   9960
caaccaaaat agccatatat acccaccgga tcaaccattc aatgaaatcc attggacctc  10020
tcaagacttg attgatgcaa ctcaaaattt tctacaacat ctaggtatta ctgatgatat  10080
atacacaata tatatattag tgtcataata ctcaatccta atacttacca catcatcaaa  10140
ttattaactc aaacaattca agctatggga caaaatggat cccattatta gtggaaattc  10200
tgctaatgtt tatctaactg atagttattt aaaaggtgtt atttctttct cagaatgtaa  10260
cgctttagga agttacatat tcaatggtcc ttatctcaaa aatgattata ccaacttaat  10320
```

```
tagtagacaa aatccattaa tagaacacat aaatctaaag aaactaaata taacacagtc  10380
cttaatatct aagtatcata aaggtgaaat aaaaatagaa gaacctactt actttcagtc  10440
attacttatg acatacaaga gtatgacctc ttcagaacag actactacta ctaatttact  10500
taaaaagata ataagaagag ctatagaaat cagtgatgtc aaagtctatg ctatattgaa  10560
taaactgggg ctcaaagaaa aagacaagat taaatccaat aatggacaag atgaagacaa  10620
ctcagtcatt actaccataa tcaaagatga tatactttta gctgtcaagg ataatcaatc  10680
tcatcttaaa gcagacaaaa atcaatccac aaaacaaaaa gatacaatca aaacaacact  10740
tttgaagaaa ttaatgtgtt cgatgcaaca tcctccatca tggttaatac attggtttaa  10800
tttatacaca aaattaaaca gcatattaac acaatatcga tctagtgagg taaaaaacca  10860
tggttttata ttgatagata atcatactct tagtggattc caatttattt tgaatcaata  10920
tggttgtata gtttatcata aggaactcaa aagaattact gtgacaactt ataatcaatt  10980
cttgacatgg aaagatatta gccttagtag attaaatgtt tgtttgatta catggattag  11040
taactgtttg aacacattaa acaaaagctt aggcttaaga tgtggattca ataatgttat  11100
cttgacacaa ttattccttt atggagattg tatactaaaa ctattccaca atgaggggtt  11160
ctacataata aaagaggtag agggatttat tatgtctcta attttaaata taacagaaga  11220
agatcaattc agaaaacggt tttataatag tatgctcaac aacatcacag atgccgccaa  11280
caaagctcaa aaaaatctgc tatcaagagt atgtcataca ttattagata agacaatatc  11340
agataatata ataaatggca gatggataat tctattgagt aagttcctaa aattaattaa  11400
gcttgcaggt gacaataacc tcaacaatct gagtgaatta tattttttgt tcagaatatt  11460
tggacaccca atggtagatg aaagacaagc catggatgct gttaaagtta attgcaacga  11520
gaccaaattt tatttgttaa gtagtttgag tatgttaaga ggagctttta tatatagaat  11580
tataaaaggg tttgtaaata attacaacag atggcctact ttaagaaatg ccattgtctt  11640
acccttaaga tggttaactt actataaact aaacacttat ccttccttgt tggaacttac  11700
agaaagagat ttgattgttc tatcaggact acgtttctat cgagagtttc ggttgcctaa  11760
aaaagtggat cttgaaatga tcataaatga taaggctata tcacctccta aaaatttaat  11820
atggactagt ttccctagaa attatatgcc gtcacacata caaaattata tagaacatga  11880
aaaattaaaa ttctctgata gtgataaatc aagaagagta ttagagtatt atttaagaga  11940
taacaaattc aatgaatgtg atttacacaa ctgtgtagtt aatcaaagtt atcttaacaa  12000
cccgaatcat gtggtatcat tgacaggcaa agaaagagaa ctcagtgtag gtagaatgtt  12060
tgcaatgcaa ccaggaatgt tcagacaagt tcaaatatta gcagagaaaa tgatagcaga  12120
aaacatatta caatttttcc ctgaaagtct tacaagatat ggtgatctag aactacagaa  12180
aatattagaa ttgaaagcag gaataagtaa caaatcaaat cgttacaatg ataattacaa  12240
caattacatt agtaagtgct ctatcatcac agatctcagc aaattcaatc aagcatttcg  12300
atatgaaaca tcatgtattt gtagtgatgt actggatgaa ctgcatggtg tacaatctct  12360
attttcctgg ttacatttaa ctattcctca tgtcacaata atatgcacat ataggcatgc  12420
accccccctat ataaaggatc atattgtaga tcttaacaat gtagatgagc aaagtggact  12480
atatagatat catatgggtg gtatcgaagg gtggtgtcaa aaactatgga ccatagaagc  12540
tatatcacta ttagatctaa tatctctcaa agggaaattc tcaattactg ctttaattaa  12600
tggtgacaat caatcaatag atataagtaa accagtcaga ctcatggaag gtcaaactca  12660
tgctcaagca gattatttgc tagcattaaa tagtctcaaa ttactgtata aagagtatgc  12720
```

aggaataggc cacaaattaa aaggaactga gacttatata tcgagagata tgcaatttat 12780
gagtaaaacg atccaacata acggtgtata ttacccagct agtataaaga aagtcctaag 12840
agtgggaccg tggataaaca ctatacttga tgacttcaaa gtgagtctag aatctatagg 12900
tagtttgaca caagaattag aatatagagg tgaaagtcta ttatgcagtt taatatttag 12960
aaatgtatgg ttatataatc aaattgcatt acaacttaaa aatcatgcat tatgtaacaa 13020
caaattatat ttggatatat taaaagttct aaaacactta aaaacctttt ttaatcttga 13080
taacattgat acagcattaa cattgtatat gaatttgccc atgttatttg gtggtggtga 13140
tcccaacttg ttatatcgaa gtttctatag aagaactcct gatttcctca cagaggctat 13200
agttcactct gtgttcatac ttagttatta tacaaaccat gatttaaaag ataaacttca 13260
agatctgtca gatgatagat tgaataagtt cttaacatgc ataatcacgt ttgataaaaa 13320
ccccaatgct gaattcgtta cattgatgag agatcctcaa gctttaggat ctgagaggca 13380
agctaaaatt actagcgaaa tcaatagact ggcagttacc gaggttttga gcacagctcc 13440
aaacaaaata ttttccaaaa gtgcacaaca ctataccact acagagatag atcttaatga 13500
tattatgcaa aatatagaac ctacatatcc tcacgggcta agagttgttt atgagagttt 13560
accctttat aaagcagaga aaatagtaaa tcttatatcc ggtacaaaat ctataactaa 13620
catactggaa aagacttctg ccatagactt aacagatatt gatagagcca ctgagatgat 13680
gaggaaaaac ataactttgc ttataaggat attaccatta gattgtaaca gagataaaag 13740
agaaatattg agtatggaaa acctaagtat tactgaatta agcaaatacg ttagagaaag 13800
atcttggtct ttatccaata tagttggtgt tacatcaccc agtatcatgt atacaatgga 13860
cataaaatat acaacaagca ctatagctag tggcataatc atagagaaat ataatgtcaa 13920
cagtttaaca cgtggtgaga gaggacccac taaaccatgg gttggttcat ctacacaaga 13980
gaaaaagaca atgccagttt ataatagaca agttttaacc aaaaaacaga gagatcaaat 14040
agatctatta gcaaaattgg attgggtgta tgcatctata gataacaagg atgaatttat 14100
ggaggaactt agcataggaa ctcttgggtt aacatatgag aaggccaaaa aattattccc 14160
acaatatttg agtgttaact atttgcatcg tcttacagtc agtagtagac catgtgaatt 14220
ccctgcatct ataccagctt atagaactac aaattatcac tttgatacta gccctattaa 14280
tcgcatatta acagaaaagt atggtgatga agatattgat atagtattcc aaaactgtat 14340
aagctttggc cttagcttaa tgtctgtagt agaacaattt actaatgtat gtcctaacag 14400
aattattctc atacccaagc ttaatgagat acatttgatg aaacctccca tattcacagg 14460
cgatgttgat attcacaagt taaaacaagt gatacaaaaa caacatatgt tttaccaga 14520
caaaataagt ttgactcaat atgtggaatt attcttaagt aataaaacac tcaaatctgg 14580
atctaatgtt aattctaatt taatattggc gcataagata tctgactatt ttcataatac 14640
ttacatttg agtactaatt tagctggaca ttggattctt attatacaac ttatgaaaga 14700
ttctaagggt atttttgaaa aagattgggg agagggatat ataactgatc atatgttcat 14760
taatttgaaa gttttcttca atgcttataa gacatatctc ttgtgttttc ataaaggtta 14820
cggcagagca aagctggagt gtgatatgaa tacttcagat ctcctatgtg tattggaatt 14880
aatagacagt agttattgga agtctatgtc taaggtgttt ttagaacaaa aagttatcaa 14940
atacattctt agccaggatg caagtttaca tagagtaaaa ggatgtcata gcttcaaact 15000
atggtttctt aaacgtctta atgtagcaga attcacagtt tgcccttggg ttgttaacat 15060

-continued

```
agattatcat ccaacacata tgaaagcaat attaacttat attgatcttg ttagaatggg  15120

attgataaat atagatagaa tatacattaa aaataaacac aagttcaatg atgagtttta  15180

tacttctaat ctgttttaca ttaattataa cttctcagat aatactcatc tattaactaa  15240

acatataagg attgctaatt ccgaattaga aagtaattac aacaaattat atcatcctac  15300

accagaaacc ctagaaaata tactaaccaa tccggttaaa agtaatgaga aaaagacact  15360

gagtgactat tgtataggta aaaatgttga ctcaataatg ttaccatcgt tatctaataa  15420

gaagcttatt aaatcgtcta caatgattag aaccaattac agcagacaag atttgtataa  15480

tttatttcct acggttgtga ttgataaaat tatagatcat tcaggtaata cagccaaatc  15540

taaccaactt tacactacta cttctcatca aatatcctta gtgcacaata gcacatcact  15600

ttattgcatg cttccttggc atcatattaa tagattcaat tttgtattta gttctacagg  15660

ttgtaaaatt agtatagagt atattttaaa agatcttaaa attaaggatc ctaattgtat  15720

agcattcata ggtgaaggag cagggaattt attattgcgt acagtagtgg aacttcatcc  15780

tgatataaga tatatttaca gaagtctgaa agattgcaat gatcatagtt taccaattga  15840

gtttttaagg ctgtacaatg gacatatcaa cattgattat ggtgaaaatt tgaccattcc  15900

tgctacagat gcaaccaaca acattcattg gtcttattta catataaagt ttgctgaacc  15960

tatcagtctt tttgtctgtg atgctgaatt gcctgtaaca gtcaactgga gtaagattat  16020

aatagagtgg agcaagcatg taagaaaatg caagtactgt tcttcagtta ataaatgtac  16080

attgatagta aaatatcatg ctcaagatga tatcgatttc aaattagaca acataactat  16140

attaaaaact tatgtatgct taggtagtaa gttaaaggga tctgaagttt acttagtcct  16200

tacaataggt cctgcaaatg tgttcccagt atttaatgta gtacaaaatg ctaaattgat  16260

actatcaaga actaaaaatt tcatcatgcc taaaaaagct gataaagagt ctattgatgc  16320

aaatattaag agtttgatac cctttctttg ttaccctata acaaaaaaag gaattaatac  16380

tgcattgtct aaattaaaga gtgttgttag tggagatata ctatcatatt ctatagctgg  16440

acgtaatgaa gttttcagca ataaacttat aaatcataag catatgaaca tcttaaagtg  16500

gttcaatcat gttttaaatt tcagatcaac agaattaaac tataatcatt tatatatggt  16560

agaatctact tatcctcatc taagtgaatt gttaaacagc ttgacaacca atgaacttaa  16620

aaaactgatt aaaatcacag gtagtttgtt atacaacttt tataatgaat aatgagcaaa  16680

aatcttataa caaaaatagc tacacactaa cattgtattc aattatagtt attgaaaatt  16740

aataattata taatttttaa taacttctag tgaactaatc ctaaaattat cattttgatc  16800

taggaagaat aagtttaaat ccaaatctaa ttggtttata tgtatattaa ctaaattacg  16860

agatattagt ttttgacact ttttttctcg tggccggcat ggtcccagcc tcctcgctgg  16920

cgccggctgg gcaacatgct tcggcatggc gaatgggact agcataaccc cttggggcct  16980

ctaaacgggt cttgaggggt tttttg                                       17006
```

<210> SEQ ID NO 26
<211> LENGTH: 15494
<212> TYPE: DNA
<213> ORGANISM: Artificial Sequence
<220> FEATURE:
<223> OTHER INFORMATION: antigenic cDNA encoding cRSVA_ mF1

<400> SEQUENCE: 26

```
taatacgact cactataggt tttttcgcgt ctgatgaggc cgttaggccg aaactcctct     60

ccggagtcac gcgaaaaaat gcgtacaaca aacttgcgta aaccaaaaaa atggggcaaa    120
```

```
taagaatttg ataagtacca cttaaattta actcctttgg ttagaggcgc gccatgggca    180
gcaactcatt gagtatgata aaagttagat tgcaaaatct gtttgacaat gatgaagtag    240
cattgttaaa aataacatgc tatactgaca aattaataca gttaactaat gctttggcta    300
aggcagttat acatacaatc aaattgaatg gcattgtatt tgtgcatgtt attacaagta    360
gtgatatttg ccctaataat aatattgtag tgaaatccaa tttcacaaca atgccagtat    420
tacaaaatgg aggttatata tgggaaatga tggaattaac acactgctct caacctaatg    480
gcctaataga tgacaattgt gaaattaaat tctccaaaaa actaagtgat tcaacaatga    540
ccaattatat gaatcaatta tctgaattac ttggatttga cctcaatcca taaatcataa    600
taaatatcaa ctagcaaatc aatgtcacta acaccattag ttaatataaa acttgacaga    660
agataaaaat ggggcaaata aatcaattca gccgacccaa ccatggacac aacacacaat    720
gataccacac cacaaagact gatgatcaca gacatgaggc cattatcgct tgagactata    780
ataacatctc taaccagaga tatcataaca cataaattta tatacttgat aaatcatgaa    840
tgcatagtaa gaaaacttga tgaaagacag gccacattta catttctggt caactatgaa    900
atgaaactat tgcacaaagt gggaagcact aaatataaaa aatatactga atacaacaca    960
aaatatggca ctttccctat gccaatattt atcaatcatg atgggttctt agaatgcatt   1020
ggcattaagc ctaccaagca cacacccata atatacaagt atgatctcaa tccatgaata   1080
tcaaaccaag attcaaacaa tccgaaataa caactttatg cataatcaca ctccatagtc   1140
caaatggagc ctgaaaatta tagttattta aaattcctgc aggaaggaga gacataagat   1200
gaaagatggg gcaaatacaa aaatggctct tagcaaagtc aagttgaatg atacactcaa   1260
caaagatcaa cttctatcat ccagcaaata taccatccaa cggagcacag gagacagcat   1320
tgacactcct aattatgatg tgcagaaaca cattaataag ttatgtggca tgttattaat   1380
cacagaagat gctaatcata aattcactgg gttaataggt atgttatatg ctatgtctag   1440
attaggaaga gaagacacca taaaaatact caaagatgcg ggatatcatg ttaaggcaaa   1500
tggagtggat gtaacaacac atcgtcaaga cattaatggg aaagaaatga aatttgaagt   1560
gttaacatta gcaagcttaa caactgaaat tcaaatcaac attgagatag aatctagaaa   1620
atcctacaaa aaaatgctaa aagaaatggg agaggtggct ccagaataca ggcatgactc   1680
tcctgattgt gggatgataa tattatgtat agcggcatta gtaataacca aattagcagc   1740
aggagataga tcaggtctta cagctgtgat taggagagct aataatgtcc taaaaaatga   1800
aatgaaacgt tataaaggtt tattacccaa ggatatagcc aacagcttct atgaagtgtt   1860
tgaaaaatat cctcacttta tagatgtttt tgttcatttt ggtatagcac aatcttctac   1920
cagaggtggc agtagagttg aagggatttt tgcaggattg tttatgaatg cctatggtgc   1980
agggcaagtg atgttacggt ggggggtctt agcaaaatca gttaaaaaca ttatgttagg   2040
acacgctagt gtacaagcag aaatggaaca agttgtggag gtgtatgagt atgctcagaa   2100
attgggtgga gaagcaggat tctaccatat attgaacaac ccaaaagcat cactattatc   2160
tttgactcaa tttcctcact tctctagtgt agtattgggc aatgctgctg gcctaggcat   2220
aatgggagaa tacagaggta caccaaggaa tcaagattta tatgatgctg caaaagcata   2280
tgctgaacaa ctcaaagaaa atggtgtgat taactacagt gtattagatt tgacagcaga   2340
agaactagag gctatcaaac atcagcttaa tccaaaagat aatgatgtag agctttgagt   2400
taataaaaaa gtggggcaaa taaatcatca tggaaaagtt tgctcctgaa ttccatggag   2460
```

-continued

```
aagatgcaaa caacagagcc accaaattcc tagaatcaat aaagggcaaa ttcacatcac   2520
ccaaagatcc caagaaaaaa gatagtatca tatctgtcaa ctcaatagat atagaagtaa   2580
ccaaagaaag ccctataaca tcaaattcaa ccattataaa cccaataaat gagacagatg   2640
atactgtagg gaacaagccc aattatcaaa gaaagcctct agtaagtttc aaagaagacc   2700
ctacgccaag tgataatcct ttttcaaaac tatacaaaga aaccatagaa acatttgata   2760
acaatgaaga agaatctagc tattcatatg aagaaataaa tgatcagaca aacgataata   2820
taacagcaag attagatagg attgatgaga aattaagtga aatactagga atgcttcaca   2880
cattagtagt agcgagtgca ggacccacat ctgctcggga tggtataaga gatgccatgg   2940
ttggtttaag agaagaaatg atagaaaaaa tcagaactga agcattaatg accaatgaca   3000
gactagaagc tatggcaaga ctcaggaatg aagaaagtga aaagatggca aaagacacat   3060
cagatgaagt gtctctcaat ccaacatcag agaaactgaa caacctgttg gaagggaatg   3120
atagtgacaa tgatctatca cttgaagatt tctgattagc taccaaactg tacatcaaaa   3180
cacaacacca atagaaaacc aacaaacaaa ccaactcacc catccaacca aacatctatc   3240
tgctgattag ccaaccagcc aaaaaacaac cagccaatct aaaactagcc acccggaaaa   3300
aatcgatact atagttacaa aaaaagatgg ggcaaatatg gaaacatacg tgaataaact   3360
tcacgagggc tccacataca cagctgctgt tcaatacaat gtcctagaaa aagacgatga   3420
tcctgcatca cttacaatat gggtgcccat gttccaatca tccatgccag cagatctact   3480
cataaaagaa ctagccaatg tcaatatact agtgaaacaa atatccacac ccaagggacc   3540
ctcattaaga gtcatgataa actcaagaag tgcagtgcta gcacaaatgc ccagcaaatt   3600
taccatatgt gccaatgtgt ccttggatga aagaagcaag ctggcatatg atgtaaccac   3660
accctgtgaa attaaggcat gcagtctaac atgcctaaaa tcaaaaaata tgttaactac   3720
agttaaagat ctcactatga aaacactcaa cccaacacat gacatcattg ctttatgtga   3780
atttgaaaat atagtaacat caaaaaaagt cataatacca acatacctaa gatctatcag   3840
cgtcagaaat aaagatctga acacacttga aaatataaca accactgaat tcaaaaatgc   3900
cattacaaat gcaaaaatca tcccttactc aggattattg ttagtcatca cagtgactga   3960
caacaaagga gcattcaaat acataaagcc acaaagtcaa ttcatagtag atcttggagc   4020
ttacctagaa aaagaaagta tatattatgt tacaacaaat tggaagcaca cagctacacg   4080
atttgcaatc aaacccatgg aagattaacc tttttcctct acatcaatga gtagattcat   4140
acaaactttc taactacatt cttcacttca caatcataat caccaaccct ctgtggttca   4200
atcaatcaaa caaaactcat caagagttcc agatcatccc aagtcattgt tcatcagatc   4260
cagtactcaa ataagttaat aaaaaatcca catggggcaa ataatcattg agggaaatcc   4320
aactaatcac aacatctgtc aacatagaca agtcaacacg ctagataaaa tcaaccaatg   4380
gaaaatacat ccataactat agaattctca agcaaattct ggccttactt tacactaata   4440
cacatgataa caacaataat ctctttgata atcataatct ccatcatgat tgcaatacta   4500
aacaaactct gcgaatataa tgtattccat aacaaaacct ttgagctacc aagagctcga   4560
gtcaatacat agcattcacc aatctgatag ctcaaaacag taaccttgca tttgtaaatg   4620
aactaccctc acttcttcac aaaaccacat caacatctca ccatgcaagc catcatctat   4680
accataaagt agttaattaa aaatggccgg ccagtcataa caatgaacta ggatattaag   4740
accaaaaaca acgctggggc aaatgcaaac atgtccaaaa ccgaggacca acgcaccgcc   4800
aagacactag aaaggacctg ggacactttt aatcatctat tattcatatc atcgtgctta   4860
```

-continued

```
tacaagttaa atcttaaatc tatagcacaa atcacattat ctattttggc aattataatc   4920
tcaacctcac ttataattgc agccatcata ttcatagcct cggcaaacca caaagtcaca   4980
ctaacaactg caatcataca agatgcaacg aaccagatca agaacacaac cccaacatac   5040
ctcacccaga atccccagca tggaatcagc ttctccaatc tgtccggaac tacatcacaa   5100
tccaccacca tactagcttc aacaacacca agtgctgatt caaccccaca atccacaaca   5160
gtcaagatca aaaacacaac aacaacccaa atattaccta gcaaacccac cacaaaacaa   5220
cgccaaaata aaccacaaaa caaacccaac aatgattttc actttgaagt gttcaatttt   5280
gtaccctgca gcatatgcag caacaatcca acctgctggg ccatctgcaa gagaatacca   5340
aacaaaaaac ctggaaagaa aaccaccacc aagcccacaa aaaaaccaac cctcaagaca   5400
accaaaaaag atcccaaatc ccaaaccaca aaaccaaagg aagtactcac taccaagcct   5460
acaggaaagc caaccatcaa caccactaaa acaaacatca gaactacact gctcacctcc   5520
aacaccaaag gaaatccaga acacacaagt caagaggaaa ccctccactc aaccacctcc   5580
gaaggctatc caagcccatc acaagtccac acaacatccg gtcaagagga aaccctccac   5640
tcaaccacct ccgaaggcta tccaagccca tcacaagtct acacaacatc cgagtaccta   5700
tcacaatctc tatcttcatc caacacaaca aaatgatagt cattaaaaag cacgcgtgta   5760
ttgttgcaaa aagccatgac caaatcaaac agaatcaaaa tcaactctgg ggcaaataac   5820
aatggagttg ccaatcctca aaacaaatgc tattaccaca atccttgctg cagtcacact   5880
ctgtttcgct tccagtcaaa acatcactga agaattttat caatcaacat gcagtgcagt   5940
cagcaaaggc tatcttagtg ctctaagaac tggttggtat actagtgtta taactataga   6000
attaagtaat atcaaggaaa ataagtgtaa tggtacagac gctaaggtaa aattaataaa   6060
acaagaatta gataaatata aaaatgctgt aacagaattg cagttgctca tgcaaagcac   6120
accagcagcc aacaatcgac cctccaagga actaccaaga tttatgaatt atacactcaa   6180
caataccaaa aacaccaatg taacattaag taagaaaagg aaaagaagat ttcttggatt   6240
tttgttaggt gttggatctg caatcgccag tggcattgcc gtatccaagg tcctgcacct   6300
agaaggggaa gtgaacaaaa tcaaaagtgc tctactatcc acaaacaagg ctgtagtcag   6360
cttatctaat ggagtcagtg tcttaaccag caaggtgtta gacctcaaaa actatataga   6420
taaacagttg ttacctattg ttaacaagca aagctgcagc atatcaaaca ttgaaactgt   6480
gatagagttc caacaaaaga acaacagact actagagatt accagagaat ttagtgttaa   6540
tgcaggtgta actactcctg taagcactta tatgttaact aatagtgagt tattatcatt   6600
aatcaatgat atgcctataa caaatgatca gaaaaagtta atgtccagca atgttcaaat   6660
agttagacag caaagttact ctatcatgtc aataataaaa gaggaagtct tggcatatgt   6720
agtacaatta ccactatatg gtgtaataga tactccttgt tggaaactac acacatcccc   6780
tttatgtaca accaacacaa aggaaggatc caacatctgc ttaacaagaa ccgacagagg   6840
atggtactgt gacaatgcag gatcagtatc ctttttccca caagctgaaa catgtaaagt   6900
tcaatcgaat cgggtgtttt gtgacacaat gaacagttta acattaccaa gtgaggtaaa   6960
tctctgcaac attgacatat tcaaccccaa atatgattgc aaaattatga cttcaaaaac   7020
agatgtaagc agctccgtta tcacatctct aggagccatt gtgtcatgct atggcaaaac   7080
caaatgtaca gcatccaata aaaatcgtgg gatcataaag acattctcta acgggtgtga   7140
ttatgtatca aataaggggg tggatactgt gtctgtaggt aatacattat attatgtaaa   7200
```

-continued

```
taagcaagaa ggcaaaagtc tctatgtaaa aggtgaacca ataataaatt tctatgatcc   7260
attagtgttc ccctctgatg aatttgatgc atcaatatct caagtcaatg agaaaattaa   7320
tcagagtcta gcatttatcc gtaaatcaga tgaattatta cataatgtaa atgctggtaa   7380
atccaccaca aatatcatga taactaccat aattatagta attatagtaa tattgttagc   7440
attaattgca gttggactgc ttctatactg caaggccaga agcacaccag tcacattaag   7500
taaggatcaa ctgagtggta taaataatat tgcatttagt aactgaataa aaatagcacc   7560
taatcatatt cttacaatgg ttcgctattt gaccatagat aacccatcta tcattagatt   7620
atcctaaaat ttgaacttca tcacaacttt catctataaa ccatctcact tacacttttt   7680
aagtagattt ctattttata gttatataaa acagggccca ttgaatacca aattaactta   7740
ctatttgtaa aaatgagaat tggggcaaat atgtcacgaa ggaatccttg caaattcgaa   7800
attcgaggtc attgcttgaa tggtaaaagg tgtcatttta gtcataatta ttttgaatgg   7860
ccaccccatg cactgcttgt aagacaaaac tttatgttaa acagaatact taagtctatg   7920
gataaaagca tagatacttt gtcagaaata agtggagctg cagagttgga cagaacagaa   7980
gagtatgccc tcggtgtagt tggagtgcta gagagttata taggatcaat aaataatata   8040
actaaacaat cagcatgtgt tgccatgagc aaactcctta ctgaactcaa cagcgatgac   8100
atcaaaaaac taagggacaa tgaagagcca aactcaccca aagtaagagt gtacaatact   8160
gtcatatcat atattgaaag caacaggaag aacaataaac aaactatcca tctgttaaaa   8220
agattgccag cagacgtatt gaagaaaacc atcaaaaaca cattggatat ccacaagagc   8280
ataaccatca ataacccaaa agaatcaact gttagtgata cgaacgacca tgccaaaaat   8340
aatgatacta cctgacaaat atccttgtag tataaattcc atactaataa caagtaattg   8400
tagagtcact atgtataatc aaaaaaacac actatatatc aatcaaaaca accaaaatag   8460
ccatatatac ccaccggatc aaccattcaa tgaaatccat tggacctctc aagacttgat   8520
tgatgcaact caaaatttc tacaacatct aggtattact gatgatatat acacaatata   8580
tatattagtg tcataatact caatcctaat acttaccaca tcatcaaatt attaactcaa   8640
acaattcaag ctatgggaca aaatggatcc cattattagt ggaaattctg ctaatgttta   8700
tctaactgat agttatttaa aaggtgttat ttctttctca gaatgtaacg ctttaggaag   8760
ttacatattc aatggtcctt atctcaaaaa tgattatacc aacttaatta gtagacaaaa   8820
tccattaata gaacacataa atctaaagaa actaaatata acacagtcct taatatctaa   8880
gtatcataaa ggtgaaataa aaatagaaga acctacttac tttcagtcat tacttatgac   8940
atacaagagt atgacctctt cagaacagac tactactact aatttactta aaaagataat   9000
aagaagagct atagaaatca gtgatgtcaa agtctatgct atattgaata aactggggct   9060
caaagaaaaa gacaagatta aatccaataa tggacaagat gaagacaact cagtcattac   9120
taccataatc aaagatgata tacttttagc tgtcaaggat aatcaatctc atcttaaagc   9180
agacaaaaat caatccacaa aacaaaaaga tacaatcaaa acaacacttt tgaagaaatt   9240
aatgtgttcg atgcaacatc ctccatcatg gttaatacat tggtttaatt tatacacaaa   9300
attaaacagc atattaacac aatatcgatc tagtgaggta aaaaaccatg gttttatatt   9360
gatagataat catactctta gtggattcca atttattttg aatcaatatg gttgtatagt   9420
ttatcataag gaactcaaaa gaattactgt gacaacttat aatcaattct tgacatggaa   9480
agatattagc cttagtagat taaatgtttg tttgattaca tggattagta actgtttgaa   9540
cacattaaac aaaagcttag gcttaagatg tggattcaat aatgttatct tgacacaatt   9600
```

-continued

```
attcctttat ggagattgta tactaaaact attccacaat gaggggttct acataataaa   9660
agaggtagag ggatttatta tgtctctaat tttaaatata acagaagaag atcaattcag   9720
aaaacggttt tataatagta tgctcaacaa catcacagat gccgccaaca aagctcaaaa   9780
aaatctgcta tcaagagtat gtcatacatt attagataag acaatatcag ataatataat   9840
aaatggcaga tggataattc tattgagtaa gttcctaaaa ttaattaagc ttgcaggtga   9900
caataacctc aacaatctga gtgaattata tttttgttc agaatatttg gacacccaat   9960
ggtagatgaa agacaagcca tggatgctgt taaagttaat tgcaacgaga ccaaatttta  10020
tttgttaagt agtttgagta tgttaagagg agcttttata tatagaatta taaaagggtt  10080
tgtaaataat tacaacagat ggcctacttt aagaaatgcc attgtcttac ccttaagatg  10140
gttaacttac tataaactaa acacttatcc ttccttgttg gaacttacag aaagagattt  10200
gattgttcta tcaggactac gtttctatcg agagtttcgg ttgcctaaaa aagtggatct  10260
tgaaatgatc ataaatgata aggctatatc acctcctaaa aatttaatat ggactagttt  10320
ccctagaaat tatatgccgt cacacataca aaattatata gaacatgaaa aattaaaatt  10380
ctctgatagt gataaatcaa gaagagtatt agagtattat ttaagagata acaaattcaa  10440
tgaatgtgat ttacacaact gtgtagttaa tcaaagttat cttaacaacc cgaatcatgt  10500
ggtatcattg acaggcaaag aaagagaact cagtgtaggt agaatgtttg caatgcaacc  10560
aggaatgttc agacaagttc aaatattagc agagaaaatg atagcagaaa acatattaca  10620
atttttccct gaaagtctta caagatatgg tgatctagaa ctacagaaaa tattagaatt  10680
gaaagcagga ataagtaaca aatcaaatcg ttacaatgat aattacaaca attacattag  10740
taagtgctct atcatcacag atctcagcaa attcaatcaa gcatttcgat atgaaacatc  10800
atgtatttgt agtgatgtac tggatgaact gcatggtgta caatctctat tttcctggtt  10860
acatttaact attcctcatg tcacaataat atgcacatat aggcatgcac ccccctatat  10920
aaaggatcat attgtagatc ttaacaatgt agatgagcaa agtggactat atagatatca  10980
tatgggtggt atcgaagggt ggtgtcaaaa actatggacc atagaagcta tatcactatt  11040
agatctaata tctctcaaag ggaaattctc aattactgct ttaattaatg gtgacaatca  11100
atcaatagat ataagtaaac cagtcagact catggaaggt caaactcatg ctcaagcaga  11160
ttatttgcta gcattaaata gtctcaaatt actgtataaa gagtatgcag gaataggcca  11220
caaattaaaa ggaactgaga cttatatatc gagagatatg caatttatga gtaaaacgat  11280
ccaacataac ggtgtatatt acccagctag tataaagaaa gtcctaagag tgggaccgtg  11340
gataaacact atacttgatg acttcaaagt gagtctagaa tctataggta gtttgacaca  11400
agaattagaa tatagaggtg aaagtctatt atgcagttta atatttagaa atgtatggtt  11460
atataatcaa attgcattac aacttaaaaa tcatgcatta tgtaacaaca aattatattt  11520
ggatatatta aaagttctaa aacacttaaa aacctttttt aatcttgata acattgatac  11580
agcattaaca ttgtatatga atttgcccat gttatttggt ggtggtgatc ccaacttgtt  11640
atatcgaagt ttctatagaa gaactcctga tttcctcaca gaggctatag ttcactctgt  11700
gttcatactt agttattata caaaccatga tttaaaagat aaacttcaag atctgtcaga  11760
tgatagattg aataagttct taacatgcat aatcacgttt gataaaaacc ccaatgctga  11820
attcgttaca ttgatgagag atcctcaagc tttaggatct gagaggcaag ctaaaattac  11880
tagcgaaatc aatagactgg cagttaccga ggttttgagc acagctccaa acaaaatatt  11940
```

-continued

```
ttccaaaagt gcacaacact ataccactac agagatagat cttaatgata ttatgcaaaa  12000
tatagaacct acatatcctc acgggctaag agttgtttat gagagtttac ccttttataa  12060
agcagagaaa atagtaaatc ttatatccgg tacaaaatct ataactaaca tactggaaaa  12120
gacttctgcc atagacttaa cagatattga tagagccact gagatgatga ggaaaaacat  12180
aactttgctt ataaggatat taccattaga ttgtaacaga gataaaagag aaatattgag  12240
tatggaaaac ctaagtatta ctgaattaag caaatacgtt agagaaagat cttggtcttt  12300
atccaatata gttggtgtta catcacccag tatcatgtat acaatggaca taaaatatac  12360
aacaagcact atagctagtg gcataatcat agagaaatat aatgtcaaca gtttaacacg  12420
tggtgagaga ggacccacta aaccatgggt tggttcatct acacaagaga aaaagacaat  12480
gccagtttat aatagacaag ttttaaccaa aaaacagaga gatcaaatag atctattagc  12540
aaaattggat tgggtgtatg catctataga taacaaggat gaatttatgg aggaacttag  12600
cataggaact cttgggttaa catatgagaa ggccaaaaaa ttattcccac aatatttgag  12660
tgttaactat ttgcatcgtc ttacagtcag tagtagacca tgtgaattcc ctgcatctat  12720
accagcttat agaactacaa attatcactt tgatactagc cctattaatc gcatattaac  12780
agaaaagtat ggtgatgaag atattgatat agtattccaa aactgtataa gctttggcct  12840
tagcttaatg tctgtagtag aacaatttac taatgtatgt cctaacagaa ttattctcat  12900
acccaagctt aatgagatac atttgatgaa acctcccata ttcacaggcg atgttgatat  12960
tcacaagtta aaacaagtga tacaaaaaca acatatgttt ttaccagaca aaataagttt  13020
gactcaatat gtggaattat tcttaagtaa taaaacactc aaatctggat ctaatgttaa  13080
ttctaattta atattggcgc ataagatatc tgactatttt cataatactt acattttgag  13140
tactaattta gctggacatt ggattcttat tatacaactt atgaaagatt ctaagggtat  13200
ttttgaaaaa gattggggag agggatatat aactgatcat atgttcatta atttgaaagt  13260
tttcttcaat gcttataaga catatctctt gtgttttcat aaaggttacg gcagagcaaa  13320
gctggagtgt gatatgaata cttcagatct cctatgtgta ttggaattaa tagacagtag  13380
ttattggaag tctatgtcta aggtgttttt agaacaaaaa gttatcaaat acattcttag  13440
ccaggatgca agtttacata gagtaaaagg atgtcatagc ttcaaactat ggtttcttaa  13500
acgtcttaat gtagcagaat tcacagtttg cccttgggtt gttaacatag attatcatcc  13560
aacacatatg aaagcaatat taacttatat tgatcttgtt agaatgggat tgataaatat  13620
agatagaata tacattaaaa ataaacacaa gttcaatgat gagttttata cttctaatct  13680
gttttacatt aattataact tctcagataa tactcatcta ttaactaaac atataaggat  13740
tgctaattcc gaattagaaa gtaattacaa caaattatat catcctacac cagaaaccct  13800
agaaaatata ctaaccaatc cggttaaaag taatgagaaa aagacactga gtgactattg  13860
tataggtaaa aatgttgact caataatgtt accatcgtta tctaataaga agcttattaa  13920
atcgtctaca atgattagaa ccaattacag cagacaagat ttgtataatt tatttcctac  13980
ggttgtgatt gataaaatta tagatcattc aggtaataca gccaaatcta accaacttta  14040
cactactact tctcatcaaa tatccttagt gcacaatagc acatcacttt attgcatgct  14100
tccttggcat catattaata gattcaattt tgtatttagt tctacaggtt gtaaaattag  14160
tatagagtat attttaaaag atcttaaaat taaggatcct aattgtatag cattcatagg  14220
tgaaggagca gggaatttat tattgcgtac agtagtggaa cttcatcctg atataagata  14280
tatttacaga agtctgaaag attgcaatga tcatagttta ccaattgagt ttttaaggct  14340
```

gtacaatgga catatcaaca ttgattatgg tgaaaatttg accattcctg ctacagatgc 14400
aaccaacaac attcattggt cttatttaca tataaagttt gctgaaccta tcagtctttt 14460
tgtctgtgat gctgaattgc ctgtaacagt caactggagt aagattataa tagagtggag 14520
caagcatgta agaaaatgca agtactgttc ttcagttaat aaatgtacat tgatagtaaa 14580
atatcatgct caagatgata tcgatttcaa attagacaac ataactatat taaaaactta 14640
tgtatgctta ggtagtaagt taaagggatc tgaagtttac ttagtcctta caataggtcc 14700
tgcaaatgtg ttcccagtat ttaatgtagt acaaaatgct aaattgatac tatcaagaac 14760
taaaaatttc atcatgccta aaaaagctga taaagagtct attgatgcaa atattaagag 14820
tttgataccc tttctttgtt accctataac aaaaaaagga attaatactg cattgtctaa 14880
attaaagagt gttgttagtg gagatatact atcatattct atagctggac gtaatgaagt 14940
tttcagcaat aaacttataa atcataagca tatgaacatc ttaaagtggt tcaatcatgt 15000
tttaaatttc agatcaacag aattaaacta taatcattta tatatggtag aatctactta 15060
tcctcatcta agtgaattgt taaacagctt gacaaccaat gaacttaaaa aactgattaa 15120
aatcacaggt agtttgttat acaactttta taatgaataa tgagcaaaaa tcttataaca 15180
aaaatagcta cacactaaca ttgtattcaa ttatagttat tgaaaattaa taattatata 15240
atttttaata acttctagtg aactaatcct aaaattatca ttttgatcta ggaagaataa 15300
gtttaaatcc aaatctaatt ggtttatatg tatattaact aaattacgag atattagttt 15360
ttgacacttt ttttctcgtg gccggcatgg tcccagcctc ctcgctggcg ccggctgggc 15420
aacatgcttc ggcatggcga atgggactag cataacccct tggggcctct aaacgggtct 15480
tgaggggttt tttg 15494

<210> SEQ ID NO 27
<211> LENGTH: 15494
<212> TYPE: DNA
<213> ORGANISM: Artificial Sequence
<220> FEATURE:
<223> OTHER INFORMATION: antigenic cDNA encoding cRSVA_ mF2

<400> SEQUENCE: 27
taatacgact cactataggt tttttcgcgt ctgatgaggc cgttaggccg aaactcctct 60
ccggagtcac gcgaaaaaat gcgtacaaca aacttgcgta aaccaaaaaa atggggcaaa 120
taagaatttg ataagtacca cttaaattta actcctttgg ttagaggcgc gccatgggca 180
gcaactcatt gagtatgata aaagttagat tgcaaaatct gtttgacaat gatgaagtag 240
cattgttaaa aataacatgc tatactgaca aattaataca gttaactaat gctttggcta 300
aggcagttat acatacaatc aaattgaatg gcattgtatt tgtgcatgtt attacaagta 360
gtgatatttg ccctaataat aatattgtag tgaaatccaa tttcacaaca atgccagtat 420
tacaaaatgg aggttatata tgggaaatga tggaattaac acactgctct caacctaatg 480
gcctaataga tgacaattgt gaaattaaat tctccaaaaa actaagtgat tcaacaatga 540
ccaattatat gaatcaatta tctgaattac ttggatttga cctcaatcca taaatcataa 600
taaatatcaa ctagcaaatc aatgtcacta acaccattag ttaatataaa acttgacaga 660
agataaaaat ggggcaaata aatcaattca gccgacccaa ccatggacac aacacacaat 720
gataccacac cacaaagact gatgatcaca gacatgaggc cattatcgct tgagactata 780
ataacatctc taaccagaga tatcataaca cataaattta tatacttgat aaatcatgaa 840

-continued

```
tgcatagtaa gaaaacttga tgaaagacag gccacattta catttctggt caactatgaa    900
atgaaactat tgcacaaagt gggaagcact aaatataaaa aatatactga atacaacaca    960
aaatatggca ctttccctat gccaatattt atcaatcatg atgggttctt agaatgcatt   1020
ggcattaagc ctaccaagca cacacccata atatacaagt atgatctcaa tccatgaata   1080
tcaaaccaag attcaaacaa tccgaaataa caactttatg cataatcaca ctccatagtc   1140
caaatggagc ctgaaaatta tagttattta aaattcctgc aggaaggaga gacataagat   1200
gaaagatggg gcaaatacaa aaatggctct tagcaaagtc aagttgaatg atacactcaa   1260
caaagatcaa cttctatcat ccagcaaata taccatccaa cggagcacag gagacagcat   1320
tgacactcct aattatgatg tgcagaaaca cattaataag ttatgtggca tgttattaat   1380
cacagaagat gctaatcata aattcactgg gttaataggt atgttatatg ctatgtctag   1440
attaggaaga gaagacacca taaaaatact caaagatgcg ggatatcatg ttaaggcaaa   1500
tggagtggat gtaacaacac atcgtcaaga cattaatggg aaagaaatga aatttgaagt   1560
gttaacatta gcaagcttaa caactgaaat tcaaatcaac attgagatag aatctagaaa   1620
atcctacaaa aaaatgctaa aagaaatggg agaggtggct ccagaataca ggcatgactc   1680
tcctgattgt gggatgataa tattatgtat agcggcatta gtaataacca aattagcagc   1740
aggagataga tcaggtctta cagctgtgat taggagagct aataatgtcc taaaaaatga   1800
aatgaaacgt tataaaggtt tattacccaa ggatatagcc aacagcttct atgaagtgtt   1860
tgaaaaatat cctcacttta tagatgtttt tgttcatttt ggtatagcac aatcttctac   1920
cagaggtggc agtagagttg aagggatttt tgcaggattg tttatgaatg cctatggtgc   1980
agggcaagtg atgttacggt ggggggtctt agcaaaatca gttaaaaaca ttatgttagg   2040
acacgctagt gtacaagcag aaatggaaca agttgtggag gtgtatgagt atgctcagaa   2100
attgggtgga gaagcaggat tctaccatat attgaacaac ccaaaagcat cactattatc   2160
tttgactcaa tttcctcact tctctagtgt agtattgggc aatgctgctg gcctaggcat   2220
aatgggagaa tacagaggta caccaaggaa tcaagattta tatgatgctg caaaagcata   2280
tgctgaacaa ctcaaagaaa atggtgtgat taactacagt gtattagatt tgacagcaga   2340
agaactagag gctatcaaac atcagcttaa tccaaaagat aatgatgtag agctttgagt   2400
taataaaaaa gtggggcaaa taaatcatca tggaaaagtt tgctcctgaa ttccatggag   2460
aagatgcaaa caacagagcc accaaattcc tagaatcaat aaagggcaaa ttcacatcac   2520
ccaaagatcc caagaaaaaa gatagtatca tatctgtcaa ctcaatagat atagaagtaa   2580
ccaaagaaag ccctataaca tcaaattcaa ccattataaa cccaataaat gagacagatg   2640
atactgtagg gaacaagccc aattatcaaa gaaagcctct agtaagtttc aaagaagacc   2700
ctacgccaag tgataatcct tttcaaaac tatacaaaga aaccatagaa acatttgata   2760
acaatgaaga agaatctagc tattcatatg aagaaataaa tgatcagaca aacgataata   2820
taacagcaag attagatagg attgatgaga aattaagtga aatactagga atgcttcaca   2880
cattagtagt agcgagtgca ggacccacat ctgctcggga tggtataaga gatgccatgg   2940
ttggtttaag agaagaaatg atagaaaaaa tcagaactga agcattaatg accaatgaca   3000
gactagaagc tatggcaaga ctcaggaatg aagaaagtga aaagatggca aaagacacat   3060
cagatgaagt gtctctcaat ccaacatcag agaaactgaa caacctgttg gaagggaatg   3120
atagtgacaa tgatctatca cttgaagatt tctgattagc taccaaactg tacatcaaaa   3180
cacaacacca atagaaaacc aacaaacaaa ccaactcacc catccaacca aacatctatc   3240
```

tgctgattag ccaaccagcc aaaaaacaac cagccaatct aaaactagcc acccggaaaa 3300
aatcgatact atagttacaa aaaaagatgg ggcaaatatg gaaacatacg tgaataaact 3360
tcacgagggc tccacataca cagctgctgt tcaatacaat gtcctagaaa aagacgatga 3420
tcctgcatca cttacaatat gggtgcccat gttccaatca tccatgccag cagatctact 3480
cataaaagaa ctagccaatg tcaatatact agtgaaacaa atatccacac ccaagggacc 3540
ctcattaaga gtcatgataa actcaagaag tgcagtgcta gcacaaatgc ccagcaaatt 3600
taccatatgt gccaatgtgt ccttggatga aagaagcaag ctggcatatg atgtaaccac 3660
accctgtgaa attaaggcat gcagtctaac atgcctaaaa tcaaaaaata tgttaactac 3720
agttaaagat ctcactatga aaacactcaa cccaacacat gacatcattg ctttatgtga 3780
atttgaaaat atagtaacat caaaaaaagt cataatacca acatacctaa gatctatcag 3840
cgtcagaaat aaagatctga acacacttga aaatataaca accactgaat tcaaaaatgc 3900
cattacaaat gcaaaaatca tcccttactc aggattattg ttagtcatca cagtgactga 3960
caacaaagga gcattcaaat acataaagcc acaaagtcaa ttcatagtag atcttggagc 4020
ttacctagaa aaagaaagta tatattatgt tacaacaaat tggaagcaca cagctacacg 4080
atttgcaatc aaacccatgg aagattaacc tttttcctct acatcaatga gtagattcat 4140
acaaactttc taactacatt cttcacttca caatcataat caccaaccct ctgtggttca 4200
atcaatcaaa caaaactcat caagagttcc agatcatccc aagtcattgt tcatcagatc 4260
cagtactcaa ataagttaat aaaaaatcca catggggcaa ataatcattg agggaaatcc 4320
aactaatcac aacatctgtc aacatagaca agtcaacacg ctagataaaa tcaaccaatg 4380
gaaaatacat ccataactat agaattctca agcaaattct ggccttactt tacactaata 4440
cacatgataa caacaataat ctctttgata atcataatct ccatcatgat tgcaatacta 4500
aacaaactct gcgaatataa tgtattccat aacaaaacct ttgagctacc aagagctcga 4560
gtcaatacat agcattcacc aatctgatag ctcaaaacag taaccttgca tttgtaaatg 4620
aactaccctc acttcttcac aaaaccacat caacatctca ccatgcaagc catcatctat 4680
accataaagt agttaattaa aaatggccgg ccagtcataa caatgaacta ggatattaag 4740
accaaaaaca acgctggggc aaatgcaaac atgtccaaaa ccgaggacca acgcaccgcc 4800
aagacactag aaaggacctg ggacactttt aatcatctat tattcatatc atcgtgctta 4860
tacaagttaa atcttaaatc tatagcacaa atcacattat ctattttggc aattataatc 4920
tcaacctcac ttataattgc agccatcata ttcatagcct cggcaaacca caaagtcaca 4980
ctaacaactg caatcataca agatgcaacg aaccagatca agaacacaac cccaacatac 5040
ctcacccaga atccccagca tggaatcagc ttctccaatc tgtccggaac tacatcacaa 5100
tccaccacca tactagcttc aacaacacca agtgctgatt caaccccaca atccacaaca 5160
gtcaagatca aaaacacaac aacaacccaa atattaccta gcaaacccac cacaaaacaa 5220
cgccaaaata aaccacaaaa caaacccaac aatgattttc actttgaagt gttcaatttt 5280
gtaccctgca gcatatgcag caacaatcca acctgctggg ccatctgcaa gagaatacca 5340
aacaaaaaac ctggaaagaa aaccaccacc aagcccacaa aaaaaccaac cctcaagaca 5400
accaaaaaag atcccaaatc ccaaaccaca aaaccaaagg aagtactcac taccaagcct 5460
acaggaaagc caaccatcaa caccactaaa acaaacatca gaactacact gctcacctcc 5520
aacaccaaag gaaatccaga acacacaagt caagaggaaa ccctccactc aaccacctcc 5580

```
gaaggctatc caagcccatc acaagtccac acaacatccg gtcaagagga aaccctccac   5640
tcaaccacct ccgaaggcta tccaagccca tcacaagtct acacaacatc cgagtaccta   5700
tcacaatctc tatcttcatc caacacaaca aaatgatagt cattaaaaag cacgcgtgta   5760
ttgttgcaaa aagccatgac caaatcaaac agaatcaaaa tcaactctgg ggcaaataac   5820
aatggagttg ccaatcctca aaacaaatgc tattaccaca atccttgctg cagtcacact   5880
ctgtttcgct tccagtcaaa acatcactga agaattttat caatcaacat gcagtgcagt   5940
cagcaaaggc tatcttagtg ctctaagaac tggttggtat actagtgtta taactataga   6000
attaagtaat atcaaggaaa ataagtgtaa tggtacagac gctaaggtaa aattaataaa   6060
acaagaatta gataaatata aaaatgctgt aacagaattg cagttgctca tgcaaagcac   6120
accagcagcc aacaatcgag ccagaagaga actaccaaga tttatgaatt atacactcaa   6180
caataccaaa aacaccaatg taacattaag taagaaaagg aaaagaaagt ttcttggatt   6240
tttgttaggt gttggatctg caatcgccag tggcattgcc gtatccaagg tcctgcacct   6300
agaaggggaa gtgaacaaaa tcaaaagtgc tctactatcc acaaacaagg ctgtagtcag   6360
cttatctaat ggagtcagtg tcttaaccag caaggtgtta gacctcaaaa actatataga   6420
taaacagttg ttacctattg ttaacaagca aagctgcagc atatcaaaca ttgaaactgt   6480
gatagagttc caacaaaaga acaacagact actagagatt accagagaat ttagtgttaa   6540
tgcaggtgta actactcctg taagcactta tatgttaact aatagtgagt tattatcatt   6600
aatcaatgat atgcctataa caaatgatca gaaaaagtta atgtccagca atgttcaaat   6660
agttagacag caaagttact ctatcatgtc aataataaaa gaggaagtct tggcatatgt   6720
agtacaatta ccactatatg gtgtaataga tactccttgt tggaaactac acacatcccc   6780
tttatgtaca accaacacaa aggaaggatc caacatctgc ttaacaagaa ccgacagagg   6840
atggtactgt gacaatgcag gatcagtatc ctttttccca caagctgaaa catgtaaagt   6900
tcaatcgaat cgggtgtttt gtgacacaat gaacagttta acattaccaa gtgaggtaaa   6960
tctctgcaac attgacatat tcaaccccaa atatgattgc aaaattatga cttcaaaaac   7020
agatgtaagc agctccgtta tcacatctct aggagccatt gtgtcatgct atggcaaaac   7080
caaatgtaca gcatccaata aaaatcgtgg gatcataaag acattctcta acgggtgtga   7140
ttatgtatca aataaggggg tggatactgt gtctgtaggt aatacattat attatgtaaa   7200
taagcaagaa ggcaaaagtc tctatgtaaa aggtgaacca ataataaatt tctatgatcc   7260
attagtgttc ccctctgatg aatttgatgc atcaatatct caagtcaatg agaaaattaa   7320
tcagagtcta gcatttatcc gtaaatcaga tgaattatta cataatgtaa atgctggtaa   7380
atccaccaca aatatcatga taactaccat aattatagta attatagtaa tattgttagc   7440
attaattgca gttggactgc ttctatactg caaggccaga agcacaccag tcacattaag   7500
taaggatcaa ctgagtggta taaataatat tgcatttagt aactgaataa aaatagcacc   7560
taatcatatt cttacaatgg ttcgctattt gaccatagat aacccatcta tcattagatt   7620
atcctaaaat ttgaacttca tcacaacttt catctataaa ccatctcact tacacttttt   7680
aagtagattt ctattttata gttatataaa acagggccca ttgaatacca aattaactta   7740
ctatttgtaa aaatgagaat tggggcaaat atgtcacgaa ggaatccttg caaattcgaa   7800
attcgaggtc attgcttgaa tggtaaaagg tgtcatttta gtcataatta ttttgaatgg   7860
ccaccccatg cactgcttgt aagacaaaac tttatgttaa acagaatact taagtctatg   7920
gataaaagca tagatacttt gtcagaaata agtggagctg cagagttgga cagaacagaa   7980
```

```
gagtatgccc tcggtgtagt tggagtgcta gagagttata taggatcaat aaataatata   8040
actaaacaat cagcatgtgt tgccatgagc aaactcctta ctgaactcaa cagcgatgac   8100
atcaaaaaac taagggacaa tgaagagcca aactcaccca aagtaagagt gtacaatact   8160
gtcatatcat atattgaaag caacaggaag aacaataaac aaactatcca tctgttaaaa   8220
agattgccag cagacgtatt gaagaaaacc atcaaaaaca cattggatat ccacaagagc   8280
ataaccatca ataacccaaa agaatcaact gttagtgata cgaacgacca tgccaaaaat   8340
aatgatacta cctgacaaat atccttgtag tataaattcc atactaataa caagtaattg   8400
tagagtcact atgtataatc aaaaaaacac actatatatc aatcaaaaca accaaaatag   8460
ccatatatac ccaccggatc aaccattcaa tgaaatccat tggacctctc aagacttgat   8520
tgatgcaact caaaattttc tacaacatct aggtattact gatgatatat acacaatata   8580
tatattagtg tcataatact caatcctaat acttaccaca tcatcaaatt attaactcaa   8640
acaattcaag ctatgggaca aaatggatcc cattattagt ggaaattctg ctaatgttta   8700
tctaactgat agttatttaa aaggtgttat ttctttctca gaatgtaacg ctttaggaag   8760
ttacatattc aatggtcctt atctcaaaaa tgattatacc aacttaatta gtagacaaaa   8820
tccattaata gaacacataa atctaaagaa actaaatata acacagtcct taatatctaa   8880
gtatcataaa ggtgaaataa aaatagaaga acctacttac tttcagtcat tacttatgac   8940
atacaagagt atgacctctt cagaacagac tactactact aatttactta aaaagataat   9000
aagaagagct atagaaatca gtgatgtcaa agtctatgct atattgaata aactggggct   9060
caaagaaaaa gacaagatta aatccaataa tggacaagat gaagacaact cagtcattac   9120
taccataatc aaagatgata tacttttagc tgtcaaggat aatcaatctc atcttaaagc   9180
agacaaaaat caatccacaa aacaaaaaga tacaatcaaa acaacacttt tgaagaaatt   9240
aatgtgttcg atgcaacatc ctccatcatg gttaatacat tggtttaatt tatacacaaa   9300
attaaacagc atattaacac aatatcgatc tagtgaggta aaaaaccatg gttttatatt   9360
gatagataat catactctta gtggattcca atttattttg aatcaatatg gttgtatagt   9420
ttatcataag gaactcaaaa gaattactgt gacaacttat aatcaattct tgacatggaa   9480
agatattagc cttagtagat taaatgtttg tttgattaca tggattagta actgtttgaa   9540
cacattaaac aaaagcttag gcttaagatg tggattcaat aatgttatct tgacacaatt   9600
attcctttat ggagattgta tactaaaact attccacaat gaggggttct acataataaa   9660
agaggtagag ggatttatta tgtctctaat tttaaatata acagaagaag atcaattcag   9720
aaaacggttt tataatagta tgctcaacaa catcacagat gccgccaaca aagctcaaaa   9780
aaatctgcta tcaagagtat gtcatacatt attagataag acaatatcag ataatataat   9840
aaatggcaga tggataattc tattgagtaa gttcctaaaa ttaattaagc ttgcaggtga   9900
caataacctc aacaatctga gtgaattata tttttgttc agaatatttg gacacccaat    9960
ggtagatgaa agacaagcca tggatgctgt taaagttaat tgcaacgaga ccaaattta    10020
tttgttaagt agtttgagta tgttaagagg agcttttata tatagaatta taaaagggtt  10080
tgtaaataat tacaacagat ggcctacttt aagaaatgcc attgtcttac ccttaagatg  10140
gttaacttac tataaactaa acacttatcc ttccttgttg gaacttacag aaagagattt  10200
gattgttcta tcaggactac gtttctatcg agagtttcgg ttgcctaaaa aagtggatct  10260
tgaaatgatc ataaatgata aggctatatc acctcctaaa aatttaatat ggactagttt  10320
```

```
ccctagaaat tatatgccgt cacacataca aaattatata gaacatgaaa aattaaaatt  10380
ctctgatagt gataaatcaa gaagagtatt agagtattat ttaagagata acaaattcaa  10440
tgaatgtgat ttacacaact gtgtagttaa tcaaagttat cttaacaacc cgaatcatgt  10500
ggtatcattg acaggcaaag aaagagaact cagtgtaggt agaatgtttg caatgcaacc  10560
aggaatgttc agacaagttc aaatattagc agagaaaatg atagcagaaa acatattaca  10620
atttttccct gaaagtctta caagatatgg tgatctagaa ctacagaaaa tattagaatt  10680
gaaagcagga ataagtaaca aatcaaatcg ttacaatgat aattacaaca attacattag  10740
taagtgctct atcatcacag atctcagcaa attcaatcaa gcatttcgat atgaaacatc  10800
atgtatttgt agtgatgtac tggatgaact gcatggtgta caatctctat tttcctggtt  10860
acatttaact attcctcatg tcacaataat atgcacatat aggcatgcac ccccctatat  10920
aaaggatcat attgtagatc ttaacaatgt agatgagcaa agtggactat atagatatca  10980
tatgggtggt atcgaagggt ggtgtcaaaa actatggacc atagaagcta tatcactatt  11040
agatctaata tctctcaaag ggaaattctc aattactgct ttaattaatg gtgacaatca  11100
atcaatagat ataagtaaac cagtcagact catggaaggt caaactcatg ctcaagcaga  11160
ttatttgcta gcattaaata gtctcaaatt actgtataaa gagtatgcag gaataggcca  11220
caaattaaaa ggaactgaga cttatatatc gagagatatg caatttatga gtaaaacgat  11280
ccaacataac ggtgtatatt acccagctag tataaagaaa gtcctaagag tgggaccgtg  11340
gataaacact atacttgatg acttcaaagt gagtctagaa tctataggta gtttgacaca  11400
agaattagaa tatagaggtg aaagtctatt atgcagttta atatttagaa atgtatggtt  11460
atataatcaa attgcattac aacttaaaaa tcatgcatta tgtaacaaca aattatattt  11520
ggatatatta aaagttctaa aacacttaaa aacctttttt aatcttgata acattgatac  11580
agcattaaca ttgtatatga atttgcccat gttatttggt ggtggtgatc ccaacttgtt  11640
atatcgaagt ttctatagaa gaactcctga tttcctcaca gaggctatag ttcactctgt  11700
gttcatactt agttattata caaaccatga tttaaaagat aaacttcaag atctgtcaga  11760
tgatagattg aataagttct taacatgcat aatcacgttt gataaaaacc ccaatgctga  11820
attcgttaca ttgatgagag atcctcaagc tttaggatct gagaggcaag ctaaaattac  11880
tagcgaaatc aatagactgg cagttaccga ggttttgagc acagctccaa acaaaatatt  11940
ttccaaaagt gcacaacact ataccactac agagatagat cttaatgata ttatgcaaaa  12000
tatagaacct acatatcctc acgggctaag agttgtttat gagagtttac ccttttataa  12060
agcagagaaa atagtaaatc ttatatccgg tacaaaatct ataactaaca tactggaaaa  12120
gacttctgcc atagacttaa cagatattga tagagccact gagatgatga ggaaaaacat  12180
aactttgctt ataaggatat taccattaga ttgtaacaga gataaaagag aaatattgag  12240
tatggaaaac ctaagtatta ctgaattaag caaatacgtt agagaaagat cttggtcttt  12300
atccaatata gttggtgtta catcacccag tatcatgtat acaatggaca taaaatatac  12360
aacaagcact atagctagtg gcataatcat agagaaatat aatgtcaaca gtttaacacg  12420
tggtgagaga ggacccacta aaccatgggt tggttcatct acacaagaga aaaagacaat  12480
gccagtttat aatagacaag ttttaaccaa aaaacagaga gatcaaatag atctattagc  12540
aaaattggat tgggtgtatg catctataga taacaaggat gaatttatgg aggaacttag  12600
cataggaact cttgggttaa catatgagaa ggccaaaaaa ttattcccac aatatttgag  12660
tgttaactat ttgcatcgtc ttacagtcag tagtagacca tgtgaattcc ctgcatctat  12720
```

accagcttat agaactacaa attatcactt tgatactagc cctattaatc gcatattaac 12780
agaaaagtat ggtgatgaag atattgatat agtattccaa aactgtataa gctttggcct 12840
tagcttaatg tctgtagtag aacaatttac taatgtatgt cctaacagaa ttattctcat 12900
acccaagctt aatgagatac atttgatgaa acctcccata ttcacaggcg atgttgatat 12960
tcacaagtta aaacaagtga tacaaaaaca acatatgttt ttaccagaca aaataagttt 13020
gactcaatat gtggaattat tcttaagtaa taaaacactc aaatctggat ctaatgttaa 13080
ttctaattta atattggcgc ataagatatc tgactatttt cataatactt acattttgag 13140
tactaattta gctggacatt ggattcttat tatacaactt atgaaagatt ctaagggtat 13200
ttttgaaaaa gattggggag agggatatat aactgatcat atgttcatta atttgaaagt 13260
tttcttcaat gcttataaga catatctctt gtgttttcat aaaggttacg gcagagcaaa 13320
gctggagtgt gatatgaata cttcagatct cctatgtgta ttggaattaa tagacagtag 13380
ttattggaag tctatgtcta aggtgttttt agaacaaaaa gttatcaaat acattcttag 13440
ccaggatgca agtttacata gagtaaaagg atgtcatagc ttcaaactat ggtttcttaa 13500
acgtcttaat gtagcagaat tcacagtttg cccttgggtt gttaacatag attatcatcc 13560
aacacatatg aaagcaatat taacttatat tgatcttgtt agaatgggat tgataaatat 13620
agatagaata tacattaaaa ataaacacaa gttcaatgat gagttttata cttctaatct 13680
gttttacatt aattataact tctcagataa tactcatcta ttaactaaac atataaggat 13740
tgctaattcc gaattagaaa gtaattacaa caaattatat catcctacac cagaaaccct 13800
agaaaatata ctaaccaatc cggttaaaag taatgagaaa aagacactga gtgactattg 13860
tataggtaaa aatgttgact caataatgtt accatcgtta tctaataaga agcttattaa 13920
atcgtctaca atgattagaa ccaattacag cagacaagat ttgtataatt tatttcctac 13980
ggttgtgatt gataaaatta tagatcattc aggtaataca gccaaatcta accaacttta 14040
cactactact tctcatcaaa tatccttagt gcacaatagc acatcacttt attgcatgct 14100
tccttggcat catattaata gattcaattt tgtatttagt tctacaggtt gtaaaattag 14160
tatagagtat attttaaaag atcttaaaat taaggatcct aattgtatag cattcatagg 14220
tgaaggagca gggaatttat tattgcgtac agtagtggaa cttcatcctg atataagata 14280
tatttacaga agtctgaaag attgcaatga tcatagttta ccaattgagt ttttaaggct 14340
gtacaatgga catatcaaca ttgattatgg tgaaaatttg accattcctg ctacagatgc 14400
aaccaacaac attcattggt cttatttaca tataaagttt gctgaaccta tcagtctttt 14460
tgtctgtgat gctgaattgc ctgtaacagt caactggagt aagattataa tagagtggag 14520
caagcatgta agaaaatgca agtactgttc ttcagttaat aaatgtacat tgatagtaaa 14580
atatcatgct caagatgata tcgatttcaa attagacaac ataactatat taaaaactta 14640
tgtatgctta ggtagtaagt taaagggatc tgaagtttac ttagtcctta caataggtcc 14700
tgcaaatgtg ttcccagtat ttaatgtagt acaaaatgct aaattgatac tatcaagaac 14760
taaaaatttc atcatgccta aaaaagctga taaagagtct attgatgcaa atattaagag 14820
tttgataccc tttctttgtt accctataac aaaaaaagga attaatactg cattgtctaa 14880
attaaagagt gttgttagtg gagatatact atcatattct atagctggac gtaatgaagt 14940
tttcagcaat aaacttataa atcataagca tatgaacatc ttaaagtggt tcaatcatgt 15000
tttaaatttc agatcaacag aattaaacta taatcattta tatatggtag aatctactta 15060
tcctcatcta agtgaattgt taaacagctt gacaaccaat gaacttaaaa aactgattaa 15120
aatcacaggt agtttgttat acaactttta taatgaataa tgagcaaaaa tcttataaca 15180
aaaatagcta cacactaaca ttgtattcaa ttatagttat tgaaaattaa taattatata 15240
atttttaata acttctagtg aactaatcct aaaattatca ttttgatcta ggaagaataa 15300
gtttaaatcc aaatctaatt ggtttatatg tatattaact aaattacgag atattagttt 15360
ttgacacttt ttttctcgtg gccggcatgg tcccagcctc ctcgctggcg ccggctgggc 15420
aacatgcttc ggcatggcga atgggactag cataacccct tggggcctct aaacgggtct 15480
tgaggggttt tttg 15494

<210> SEQ ID NO 28
<211> LENGTH: 1638
<212> TYPE: DNA
<213> ORGANISM: Artificial Sequence
<220> FEATURE:
<223> OTHER INFORMATION: cDNA encoding a soluble pre F trimer

<400> SEQUENCE: 28
atggagttgc caatcctcaa aacaaatgct attaccacaa tccttgctgc agtcacactc 60
tgtttcgctt ccagtcaaaa catcactgaa gaattttatc aatcaacatg cagtgcagtc 120
agcaaaggct atcttagtgc tctaagaact ggttggtata ctagtgttat aactatagaa 180
ttaagtaata tcaaggaaaa taagtgtaat ggtacagacg ctaaggtaaa attaataaaa 240
caagaattag ataaatataa aaatgctgta acagaattgc agttgctcat gcaaagcaca 300
ccagcagcca acaatcgagc cagaagagaa ctaccaagat ttatgaatta tacactcaac 360
aataccaaaa acaccaatgt aacattaagt aagaaaagga aaagaagatt tcttggattt 420
ttgttaggtg ttggatctgc aatcgccagt ggcattgccg tatccaaggt cctgcaccta 480
gaaggggaag tgaacaaaat caaaagtgct ctactatcca caaacaaggc tgtagtcagc 540
ttatctaatg gagtcagtgt cttaaccagc aaggtgttag acctcaaaaa ctatatagat 600
aaacagttgt tacctattgt taacaagcaa agctgcagca tatcaaacat tgaaactgtg 660
atagagttcc aacaaaagaa caacagacta ctagagatta ccagagaatt tagtgttaat 720
gcaggtgtaa ctactcctgt aagcacttat atgttaacta atagtgagtt attatcatta 780
atcaatgata tgcctataac aaatgatcag aaaaagttaa tgtccagcaa tgttcaaata 840
gttagacagc aaagttactc tatcatgtca ataataaaag aggaagtctt ggcatatgta 900
gtacaattac cactatatgg tgtaatagat actccttgtt ggaaactaca cacatcccct 960
ttatgtacaa ccaacacaaa ggaaggatcc aacatctgct taacaagaac cgacagagga 1020
tggtactgtg acaatgcagg atcagtatcc tttttcccac aagctgaaac atgtaaagtt 1080
caatcgaatc gggtgttttg tgacacaatg aacagtttaa cattaccaag tgaggtaaat 1140
ctctgcaaca ttgacatatt caaccccaaa tatgattgca aaattatgac ttcaaaaaca 1200
gatgtaagca gctccgttat cacatctcta ggagccattg tgtcatgcta tggcaaaacc 1260
aaatgtacag catccaataa aaatcgtggg atcataaaga cattctctaa cgggtgtgat 1320
tatgtatcaa ataagggggt ggatactgtg tctgtaggta atacattata ttatgtaaat 1380
aagcaagaag gcaaaagtct ctatgtaaaa ggtgaaccaa taataaattt ctatgatcca 1440
ttagtgttcc cctctctcct gtgggatgca tcaatatctc aagtcaatga gaaaattaat 1500
cagagtctag catttatccg taaatcagat gaattattag gctctggcgg aagcggatac 1560
atccctgagg caccaaggga cggacaggcc tacgtgcgca aggatggcga gtgggtgctg 1620
ctgtccacct ttctgtga 1638

<210> SEQ ID NO 29
<211> LENGTH: 545
<212> TYPE: PRT
<213> ORGANISM: Artificial Sequence
<220> FEATURE:
<223> OTHER INFORMATION: soluble pre F trimer

<400> SEQUENCE: 29

```
Met Glu Leu Pro Ile Leu Lys Thr Asn Ala Ile Thr Thr Ile Leu Ala
1               5                   10                  15

Ala Val Thr Leu Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Asn Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Ser Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350
```

```
Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Ile
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Leu Leu Trp Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu Gly Ser Gly Gly Ser Gly Tyr Ile Pro Glu Ala Pro Arg Asp Gly
        515                 520                 525

Gln Ala Tyr Val Arg Lys Asp Gly Glu Trp Val Leu Leu Ser Thr Phe
    530                 535                 540

Leu
545
```

<210> SEQ ID NO 30
<211> LENGTH: 1656
<212> TYPE: DNA
<213> ORGANISM: Artificial Sequence
<220> FEATURE:
<223> OTHER INFORMATION: cDNA encoding a preFsc

<400> SEQUENCE: 30

```
atggagttgc caatcctcaa aacaaatgct attaccacaa tccttgctgc agtcacactc     60

tgtttcgctt ccagtcaaaa catcactgaa gaattttatc aatcaacatg cagtgcagtc    120

agcaaaggct atcttagtgc tctaagaact ggttggtata ctagtgttat aactatagaa    180

ttaagtaata tcaaggaaaa taagtgtaat ggtacagacg ctaaggtaaa attaataaaa    240

caagaattag ataaatataa aaatgctgta acagaattgc agttgctcat gcaaagcaca    300

ccagcagcca acaatggagc cagaggctct ggcggaagcg gacttggatt tttgttaggt    360

gttggatctg caatcgccag tggcattgcc gtatccaagg tcctgcacct agaaggggaa    420

gtgaacaaaa tcaaaagtgc tctactatcc acaaacaagg ctgtagtcag cttatctaat    480

ggagtcagtg tcttaaccag caaggtgtta gacctcaaaa actatataga taaacagttg    540

ttacctattg ttaacaagca aagctgcagc atatcaaaca ttgaaactgt gatagagttc    600

caacaaaaga acaacagact actagagatt accagagaat ttagtgttaa tgcaggtgta    660

actactcctg taagcactta tatgttaact aatagtgagt tattatcatt aatcaatgat    720

atgcctataa caaatgatca gaaaaagtta atgtccagca atgttcaaat agttagacag    780

caaagttact ctatcatgtc aataataaaa gaggaagtct tggcatatgt agtacaatta    840

ccactatatg gtgtaataga tactccttgt tggaaactac acacatcccc tttatgtaca    900
```

accaacacaa aggaaggatc caacatctgc ttaacaagaa ccgacagagg atggtactgt 960
gacaatgcag gatcagtatc ctttttccca caagctgaaa catgtaaagt tcaatcgaat 1020
cgggtgtttt gtgacacaat gaacagttta acattaccaa gtgaggtaaa tctctgcaac 1080
attgacatat tcaaccccaa atatgattgc aaaattatga cttcaaaaac agatgtaagc 1140
agctccgtta tcacatctct aggagccatt gtgtcatgct atggcaaaac caaatgtaca 1200
gcatccaata aaaatcgtgg gatcataaag acattctcta acgggtgtga ttatgtatca 1260
aataaggggg tggatactgt gtctgtaggt aatacattat attatgtaaa taagcaagaa 1320
ggcaaaagtc tctatgtaaa aggtgaacca ataataaatt tctatgatcc attagtgttc 1380
ccctctgatg aatttgatgc atcaatatct caagtcaatg agaaaattaa tcagagtcta 1440
gcatttatcc gtaaatcaga tgaattatta cataatgtaa atgctggtaa atccaccaca 1500
aatatcatga taactaccat aattatagta attatagtaa tattgttagc attaattgca 1560
gttggactgc ttctatactg caaggccaga agcacaccag tcacattaag taaggatcaa 1620
ctgagtggta taaataatat tgcatttagt aactga 1656

<210> SEQ ID NO 31
<211> LENGTH: 551
<212> TYPE: PRT
<213> ORGANISM: Artificial Sequence
<220> FEATURE:
<223> OTHER INFORMATION: preFsc

<400> SEQUENCE: 31

Met Glu Leu Pro Ile Leu Lys Thr Asn Ala Ile Thr Thr Ile Leu Ala
1 5 10 15

Ala Val Thr Leu Cys Phe Ala Ser Ser Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Pro Ala Ala Asn Asn Gly Ala Arg Gly Ser Gly Gly
100 105 110

Ser Gly Leu Gly Phe Leu Leu Gly Val Gly Ser Ala Ile Ala Ser Gly
115 120 125

Ile Ala Val Ser Lys Val Leu His Leu Glu Gly Glu Val Asn Lys Ile
130 135 140

Lys Ser Ala Leu Leu Ser Thr Asn Lys Ala Val Val Ser Leu Ser Asn
145 150 155 160

Gly Val Ser Val Leu Thr Ser Lys Val Leu Asp Leu Lys Asn Tyr Ile
165 170 175

Asp Lys Gln Leu Leu Pro Ile Val Asn Lys Gln Ser Cys Ser Ile Ser
180 185 190

Asn Ile Glu Thr Val Ile Glu Phe Gln Gln Lys Asn Asn Arg Leu Leu
195 200 205

Glu Ile Thr Arg Glu Phe Ser Val Asn Ala Gly Val Thr Thr Pro Val
210 215 220

Ser Thr Tyr Met Leu Thr Asn Ser Glu Leu Leu Ser Leu Ile Asn Asp

-continued

```
225                 230                 235                 240

Met Pro Ile Thr Asn Asp Gln Lys Lys Leu Met Ser Ser Asn Val Gln
                245                 250                 255

Ile Val Arg Gln Gln Ser Tyr Ser Ile Met Ser Ile Ile Lys Glu Glu
            260                 265                 270

Val Leu Ala Tyr Val Val Gln Leu Pro Leu Tyr Gly Val Ile Asp Thr
        275                 280                 285

Pro Cys Trp Lys Leu His Thr Ser Pro Leu Cys Thr Thr Asn Thr Lys
    290                 295                 300

Glu Gly Ser Asn Ile Cys Leu Thr Arg Thr Asp Arg Gly Trp Tyr Cys
305                 310                 315                 320

Asp Asn Ala Gly Ser Val Ser Phe Phe Pro Gln Ala Glu Thr Cys Lys
                325                 330                 335

Val Gln Ser Asn Arg Val Phe Cys Asp Thr Met Asn Ser Leu Thr Leu
            340                 345                 350

Pro Ser Glu Val Asn Leu Cys Asn Ile Asp Ile Phe Asn Pro Lys Tyr
        355                 360                 365

Asp Cys Lys Ile Met Thr Ser Lys Thr Asp Val Ser Ser Ser Val Ile
    370                 375                 380

Thr Ser Leu Gly Ala Ile Val Ser Cys Tyr Gly Lys Thr Lys Cys Thr
385                 390                 395                 400

Ala Ser Asn Lys Asn Arg Gly Ile Ile Lys Thr Phe Ser Asn Gly Cys
                405                 410                 415

Asp Tyr Val Ser Asn Lys Gly Val Asp Thr Val Ser Val Gly Asn Thr
            420                 425                 430

Leu Tyr Tyr Val Asn Lys Gln Glu Gly Lys Ser Leu Tyr Val Lys Gly
        435                 440                 445

Glu Pro Ile Ile Asn Phe Tyr Asp Pro Leu Val Phe Pro Ser Asp Glu
    450                 455                 460

Phe Asp Ala Ser Ile Ser Gln Val Asn Glu Lys Ile Asn Gln Ser Leu
465                 470                 475                 480

Ala Phe Ile Arg Lys Ser Asp Glu Leu Leu His Asn Val Asn Ala Gly
                485                 490                 495

Lys Ser Thr Thr Asn Ile Met Ile Thr Thr Ile Ile Ile Val Ile Ile
            500                 505                 510

Val Ile Leu Leu Ala Leu Ile Ala Val Gly Leu Leu Leu Tyr Cys Lys
        515                 520                 525

Ala Arg Ser Thr Pro Val Thr Leu Ser Lys Asp Gln Leu Ser Gly Ile
    530                 535                 540

Asn Asn Ile Ala Phe Ser Asn
545                 550
```

<210> SEQ ID NO 32
<211> LENGTH: 420
<212> TYPE: DNA
<213> ORGANISM: Artificial Sequence
<220> FEATURE:
<223> OTHER INFORMATION: deoptimized NS1

<400> SEQUENCE: 32

```
atgggttcga attcgctatc gatgataaaa gtacgtctac aaaatctatt tgataatgat     60

gaagtagcgc tactaaaaat aacgtgttat acggataaac taatacaact aacgaatgcg    120

ctagcgaaag cggtaataca tacgataaaa ctaaatggta tagtatttgt acatgtaata    180

acgtcgtcgg atatatgtcc gaataataat atagtagtaa aatcgaattt tacgacgatg    240
```

```
ccggtactac aaaatggtgg ttatatatgg gaaatgatgg aactaacgca ttgttcgcaa    300

ccgaatggtc taatagatga taattgtgaa ataaaatttt cgaaaaaact atcggattcg    360

acgatgacga attatatgaa tcaactatcg gaactactag gttttgatct aaatccgtaa    420
```

<210> SEQ ID NO 33
<211> LENGTH: 375
<212> TYPE: DNA
<213> ORGANISM: Artificial Sequence
<220> FEATURE:
<223> OTHER INFORMATION: deoptimized NS2

<400> SEQUENCE: 33

```
atggatacga cgcataatga tacgacgccg caacgtctaa tgataacgga tatgcgtccg     60

ctatcgctag aaacgataat aacgtcgcta acgcgagata taataacgca taaatttata    120

tatctaataa atcatgaatg tatagtacgt aaactagatg aacgtcaagc gacgtttacg    180

tttctagtaa attatgaaat gaaactacta cataaagtag gttcgacgaa atataaaaaa    240

tatacggaat ataatacgaa atatggtacg tttccgatgc cgatatttat aaatcatgat    300

ggttttctag aatgtatagg tataaaaccg acgaaacata cgccgataat atataaatat    360

gatctaaatc cgtga                                                     375
```

<210> SEQ ID NO 34
<211> LENGTH: 1176
<212> TYPE: DNA
<213> ORGANISM: respiratory syncytial virus

<400> SEQUENCE: 34

```
atggctctta gcaaagtcaa gttgaatgat acactcaaca aagatcaact tctatcatcc     60

agcaaatata ccatccaacg gagcacagga gacagcattg acactcctaa ttatgatgtg    120

cagaaacaca ttaataagtt atgtggcatg ttattaatca cagaagatgc taatcataaa    180

ttcactgggt taataggtat gttatatgct atgtctagat taggaagaga agacaccata    240

aaaatactca aagatgcggg atatcatgtt aaggcaaatg gagtggatgt aacaacacat    300

cgtcaagaca ttaatgggaa agaaatgaaa tttgaagtgt taacattagc aagcttaaca    360

actgaaattc aaatcaacat tgagatagaa tctagaaaat cctacaaaaa aatgctaaaa    420

gaaatgggag aggtggctcc agaatacagg catgactctc ctgattgtgg gatgataata    480

ttatgtatag cggcattagt aataaccaaa ttagcagcag gagatagatc aggtcttaca    540

gctgtgatta ggagagctaa taatgtccta aaaaatgaaa tgaaacgtta taaaggttta    600

ttacccaagg atatagccaa cagcttctat gaagtgtttg aaaaatatcc tcactttata    660

gatgtttttg ttcattttgg tatagcacaa tcttctacca gaggtggcag tagagttgaa    720

gggatttttg caggattgtt tatgaatgcc tatggtgcag ggcaagtgat gttacggtgg    780

ggggtcttag caaaatcagt taaaaacatt atgttaggac acgctagtgt acaagcagaa    840

atggaacaag ttgtggaggt gtatgagtat gctcagaaat tgggtggaga agcaggattc    900

taccatatat tgaacaaccc aaaagcatca ctattatctt tgactcaatt tcctcacttc    960

tctagtgtag tattgggcaa tgctgctggc ctaggcataa tgggagaata cagaggtaca   1020

ccaaggaatc aagatttata tgatgctgca aaagcatatg ctgaacaact caaagaaaat   1080

ggtgtgatta actacagtgt attagatttg acagcagaag aactagaggc tatcaaacat   1140

cagcttaatc caaaagataa tgatgtagag ctttga                             1176
```

<210> SEQ ID NO 35
<211> LENGTH: 726
<212> TYPE: DNA
<213> ORGANISM: respiratory syncytial virus

<400> SEQUENCE: 35
atggaaaagt ttgctcctga attccatgga gaagatgcaa acaacagagc caccaaattc 60
ctagaatcaa taaagggcaa attcacatca cccaaagatc ccaagaaaaa agatagtatc 120
atatctgtca actcaataga tatagaagta accaaagaaa gccctataac atcaaattca 180
accattataa acccaataaa tgagacagat gatactgtag ggaacaagcc caattatcaa 240
agaaagcctc tagtaagttt caaagaagac cctacgccaa gtgataatcc tttttcaaaa 300
ctatacaaag aaaccataga aacatttgat aacaatgaag aagaatctag ctattcatat 360
gaagaaataa atgatcagac aaacgataat ataacagcaa gattagatag gattgatgag 420
aaattaagtg aaatactagg aatgcttcac acattagtag tagcgagtgc aggacccaca 480
tctgctcggg atggtataag agatgccatg gttggtttaa gagaagaaat gatagaaaaa 540
atcagaactg aagcattaat gaccaatgac agactagaag ctatggcaag actcaggaat 600
gaagaaagtg aaaagatggc aaaagacaca tcagatgaag tgtctctcaa tccaacatca 660
gagaaactga acaacctgtt ggaagggaat gatagtgaca atgatctatc acttgaagat 720
ttctga 726

<210> SEQ ID NO 36
<211> LENGTH: 585
<212> TYPE: DNA
<213> ORGANISM: respiratory syncytial virus

<400> SEQUENCE: 36
atgtcacgaa ggaatccttg caaattcgaa attcgaggtc attgcttgaa tggtaaaagg 60
tgtcatttta gtcataatta ttttgaatgg ccaccccatg cactgcttgt aagacaaaac 120
tttatgttaa acagaatact taagtctatg gataaaagca tagatacttt gtcagaaata 180
agtggagctg cagagttgga cagaacagaa gagtatgccc tcggtgtagt tggagtgcta 240
gagagttata taggatcaat aaataatata actaaacaat cagcatgtgt tgccatgagc 300
aaactcctta ctgaactcaa cagcgatgac atcaaaaaac taagggacaa tgaagagcca 360
aactcaccca aagtaagagt gtacaatact gtcatatcat atattgaaag caacaggaag 420
aacaataaac aaactatcca tctgttaaaa agattgccag cagacgtatt gaagaaaacc 480
atcaaaaaca cattggatat ccacaagagc ataaccatca ataacccaaa agaatcaact 540
gttagtgata cgaacgacca tgccaaaaat aatgatacta cctga 585

<210> SEQ ID NO 37
<211> LENGTH: 6498
<212> TYPE: DNA
<213> ORGANISM: respiratory syncytial virus

<400> SEQUENCE: 37
atggatccca ttattagtgg aaattctgct aatgtttatc taactgatag ttatttaaaa 60
ggtgttattt ctttctcaga atgtaacgct ttaggaagtt acatattcaa tggtccttat 120
ctcaaaaatg attataccaa cttaattagt agacaaaatc cattaataga acacataaat 180
ctaaagaaac taaatataac acagtcctta atatctaagt atcataaagg tgaaataaaa 240
atagaagaac ctacttactt tcagtcatta cttatgacat acaagagtat gacctcttca 300

```
gaacagacta ctactactaa tttacttaaa aagataataa gaagagctat agaaatcagt    360
gatgtcaaag tctatgctat attgaataaa ctggggctca aagaaaaaga caagattaaa    420
tccaataatg gacaagatga agacaactca gtcattacta ccataatcaa agatgatata    480
cttttagctg tcaaggataa tcaatctcat cttaaagcag acaaaaatca atccacaaaa    540
caaaaagata caatcaaaac aacacttttg aagaaattaa tgtgttcgat gcaacatcct    600
ccatcatggt taatacattg gtttaattta tacacaaaat taaacagcat attaacacaa    660
tatcgatcta gtgaggtaaa aaaccatggt tttatattga tagataatca tactcttagt    720
ggattccaat ttattttgaa tcaatatggt tgtatagttt atcataagga actcaaaaga    780
attactgtga caacttataa tcaattcttg acatggaaag atattagcct tagtagatta    840
aatgtttgtt tgattacatg gattagtaac tgtttgaaca cattaaacaa aagcttaggc    900
ttaagatgtg gattcaataa tgttatcttg acacaattat tcctttatgg agattgtata    960
ctaaaactat tccacaatga ggggttctac ataataaaag aggtagaggg atttattatg   1020
tctctaattt taaatataac agaagaagat caattcagaa aacggtttta taatagtatg   1080
ctcaacaaca tcacagatgc cgccaacaaa gctcaaaaaa atctgctatc aagagtatgt   1140
catacattat tagataagac aatatcagat aatataataa atggcagatg gataattcta   1200
ttgagtaagt tcctaaaatt aattaagctt gcaggtgaca ataacctcaa caatctgagt   1260
gaattatatt ttttgttcag aatatttgga cacccaatgg tagatgaaag acaagccatg   1320
gatgctgtta aagttaattg caacgagacc aaattttatt tgttaagtag tttgagtatg   1380
ttaagaggag cttttatata tagaattata aaagggtttg taaataatta caacagatgg   1440
cctactttaa gaaatgccat tgtcttaccc ttaagatggt taacttacta taaactaaac   1500
acttatcctt ccttgttgga acttacagaa agagatttga ttgttctatc aggactacgt   1560
ttctatcgag agtttcggtt gcctaaaaaa gtggatcttg aaatgatcat aaatgataag   1620
gctatatcac ctcctaaaaa tttaatatgg actagtttcc ctagaaatta tatgccgtca   1680
cacatacaaa attatataga acatgaaaaa ttaaaattct ctgatagtga taaatcaaga   1740
agagtattag agtattattt aagagataac aaattcaatg aatgtgattt acacaactgt   1800
gtagttaatc aaagttatct taacaacccg aatcatgtgg tatcattgac aggcaaagaa   1860
agagaactca gtgtaggtag aatgtttgca atgcaaccag gaatgttcag acaagttcaa   1920
atattagcag agaaaatgat agcagaaaac atattacaat tttccctgaa aagtcttaca   1980
agatatggtg atctagaact acagaaaata ttagaattga aagcaggaat aagtaacaaa   2040
tcaaatcgtt acaatgataa ttacaacaat tacattagta agtgctctat catcacagat   2100
ctcagcaaat tcaatcaagc atttcgatat gaaacatcat gtatttgtag tgatgtactg   2160
gatgaactgc atggtgtaca atctctattt tcctggttac atttaactat tcctcatgtc   2220
acaataatat gcacatatag gcatgcaccc ccctatataa aggatcatat tgtagatctt   2280
aacaatgtag atgagcaaag tggactatat agatatcata tgggtggtat cgaagggtgg   2340
tgtcaaaaac tatggaccat agaagctata tcactattag atctaatatc tctcaaaggg   2400
aaattctcaa ttactgcttt aattaatggt gacaatcaat caatagatat aagtaaacca   2460
gtcagactca tggaaggtca aactcatgct caagcagatt atttgctagc attaaatagt   2520
ctcaaattac tgtataaaga gtatgcagga ataggccaca aattaaaagg aactgagact   2580
tatatatcga gagatatgca atttatgagt aaaacgatcc aacataacgg tgtatattac   2640
```

-continued

```
ccagctagta taaagaaagt cctaagagtg ggaccgtgga taaacactat acttgatgac   2700
ttcaaagtga gtctagaatc tataggtagt ttgacacaag aattagaata tagaggtgaa   2760
agtctattat gcagtttaat atttagaaat gtatggttat ataatcaaat tgcattacaa   2820
cttaaaaatc atgcattatg taacaacaaa ttatatttgg atatattaaa agttctaaaa   2880
cacttaaaaa cctttttttaa tcttgataac attgatacag cattaacatt gtatatgaat   2940
ttgcccatgt tatttggtgg tggtgatccc aacttgttat atcgaagttt ctatagaaga   3000
actcctgatt tcctcacaga ggctatagtt cactctgtgt tcatacttag ttattataca   3060
aaccatgatt taaaagataa acttcaagat ctgtcagatg atagattgaa taagttctta   3120
acatgcataa tcacgtttga taaaaacccc aatgctgaat tcgttacatt gatgagagat   3180
cctcaagctt taggatctga gaggcaagct aaaattacta gcgaaatcaa tagactggca   3240
gttaccgagg ttttgagcac agctccaaac aaaatatttt ccaaaagtgc acaacactat   3300
accactacag agatagatct taatgatatt atgcaaaata tagaacctac atatcctcac   3360
gggctaagag ttgtttatga gagtttaccc ttttataaag cagagaaaat agtaaatctt   3420
atatccggta caaaatctat aactaacata ctggaaaaga cttctgccat agacttaaca   3480
gatattgata gagccactga gatgatgagg aaaaacataa ctttgcttat aaggatatta   3540
ccattagatt gtaacagaga taaaagagaa atattgagta tggaaaacct aagtattact   3600
gaattaagca aatacgttag agaaagatct tggtctttat ccaatatagt tggtgttaca   3660
tcacccagta tcatgtatac aatggacata aaatatacaa caagcactat agctagtggc   3720
ataatcatag agaaatataa tgtcaacagt ttaacacgtg gtgagagagg acccactaaa   3780
ccatgggttg gttcatctac acaagagaaa aagacaatgc cagtttataa tagacaagtt   3840
ttaaccaaaa aacagagaga tcaaatagat ctattagcaa aattggattg ggtgtatgca   3900
tctatagata acaaggatga atttatggag gaacttagca taggaactct tgggttaaca   3960
tatgagaagg ccaaaaaatt attcccacaa tatttgagtg ttaactattt gcatcgtctt   4020
acagtcagta gtagaccatg tgaattccct gcatctatac cagcttatag aactacaaat   4080
tatcactttg atactagccc tattaatcgc atattaacag aaaagtatgg tgatgaagat   4140
attgatatag tattccaaaa ctgtataagc tttggcctta gcttaatgtc tgtagtagaa   4200
caatttacta atgtatgtcc taacagaatt attctcatac ccaagcttaa tgagatacat   4260
ttgatgaaac ctcccatatt cacaggcgat gttgatattc acaagttaaa acaagtgata   4320
caaaaacaac atatgttttt accagacaaa ataagtttga ctcaatatgt ggaattattc   4380
ttaagtaata aaacactcaa atctggatct aatgttaatt ctaatttaat attggcgcat   4440
aagatatctg actattttca taatacttac attttgagta ctaatttagc tggacattgg   4500
attcttatta tacaacttat gaaagattct aagggtattt ttgaaaaaga ttggggagag   4560
ggatatataa ctgatcatat gttcattaat ttgaaagttt tcttcaatgc ttataagaca   4620
tatctcttgt gttttcataa aggttacggc agagcaaagc tggagtgtga tatgaatact   4680
tcagatctcc tatgtgtatt ggaattaata gacagtagtt attggaagtc tatgtctaag   4740
gtgtttttag aacaaaaagt tatcaaatac attcttagcc aggatgcaag tttacataga   4800
gtaaaaggat gtcatagctt caaactatgg tttcttaaac gtcttaatgt agcagaattc   4860
acagtttgcc cttgggttgt taacatagat tatcatccaa cacatatgaa agcaatatta   4920
acttatattg atcttgttag aatgggattg ataaatatag atagaatata cattaaaaat   4980
aaacacaagt tcaatgatga gttttatact tctaatctgt tttacattaa ttataacttc   5040
```

```
tcagataata ctcatctatt aactaaacat ataaggattg ctaattccga attagaaagt   5100

aattacaaca aattatatca tcctacacca gaaaccctag aaaatatact aaccaatccg   5160

gttaaaagta atgagaaaaa gacactgagt gactattgta taggtaaaaa tgttgactca   5220

ataatgttac catcgttatc taataagaag cttattaaat cgtctacaat gattagaacc   5280

aattacagca gacaagattt gtataattta tttcctacgg ttgtgattga taaaattata   5340

gatcattcag gtaatacagc caaatctaac caactttaca ctactacttc tcatcaaata   5400

tccttagtgc acaatagcac atcactttat tgcatgcttc cttggcatca tattaataga   5460

ttcaattttg tatttagttc tacaggttgt aaaattagta tagagtatat tttaaaagat   5520

cttaaaatta aggatcctaa ttgtatagca ttcataggtg aaggagcagg gaatttatta   5580

ttgcgtacag tagtggaact tcatcctgat ataagatata tttacagaag tctgaaagat   5640

tgcaatgatc atagtttacc aattgagttt ttaaggctgt acaatggaca tatcaacatt   5700

gattatggtg aaaatttgac cattcctgct acagatgcaa ccaacaacat tcattggtct   5760

tatttacata taaagtttgc tgaacctatc agtctttttg tctgtgatgc tgaattgcct   5820

gtaacagtca actggagtaa gattataata gagtggagca agcatgtaag aaaatgcaag   5880

tactgttctt cagttaataa atgtacattg atagtaaaat atcatgctca agatgatatc   5940

gatttcaaat tagacaacat aactatatta aaaacttatg tatgcttagg tagtaagtta   6000

aagggatctg aagtttactt agtccttaca ataggtcctg caaatgtgtt cccagtattt   6060

aatgtagtac aaaatgctaa attgatacta tcaagaacta aaaatttcat catgcctaaa   6120

aaagctgata aagagtctat tgatgcaaat attaagagtt tgataccctt tctttgttac   6180

cctataacaa aaaaaggaat taatactgca ttgtctaaat taaagagtgt tgttagtgga   6240

gatatactat catattctat agctggacgt aatgaagttt tcagcaataa acttataaat   6300

cataagcata tgaacatctt aaagtggttc aatcatgttt taaatttcag atcaacagaa   6360

ttaaactata atcatttata tatggtagaa tctacttatc ctcatctaag tgaattgtta   6420

aacagcttga caaccaatga acttaaaaaa ctgattaaaa tcacaggtag tttgttatac   6480

aacttttata atgaataa                                                 6498
```

<210> SEQ ID NO 38
<211> LENGTH: 4
<212> TYPE: PRT
<213> ORGANISM: respiratory syncytial virus

<400> SEQUENCE: 38

Arg Ala Arg Arg
1

<210> SEQ ID NO 39
<211> LENGTH: 4
<212> TYPE: PRT
<213> ORGANISM: Artificial Sequence
<220> FEATURE:
<223> OTHER INFORMATION: the amino acid sequence of modified Furin
cleavage site II

<400> SEQUENCE: 39

Arg Pro Ser Lys
1

<210> SEQ ID NO 40
<211> LENGTH: 4

<212> TYPE: PRT
<213> ORGANISM: respiratory syncytial virus

<400> SEQUENCE: 40

Arg Lys Arg Arg
1

<210> SEQ ID NO 41
<211> LENGTH: 4
<212> TYPE: PRT
<213> ORGANISM: Artificial Sequence
<220> FEATURE:
<223> OTHER INFORMATION: the amino acid sequence of modified Furin cleavage site I

<400> SEQUENCE: 41

Arg Lys Arg Lys
1

<210> SEQ ID NO 42
<211> LENGTH: 12
<212> TYPE: DNA
<213> ORGANISM: respiratory syncytial virus

<400> SEQUENCE: 42
cgagccagaa ga 12

<210> SEQ ID NO 43
<211> LENGTH: 12
<212> TYPE: DNA
<213> ORGANISM: Artificial Sequence
<220> FEATURE:
<223> OTHER INFORMATION: the nucleotide sequence of modified Furin cleavage site II

<400> SEQUENCE: 43
cgaccctcca ag 12

<210> SEQ ID NO 44
<211> LENGTH: 12
<212> TYPE: DNA
<213> ORGANISM: respiratory syncytial virus

<400> SEQUENCE: 44
aggaaaagaa ga 12

<210> SEQ ID NO 45
<211> LENGTH: 12
<212> TYPE: DNA
<213> ORGANISM: Artificial Sequence
<220> FEATURE:
<223> OTHER INFORMATION: the nucleotide sequence of modified Furin cleavage site I

<400> SEQUENCE: 45
aggaaaagaa ag 12

<210> SEQ ID NO 46
<211> LENGTH: 5
<212> TYPE: PRT
<213> ORGANISM: Artificial Sequence
<220> FEATURE:
<223> OTHER INFORMATION: GSGGS linker peptide

<400> SEQUENCE: 46

Gly Ser Gly Gly Ser 1 5

<210> SEQ ID NO 47
<211> LENGTH: 19
<212> TYPE: DNA
<213> ORGANISM: Artificial Sequence
<220> FEATURE:
<223> OTHER INFORMATION: the nucleotide sequence of T7 promoter

<400> SEQUENCE: 47
taatacgact cactatagg 19

<210> SEQ ID NO 48
<211> LENGTH: 49
<212> TYPE: DNA
<213> ORGANISM: Artificial Sequence
<220> FEATURE:
<223> OTHER INFORMATION: the sequence of hammerhead ribozyme

<400> SEQUENCE: 48 tttttcgcg tctgatgagg ccgttaggcc gaaactcctc tccggagtc 49

<210> SEQ ID NO 49
<211> LENGTH: 68
<212> TYPE: DNA
<213> ORGANISM: Artificial Sequence
<220> FEATURE:
<223> OTHER INFORMATION: the sequene of the hepatitis delta virus ribozyme

<400> SEQUENCE: 49
ggccggcatg gtcccagcct cctcgctggc gccggctggg caacatgctt cggcatggcg 60
aatgggac 68

<210> SEQ ID NO 50
<211> LENGTH: 47
<212> TYPE: DNA
<213> ORGANISM: Artificial Sequence
<220> FEATURE:
<223> OTHER INFORMATION: the sequene of T7 terminator

<400> SEQUENCE: 50
tagcataacc ccttggggcc tctaaacggg tcttgagggg ttttttg 47

<210> SEQ ID NO 51
<211> LENGTH: 21
<212> TYPE: DNA
<213> ORGANISM: Artificial Sequence
<220> FEATURE:
<223> OTHER INFORMATION: 3' leader sequence

<400> SEQUENCE: 51
acgcgaaaaa atgcgtacaa c 21

<210> SEQ ID NO 52
<211> LENGTH: 23
<212> TYPE: DNA
<213> ORGANISM: Artificial Sequence
<220> FEATURE:
<223> OTHER INFORMATION: 5' trailer sequence

<400> SEQUENCE: 52
gtttttgaca cttttttct cgt 23

<210> SEQ ID NO 53

<211> LENGTH: 20
<212> TYPE: PRT
<213> ORGANISM: Artificial Sequence
<220> FEATURE:
<223> OTHER INFORMATION: the cytoplasmic tail region of the Vesicular stomatitis virus (VSV) G protein

<400> SEQUENCE: 53

```
Leu Lys His Thr Lys Lys Arg Gln Ile Tyr Thr Asp Ile Glu Met Asn
1               5                   10                  15

Arg Leu Gly Lys
            20
```

<210> SEQ ID NO 54
<211> LENGTH: 23
<212> TYPE: PRT
<213> ORGANISM: Artificial Sequence
<220> FEATURE:
<223> OTHER INFORMATION: the cytoplasmic tail region of the wild type human respiratory syncytial virus

<400> SEQUENCE: 54

```
Ala Arg Ser Thr Pro Val Thr Leu Ser Lys Asp Gln Leu Ser Gly Ile
1               5                   10                  15

Asn Asn Ile Ala Phe Ser Asn
            20
```

<210> SEQ ID NO 55
<211> LENGTH: 51
<212> TYPE: DNA
<213> ORGANISM: Artificial Sequence
<220> FEATURE:
<223> OTHER INFORMATION: the inter-gene between G gene and F gene

<400> SEQUENCE: 55

```
gtattgttgc aaaaagccat gaccaaatca aacagaatca aaatcaactc t              51
```

<210> SEQ ID NO 56
<211> LENGTH: 43
<212> TYPE: DNA
<213> ORGANISM: Artificial Sequence
<220> FEATURE:
<223> OTHER INFORMATION: the inter-gene between SH gene and G gene

<400> SEQUENCE: 56

```
agtcataaca atgaactagg atattaagac caaaaacaac gct                      43
```

<210> SEQ ID NO 57
<211> LENGTH: 29
<212> TYPE: PRT
<213> ORGANISM: respiratory syncytial virus

<400> SEQUENCE: 57

```
Arg Glu Leu Pro Arg Phe Met Asn Tyr Thr Leu Asn Asn Thr Lys Asn
1               5                   10                  15

Thr Asn Val Thr Leu Ser Lys Lys Arg Lys Arg Arg Phe
            20                  25
```

<210> SEQ ID NO 58
<211> LENGTH: 6
<212> TYPE: PRT
<213> ORGANISM: Artificial Sequence -continued

```
<220> FEATURE:
<223> OTHER INFORMATION: GSGGSG linker peptide

<400> SEQUENCE: 58

Gly Ser Gly Gly Ser Gly
1               5
```

RECOMBINANT RSV LIVE VACCINE STRAIN AND THE PREPARING METHOD THEREOF

CROSS-REFERENCE TO RELATED APPLICATION

The present application claims priority to U.S. Provisional Application No. 63/173,577 filed on Apr. 12, 2021 and Korean Patent Application No. 10-2021-0129272 filed on Sep. 29, 2021, the entire contents disclosed in the description and drawings of the corresponding applications are incorporated by reference in the present application.

SEQUENCE LISTING

The instant application contains a Sequence Listing which has been submitted electronically in ASCII format and is hereby incorporated by reference in its entirety. Said ASCII copy, created on 29 Sep. 2023, is named 0393_0008-NP-US_SL.txt and is 513 KB in size.

TECHNICAL FIELD

The present invention relates to a recombinant attenuated RSV, a method for preparing the same, or a vaccine comprising the same, and more specifically, it relates to a recombinant attenuated RSV capable of producing a live vaccine strain with excellent stability and safety, a method for preparing the same, or a vaccine comprising the same.

BACKGROUND ART

Respiratory Syncytial Virus (RSV) is a virus that is prevalent around the world, and it is a virus that causes respiratory diseases and particularly, is the main cause of death from severe respiratory infection in infants and children. Although infants and children are the main target of infection, it is known that it causes fatal respiratory diseases by inducing infection in patients with weakened immunity and respiratory disease in the elderly. It is the second highest cause of respiratory disease after influenza, but it is known that the annual mortality rate from RSV per 100,000 children under 1 year is 1.3~2.5 times higher than that of influenza. According to the report of WHO in 2002, 64 million people are infected with RSV every year, of which 160,000 die.

Initially, a vaccine using an inactivated virus (inactivated vaccine) was developed for the purpose of protecting against RSV disease, but the use of the inactivated vaccine became impossible due to occurrence of serious side effects (ERD (enhanced respiratory disease)) such as a more severe induction of disease symptoms.

Accordingly, researchers have tried to develop a vaccine that does not induce ERD and has excellent ability to induce neutralizing antibodies.

In particular, the live vaccine has an advantage that it does not cause ERD and has excellent ability to induce neutralizing antibodies, but there were difficulties in vaccine development, when considering both the stability issue and safety issue of the virus, since RSV is very metastable.

RSV belongs to the subfamily Orthopneumoviridae, belonging to the order Mononegavirales, the family Pneumoviridae. RSV is known as a medium-sized virus of about 120-200 nm. The wild type (wt) RSV genome or antigenome consists of 10 genes and 11 virus proteins below. The 11 RSV proteins RNA-binding nucleoprotein (N), phosphoprotein (P), large polymerase protein (L), attachment glycoprotein (G), fusion protein (F), small hydrophobic (SH) surface glycoprotein, internal matrix protein (M), two non-structural proteins NS1 and NS2, and M2-1 and M2-2 proteins. The complete amino acid sequences of these proteins are known in the art. The RSV gene sequence is 3'-NS1-NS2-N-P-M-SH-G-F-M2-L. Transcription begins with a single promoter at the 3' end and proceeds sequentially. The genome of the RSV is a single strand of 15.2 kb non-segmented negative sense RNA. Herein, the RSV F protein is an important component for early virus entry and fusion with cell membrane, and is known as a major target for vaccines and antiviral drugs. However, the F protein antigen is difficult to produce and purify in a stabilized form of the pre-fusion type protein, and it has a problem in that it is difficult to secure stability and it is not easy to maintain efficacy.

Accordingly, the inventors of the present invention are to overcome the instability of the F protein and develop a safe vaccine using a new type of attenuated RSV.

DISCLOSURE

Technical Problem

Accordingly, a problem to be solved by the present invention is to provide a new type of vaccine capable of operating an effective immune system.

A problem to be solved by the present invention is to provide a live RSV vaccine strain with excellent stability and safety.

Technical Solution

One embodiment provides a recombinant attenuated respiratory syncytial virus comprising a stabilized pre-fusion RSV F protein, or comprising a nucleic acid encoding a chimeric vesicular virus (Vesicular stomatitis Indiana virus, VSV) G protein or analogue, variant or fragment thereof. Preferably, the G protein comprises a recombinant virus consisting of the amino acid sequence of SEQ ID NO: 2.

One embodiment provides a recombinant attenuated respiratory syncytial virus comprising stability inducing mutation or safety inducing mutation. The recombinant attenuated respiratory syncytial virus (RSV) comprising a nucleic acid encoding the chimeric vesicular virus (Vesicular stomatitis Indiana virus, VSV) G protein or analogue, variant or fragment thereof may further comprise i) deletion of a nucleic acid encoding at least one or more selected from the group consisting of SH, G and F proteins of RSV, ii) substitution it with another nucleic acid, or iii) deletion of any one of nucleic acids encoding the proteins and the others are substituted with other nucleic acids.

For inducing stability, mutation for maintaining the F protein of RSV in a prefusion form is comprised or (or comprised and) a protein consisting of the amino acid sequence represented by SEQ ID NO: 2 or functional fragment thereof (that is, chimeric VSV G protein) is comprised. In order to maintain it in a prefusion form, 1) mutation for structurally stabilizing the F protein (D486L/E487L/F488W) may be introduced, or 2) a furin cleavage site of the F protein may be modified to control cleavage of protein, thereby maintaining it in a prefusion form.

1) Specifically, it may be produced by deleting 514-575 residues corresponding to the transmembrane domain and cytoplasmic tail and adding a foldon sequence which is a heterologous trimer domain so that it is expressed as a soluble prefusion trimer F protein in which this mutant F protein is not present on a virus surface and is secreted outside the infected cell together with structural stabilization mutation (D486L/E487L/F488W). Accordingly, this soluble prefusion trimer F protein may have an advantage of inducing immune response without affecting instability of the virus.

2) Specifically, in the mutated F protein, in which at least one among the furin cleavage sites of the F protein of the recombinant attenuated respiratory syncytial virus (RSV) has mutation, the amino acid RARR (SEQ ID NO: 38) corresponding to the furin cleavage site II of the F gene which is the 106~109th amino acid sequence of the F protein may be modified into RPSK (SEQ ID NO: 39), or the amino acid RKRR (SEQ ID NO: 40) corresponding to the furin cleavage site I of the F gene which is the 133~136th amino acids may be substituted with RKRK (SEQ ID NO: 41). Otherwise, by connecting two furin cleavage sites with a linker sequence (GSGGS; SEQ ID NO: 46), it may be modified so that it is maintained in a single chain form without cleavage. Therefore, the stability of the virus is to be increased by maintaining the F protein in the prefusion form.

In addition, in another embodiment, for increasing safety, the RSV protein (SH or G or F) may be deleted or an NS1 or NS2 gene is further deoptimized for inhibiting an immune escaping mechanism.

A recombinant attenuated respiratory syncytial virus is provided through a combination of mutations for increased stability and safety as described above.

In one embodiment, the recombinant attenuated respiratory syncytial virus may be provided in a form which comprises a protein consisting of the amino acid sequence represented by SEQ ID NO: 2 or functional fragment thereof, and comprises i) deletion of at least one or more proteins selected from the group consisting of SH, G and F proteins of RSV, or ii) substitution of at least one protein selected from the group consisting of the SH, G and F proteins, or iii) deletion of at least one protein selected from the group consisting of the SH, G and F proteins and substitution of a protein other than the deleted protein with a new protein.

In one embodiment, in case of the ii), a nucleic acid sequence consisting of SEQ ID NO: 11 or SEQ ID NO: 14, preferably, an amino acids sequence encoded by a cDNA sequence may be comprised.

In other embodiment, in case of the iii), a nucleic acid sequence consisting of SEQ ID NO: 12 or SEQ ID NO: 13, preferably, an amino acid sequence encoded by a cDNA sequence may be comprised.

In one embodiment, in the mutated F protein, having at least one mutation among furin cleavage sites of F protein of the recombinant attenuated respiratory syncytial virus (RSV), the amino acid RARR (SEQ ID NO: 38) corresponding to the furin cleavage site II of the F gene which is the 106~109th amino acids sequence of F protein is modified into RPSK (SEQ ID NO: 39), or the amino acid RKRR (SEQ ID NO: 40) corresponding to the furin cleavage site I of the F gene which is the 133~136th amino acids are substituted with RKRK (SEQ ID NO: 41). In addition, two furin cleavage sites are linked with a linker sequence (GSGGS; SEQ ID NO: 46) to prevent cleavage, so that it can be modified to maintain a single chain form.

In other embodiment, a gene encoding NS1 and NS2 proteins comprised in the virus may be further substituted, and the antigenomic cDNA of the substituted gene may consist of the nucleotide sequence represented by SEQ ID NOs: 32 and 33, respectively.

One example of the present invention provides an isolated polynucleotide molecule comprising the nucleotide sequence of the recombinant attenuated RSV genome or antigenomic cDNA or RNA of the recombinant RSV genome. The polynucleotide molecule may be preferably cDNA, and may be used for co-transfection with an expression vector encoding a part of protein of RSV.

One embodiment of the present invention may provide a novel use of the recombinant attenuated RSV or polynucleotide molecule thereof, for preparing a medicine for preventing or treating RSV infection.

In one embodiment, the isolated polynucleotide molecule may be cDNA consisting of the polynucleotide represented by any one or more sequences selected from the group consisting of SEQ ID NOs: 6 to 16. The cDNA sequence may have the sequence identity of at least 70%, at least 80%, at least 85%, at least 90%, at least 91%, at least 92%, at least 93%, at least 94%, at least 95%, at least 96%, at least 97%, at least 98%, at least 99%, or 100% to the above any one or more polynucleotide sequences selected from the group consisting of SEQ ID NOs: 6 to 16.

One embodiment provides a vector comprising the isolated polynucleotide molecule. The vector is an expression vector encoding N, P, L, M2-ORF1 proteins of RSV and may be used for co-transfection.

One embodiment provides a cell comprising the isolated polynucleotide molecule or vector.

One embodiment provides a pharmaceutical composition comprising a recombinant attenuated RSV; and a pharmaceutically acceptable carrier.

One embodiment provides a method for inducing immune response against RSV in a subject, comprising administering the pharmaceutical composition in an effective dose to generate immunity to a subject.

One embodiment provides a use of a recombinant RSV, for inducing immune response against RSV in a subject.

One embodiment provides a method for producing a recombinant attenuated RSV comprising the following.

Specifically, the method may comprise transfecting the vector with a host cell, culturing the cell or culture thereof during time enough for allowing virus replication, and separating the replicated recombinant RSV.

One embodiment provides a recombinant attenuated RSV produced by the method.

One embodiment provides a recombinant attenuated RSV used as a live vaccine strain for preventing RSV infection.

One embodiment may provide a pharmaceutical composition for preparation of a medicine for preventing or treating RSV infection, wherein the composition is a composition comprising cDNA molecule of the recombinant RSV or functional fragment or analogue thereof.

The cDNA molecule of the recombinant RSV may comprise a composition comprising any one selected from the group consisting of SEQ ID NOs: 6 to 16.

The vector comprises a T7 promoter, hammerhead ribozyme, hepatitis delta virus ribozyme, and a T7 terminator required for producing a recombinant virus, and may comprise cDNA of any one selected from the group consisting of SEQ ID NOs: 17 to 27.

Advantageous Effects

The present invention provides a live RSV vaccine strain with excellent stability and safety.

The present invention provides a new type of RSV vaccine capable of inducing a defense mechanism against RSV.

The recombinant attenuated RSV of the present invention can overcome instability of the virus by expressing a prefusion form of F protein on a virus surface.

The recombinant attenuated RSV of the present invention can not only resolve instability of the virus but also induce immunity due to F protein by expressing a prefusion form of soluble trimer F protein.

The recombinant attenuated RSV of the present invention can resolve instability of the virus by allowing VSV G to perform a role of virus infection instead of the F protein.

The recombinant attenuated RSV of the present invention can resolve instability of the virus by removing F protein.

The recombinant attenuated RSV of the present invention provides a new type of vaccine capable of operating an effective immune system by inhibiting an immune escaping mechanism as it does not produce secreted G.

The recombinant attenuated RSV of the present invention can reduce the expression level of NS1 or NS2 protein, and thereby can inhibit an immune escaping mechanism and operate an effective immune system.

The present invention can attenuate a recombinant RSV by removing SH protein or G protein or F protein of RSV, thereby increasing safety of a vaccine. The present invention provides a new recombinant RSV.

BRIEF DESCRIPTION OF THE DRAWINGS

The following drawings attached to the present description illustrate preferable examples of the present invention, and play a role of further understanding the technical spirit of the present invention with the aforementioned content of the invention, so the present invention should not be interpreted as limited only to the matters described in those drawings.

FIG. 1 is a schematic diagram of the genome structure of the RSV and is a diagram showing the RSV genome and morphology.

FIG. 2 is a vector map and shows the antigenomic cDNA and cloning vector of the recombinant A backbone.

FIG. 3 is a schematic diagram of the negative-sense RSV genome structure of CRSVA_VSVG_A and a recombinant chimeric VSV G gene is inserted between the SH gene and G gene of the recombinant RSV A backbone.

FIG. 4 is a schematic diagram of the negative-sense RSV genome structure of CRSVA_VSVG_A_ASH and the SH gene of the recombinant RSV A backbone is deleted and the recombinant chimeric VSV G gene is inserted upstream of the G gene.

FIG. 5 is a schematic diagram of the negative-sense RSV genome structure of CRSVA_VSVG_A_ASH_AG and the SH gene and G gene of the recombinant RSV A backbone are deleted and the recombinant chimeric VSV G gene is inserted.

FIG. 6 is a schematic diagram of the negative-sense RSV genome structure of CRSVA_VSVG_A_ASH_AF and the SH gene and F gene of the recombinant RSV A backbone are deleted and the recombinant chimeric VSV G gene is inserted upstream of the G gene.

FIG. 7 is a schematic diagram of the negative-sense RSV genome structure of CRSVA_VSVG_S and the F gene of the recombinant RSV A backbone is substituted with the recombinant chimeric VSV G gene.

FIG. 8 is a schematic diagram of the negative-sense RSV genome structure of CRSVA_VSVG_A_preF_ef and the recombinant chimeric VSV G gene is inserted upstream of the F gene of the recombinant RSV A backbone, and in the F gene, prefusion stabilization mutation (D486L, E487L, F488W) and 514~575 residues deletion mutation, and GSGGS (SEQ ID NO: 46) linker and foldon insertion mutation are introduced. VSV G performs a role of cell infection instead of unstable RSV F, and RSV F is inserted in an ectodomain form, and thus, it is not expressed on the cell and virus surfaces, and therefore, it does not play a role of infection. Instead, when the virus infects a cell, the RSV F is expressed in the cell and secreted outside the cell to induce immune response. In the F ectodomain, mutation stabilizing by prefusion and a trimerization domain are added, and therefore, it is expressed into a soluble preF trimer.

FIG. 9 is a schematic diagram of the negative-sense RSV genome structure of CRSVA_VSVG_S_preF_ef and it is a further attenuated type by further deleting the G gene in FIG. 8.

FIG. 10 is a schematic diagram of the negative-sense RSV genome structure of cRSVA_VSVG_S_preF_sc and it is one that preF ectodomain-foldon is substituted with single chain F in FIG. 9. The single chain F is expressed on the cell and virus surfaces, but it is not modified into a postfusion form, and therefore it does not cause infection and can play an immune inducing role. It is expressed as attached to a non-soluble cell or virus membrane and is expected to induce immune response more similar to that of an actual virus.

FIG. 11 is a schematic diagram of the negative-sense RSV genome structure of cRSVA_VSVG_A_preF_ef_NS1/NS2deop and it is one that a DNA sequence encoding NS1 and NS2 proteins is deoptimized for a human codon. When this codon deoptimization reduces the expression level in a human cell, the virus is attenuated.

FIG. 12 shows a schematic diagram of the negative-sense RSV genome structure of cRSVA_mF1.

FIG. 13 shows a schematic diagram of the negative-sense RSV genome structure of cRSVA_mF2.

FIG. 14 shows an example of the recombinant RSV recovered from the recombinant RSV antigenomic cDNA through reverse genetics.

FIG. 15 is the result of confirming the protein expression into a prefusion form due to prefusion stabilization mutation (D486L, E487L, F488W) comprised in SEQ ID NO: 11. It was confirmed by detecting with a prefusion F-specific antibody.

MODE FOR INVENTION

In order to solve the above problems, the present invention provides a recombinant attenuated respiratory syncytial virus (RSV) with excellent stability or safety. The RSV may be used preferably as a live vaccine strain for preventing RSV infection. The recombinant RSV of the present invention may be produced using "reverse genetic engineering". Reverse genetic engineering is also called reverse genetics, and may be used for production of various RNA viruses comprising positive (+) stranded RNA viruses, negative (−) stranded RNA viruses and double stranded RNA viruses. The present invention provides a method for producing a recombinant virus obtained by using the reverse genetic engineering method of the present invention.

Reverse genetic engineering may be performed using a conventional method and means well known to those skilled in the art, and those skilled in the art may obtain a recombinant RSV without difficulty through a method well known in the art and the description below. For example, a desired recombinant virus may be produced by converting an amino acid sequence of a target protein or polypeptide into a corresponding nucleic acid sequence, modifying the nucleic acid sequence into a nucleic acid sequence which can be recognized by a host cell and encodes the target protein, synthesizing the modified nucleic acid using primers in vitro to produce a plasmid, and transforming the plasmid. As references, i) Stobart, Christopher C., et al. "BAC-based recovery of recombinant respiratory syncytial virus (RSV)." Reverse Genetics of RNA Viruses. Humana Press, New York, NY, 2017. 111-124., ii) Collins, Peter L., Rachel Fearns, and Barney S. Graham. "Respiratory syncytial virus: virology, reverse genetics, and pathogenesis of disease." Challenges and opportunities for respiratory syncytial virus vaccines (2013): 3-38., iii) Hu, Bing, et al. "Development of a reverse genetics system for respiratory syncytial virus long strain and an immunogenicity study of the recombinant virus." Virology journal 11.1 (2014): 1-16. and the like may be referred.

"Recombinant" may mean a case in which cells, proteins or genes with different genetic traits are present together in one organism, and in particular, "recombinant" used in herein means a case in which genetic information (nucleic acid) of different individuals is inserted based on a single genetic backbone to generate new genetic mutation.

The recombinant RSV (rRSV) means an RSV or RSV-like virus derived directly or indirectly from a recombinant expression system or proliferated from a virus or subvirus produced therefrom. The expression structure encoding a virus RNA molecule to be used in the present invention may be any expression structure commonly used in the art for virus rescue. The expression structure may be a plasmid or vector such as other episome structures. These vectors may comprise at least one replication origins of bacteria and/or eukaryotes. Furthermore, the vector may comprise a selective marker. The example of this selective marker may comprise a gene giving resistance to an antibiotic such as chloramphenicol, ampicillin or kanamycin. The vector may comprise one or more various cloning sites capable of cloning of the DNA sequence.

The recombinant expression system may comprise a recombinant expression vector. "Vector" means a DNA structure containing a DNA sequence operably linked to an appropriate regulatory sequence capable of performing expression of DNA in an appropriate host. It comprises a functionally linked transcription unit, comprising at least one genetic element or a combination of elements which has regulatory function in expression of cDNA of the RSV gene, and the example of the element includes a promoter, a structure or coding sequence transcribed to RSV mRNA, and an appropriate transcription initiation and termination sequence. The vector of the present invention may use any vector known in the art, and for example, it may be a plasmid, cosmid, phage particle, or virus vector, and as long as it can replicate in a cell, it is not particularly limited thereto.

In the present invention, "recombinant vector" may be used as an expression vector of a target polypeptide capable of expressing the target polypeptide with high efficiency in an appropriate host cell, when an encoding gene of a target polypeptide to be expressed is operably linked, and the recombinant vector may be expressed in a host cell. Depending on the type of the host cell, an expression regulatory sequence such as a promoter, a terminator and an enhancer, a sequence for membrane targeting or secretion, and the like may be appropriately selected and variously combined according to the purpose. In the present invention, the host cell may be preferably a eukaryote, and according to one embodiment of the present invention, it may be Vero cell, but not limited thereto.

The term "operably linked" used in the present invention refers to that a gene which requires expression and its regulatory sequence are functionally linked to each other and linked in such a way as to enable gene expression.

There is no particularly limited in the method for introducing DNA in a vector form to a cell, and for example, it may be conducted according to a method well known to those skilled in the art to which the present invention pertains such as nucleofection, transient transfection, cell fusion, liposome-mediated transfection, polybrene-mediated transfection, transfection using calcium phosphate, transfection by DEAE dextran, transfection by microinjection, transfection by cationic lipids, electroporation, transduction or transfection, and the like.

"Genome" used herein is the total nucleotide sequence of a gene of one individual and means an assembly of all genetic information of one organism. For example, genome of a virus is used as a meaning encompassing all genetic information sequences of the whole virus.

"Gene" used herein may be understood as a part encoding protein, and may be DNA or RNA.

The expression used herein, "cDNA or cDNA sequence" means a DNA form of a virus genome RNA sequence, and this means a sequence different from an RNA sequence in that a ribonucleotide is substituted with corresponding deoxyribonucleotide in the RNA sequence.

Herein, the meaning of "a new gene was introduced into genome" may mean that a part of the total gene nucleotide sequence of an original individual may be substituted or inserted with a gene derived from a new individual. Due to this introduction, it may be longer, shorter or maintaining the length, than the genome nucleotide sequence of the original individual (for example, backbone).

"Vaccine strain" used herein is also called a vaccine strain, and means a virus group separated to be used as a vaccine.

"Attenuated vaccine" used herein is a vaccine making a weakened respiratory syncytial virus (RSV), wherein a pathogen is still biologically active but has the weakened toxicity enough to not cause disease in a host.

"Anti-genome" used herein means a complementary (+) sense polynucleotide molecule acting as a template for synthesis of descendant RSV genome.

"Gene encoding protein" or "gene coding protein" used herein means a gene producing protein.

"Soluble prefusion F trimer protein" used herein means a fusion protein in which a linker and a heterologous trimerized domain are linked to a soluble F protein ectodomain (preF ectodomain), and in particular, D486L/E487L/F488W mutation is introduced to the wild type F protein ectodomain to stabilize protein. The heterologous trimerized domain may comprise a commonly used foldon domain. The linker is not particularly limited.

Hereinafter, an attenuated recombinant RSV with enhanced safety or stability will be described specifically.

One embodiment provides a recombinant attenuated respiratory syncytial virus comprising a chimeric vesicular virus (Vesicular stomatitis Indiana virus, VSV) G protein (preferably, protein consisting of the amino acid sequence represented by SEQ ID NO: 2) or analogue, variant or fragment thereof, or comprising F protein in which at least one of furin cleavage sites of F protein of RSV. Specifically, for example, the recombinant attenuated respiratory syncytial virus provided herein is to provide a live RSV vaccine strain with excellent stability and safety by inserting a surface glycoprotein based on RSV genome or substituting F protein or G protein with a surface glycoprotein of a heterologous virus.

Herein, the protein consisting of the amino acid sequence represented by SEQ ID NO: 2 may be understood as showing a surface glycoprotein G of a recombinant Indiana vesicular virus (Vesicular stomatitis Indiana virus; VSV) (hereinafter, represented by rVSV G protein). This may be encoded by SEQ ID NO: 3 or a polynucleotide sequence having the sequence homology of at least 70% or more thereto. The cytoplasmic tail (CT) domain of the VSV G protein may be derived from RSV F protein. Preferably, the recombinant RSV may comprise protein consisting of the amino acid sequence represented by SEQ ID NO: 2, as well as analogue, variant or fragment thereof, and may comprise even a functional fragment. Herein, 'functional fragment' may be understood as comprising protein having the sequence homology of at least 80% or more, 85% or more, 90% or more, 95% or more, 98% or more, or 100% thereto, while maintaining the function of the recombinant VSV G protein. For example, the cytoplasmic tail (CT) domain of the recombinant VSV G protein may also comprise a case in that the cytoplasmic tail (CT) domain of the original VSV G protein is linked instead of the RSV F protein.

The VSV is a safe virus for humans and is similar to RSV in an aspect of virus classification. Both the VSV and RSV have (−) ssRNA as a genetic substance and are enveloped viruses. In particular, it has been confirmed that the VSV G protein is a membrane protein playing a role similar to the RSV F protein, and is a protein having activity alone (not requiring help of other protein), and has stabilized properties under a condition such as temperature and pH, and therefore, a safe vaccine with excellent stability can be produced when using it.

One embodiment may provide the recombinant attenuated respiratory syncytial virus in a form of comprising (or comprises) protein consisting of the amino acid sequence represented by SEQ ID NO: 2 or functional fragment thereof, additionally having i) deletion of at least one protein selected from the group consisting of SH, G and F proteins of RSV, ii) substitution of at least one protein selected from the group consisting of the SH, G and F proteins, or iii) deletion of at least one protein selected from the group consisting of the SH, G and F proteins, and substitution of protein(s) other than the deleted protein(s) with new protein. Herein, 'at least one' may be understood as a meaning of comprising one or more, 2 or more or 3. Herein, 'substitution of protein' may be understood as a broad meaning of comprising a case in that one or more amino acid sequences are changed to other sequences and comprising substitution of a domain.

In one embodiment, in case of the ii), preferably, substitution of F protein of RSV may be included. Preferably, the substitution of F protein of RSV may be substituting with a new domain capable of reducing infectability of RSV. Preferably, the new domain May 1) comprise a fusion protein domain in which a linker and a heterologous trimerized domain are linked to a soluble F protein ectodomain, or 2) comprise a F protein domain comprising mutation increasing stability of a prefusion form. Specifically, it may be substituted with the polynucleotide sequence consisting of SEQ ID NO: 11 or 14, preferably, amino acids encoded by cDNA.

In other embodiment, in case of the iii), together with deletion of G protein of RSV, the F protein of RSV may be substituted with the aforementioned new domain capable of reducing infectability of RSV, and preferably, this may be substituted with a polynucleotide sequence consisting of SEQ ID NO: 12 or SEQ ID NO: 13, preferably, amino acids encoded by cDNA.

Specifically, in the 1) fusion protein domain in which a linker and a heterologous trimerized domain are linked to a soluble F protein ectodomain, the G protein of the recombinant VSV performs a cell infection role instead of the unstable F protein of RSV, and the RSV F is inserted in an ectodomain form and therefore it is not expressed on cell and virus surfaces, and thus it cannot perform an infection role. Instead, the RSV F is expressed in a cell when infection the cell and secreted outside the cell, thereby inducing only immune response. As a mutation and trimerization domain stabilizing into prefusion is added in the F ectodomain, it may be expressed as a soluble prefusion F trimer. The fusion protein domain in which a linker and a heterologous trimerized domain are linked to the soluble F protein ectodomain consists of the amino acid sequence represented by SEQ ID NO: 29. The 2) F protein domain comprising mutation increasing the stability of the prefusion form substitutes the pre fusion F ectodomain-foldon with single chain F. This consists of the amino acid sequence represented by SEQ ID NO: 31. Since the single chain F is expressed on cell and virus surfaces, but is not modified into a postfusion form, and therefore, it cannot cause infection, and it can play only an immune inducing role. It is expressed in a state attached to an insoluble cell or virus membrane, and therefore, it can induce immune response more similar to an actual virus.

In other embodiment, the recombinant attenuated respiratory syncytial virus (RSV) may comprise mutated F protein having mutation in at least one of furin cleavage sites of F protein of RSV. Preferably, in the mutated F protein, the furin cleavage I or II of F protein of RSV may be modified into other protease cleavage sites such as trypsin, MMP, trypsin-like protease, and the like, and more preferably, the amino acid RARR (SEQ ID NO: 38) corresponding to the furin cleavage site II of the F gene which is the 106~109th amino acid sequence of the F protein may be modified into RPSK (SEQ ID NO: 39), or the amino acid RKRR (SEQ ID NO: 40) corresponding to the furin cleavage site I of the F gene which are the 133~136th amino acids may be substituted with RKRK (SEQ ID NO: 41). The F protein is cleaved after transcription by ER-rich furin protease, and is divided into F1/F2 subdomains and becomes metastable. Preferably, when the furin cleavage site I or II is modified into a cleavage site by cleavage enzyme rich in lysosome, cleavage after transcription does not occur, and it may be present on a virus surface in a single chain F form with high stability, and it is effective in inducing immune response.

In other embodiment, in the virus, a gene encoding NS1 and NS2 proteins comprised in the virus is further substituted, and the antigenomic cDNA of the substituted gene may consist of the nucleotide sequence represented by SEQ ID NOs: 32 and 33, respectively.

Specifically, a recombinant attenuated RSV with increased safety by deoptimization of codons of polynucleotides encoding NS1 protein, NS2 protein or both NS1 and NS2 proteins for human codons may be provided. When conducting codon optimization of the NS1 and/or NS2 proteins, the expression level in a human body of NS1 or NS2 protein is reduced and the recombinant virus is attenuated, and thereby, the safety may be increased.

The recombinant RSV may be used safely as a live vaccine strain.

One example of the present invention provides a nucleotide molecule composing the recombinant attenuated RSV, and this comprises genome or antigenome of RSV. One embodiment provides a recombinant vector of a recombinant attenuated RSV comprising thereof, and the antigenomic cDNA sequence comprised in the vector consists of any one or more nucleotide sequences selected from the group consisting of SEQ ID NOs: 6 to 16.

The recombinant vector comprises a nucleotide sequence encoding the rVSV G protein. Preferably, the nucleotide sequence encoding the rVSV G protein may be positioned between the SH gene and G gene of RSV, and this may be represented by SEQ ID NO: 3.

The genome of the recombinant attenuated RSV may be provided in a form of comprising a nucleotide sequence encoding the rVSV G protein, and having i) deletion of a nucleotide sequence encoding at least one or more proteins selected from the group consisting of SH, G and F proteins or a gene encoding the proteins, ii) substitution of a nucleotide sequence encoding at least one proteins selected from the group consisting of SH, G and F proteins or a gene encoding the proteins, or iii) deletion of a nucleotide sequence encoding at least one proteins selected from the group consisting of SH, G and F proteins or a gene encoding the proteins and substitution of a nucleotide sequence encoding protein(s) other than the deleted protein(s) with other sequence.

In one embodiment, in case of the ii), the nucleotide encoding F protein of RSV may be substituted with a nucleotide sequence encoding soluble preF trimer protein or preFsc protein. Preferably, the cDNA sequence of the recombinant RSV may comprise a nucleotide consisting of SEQ ID NO: 11 or SEQ ID NO: 14, respectively, or functional fragment thereof.

In other embodiment, in case of the iii), the nucleotide encoding G protein of RSV or nucleotide encoding F protein or RSV may be substituted with a nucleotide sequence encoding soluble preF trimer protein or preFsc protein. Preferably, the cDNA sequence of the recombinant RSV may preferably comprise a nucleotide consisting of SEQ ID NO: 12 or SEQ ID NO: 13, respectively, or functional fragment thereof.

In one embodiment, the genome of the recombinant attenuated respiratory syncytial virus (RSV) may have mutation in at least one or more of proteins encoding furin cleavage sites of F protein. In the nucleotide sequence encoding mutated F protein, the nucleotide sequence corresponding to furin cleavage site II of the F gene positioned from 6137 to 6148 of the nucleotide sequence encoding F protein, CGAGCCAGAAGA (SEQ ID NO: 42) may be modified into CGACCCTCCAAG (SEQ ID NO: 43), or the nucleotide sequence corresponding to furin cleavage site I of the F gene positioned from 6218 to 6229, AGGAAAAGAAGA (SEQ ID NO: 44) may be substituted with AGGAAAAGAAAG (SEQ ID NO: 45).

In other embodiment, the genes encoding NS1 and NS2 proteins of the virus may be provided as substituted with genes consisting of the nucleotide sequence represented by SEQ ID NOs: 32 and 33, respectively.

That the gene arrangement order of RSV is present as arranged as 3'leader-NS1, NS2, N, P, M, SH, G, F, M2, L-5' trailer is a fact already known in the art.

In a specific example, the nucleotide sequence of the recombinant RSV may comprise any one nucleotide sequence selected from the group consisting of SEQ ID NOs: 6 to 16. The nucleotide sequence of the recombinant RSV may be inserted into a vector for co-transfection, and in this case, it is present with a T7 promoter, hammerhead ribozyme, hepatitis delta virus ribozyme, and a T7 terminator required for producing the recombinant virus, and preferably, it may be present as inserted as any one nucleotide sequence selected from the group consisting of SEQ ID NOs: 17 to 27.

Preferably, as the RSV virus genome which is the basis of the present invention, the human RSV A virus strain of SEQ ID NO: 1 may be used. RSV virus strains are various, such as RSV A strain, RSV B strain, HRSV A strain, HRSV B strain, BRSV strain, algal RSV strain, and the like, but the RSV basic backbone in which a foreign gene on the purpose of the present invention is inserted may be preferably an RSV A virus strain.

One example of the present invention provides an isolated polynucleotide molecule comprising a genome nucleotide sequence of the recombinant attenuated RSV genome or antigenomic cDNA or RNA of the recombinant attenuated RSV genome. Preferably, the polynucleotide molecule comprises antigenomic cDNA of the recombinant attenuated RSV, and the cDNA comprises a polynucleotide encoding antigenome of the recombinant attenuated RSV. In one embodiment, the isolated polynucleotide molecule may provide a polynucleotide molecule which is cDNA consisting of a polynucleotide represented by any one or more sequences selected from the group consisting of SEQ ID NOs: 6 to 16.

One embodiment provides a vector comprising the isolated polynucleotide molecule, preferably, the antigenomic cDNA. One embodiment provides a cell comprising the isolated polynucleotide molecule or vector.

The polynucleotide may be comprised in the vector or expressed by the vector to produce a recombinant RSV. Accordingly, a cell transfected by the isolated polynucleotide or vector also belongs to the scope of the present invention and is illustrated herein. In a related aspect of the present invention, a composition and a method for producing a recombinant RSV (e.g., isolated polynucleotide and vector incorporating RSV-incorporating cDNA) are also provided. In addition, a same or different expression vector comprising one or more isolated polynucleotide molecules encoding the RSV protein is also provided. This protein may be directly expressed from the genomic or antigenomic cDNA. The vector(s) may be expressed or co-expressed in a cell or culture culturing the cell to produce a recombinant attenuated RSV.

One embodiment provides a method for producing a recombinant attenuated RSV comprising the following. S1) transfecting the vector with a host cell, S2) culturing the cell or its culture for time sufficient for allowing virus replication, and S3) separating the replicated recombinant RSV may be comprised.

Specifically, in the S1) transfecting, one or more of the vectors may be used, and preferably, 2 or more may be used. Specifically, the vector may comprise the first expression vector comprising the recombinant antigenomic cDNA and the second expression vector comprising a polynucleotide encoding any one or more proteins selected from the group consisting of N, P, L, and M2-1 proteins. RSV is a negative sense RNA virus, and during virus production in vitro using reverse genetics, a separate helper gene required for gene synthesis is needed. The recombinant RSV antigenome and polynucleotides encoding each of N, P, L, M2-1 proteins may be introduced into a cell by a method such as transfection, electroporation, mechanical insertion, and transduction, and any method for cell infection of a plasmid commonly used in the art may be used. Preferably, as the cell, a cell such as Vero cell may be used, and production of the recombinant RSV virus of the present invention may be advantageous in the Vero cell. The method for introducing the recombinant RSV antigenomic cDNA and polynucleotide encoding each of N, P, L, M2-1 proteins may use a method commonly used in the art, and it is not particularly limited. In other embodiment, it may be synthesized by synthesizing the RSV antigenomic RNA in vitro and transfecting into a cell expressing RSV protein. Preferably, the vector comprising the recombinant RSV antigenome may be a cloning vector comprising cDNA of a polynucleotide comprising a T7 promoter, hammerhead ribozyme, RSV antigenome (or antigenomic cDNA), hepatitis delta virus ribozyme and a T7 terminator.

The polynucleotide encoding recombinant RSV antigenome may be comprised in the first expression vector, and the helper gene may be comprised in another vector different from the first expression vector (the second expression vector) or may be comprised in the same vector.

The vector comprising the polynucleotide encoding the recombinant RSV antigenome or antigenomic cDNA may illustratively use a pCC1 plasmid, and the recombinant RSV antigenome may be stabilized, and as long as the object of the present invention is not impaired, the type of the vector may be used without limitation. In the vector comprising the polynucleotide encoding the recombinant RSV antigenome or antigenomic cDNA, for the purpose of facilitating gene combination, mutation may be induced, or a restriction enzyme site may be modified, or a vector may be modified by inserting a synthesized polylinker comprising a controlled restriction enzyme site.

One embodiment provides a recombinant attenuated RSV produced by the method.

In one aspect, the present invention comprises a method for producing RSV comprising infecting a host cell in which RSV infection is allowed under a condition allowing RSV proliferation in an infected cell with a recombinant RSV. After a period of replication in the culture, the cell is lysed and the recombinant RSV is isolated therefrom. One or more desired RSVs are isolated as needed to produce one or more RSVs for vaccine, diagnostic and other uses.

One embodiment provides a pharmaceutical composition comprising a recombinant attenuated RSV; and a pharmaceutically acceptable carrier. The recombinant attenuated RSV prepared by one embodiment of the present invention may be used as a vaccine strain, preferably, live vaccine strain for preventing RSV infection, and when using the recombinant RSV in a vaccine use, the virus prepared according to the present invention may be directly used, used by freeze drying or used by mixing in liquid as a vaccine preparation. The vaccine composition of the present invention comprises any pharmaceutical substance which does not cause immune response harmful for a vertebrate to be administered by this composition, and comprises a pharmaceutically acceptable carrier comprising any appropriate diluent or excipient to be administered with the recombinant RSV vaccine strain without toxicity. In addition, if necessary, a pharmaceutically acceptable vaccine protective agent, an immunopotentiator, a diluent, an absorption accelerator, and the like may be comprised. The vaccine protective agent comprises for example, a lactose phosphate glutamate gelatin mixture, but not limited thereto. When the vaccine is a liquid or injection, if necessary, propylene glycol and sodium chloride in an amount sufficient for preventing hemolysis (e.g.: about 1%) may be contained. The term "pharmaceutically acceptable" means as listed in the United States Pharmacopoeia, European Pharmacopoeia or other commonly recognized pharmacopoeias for use in vertebrates, more specifically, humans. The RSV live vaccine strain of the present invention is administered in an effective dose or amount sufficient for stimulating immune response against one or more strains of the RSV virus (defined above). This composition may be used as a vaccine and/or an immunogenic composition for inducing protective immune response.

In the present invention, the vaccine composition may further comprise an adjuvant. "Adjuvant" means any substance added to the vaccine composition for enhancing antigenicity of the RSV virus. A substance used as the adjuvant is not particularly limited, and for example, it may be aluminum hydroxide, MPL (monophosphoryl lipid A), or an auxiliary molecule added to an oil or vaccine or generated by a body after each induction by such an additional component. In the present invention, the vaccine composition may induce cytokine production against RSV, and the cytokine may be one or more selected from the group consisting of Interferon-gamma (hereinafter, IFN-$\gamma$), Interleukin-12 (hereinafter, IL-12), and tumor necrosis factor-alpha (hereinafter, TNF-$\alpha$), but not limited thereto.

In one example of the present invention, the vaccine composition may induce production of antibodies against RSV and/or Indiana vesicular virus (Vesicular stomatitis Indiana virus; VSV). The vaccine composition may induce production of neutralizing antibodies against RSV and/or VSV.

The vaccine or immunogenic composition of the present invention may be administered in a subject to induce immune response against RSV. In one embodiment, the subject means a subject in need of preventing RSV infection, and specifically, includes an animal, and the animal may include a mammal such as a human, a non-human primate, a mouse, a rat, a cat, a dog and a horse. Conventionally, the dosage may be adjusted in this range based on for example, age, body condition, body weight, age, food, administration time and other clinical factors. The present invention comprises a method for formulating a vaccine or immunogenic composition which induce substantial immunity for infection of a subject or at least one symptom thereof, comprising adding an effective dose of immunogen into the preparation. A stimulus of substantial immunity by a single dosage is preferable, but in order to obtain a desired effect, an additional dosage may be administered through the same or different route. In newborns and infants, for example, in order to induce immunity at a sufficient level, a plurality of administrations may be needed. In one non-limitative embodiment, the dosage of the recombinant RSV live vaccine strain comprised in the vaccine may be commonly in a range of about 3.0 $\log_{10}$ to about 6.0 $\log_{10}$ plaque forming units ("PFU") or more of viruses per patient, more generally, about 4.0 $\log_{10}$ to 5.0 log 10 PFU of viruses. In one embodiment, about 5.0 $\log_{10}$ to 6.0 $\log_{10}$ PFU per patient may be administered for example, during the infancy between 1 and 6 months after birth, and one or more times of additional booster dosages may be administered for 2 to 6 months or longer after the first dosage. In other embodiment, young infants may be administered in a dosage of about 5.0 $\log_{10}$ to 6.0 $\log_{10}$ PFU at about 2, 4 or 6 months. Administration may be continued at intervals throughout childhood if necessary to maintain a sufficient level of protection against infection. In one embodiment, a method for inducing substantial immunity against virus infection or at least one symptom thereof in a subject comprises administering at least one effective dose of RSV recombinant virus. A method for administering a vaccine and/or immunogenic preparation includes parenteral administration (for example, endothelial, intramuscular, intravenous and subcutaneous), epidural and mucosal (for example, intranasal and oral or pulmonary route or suppository) administration, but not limited thereto. In a specific embodiment, the composition is administered intramuscularly, intravenously, subcutaneously, orally, intradermally, or intranasally. The composition may be administered by any convenient route by for example, injection or bolus injection, and absorption through the epithelium or inside the mucous membrane (for example, oral mucosa, colon, conjunctiva, nasopharyngeal cavity, mid-pharyngeal, vagina, urinary tract, bladder, intestinal mucosa, etc.), and may be administered with other biologically active substances. Administration may be systemic or local. The preventive vaccine preparation is systemically administered by subcutaneous or intramuscular injection or a needleless injection device using a needle and an injection. Selectively, the vaccine preparation is administered intranasally by drops, large particle aerosol (larger than about 10 microns) or spray into the upper respiratory tract. While any of the above routes of delivery causes immune response, intranasal administration provides an increased effect of inducing mucosal immunity at the position of penetration of the virus. In other embodiment, the vaccine and/or immunogenic preparation may be administered in a manner that targets mucosal tissue to induce immune response at the site of immunization. The administration site is not limited.

One embodiment of the present invention provides a method for preventing respiratory syncytial virus (RSV) infection by administering the RSV vaccine strain of the present application to a subject.

One embodiment provides a method for inducing immune response against RSV in a subject, comprising administering the pharmaceutical composition in an effective dose to generate immunity to a subject.

One embodiment provides a use of the recombinant RSV, for inducing immune response against RSV in a subject.

One embodiment provides a recombinant attenuated RSV used as a live vaccine strain for preventing RSV infection. The viruses of the present invention may be attenuated to reduce one or more functional properties of the virus. In a specific example, attenuation may be measured, compared to the wild type virus strain derived by the attenuated virus. In another example, attenuation may be determined, compared to the growth of the attenuated virus in other host system. The recombinant viruses of the present invention show an attenuated phenotype so that a virus can be administered as a vaccine. Attenuation may be achieved by any method known to those skilled in the art. The recombinant virus may be composed by the attenuated phenotype regardless of any theory.

The protein described in the present description may be understood as comprising a peptide or polypeptide as a set of amino acid sequences, and may be used interchangeably.

The nucleotide used in the present description may be used as a meaning including a polynucleotide, and may be used interchangeably.

The nucleotide used in the present description may be understood as comprising functional fragment thereof. For example, when a desired function or effect in a sequence having the sequence homology of 85% or more, 90% or more, 95% or more, 99% or more or 100% is shown, it may be understood that the right of the present invention extends to the case of having the sequence homology.

The protein used in the present description may be understood as comprising functional fragment thereof. For example, when a desired function or effect in a sequence having the sequence homology of 85% or more, 90% or more, 95% or more, 99% or more or 100% is shown, it may be understood that the right of the present invention extends to the case of having the sequence homology.

Hereinafter, the present invention will be described in detail by examples and the like to help understanding of the present invention. However, examples according to the present invention may be modified into various other forms, and the scope of the present invention should not be construed as being limited to the following examples. The examples of the present invention are provided to more completely explain the present invention to those skilled in the art to which the present invention pertains.

1. Wild Type RSV a Virus Strain Preparation

A wild type RSV A virus strain having the following information was prepared as follows.

Definition; Human respiratory syncytial virus strain RSVA/TH_10654/complete genome Accession No.; KU950464.1

Length; 15232 bp

Host; *Homo sapiens*/female/12 weeks

Collection date; 19 Feb. 2014

Country; USA

Subtype; RSV A

2. Surface Glycoprotein Donor Virus Selection

As a surface glycoprotein donor, Indiana vesicular virus (Vesicular stomatitis Indiana virus; VSV) was selected.

3. Preparation of cDNA Encoding RSV Antigenome

Backbone construct A below was produced as a basis.

(1) Design of backbone construct A

The gene sequence is in the order of 5'—T7 promoter—hammerhead ribozyme—RSV anti-genome (mutant part)-hepatitis delta virus ribozyme—T7 terminator—3'. The mutant part is based on SEQ ID NO: 1.

A T7 promoter sequence (TAATACGACTCACTATAGG; SEQ ID NO: 47) was inserted into the 5' end. Followed by the T7 promoter, a hammerhead ribozyme sequence (T TTTTTCGCGT CTGATGAGGC CGTTAGGCCG AAACTCCTCT CCGGAGTC; SEQ ID NO: 48) was inserted. Followed by the hammerhead ribozyme sequence, a wild type RSV anti-genome sequence was inserted and the following mutation was applied. In other words, the mutant part was produced so that any one cDNA sequence selected from the group consisting of SEQ ID NOs: 6-16 was inserted, instead of SEQ ID NO: 1.

The process for producing cDNA in which the mutant part is introduced as follows:

Based on the anti-genome sequence of the wild type RSV, produce AscI restriction enzyme sequence by inserting GCGCGCC between 77nt and 78nt. (insert only GCGCGCC<7 bp> as the AscI restriction enzyme sequence is GGCGCGCC<8 bp> but the sequence of 77nt is G)

1) Insert CCTGCAGG (SbfI restriction enzyme) sequence between 1079nt and 1080nt.
2) Insert GGCCGGCC (FseI restriction enzyme) sequence between 4590nt and 4591nt.
3) Substitute ATG (M) which are 4799nt and 4802nt nucleotides with ATT (I) sequence.
4) Insert ACGCGT (MluI restriction enzyme) sequence between 5639nt and 5640nt.
5) Insert GGGCCC (ApaI restriction enzyme) sequence between 7595nt and 7596nt.
6) Insert hepatitis delta virus ribozyme sequence (GGCCGGCATGGTCCCAGCCTCCT CGCTGGCGCCGGCTGGGCAACATGCTTCGG- CATGGCGAATGGGAC; SEQ ID NO: 49) followed by the wild type RSV antigenome sequence.

7) Insert a T7 terminator sequence (TAGCATAACCCCTTGGGGCCTCTAAACGGGTCTTGAGGGGTTTTTTG; SEQ ID NO: 50) into a hepatitis delta virus ribozyme sequence.

8) Insert the ACGCGAAAAAATGCGTACAAC (SEQ ID NO: 51) sequence at the 5' extreme end, and the GTTTTTGACACTTTTTTTCTCGT (SEQ ID NO: 52) sequence at the 3' extreme end. Herein, the ACGCGAAAAAATGCGTACAAC (SEQ ID NO: 51) inserted at the 5' extreme end was represented by 3' leader, and the GTTTTTGACACTTTTTTTCTCGT (SEQ ID NO: 52) inserted at the 3' extreme end was represented by 5' trailer.

The designed recombinant cDNA (SEQ ID NO: 1) was synthesized in vitro, and then was cloned in front of chloramphenicol resistance gene of the pCC1 cloning vector. Herein, one point mutation induction (M481) of the G protein sequence was introduced.

Hereinafter, various mutations were introduced into the RSV anti-genome of the cDNA. The process for producing the mutant part was specifically shown in the following.

(2) Example 1. cDNA construct of modified RSV in which chimeric vesicular stomatitis virus (VSV) G is inserted (SEQ ID NO: 6)

A VSV G gene sequence was inserted between the SH gene and G gene of Backbone construct A of SEQ ID NO: 1. As the VSV G sequence, the G sequence of GenBank FJ478454.1, Indiana serotype used as a viral vector was used. Then, the cytoplasmic tail region (LKHTKKRQIYTDIEMNRLGK; SEQ ID NO: 53) of VSV G used a chimeric VSV G sequence substituted with the cytoplasmic tail region (ARSTPVTLSKDQLSGINNIAFSN; SEQ ID NO: 54) of the wild type human respiratory syncytial virus strain RSVA/TH_10654. The 5' UTR and 3' UTR used a UTR sequence of the G protein gene of the wild type human respiratory syncytial virus strain RSVA/TH_10654, and NS1/NS2 inter-gene was inserted before the 5' UTR (SEQ ID NO: 3). Backbone construct A (SEQ ID NO: 1) was digested with FseI restriction enzyme, and the designed recombinant chimeric VSV G gene (SEQ ID NO: 3) was inserted.

(3) Example 2. SH removal (SEQ ID NO: 7) in chimeric VSV G-inserted construct (SEQ ID NO: 6)

The SH gene was removed for further attenuation of the construct of SEQ ID NO: 6. In SEQ ID NO: 6, the portion from 3'UTR of M to 3'UTR-FseI of SH (4288 ~ 4712) was removed and a RsrII restriction site (CGGTCCG) site was added.

(4) Example 3. Removing G gene in SEQ ID NO: 7 (SEQ ID NO: 8)

SEQ ID NO: 7 was digested with FseI and MluI to remove the portion comprising the G gene (5896~6934) and an inter-gene (gtattgttgcaaaaagccatgaccaaatcaaacagaatcaaaatcaactct; SEQ ID NO: 55) between G/F genes of the wild type human respiratory syncytial virus strain RSVA/TH_10654 was inserted (SEQ ID NO: 8).

(5) Example 4. Removing F gene in SEQ ID NO: 7 (SEQ ID NO: 9)

SEQ ID NO: 7 was digested with MluI and ApaI to remove the portion comprising the F gene (6941-8896) and an inter-gene (gtattgttgcaaaaagccatgaccaaatcaaacagaatcaaaatcaactct; SEQ ID NO: 55) between G/F genes of the wild type human respiratory syncytial virus strain RSVA/TH_10654 was inserted (SEQ ID NO: 9).

(6) Example 5. Substituting F gene of Backbone construct A with VSV G gene (SEQ ID NO: 10).

SEQ ID NO: 1 is digested with M1uI and ApaI thereby removing the 5758~7713 portion and a recombinant chimeric VSV G (SEQ ID NO: 3) is inserted at this position.

(7) G/F inter-gene-F 5' UTR-preF ectodomain-foldon fusion gene-F 3'UTR (SEQ ID NO: 4).

G/F inter-gene of the wild type human respiratory syncytial virus strain RSVA/TH_10654, F 5' UTR, a variant gene with D486L, E487L, F488W mutations applied to the ectodomain of F protein (1~513 aa), a linker (GSGGS; SEQ ID NO: 46), a T4 fibritin foldon gene, and F 3' UTR are synthesized (SEQ ID NO: 4).

(8) Example 6. SEQ ID NO: 10 is digested with ApaI and SEQ ID NO: 4 is inserted thereto (SEQ ID NO:11).

(9) Example 7. Removing G gene in SEQ ID NO: 11 (SEQ ID NO: 12).

SEQ ID NO: 11 is digested with FseI and MluI thereby removing the 4713~5751 portion comprising G gene, and an SH/G inter-gene (AGTCATAACAATGAACTAGGATATTAAGACCAAAAACAACGCT; SEQ ID NO: 56) is inserted (SEQ ID NO: 12).

(10) F protein is cleaved at two sites by furin protease and is separated into two subunits F1 and F2 and a peptide (p27) consisting of 27 amino acids in between. Even after cleavage, F1 and F2 are connected by two disulfide bonds, but p27 is removed from F to be a prefusion form. In the prefusion form, the hydrophobic fusion peptide (FP) region located at the N-terminus of F1 is located inside the protein, but is thermodynamically very unstable, and thus it comes out easily and it is exposed to the outside, and is irreversibly transformed into a postfusion form. When the furin cleavage site is mutated to prevent cleavage and the P27 portion is removed, the FP portion located inside the protein cannot protrude to the outside, resulting in stabilization in the prefusion form. When this stabilized protein is present on the virus surface, the infectivity of the virus disappears due to inability to function of cell fusion, but when heterologous attachment/fusion protein such as VSV G is present together on the virus surface, prefusion F-specific antibodies may be induced while maintaining the infectivity.

To WT F of the wild type human respiratory syncytial virus strain RSVA/TH_10654, 1) R106G mutation is introduced, and 2) 29 amino acids corresponding to R109~F137 comprising 2 furin cleavage sites and p27 region (RELPRFMNYTLNNTKNTNVTLSKKRKRRF; SEQ ID NO: 57) are removed, and 3) G/F inter-gene and F 5' UTR are linked to the 5' and F 3' UTR is linked to the 3', of the DNA sequence encoding modified F protein in which the part that 29 amino acids are removed is linked with GSGGSG (SEQ ID NO: 58) (SEQ ID NO: 5).

(11) Example 8. A sequence in which SEQ ID NO: 12 is digested with ApaI and the 6361~8229 portion is removed and SEQ ID NO: 5 is inserted is SEQ ID NO: 13.

(12) Example 9. SEQ ID NO: 11 is digested with AscI and SbfI, and the 174-1175 portion comprising NS1 and NS2 genes is substituted with NS1 and NS2 coding regions which are deoptimized with respect to human codon (SEQ ID NO: 14). The NS1 and NS2 genes are genes involved in immune escaping, and when deoptimized with respect to human codon, the expression level in a human cell decreases, resulting in reduced virus growth, attenuation in a human body, and increased safety, but the production level is not reduced because it is not attenuated in production cells deficient in these immune mechanisms.

(13) Example 10. The furin cleavage site II (6137-6148, CGAGCCAGAAGA (SEQ ID NO: 42); RARR (SEQ ID NO: 38)) of the F gene of Backbone construct A (SEQ ID NO: 1) was mutated into CGACCCTCCAAG (SEQ ID NO: 43); RPSK (SEQ ID NO: 39) (SEQ ID NO: 15). F protein is cleaved after transcription by ER-rich furin protease, and is divided into F1/F2 subdomains and becomes metastable. When the furin cleavage site is modified into a cleavage site of a lysosome-rich cleavage enzyme such as trypsin like protease, and the like, it is expected that it will be present on the surface of the virus in a single chain F form with high stability without cleavage after transcription.

(14) Example 11. The furin cleavage site I (6218~6229, AGGAAAAGAAGA (SEQ ID NO: 44); RKRR (SEQ ID NO: 40)) of the F gene of Backbone construct A (SEQ ID NO: 1) was mutated into AGGAAAAGAAAG (SEQ ID NO: 45); RKRK (SEQ ID NO: 41) (SEQ ID NO: 16). When the furin cleavage site is modified into a cleavage site of a lysosome-rich cleavage enzyme such as trypsin like protease, and the like, it is expected that it will be present on the surface of the virus in a single chain F form with high stability without cleavage after transcription.

Into the vector for co-transfection into which the examples were introduced, the cDNA sequence of SEQ ID NOs: 17-27 was introduced.

4. Helper Gene Design (4 Kinds)

RSV is a negative sense RNA virus, and helper genes required for gene synthesis (genes encoding N, P, L, M2-1 proteins of RSV) were added together, when viruses are produced in vitro using reverse genetics.

(1) For an N protein gene, the 1119~2294 sequence of the wild type human respiratory syncytial virus strain RSVA/TH_10654 anti-genome is cloned in pCI neo vector using restriction enzymes XhoI and MluI.

(2) For a P protein gene, the 2326~3051 sequence of the wild type human respiratory syncytial virus strain RSVA/TH_10654 anti-genome is cloned in pCI neo vector using restriction enzymes XhoI and MluI.

(3) For an M2-1 protein gene, the 7647~8231 sequence of the wild type human respiratory syncytial virus strain RSVA/TH_10654 anti-genome is cloned in pCI neo vector using restriction enzymes XhoI and MluI.

(4) For an L protein gene, the 8539~15036 sequence of the wild type human respiratory syncytial virus strain RSVA/TH_10654 anti-genome is cloned in pCI neo vector using restriction enzymes XhoI and MluI.

The N protein gene was shown as SEQ ID NO: 34, and the P protein gene was shown as SEQ ID NO: 35, and the M2-1 protein gene was shown as SEQ ID NO: 36, and the L protein gene was shown as SEQ ID NO: 37, respectively.

5. Virus Rescue

Vero cell was prepared in a 12well plate at a concentration of $1\times10^5$ cell/well.

Next day, 0.5 ug of each of a total of 6 plasmids of the T7 polymerase expression vector, RSV full length anti-genome vector, helper gene vector 4 kinds (N, P, M2-1, L) was transfected in the Vero cell using lipofectamine3000 at the same time.

After 10 days, the culture solution was collected and IFA, RT-PCR and gene sequence analysis were performed for virus detection.

A total of 12 viruses were produced by reverse genetics. Hereinafter, Δ is understood as deletion. The names of cDNA vectors for mutant virus production were written on the right. A schematic diagram of the negative strand RNA (that is, viral RNA) of each cDNA is shown in FIGS. 3-13, respectively.

1) RSV backbone strain; wtRSVA_TH10654 (Wild type control)

2) RSV backbone strain-VSV G insertion; cRSVA_VSVG_A (FIG. 3)

3) RSV backbone strain-VSV G insertion, SH deletion; cRSVA_VSVG_A_ΔSH (FIG. 4)

4) RSV backbone strain-VSV G insertion, SH deletion, RSV G deletion; CRSVA_VSVG_A_ΔSH_ΔG (FIG. 5)

5) RSV backbone strain-VSV G insertion, SH deletion, F deletion; CRSVA_VSVG_A_ΔSH_ΔF (FIG. 6)

6) RSV backbone strain-VSV G substitution; cRSVA_VSVG_S (FIG. 7)

7) RSV backbone strain-VSV G insertion, preF ectodomain-foldon mutation; CRSVA_VSVG_A_preF_ef (FIG. 8)

8) RSV backbone strain-VSV G substitution, preF ectodomain-foldon mutation; CRSVA_VSVG_S_preF_ef (FIG. 9)

9) RSV backbone strain-VSV G substitution, preF single chain mutation; CRSVA_VSVG_S_preF_sc (FIG. 10)

10) RSV backbone strain-VSV G insertion, preF ectodomain-foldon mutation, NS1/NS2 deoptimization; cRSVA_VSVG_A_preF_ef_NS1/NS2deop (FIG. 11)

11) RSV backbone strain-F furin cleavage stie II mutation; cRSVA_mF1 (FIG. 12)

12) RSV backbone strain-F furin cleavage site I mutation; cRSVA_mF2 (FIG. 13)

6. In Vitro Attenuation Test

Vero cell, HEp2 cell, MRC-5, BEAS-2B, NHBE (primary normal human bronchial epithelial cell) or HAE (primary human tracheobronchial airway cell) were infected with above 12 kinds of viruses at 0.1 MOI and cultured for 7 days. The virus culture solution was collected every day, and the virus titer was analyzed using q-PCR or plaque assay, and it was confirmed that the mutant virus, vaccine strain was attenuated as the proliferation rate and proliferation titer were reduced, compared to the wild type virus.

7. In Vivo Attenuation Test

The 12 kinds of viruses were administered through an IN (Intranasal), IM (intramuscular), or IP (intraperitoneal) route to BALB/c mice, Type I KO mice or cotton rats at a concentration of $10^1$~$10^7$ pfu/mouse. Virus was detected in blood or lung at Day 1~7 using q-PCR or plaque assay, and various changes such as body weight, fatality, pulmonary inflammation, and the like were measured for 2 weeks. As a result, it was confirmed that the viruses are attenuated.

8. Virus Stability Test

The 12 kinds of viruses were stored at −20° C., 4° C., 37° C. for 1-30 days. Plaque assay was performed using samples under each condition to measure an infectious virus titer. Vero cell or HEp2 cell were infected and the virus proliferation titer analysis according to temperature conditions was performed through q-PCR or plaque assay for the samples at Day 1~10. As the result of the analysis, it was confirmed that the stability of the mutant virus was increased compared to the wild type.

9. Immunogenicity Test

Using Mock, and the 12 kinds of viruses, the total antibody titer was measured. They were inoculated IM, IN or IP to BALB/c, female 4w mice, at a concentration of $1\times10^5$ pfu/mouse, once or twice every 2 weeks. The serum of each mouse was separated and the total antibody titer through ELISA and the neutralizing antibody was measured through plaque reduction neutralization test were measured. It was confirmed that the IgG antibody specific to the RSV antigen and antibody neutralizing virus infection were sufficiently formed in all the groups except for Mock.

10. Immunological Efficacy Test

The 12 kinds of viruses were inoculated IM or IP to BALB/c mice at a concentration of $10^1$~$10^7$ pfu/mouse once~three times every 2~3 weeks. After 4 weeks, RSVA or RSVB was challenged to the mouse nasal cavity at a concentration of $10^1$~$10^7$ pfu/mouse. Virus was detected in blood at Day 1~10 through q-PCR or Plaque assay and various changes such as body weight, fatality, pulmonary inflammation, and the like were measured for 20 days. As a result, it was confirmed that the virus infection was effectively inhibited in the immune groups.

11. Confirmation Test of Prefusion Stabilization Mutation

The RSV F gene which comprises s prefusion stabilization mutation (D486L/E487L/F488W) and has 6-Histidine attached to 3' is cloned in a mammalian cell expression vector and transfected into HEK293FT cells. After 5 days, the cells are lysed and reacted in a nickel coated plate, and thereby, the expressed RSV F protein is combined. The combined RSV F protein is binded to an antibody specifically reacting to the prefusion F protein (D25). While binding to the D25 antibody, a secondary antibody with HRP is added, followed by developing with TMB solution, and the absorbance is measured at a wavelength of 450 nm with a microplate reader.

The RSV F protein comprising mutation was confirmed to bind to the prefusion F-specific antibody (D25), and it was confirmed that the F protein was expressed in the prefusion form. Therefore, it was confirmed that a mutant virus expressing the prefusion RSV F protein was successfully prepared.

The invention claimed is:

1. A recombinant attenuated respiratory syncytial virus (RSV) comprising a nucleic acid encoding a chimeric vesicular stomatitis Indiana virus (VSV) G protein, wherein the chimeric VSV G protein consists of the amino acid sequence of SEQ ID NO: 2.

2. The recombinant attenuated respiratory syncytial virus according to claim 1, wherein:

i) a nucleic acid encoding at least one selected from the group consisting of SH, G, and F proteins of RSV is deleted or substituted with another nucleic acid; or ii) a first nucleic acid encoding the SH, G, or F protein is deleted and a second nucleic acid encoding a protein other than the deleted protein is substituted with another nucleic acid.

3. The recombinant attenuated respiratory syncytial virus according to claim 2, wherein the recombinant attenuated respiratory syncytial virus comprises the nucleic acid sequence of SEQ ID NO: 11 or SEQ ID NO: 14.

4. The recombinant attenuated respiratory syncytial virus according to claim 2, wherein the recombinant attenuated respiratory syncytial virus comprises the nucleic acid sequence of SEQ ID NO: 12 or SEQ ID NO: 13.

5. A recombinant attenuated respiratory syncytial virus (RSV) comprising a nucleic acid encoding a stabilized pre-fusion RSV F protein, wherein the stabilized pre-fusion RSV F protein has at least one mutation at a furin cleavage site of the F protein, and wherein amino acid residues RARR (SEQ ID NO: 38) corresponding to furin cleavage site II of the F protein at amino acid positions 106-109 of SEQ ID NO: 29 are modified to RPSK (SEQ ID NO: 39), or amino acid residues RKRR (SEQ ID NO: 40) corresponding to furin cleavage site I of the F protein at amino acid positions 133-136 of SEQ ID NO: 29 are substituted with RKRK (SEQ ID NO: 41).

6. The recombinant attenuated respiratory syncytial virus according to claim 1, further comprising a mutation structurally stabilizing an RSV F protein.

7. The recombinant attenuated respiratory syncytial virus according to claim 2, wherein nucleic acids encoding NS1 and NS2 proteins comprised in the virus are substituted with the nucleotide sequences of SEQ ID NOs: 32 and 33, respectively.

8. An isolated polynucleotide molecule comprising a genomic nucleotide sequence of the recombinant attenuated RSV genome of claim 1 or antigenomic cDNA or RNA of the recombinant attenuated RSV genome.

9. The polynucleotide molecule according to claim 8, wherein the isolated polynucleotide molecule is a cDNA consisting of the nucleotide sequence of SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, or SEQ ID NO: 14.

10. A method for inducing an immune response against RSV in a subject, comprising administering to the subject an immunogenically effective amount of a pharmaceutical composition comprising the recombinant attenuated RSV of claim 1 and a pharmaceutically acceptable carrier.

11. An isolated polynucleotide molecule comprising a genomic nucleotide sequence of the recombinant attenuated RSV genome of claim 5 or antigenomic cDNA or RNA of the recombinant attenuated RSV genome.

12. The polynucleotide molecule according to claim 11, wherein the isolated polynucleotide molecule is a cDNA consisting of the nucleotide sequence of SEQ ID NO: 15 or SEQ ID NO: 16.

13. A method for inducing an immune response against RSV in a subject, comprising administering to the subject an immunogenically effective amount of a pharmaceutical composition comprising the recombinant attenuated RSV of claim 5 and a pharmaceutically acceptable carrier.

14. The recombinant attenuated respiratory syncytial virus according to claim 6, wherein the mutation comprises a D486L mutation, a E487L mutation, and a F488W mutation corresponding to the mutations at amino acid positions 486-488 of SEQ ID NO: 29.

* * * * *